(12) United States Patent
Nielsen et al.

(10) Patent No.: US 10,918,499 B2
(45) Date of Patent: Feb. 16, 2021

(54) HIP REPLACEMENT NAVIGATION SYSTEMS AND METHODS

(71) Applicant: OrthAlign, Inc., Aliso Viejo, CA (US)

(72) Inventors: Jonathan Nielsen, Aliso Viejo, CA (US); John Matthews, San Diego, CA (US); Nicholas van der Walt, Laguna Hills, CA (US)

(73) Assignee: OrthAlign, Inc., Aliso Viejo, CA (US)

( * ) Notice: Subject to any disclaimer, the term of this patent is extended or adjusted under 35 U.S.C. 154(b) by 52 days.

(21) Appl. No.: 15/920,216

(22) Filed: Mar. 13, 2018

(65) Prior Publication Data

US 2018/0296365 A1    Oct. 18, 2018

Related U.S. Application Data

(60) Provisional application No. 62/471,185, filed on Mar. 14, 2017, provisional application No. 62/521,097, filed on Jun. 16, 2017.

(51) Int. Cl.
*A61B 17/58* (2006.01)
*A61B 17/60* (2006.01)
(Continued)

(52) U.S. Cl.
CPC ............ *A61F 2/4657* (2013.01); *A61B 34/20* (2016.02); *A61F 2/4607* (2013.01); *A61B 46/20* (2016.02);
(Continued)

(58) Field of Classification Search
CPC combination set(s) only.
See application file for complete search history.

(56) References Cited

U.S. PATENT DOCUMENTS

| | | |
|---|---|---|
| 3,174,080 A | 3/1965 | Scott |
| 3,670,324 A | 6/1972 | Trevor, 3rd |

(Continued)

FOREIGN PATENT DOCUMENTS

| | | |
|---|---|---|
| CA | 2241359 | 12/1999 |
| CA | 2 594 874 | 7/2006 |

(Continued)

OTHER PUBLICATIONS 510 (k) Summary for Total Knee Surgetics Navigation System, in 5 pages.

(Continued)

*Primary Examiner* — Sameh R Boles
(74) *Attorney, Agent, or Firm* — Knobbe, Martens, Olson & Bear, LLP

(57) ABSTRACT

Hip joint navigation systems and methods are provided. In some embodiments, the systems and methods described herein determine a table reference plane that approximates the Anterior Pelvic Plane. In some embodiments, the systems and methods described herein measure a pre-operative and post-operative point. In some embodiments, the comparison of the pre-operative and post-operative point corresponds to changes in leg length and joint offset. In some embodiments, the systems and methods described herein determine an Adjusted Plane. In some embodiments, the Adjusted Plane adjusts for tilt by rotating the Anterior Pelvic Plane about the inter-ASIS line. In some embodiments, the Adjusted Plane improves correlation between navigated cup angles and post-operative images.

20 Claims, 54 Drawing Sheets

(51) Int. Cl.
*A61F 2/00* (2006.01)
*A61F 2/46* (2006.01)
*A61B 34/20* (2016.01)
*A61B 46/20* (2016.01)
*A61B 90/00* (2016.01)
*A61F 2/36* (2006.01)

(52) U.S. Cl.
CPC .......... *A61B 2034/2048* (2016.02); *A61B 2034/2055* (2016.02); *A61B 2034/2057* (2016.02); *A61B 2034/2072* (2016.02); *A61B 2046/205* (2016.02); *A61B 2090/061* (2016.02); *A61B 2560/0228* (2013.01); *A61F 2/36* (2013.01); *A61F 2002/469* (2013.01); *A61F 2002/4658* (2013.01); *A61F 2002/4668* (2013.01); *A61F 2002/4681* (2013.01); *A61F 2002/4687* (2013.01); *A61F 2002/4696* (2013.01)

(56) References Cited

U.S. PATENT DOCUMENTS

| | | |
|---|---|---|
| 4,349,018 A | 9/1982 | Chambers |
| 4,421,112 A | 12/1983 | Mains et al. |
| 4,436,099 A | 3/1984 | Raftopoulos |
| 4,459,985 A | 7/1984 | McKay et al. |
| 4,475,549 A | 10/1984 | Oh |
| 4,501,266 A | 2/1985 | McDaniel |
| 4,509,393 A | 4/1985 | Castiglione |
| 4,518,855 A | 5/1985 | Malak |
| 4,524,766 A | 6/1985 | Petersen |
| 4,529,348 A | 7/1985 | Johnson et al. |
| 4,567,885 A | 2/1986 | Androphy |
| 4,567,886 A | 2/1986 | Petersen |
| 4,621,630 A | 11/1986 | Kenna |
| 4,646,729 A | 3/1987 | Kenna |
| 4,716,894 A | 1/1988 | Lazzeri et al. |
| 4,718,078 A | 1/1988 | Bleidorn et al. |
| 4,738,253 A | 4/1988 | Buechel et al. |
| 4,759,350 A | 7/1988 | Dunn et al. |
| 4,823,807 A | 4/1989 | Russell et al. |
| 4,938,762 A | 7/1990 | Wehrli |
| 4,944,760 A | 7/1990 | Kenna |
| 4,945,799 A | 8/1990 | Knetzer |
| 4,952,213 A | 8/1990 | Bowman et al. |
| 5,002,547 A | 3/1991 | Poggie et al. |
| 5,053,037 A | 10/1991 | Lackey |
| 5,065,612 A | 11/1991 | Ooka et al. |
| 5,116,338 A | 5/1992 | Poggie et al. |
| 5,122,146 A | 6/1992 | Chapman et al. |
| 5,129,908 A | 7/1992 | Petersen |
| 5,141,512 A | 8/1992 | Farmer et al. |
| 5,171,244 A | 12/1992 | Caspari et al. |
| 5,213,112 A | 5/1993 | Niwa et al. |
| 5,249,581 A | 10/1993 | Horbal et al. |
| 5,251,127 A | 10/1993 | Raab |
| 5,279,309 A | 1/1994 | Taylor et al. |
| 5,296,855 A | 3/1994 | Matsuzaki et al. |
| 5,306,276 A | 4/1994 | Johnson et al. |
| 5,320,625 A | 6/1994 | Bertin |
| 5,324,293 A | 6/1994 | Rehmann |
| 5,325,029 A | 6/1994 | Janecke et al. |
| 5,329,933 A | 7/1994 | Graf |
| 5,342,367 A | 8/1994 | Ferrante et al. |
| 5,343,391 A | 8/1994 | Mushabac |
| 5,358,526 A | 10/1994 | Tornier |
| 5,376,093 A | 12/1994 | Newman |
| 5,395,377 A | 3/1995 | Petersen et al. |
| 5,417,694 A | 5/1995 | Marik et al. |
| 5,423,827 A | 6/1995 | Mumme |
| 5,431,653 A | 7/1995 | Callaway |
| 5,462,548 A | 10/1995 | Pappas et al. |
| 5,468,244 A | 11/1995 | Attfield et al. |
| 5,474,088 A | 12/1995 | Zaharkin et al. |
| 5,486,177 A | 1/1996 | Mumme et al. |
| 5,514,143 A | 5/1996 | Bonutti et al. |
| 5,529,070 A | 6/1996 | Augustine et al. |
| 5,540,696 A | 7/1996 | Booth, Jr. et al. |
| 5,540,697 A | 7/1996 | Rehmann et al. |
| 5,553,198 A | 9/1996 | Wang et al. |
| 5,576,727 A | 11/1996 | Rosenberg et al. |
| 5,584,837 A | 12/1996 | Peterson |
| 5,597,379 A | 1/1997 | Haines et al. |
| 5,611,353 A | 3/1997 | Dance et al. |
| 5,624,444 A | 4/1997 | Wixson et al. |
| 5,628,750 A | 5/1997 | Whitlock et al. |
| 5,645,077 A | 7/1997 | Foxlin |
| 5,653,764 A | 8/1997 | Murphy |
| 5,681,316 A | 10/1997 | DeOrio et al. |
| 5,683,398 A | 11/1997 | Carls et al. |
| 5,688,282 A | 11/1997 | Baron et al. |
| 5,720,752 A | 2/1998 | Elliot et al. |
| 5,724,264 A | 3/1998 | Rosenberg et al. |
| 5,748,767 A | 5/1998 | Raab |
| 5,769,861 A | 6/1998 | Vilsmeier |
| 5,776,137 A | 7/1998 | Katz |
| 5,788,700 A | 8/1998 | Morawa et al. |
| 5,824,085 A | 10/1998 | Sahay et al. |
| 5,840,047 A | 11/1998 | Stedham |
| 5,880,714 A | 3/1999 | Rosenberg et al. |
| 5,916,219 A | 6/1999 | Matsuno et al. |
| 5,919,149 A | 7/1999 | Allum |
| 5,935,086 A | 8/1999 | Beacon et al. |
| 5,976,156 A | 11/1999 | Taylor et al. |
| 6,027,507 A | 2/2000 | Anderson et al. |
| 6,036,696 A | 3/2000 | Lambrecht et al. |
| 6,056,756 A | 5/2000 | Eng et al. |
| 6,090,114 A | 7/2000 | Matsuno et al. |
| 6,094,019 A | 7/2000 | Saiki |
| 6,120,509 A | 9/2000 | Wheeler |
| 6,122,538 A | 9/2000 | Sliwa, Jr. et al. |
| 6,126,608 A | 10/2000 | Kemme et al. |
| 6,162,191 A | 12/2000 | Foxin |
| 6,167,292 A | 12/2000 | Badano et al. |
| 6,171,310 B1 | 1/2001 | Giordano |
| 6,195,615 B1 | 2/2001 | Lysen |
| 6,197,032 B1 | 3/2001 | Lawes et al. |
| 6,214,013 B1 | 4/2001 | Lambrech et al. |
| 6,214,014 B1 | 4/2001 | McGann |
| 6,216,029 B1 | 4/2001 | Paltieli |
| 6,246,898 B1 | 6/2001 | Vesely et al. |
| 6,258,095 B1 | 7/2001 | Lombardo et al. |
| 6,261,247 B1 | 7/2001 | Ishikawa et al. |
| 6,299,646 B1 | 10/2001 | Chambat et al. |
| 6,332,089 B1 | 12/2001 | Acker et al. |
| 6,348,058 B1 | 2/2002 | Melken et al. |
| 6,354,011 B1 | 3/2002 | Albrecht |
| 6,361,506 B1 | 3/2002 | Saenger et al. |
| 6,361,507 B1 | 3/2002 | Foxlin |
| 6,361,508 B1 | 3/2002 | Johnson et al. |
| 6,377,839 B1 | 4/2002 | Kalfas et al. |
| 6,381,485 B1 | 4/2002 | Hunter et al. |
| 6,383,149 B1 | 5/2002 | DeMayo |
| 6,395,005 B1 | 5/2002 | Lovell |
| 6,447,448 B1 | 9/2002 | Ishikawa et al. |
| 6,468,280 B1 | 10/2002 | Saenger et al. |
| 6,470,207 B1 | 10/2002 | Simon et al. |
| 6,471,637 B1 | 10/2002 | Green et al. |
| 6,473,635 B1 | 10/2002 | Rasche |
| 6,477,400 B1 | 11/2002 | Barrick |
| 6,477,421 B1 | 11/2002 | Andersen et al. |
| 6,478,799 B1 | 11/2002 | Williamson |
| 6,488,713 B1 | 12/2002 | Hershnerger |
| 6,499,488 B1 | 12/2002 | Hunter et al. |
| 6,514,259 B2 | 2/2003 | Picard et al. |
| 6,527,443 B1 | 3/2003 | Vilsmeier |
| 6,551,325 B2 | 4/2003 | Neubauer et al. |
| 6,585,666 B2 | 7/2003 | Suh et al. |
| 6,595,997 B2 | 7/2003 | Axelson, Jr. et al. |
| 6,595,999 B2 | 7/2003 | Marchione et al. |
| 6,607,487 B2 | 8/2003 | Chang et al. |
| 6,640,128 B2 | 10/2003 | Vilsmeier et al. |
| 6,648,896 B2 | 11/2003 | Overes et al. |

(56) References Cited

U.S. PATENT DOCUMENTS

| | | |
|---|---|---|
| 6,679,916 B1 | 1/2004 | Frankie et al. |
| 6,685,655 B2 | 2/2004 | DeMayo |
| 6,685,711 B2 | 2/2004 | Axelson et al. |
| 6,711,431 B2 | 3/2004 | Sarin et al. |
| 6,712,824 B2 | 3/2004 | Millard et al. |
| 6,715,213 B2 | 4/2004 | Richter |
| 6,725,080 B2 | 4/2004 | Melkent et al. |
| 6,725,173 B2 | 4/2004 | An |
| 6,743,235 B2 | 6/2004 | Rao |
| 6,770,078 B2 | 8/2004 | Bonutti |
| 6,786,877 B2 | 9/2004 | Foxlin |
| 6,802,864 B2 | 10/2004 | Tornier |
| 6,820,025 B2 | 11/2004 | Bachmann et al. |
| 6,827,723 B2 | 12/2004 | Carson |
| 6,917,827 B2 | 7/2005 | Kienzle, III |
| 6,923,817 B2 | 8/2005 | Carson et al. |
| 6,928,742 B2 | 8/2005 | Broers et al. |
| 6,947,783 B2 | 9/2005 | Immerz |
| 6,986,181 B2 | 1/2006 | Murphy et al. |
| 6,997,882 B1 | 2/2006 | Parker et al. |
| 7,007,699 B2 | 3/2006 | Martinelli et al. |
| 7,021,140 B2 | 4/2006 | Perkins |
| 7,027,477 B2 | 4/2006 | Sutter et al. |
| 7,037,310 B2 | 5/2006 | Murphy |
| 7,048,741 B2 | 5/2006 | Swanson |
| 7,089,148 B1 | 8/2006 | Bachmann et al. |
| 7,094,241 B2 | 8/2006 | Hodorek et al. |
| 7,104,998 B2 | 9/2006 | Yoon et al. |
| 7,105,028 B2 | 9/2006 | Murphy |
| 7,194,295 B2 | 3/2007 | Vilsmeier |
| 7,209,776 B2 | 4/2007 | Leitner |
| 7,219,033 B2 | 5/2007 | Kolen |
| 7,273,500 B2 | 9/2007 | Williamson |
| 7,331,932 B2 | 2/2008 | Leitner |
| 7,344,541 B2 | 3/2008 | Haines et al. |
| 7,392,076 B2 | 6/2008 | Moctezuma de la Barrera |
| 7,396,357 B2 | 7/2008 | Tornier et al. |
| 7,444,178 B2 | 10/2008 | Goldbach |
| 7,468,075 B2 | 12/2008 | Lang et al. |
| 7,468,077 B2 | 12/2008 | Rochetin |
| 7,497,029 B2 | 3/2009 | Plassky et al. |
| 7,520,880 B2 | 4/2009 | Claypool et al. |
| 7,547,307 B2 | 6/2009 | Carson et al. |
| 7,559,931 B2 | 7/2009 | Stone |
| 7,578,821 B2 | 8/2009 | Fisher et al. |
| 7,611,520 B2 | 11/2009 | Broers et al. |
| 7,611,522 B2 | 11/2009 | Gorek |
| 7,621,920 B2 | 11/2009 | Claypool et al. |
| 7,623,902 B2 | 11/2009 | Pacheco |
| 7,726,564 B2 | 6/2010 | Goldbach |
| 7,776,098 B2 | 8/2010 | Murphy |
| 7,831,292 B2 | 11/2010 | Quaid et al. |
| 7,834,847 B2 | 11/2010 | Boillot et al. |
| 7,846,092 B2 | 12/2010 | Murphy |
| 7,857,821 B2 | 12/2010 | Couture et al. |
| 7,885,705 B2 | 2/2011 | Murphy |
| 7,970,174 B2 | 6/2011 | Goldbach |
| 8,057,479 B2 | 11/2011 | Stone |
| 8,057,482 B2 | 11/2011 | Stone |
| 8,078,254 B2 | 12/2011 | Murphy |
| 8,118,815 B2 | 2/2012 | van der Walt |
| 8,241,296 B2 | 8/2012 | Wasielewski |
| 8,265,790 B2 | 9/2012 | Amiot et al. |
| 8,267,938 B2 | 9/2012 | Murphy |
| 8,277,455 B2 | 10/2012 | Couture et al. |
| 8,282,685 B2 | 10/2012 | Rochetin et al. |
| 8,355,773 B2 | 1/2013 | Leitner et al. |
| 8,412,308 B2 | 4/2013 | Goldbach |
| 8,421,854 B2 | 4/2013 | Zerkin |
| 8,446,473 B2 | 5/2013 | Goldbach |
| 8,512,346 B2 | 8/2013 | Couture |
| 8,551,108 B2 | 10/2013 | Pelletier et al. |
| 8,588,892 B2 | 11/2013 | Hladio et al. |
| 8,690,888 B2 | 4/2014 | Stein et al. |
| 8,718,820 B2 | 5/2014 | Amiot et al. |
| 8,734,432 B2 | 5/2014 | Tuma et al. |
| 8,764,758 B2 | 7/2014 | Echeverri |
| 8,888,786 B2 | 11/2014 | Stone |
| 8,911,447 B2 | 12/2014 | van der Walt et al. |
| 8,974,467 B2 | 3/2015 | Stone |
| 8,974,468 B2 | 3/2015 | Borja |
| 8,998,910 B2 | 4/2015 | Borja et al. |
| 9,044,218 B2 | 6/2015 | Young |
| 9,192,392 B2 | 11/2015 | van der Walt et al. |
| 9,262,802 B2 | 2/2016 | Aghazadeh |
| 9,271,756 B2 | 3/2016 | van der Walt et al. |
| 9,339,226 B2 | 5/2016 | van der Walt et al. |
| 9,375,178 B2 | 6/2016 | Aghazadeh |
| 9,456,769 B2 | 10/2016 | Stein et al. |
| 9,549,742 B2 | 1/2017 | Berend et al. |
| 9,572,586 B2 | 2/2017 | van der Walt et al. |
| 9,649,160 B2 | 5/2017 | van der Walt et al. |
| 9,775,725 B2 | 10/2017 | van der Walt et al. |
| 9,855,075 B2 | 1/2018 | van der Walt et al. |
| 9,931,059 B2 | 4/2018 | Borja |
| 10,206,714 B2 | 2/2019 | van der Walt et al. |
| 10,238,510 B2 | 3/2019 | van der Walt et al. |
| 10,321,852 B2 | 6/2019 | Borja |
| 10,363,149 B2 | 7/2019 | van der Walt et al. |
| 10,603,115 B2 | 3/2020 | van der Walt et al. |
| 10,716,580 B2 | 7/2020 | Berend et al. |
| 2002/0077540 A1 | 6/2002 | Kienzie, III |
| 2002/0103610 A1 | 8/2002 | Bachmann et al. |
| 2002/0107522 A1 | 8/2002 | Picard et al. |
| 2002/0133175 A1 | 9/2002 | Carson |
| 2002/0198451 A1 | 12/2002 | Carson |
| 2003/0019294 A1 | 1/2003 | Richter |
| 2003/0069591 A1 | 4/2003 | Carson et al. |
| 2003/0093080 A1 | 5/2003 | Brown et al. |
| 2003/0105470 A1 | 6/2003 | White |
| 2003/0120282 A1 | 6/2003 | Scouten et al. |
| 2003/0163142 A1 | 8/2003 | Paltieli et al. |
| 2003/0181919 A1 | 9/2003 | Gorek |
| 2003/0184297 A1 | 10/2003 | Jakab |
| 2003/0199882 A1 | 10/2003 | Gorek |
| 2003/0204965 A1 | 11/2003 | Hennessey |
| 2003/0229356 A1 | 12/2003 | Dye |
| 2004/0006393 A1 | 1/2004 | Burkinshaw |
| 2004/0019382 A1 | 1/2004 | Amirouche et al. |
| 2004/0034313 A1 | 2/2004 | Leitner |
| 2004/0039396 A1 | 2/2004 | Couture et al. |
| 2004/0068260 A1 | 4/2004 | Cossette et al. |
| 2004/0087958 A1 | 5/2004 | Myers et al. |
| 2004/0087962 A1 | 5/2004 | Gorek |
| 2004/0097952 A1 | 5/2004 | Sarin et al. |
| 2004/0102792 A1 | 5/2004 | Sarin et al. |
| 2004/0106916 A1 | 6/2004 | Quaid et al. |
| 2004/0122441 A1 | 6/2004 | Muratsu |
| 2004/0147926 A1 | 7/2004 | Iversen |
| 2004/0149036 A1 | 8/2004 | Foxlin et al. |
| 2004/0152970 A1 | 8/2004 | Hunter et al. |
| 2004/0153066 A1 | 8/2004 | Coon et al. |
| 2004/0153079 A1 | 8/2004 | Tsougarakis et al. |
| 2004/0181144 A1 | 9/2004 | Cinquin et al. |
| 2004/0201857 A1 | 10/2004 | Foxlin |
| 2004/0230197 A1 | 11/2004 | Tornier et al. |
| 2004/0243148 A1 | 12/2004 | Wasielewski |
| 2005/0021037 A1 | 1/2005 | McCombs et al. |
| 2005/0021044 A1 | 1/2005 | Stone et al. |
| 2005/0107799 A1 | 5/2005 | Graf et al. |
| 2005/0113846 A1 | 5/2005 | Carson |
| 2005/0149040 A1 | 7/2005 | Haines et al. |
| 2005/0197814 A1 | 9/2005 | Aram et al. |
| 2005/0209605 A1 | 9/2005 | Grimm et al. |
| 2005/0222574 A1 | 10/2005 | Giordano et al. |
| 2005/0234332 A1 | 10/2005 | Murphy |
| 2005/0251026 A1 | 11/2005 | Stone |
| 2005/0251148 A1 | 11/2005 | Friedrich |
| 2006/0009780 A1 | 1/2006 | Foley et al. |
| 2006/0015018 A1 | 1/2006 | Jutras et al. |
| 2006/0015120 A1 | 1/2006 | Richard et al. |
| 2006/0020177 A1 | 1/2006 | Seo et al. |
| 2006/0064105 A1 | 3/2006 | Raistrick et al. |
| 2006/0084977 A1 | 4/2006 | Lieberman |

(56) References Cited

U.S. PATENT DOCUMENTS

| | | |
|---|---|---|
| 2006/0089657 A1 | 4/2006 | Broers et al. |
| 2006/0094958 A1 | 5/2006 | Marquart et al. |
| 2006/0122491 A1 | 6/2006 | Murray et al. |
| 2006/0142656 A1 | 6/2006 | Malackowski et al. |
| 2006/0142657 A1 | 6/2006 | Quaid et al. |
| 2006/0149276 A1 | 7/2006 | Grimm |
| 2006/0161051 A1 | 7/2006 | Terrill-Grisoni et al. |
| 2006/0184177 A1 | 8/2006 | Echeverri |
| 2006/0217733 A1 | 9/2006 | Plassky et al. |
| 2006/0217734 A1 | 9/2006 | Sanford et al. |
| 2006/0241639 A1 | 10/2006 | Kuczynski et al. |
| 2006/0270949 A1 | 11/2006 | Mathie et al. |
| 2006/0282023 A1 | 12/2006 | Leitner |
| 2007/0032748 A1 | 2/2007 | McNeil et al. |
| 2007/0043287 A1 | 2/2007 | Degraaf |
| 2007/0043375 A1 | 2/2007 | Anissian |
| 2007/0073296 A1 | 3/2007 | Panchbhavi |
| 2007/0100346 A1 | 5/2007 | Wyss et al. |
| 2007/0162142 A1 | 7/2007 | Stone |
| 2007/0179626 A1 | 8/2007 | de la Barrera et al. |
| 2007/0179628 A1 | 8/2007 | Rochetin |
| 2007/0219559 A1 | 9/2007 | Heavener et al. |
| 2007/0219561 A1 | 9/2007 | Lavallee et al. |
| 2007/0226986 A1 | 10/2007 | Park et al. |
| 2007/0244488 A1 | 10/2007 | Metzger et al. |
| 2007/0249967 A1 | 10/2007 | Buly et al. |
| 2007/0270718 A1 | 11/2007 | Rochetin et al. |
| 2007/0270973 A1 | 11/2007 | Johnson et al. |
| 2007/0287911 A1 | 12/2007 | Haid et al. |
| 2008/0039868 A1 | 2/2008 | Tuemmler et al. |
| 2008/0058945 A1 | 3/2008 | Hajaj et al. |
| 2008/0071195 A1 | 3/2008 | Cuellar et al. |
| 2008/0103509 A1 | 5/2008 | Goldbach |
| 2008/0162074 A1 | 7/2008 | Schneider |
| 2008/0183179 A1 | 7/2008 | Siebel et al. |
| 2008/0195109 A1 | 8/2008 | Hunter et al. |
| 2008/0202200 A1 | 8/2008 | West |
| 2008/0211768 A1 | 9/2008 | Breen et al. |
| 2008/0243127 A1 | 10/2008 | Lang et al. |
| 2008/0249394 A1 | 10/2008 | Giori et al. |
| 2008/0262812 A1 | 10/2008 | Arata et al. |
| 2008/0275451 A1 | 11/2008 | McAllister et al. |
| 2008/0281328 A1 | 11/2008 | Lang et al. |
| 2008/0285805 A1 | 11/2008 | Luinge et al. |
| 2009/0000626 A1 | 1/2009 | Quaid et al. |
| 2009/0000627 A1 | 1/2009 | Quaid et al. |
| 2009/0012532 A1 | 1/2009 | Quaid et al. |
| 2009/0040224 A1 | 2/2009 | Igarashi et al. |
| 2009/0076507 A1 | 3/2009 | Claypool et al. |
| 2009/0076519 A1 | 3/2009 | Iversen |
| 2009/0088753 A1 | 4/2009 | Aram et al. |
| 2009/0099665 A1 | 4/2009 | Taylor et al. |
| 2009/0138019 A1 | 5/2009 | Wasielewski |
| 2009/0171370 A1 | 7/2009 | Yoon et al. |
| 2009/0209884 A1 | 8/2009 | Van Vorhis et al. |
| 2009/0216247 A1 | 8/2009 | Collette |
| 2009/0216285 A1 | 8/2009 | Ek |
| 2009/0234360 A1 | 9/2009 | Alexander |
| 2009/0247863 A1 | 10/2009 | Proulx et al. |
| 2009/0248044 A1 | 10/2009 | Amiot et al. |
| 2009/0264737 A1 | 10/2009 | Haechler et al. |
| 2009/0270864 A1 | 10/2009 | Poncet |
| 2009/0270865 A1 | 10/2009 | Poncet et al. |
| 2009/0270868 A1 | 10/2009 | Park et al. |
| 2009/0270869 A1 | 10/2009 | Colquhoun et al. |
| 2009/0270874 A1 | 10/2009 | Santarella et al. |
| 2009/0270875 A1 | 10/2009 | Poncet |
| 2009/0270928 A1 | 10/2009 | Stone et al. |
| 2009/0276054 A1 | 11/2009 | Clifford et al. |
| 2009/0281545 A1 | 11/2009 | Stubbs |
| 2009/0289806 A1 | 11/2009 | Thornberry |
| 2009/0292227 A1 | 11/2009 | Scholten et al. |
| 2009/0299416 A1 | 12/2009 | Haenni et al. |
| 2009/0299483 A1 | 12/2009 | Amirouche et al. |
| 2009/0306679 A1 | 12/2009 | Murphy |
| 2009/0312973 A1 | 12/2009 | Hatlestad et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0324078 A1 | 12/2009 | Wu et al. |
| 2010/0016705 A1 | 1/2010 | Stone |
| 2010/0023018 A1 | 1/2010 | Theofilos |
| 2010/0063508 A1 | 3/2010 | Borja et al. |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0087829 A1 | 4/2010 | Metzger et al. |
| 2010/0100011 A1 | 4/2010 | Roche |
| 2010/0100154 A1 | 4/2010 | Roche |
| 2010/0113980 A1 | 5/2010 | Herr et al. |
| 2010/0121334 A1 | 5/2010 | Couture et al. |
| 2010/0137869 A1 | 6/2010 | Borja et al. |
| 2010/0137871 A1 | 6/2010 | Borja |
| 2010/0153081 A1 | 6/2010 | Bellettre et al. |
| 2010/0179605 A1 | 7/2010 | Branch et al. |
| 2010/0182914 A1 | 7/2010 | DelRegno et al. |
| 2010/0192662 A1 | 8/2010 | Yanni |
| 2010/0198067 A1 | 8/2010 | Mahfouz et al. |
| 2010/0198275 A1 | 8/2010 | Chana et al. |
| 2010/0204551 A1 | 8/2010 | Roche |
| 2010/0204575 A1 | 8/2010 | Roche et al. |
| 2010/0204955 A1 | 8/2010 | Roche et al. |
| 2010/0211077 A1 | 8/2010 | Couture et al. |
| 2010/0239996 A1 | 9/2010 | Ertl |
| 2010/0241126 A1 | 9/2010 | Ghijselings |
| 2010/0249533 A1 | 9/2010 | Pierce et al. |
| 2010/0249534 A1 | 9/2010 | Pierce et al. |
| 2010/0249535 A1 | 9/2010 | Pierce et al. |
| 2010/0249659 A1 | 9/2010 | Sherman et al. |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0250276 A1 | 9/2010 | Pierce et al. |
| 2010/0250284 A1 | 9/2010 | Roche et al. |
| 2010/0250571 A1 | 9/2010 | Pierce et al. |
| 2010/0256504 A1 | 10/2010 | Moreau-Gaudry et al. |
| 2010/0261998 A1 | 10/2010 | Stiehl |
| 2010/0268067 A1 | 10/2010 | Razzaque et al. |
| 2010/0298661 A1 | 11/2010 | McCombie et al. |
| 2010/0324457 A1 | 12/2010 | Bean et al. |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331633 A1 | 12/2010 | Stein |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331683 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331735 A1 | 12/2010 | Stein |
| 2010/0331736 A1 | 12/2010 | Stein |
| 2010/0331737 A1 | 12/2010 | Stein et al. |
| 2010/0331738 A1 | 12/2010 | Stein et al. |
| 2010/0331894 A1 | 12/2010 | Stein |
| 2010/0332152 A1 | 12/2010 | Stein |
| 2011/0028865 A1 | 2/2011 | Luinge et al. |
| 2011/0032184 A1 | 2/2011 | Roche et al. |
| 2011/0093081 A1 | 4/2011 | Chana et al. |
| 2011/0208093 A1 | 8/2011 | Gross et al. |

(56) References Cited

U.S. PATENT DOCUMENTS

| | | |
|---|---|---|
| 2011/0213275 A1 | 9/2011 | Boos et al. |
| 2011/0218458 A1 | 9/2011 | Valin et al. |
| 2011/0218543 A1 | 9/2011 | van der Walt |
| 2011/0218546 A1 | 9/2011 | De La Fuente Klein et al. |
| 2011/0275957 A1 | 11/2011 | Bhandari |
| 2012/0022406 A1 | 1/2012 | Hladio et al. |
| 2012/0029389 A1 | 2/2012 | Amiot et al. |
| 2012/0053488 A1 | 3/2012 | Boutin et al. |
| 2012/0053594 A1 | 3/2012 | Pelletier et al. |
| 2012/0093377 A1 | 4/2012 | Tsougarakis et al. |
| 2012/0130279 A1 | 5/2012 | Stone |
| 2012/0157887 A1 | 6/2012 | Fanson et al. |
| 2012/0172712 A1 | 7/2012 | Bar-Tal |
| 2012/0203140 A1 | 8/2012 | Malchau et al. |
| 2012/0283599 A1 | 11/2012 | Borja |
| 2012/0316567 A1 | 12/2012 | Gross et al. |
| 2013/0079678 A1 | 3/2013 | Stein et al. |
| 2013/0079679 A1 | 3/2013 | Roche et al. |
| 2013/0079680 A1 | 3/2013 | Stein et al. |
| 2013/0079790 A1 | 3/2013 | Stein et al. |
| 2013/0079791 A1 | 3/2013 | Stein et al. |
| 2013/0079793 A1 | 3/2013 | Stein et al. |
| 2013/0190887 A1 | 7/2013 | Fanson et al. |
| 2013/0274633 A1 | 10/2013 | Hladio et al. |
| 2014/0005673 A1 | 1/2014 | Pelletier et al. |
| 2014/0031672 A1 | 1/2014 | McCaulley et al. |
| 2014/0052149 A1* | 2/2014 | van der Walt ........ A61F 2/4657 606/130 |
| 2014/0114179 A1 | 4/2014 | Muller et al. |
| 2014/0134586 A1 | 5/2014 | Stein et al. |
| 2014/0135658 A1 | 5/2014 | Hladio et al. |
| 2014/0135744 A1 | 5/2014 | Stein et al. |
| 2014/0135773 A1 | 5/2014 | Stein et al. |
| 2014/0136143 A1 | 5/2014 | Stein et al. |
| 2014/0182062 A1 | 7/2014 | Aghazadeh |
| 2014/0275940 A1 | 9/2014 | Hladio et al. |
| 2014/0276000 A1 | 9/2014 | Mullaney et al. |
| 2014/0276864 A1 | 9/2014 | Aghazadeh |
| 2014/0303631 A1 | 10/2014 | Thornberry |
| 2014/0330281 A1 | 11/2014 | Aghazadeh |
| 2014/0364858 A1 | 12/2014 | Li et al. |
| 2015/0018718 A1 | 1/2015 | Aghazadeh |
| 2015/0100058 A1 | 4/2015 | van der Walt et al. |
| 2015/0127009 A1 | 5/2015 | Berend et al. |
| 2015/0142372 A1 | 5/2015 | Singh |
| 2015/0150569 A1 | 6/2015 | van der Walt et al. |
| 2015/0164657 A1 | 6/2015 | Miles et al. |
| 2015/0238204 A1 | 8/2015 | Stone |
| 2015/0245914 A1 | 9/2015 | Langton |
| 2015/0272478 A1 | 10/2015 | Borja |
| 2015/0313723 A1 | 11/2015 | Jansen |
| 2015/0342516 A1 | 12/2015 | Nguyen et al. |
| 2016/0038242 A1 | 2/2016 | Lo Iacono et al. |
| 2016/0175055 A1 | 6/2016 | Hook et al. |
| 2016/0213383 A1 | 7/2016 | van der Walt et al. |
| 2016/0220315 A1 | 8/2016 | Falardeau |
| 2016/0220318 A1 | 8/2016 | Falardeau et al. |
| 2016/0220385 A1 | 8/2016 | Falardeau et al. |
| 2016/0242934 A1 | 8/2016 | van der Walt et al. |
| 2016/0278943 A1 | 9/2016 | van der Walt et al. |
| 2016/0346044 A1 | 12/2016 | Brown et al. |
| 2017/0196571 A1 | 7/2017 | Berend et al. |
| 2017/0238946 A1 | 8/2017 | van der Walt et al. |
| 2017/0296203 A1 | 10/2017 | Stone |
| 2017/0296274 A1 | 10/2017 | van der Walt et al. |
| 2018/0064496 A1 | 3/2018 | Hladio et al. |
| 2018/0153587 A1 | 6/2018 | van der Walt et al. |
| 2018/0168826 A1 | 6/2018 | van der Walt et al. |
| 2018/0193171 A1 | 7/2018 | van der Walt et al. |
| 2018/0206860 A1 | 7/2018 | van der Walt et al. |
| 2018/0296232 A1 | 10/2018 | Nielsen et al. |
| 2019/0254715 A1 | 8/2019 | van der Walt et al. |
| 2019/0328549 A1 | 10/2019 | van der Walt et al. |
| 2019/0350728 A1 | 11/2019 | van der Walt et al. |
| 2019/0357809 A1 | 11/2019 | Borja et al. |

FOREIGN PATENT DOCUMENTS

| | | |
|---|---|---|
| CA | 2 537 711 | 8/2007 |
| DE | 4 225 112 | 12/1993 |
| DE | 29704393 | 8/1997 |
| DE | 198 30 359 | 1/2000 |
| EP | 0 557 591 | 9/1993 |
| EP | 0 651 968 | 5/1995 |
| EP | 1 635 705 | 3/2006 |
| EP | 1 817 547 | 4/2012 |
| GB | 2 197 790 | 6/1988 |
| GB | 2 511 885 | 9/2014 |
| JP | 07-184929 | 7/1995 |
| JP | H08-240611 | 9/1996 |
| JP | 2006-314775 | 11/2006 |
| JP | 2006-528496 | 12/2006 |
| JP | 2007-503289 | 2/2007 |
| JP | 2007-534351 | 11/2007 |
| JP | 2008-521574 | 6/2008 |
| JP | 2008-537496 | 9/2008 |
| JP | 2009-511136 | 3/2009 |
| JP | 2011-502626 | 1/2011 |
| WO | WO 99/60939 | 12/1999 |
| WO | WO 2001/030247 | 5/2001 |
| WO | WO 02/000131 | 1/2002 |
| WO | WO 02/17798 | 3/2002 |
| WO | WO 2004/080323 | 9/2004 |
| WO | WO 2004/112610 | 12/2004 |
| WO | WO 2005/006993 | 1/2005 |
| WO | WO 2006/119387 | 11/2006 |
| WO | WO 2007/136784 | 11/2007 |
| WO | WO 2008/073999 | 6/2008 |
| WO | WO 2008/129414 | 10/2008 |
| WO | WO 2009/117833 | 10/2009 |
| WO | WO 2010/011978 | 1/2010 |
| WO | WO 2010/030809 | 3/2010 |
| WO | WO 2010/063117 | 6/2010 |
| WO | WO 2011/044273 | 4/2011 |
| WO | WO 2012/006172 | 1/2012 |
| WO | WO 2012/027815 | 3/2012 |
| WO | WO 2012/027816 | 3/2012 |
| WO | WO 2012/082164 | 6/2012 |
| WO | WO 2012/113054 | 8/2012 |
| WO | WO 2013/012561 | 1/2013 |
| WO | WO 2013/169674 | 11/2013 |
| WO | WO 2013/173700 | 11/2013 |
| WO | WO 2013/188960 | 12/2013 |
| WO | WO 2014/028227 | 2/2014 |
| WO | WO 2016/070288 | 5/2016 |
| WO | WO 2016/134168 | 8/2016 |
| WO | WO 2018/169980 | 9/2018 |
| WO | WO 2018/169995 | 9/2018 |

OTHER PUBLICATIONS 510 (k) Summary of Safety and Effectiveness for BrainLAB knee, in 5 pages.
Anderson MD., Kevin, et al., "Computer Assisted Navigation in Total Knee Arthroplasty", The Journal of Arthroplasty, 2005, vol. 20, No. 7, Suppl. 3, in 7 pages.
ANG, et al., An Active Hand-Held Instrument for Enhanced Microsurgical Accuracy, Medical Image Computing and Computer-Assisted Intervention, 2000, vol. 1935, pp. 878-887.
Arnold-Moore, et. al., Architecture of a Content Management Server for XML Document Applications, RMIT Multimedia Database Systems, Royal Melbourne Institute of Technology, Victoria Australia, in 12 pages.
ArthroCAD, Enhancing orthopedic outcomes through optimal alignment, 2012, pp. in 2 pages.
Bae et al., "Computer Assisted Navigation in Knee Arthroplasty", Clinics in Orthopedic Surgery, 2011, vol. 3, pp. 259-267.
Bargren, MD., et al., Alignment in Total Knee Arthroplasty, Correlated Biomechanical and Clinical Observations, Clinical Orthopaedics and Related Research, Mar. 1, 1983, Issue 173, pp. 178-183, Philadelphia.
Bathis, H. et al., "Alignment in total knee arthroplasty", The Journal of Bone & Joint Surgery (Br), 2004, 86-B, pp. 682-687, British Editorial.

(56) References Cited

OTHER PUBLICATIONS

Bhandari, Design and Prototype of a Computer Assisted Surgical Navigation System for Total Knee Replacement Surgery, May 12, 2009, pp. in 294 pages.
Biomet Orthopedics, Inc, Vision Acetabular Surgical Techniques, website brochure, pp. 16 pages.
Biomet Orthopedics, Inc., Universal Ringlock® Acetabular Series, vol. website brochure, pp. 13 pages.
BRAINLAB, "Position Determination and Calibration in optical tracking systems", FLORENUS the technology merchants, in 2 pages.
BRAINLAB, "Tracking and imaging in Navigation", FLORENUS, in 2 pages.
Brennan, et al., Quantification of Inertial Sensor-Based 3D Joint Angle Measurement Accuracy Using and Instrumented Gimbal, Gait & Posture, May 23, 2011, vol. 34, pp. 320-323.
Chauhan, et al., Computer-Assisted Knee Arthroplasty Versus a Conventional Jig-Based Technique, The Journal of Bone & Joint Surgery, 2004, vol. 86-B, pp. 372-377.
Cutti, et al., Motion Analysis of the Upper-Limb Based on Inertial Sensors: Part 1—Protocol Description, Journal of Biomechanics, Jan. 1, 2007, vol. 40, pp. S250.
Decking, MD., et al., Leg Axis After Computer-Navigated Total Knee Arthroplasty, The Journal of Arthroplasty, 2005, vol. 20, Issue 3, pp. 282-288.
Depuy, Johnson & Johnson, Co., Summit Cemented Hip System, website brochure, pp. 21 pages.
De Momi, et al., "In-vitro experimental assessment of a new robust algorithm for hip joint centre estimation", Journal of Biomechanics, Feb. 26, 2009, vol. 42, pp. 989-995.
Digioia III, MD., et al., "Comparison of a Mechanical Acetabular Alignment Guide with Computer Placement of the Socket", The Journal of Arthroplasty, Apr. 2002, vol. 17, No. 3, in 6 pages.
Eric Foxlin, Chapter 7. Motion Tracking Requirements and Technologies, Handbook of Virtual Environment Technology, 2002, vol. Kay Stanney, Ed., Issue Lawrence Erlbaum Ass.
European Office Action for Application No. 04776379.2, dated May 4, 2010, in 5 pages.
Extended European Search Report issue in European Patent Application No. 13787733.8, dated Aug. 6, 2015, in 8 pages.
Extended European Search Report issue in European Patent Application No. 13790292.0, dated Oct. 28, 2015, in 7 pages.
Favre, et al., 3D Evaluation of the Knee Joint Using Ambulatory System: Application to ACL-Deficient Knees, Journal of Biomechanics, Jan. 1, 2007, vol. 40, pp. S251.
Favre, et al., A New Ambulatory System for Comparative Evaluation of the Three-Dimensional Knee Kinematics, Applied to Anterior Cruciate Ligament Injuries, Knee Surgery, Sports Traumatology, Arthroscopy, Jan. 19, 2006, vol. 14, pp. 592-604.
Favre, et al., Ambulatory Measurement of 3D Knee Joint Angle, Journal of Biomechanics, Jan. 28, 2008, vol. 41, Issue 1029-1035.
Fixed Reference Surgical Technique, SIGMA High Performance Instruments, DePuy Orthopaedics, Inc., 2008, Warsaw, In, in 52pages.
Ganapathi et al., "Limb Length and Femoral Offset Reconstruction During THA Using CT-Free Computer Navigation", The Journal of Bone and Joint Surgery, 2009, vol. 91-B, Supplement III, p. 399.
Goniometer, AllHeart.com, 2004, website: http://allheart.com/allheart, (1 page).
Haaker et al., "Computer-Assisted Navigation Increases Precision of Component Placement in Total Knee Arthroplasty", Clinical Orthopaedics and Related Research, Apr. 2005, vol. 433, pp. 152-159.
Hofstetter, Ph.D., et al., "Computer-Assisted Fluoroscopy-Based Reduction of Femoral Fractures and Antetorsion Correction", Computer Aided Surgery, 2000, vol. 5, pp. 311-325, Wiley-Liss, Inc.
Hsieh, Pang-Hsin, et al., "Image-guided periacetabular osteotomy: computer-assisted navigation compared with the conventional technique: A randomized study of 36 patients followed for 2 years", Acta Orthopaedica, Aug. 1, 2006, 77:4, pp. 591-597.
IASSIST Knee, Surgical Technique, Zimmer, Inc., 2012.

International Preliminary Report for Application No. PCT/US2004/018244, dated Dec. 13, 2005, in 11 pages.
International Search Report and Written Opinion issued in PCT Application No. PCT/US2013/039770, dated Sep. 25, 2013.
International Preliminary Report on Patentability issued in PCT Application No. PCT/US2013/039770, dated Nov. 11, 2014.
International Search Report and Written Opinion issued in PCT Application No. PCT/US2013/041556, dated Sep. 13, 2013.
International Preliminary Report on Patentability issued in PCT Application No. PCT/US2013/041556, dated Nov. 18, 2014.
International Search Report and Written Opinion issued in PCT Application No. PCT/US2013/053182, dated Nov. 11, 2013.
International Search Report for Application No. PCT/US2004/018244, dated Feb. 15, 2005, in 4 pages.
International Search Report for International Application No. PCT/US2009/051769, dated Nov. 19, 2009, in 11 pages.
International Search Report for International Application No. PCT/US2009/051769, dated Nov. 19, 2009, in 3 pages.
International Search Report for International Application No. PCT/US2011/022162, dated Jun. 16, 2011, in 4 pages.
International Search Report for International Application No: PCT/US2009/056553, dated Nov. 4, 2009, in 12 pages.
International Preliminary Report on Patentability issued in PCT Application No. PCT/US2013/053182, dated Feb. 17, 2015, in 10 pages.
International Search Report and Written Opinion issued in International Application No. PCT/US2016/018508, dated Jun. 22, 2016, in 19 pages.
International Preliminary Report on Patentability issued in International Application No. PCT/US2016/018508, dated Aug. 22, 2017, in 11 pages.
Jenny, et al., Computer-Assisted Implantation of Total Knee Prosthesis: A Case-Control Comparative Study with Classical Instrumentation, Computer Aided Surgery, 2001, vol. 6, pp. 217-220.
Konyves et al., "The importance of leg length discrepancy after total hip arthroplasty", The Journal of Bone & Joint Surgery (Br), Feb. 2005, vol. 87-B, No. 2, pp. 155-157.
Leenders, MD., et al., "Reduction in Variability of Acetabular Cup Abduction Using Computer Assisted Surgery: A Prospective and Randomized Study", Computer Aided Surgery, 2002, vol. 7, pp. 99-106.
Leung, et al., Intraobserver Errors in Obtaining Visually Selected Anatomic Landmarks During Registration Process in Nonimage-based Navigation-assisted Total Knee Arthroplasty, The Journal of Arthroplasty, 2005, vol. 20, Issue 5, pp. 591-601.
Liebergall, Meir, et al., "Computerized Navigation for the Internal Fixation of Femoral Neck Fractures", The Journal of Bone & Joint Surgery Am, 2006, vol. 88, pp. 1748-1754.
Longo, et al., Mika Surgical Technique, DJO Surgical, 2008, Austin Texas in 14 pages.
Luinge, Inertial Sensing of Human Movement, Twente University Press, Feb. 15, 1973, pp. in 88 pages.
Mackenzie, et al., A Two-Ball Mouse Affords Three Degrees of Freedom, Extended Abstracts of the CHI '97 Conference on Human Factors in Compounding Systems (as printed from the internet on Jun. 13, 2012 URL: http://www.yorku.ca/mack/CHI97a.htm), 1997, pp. 303-304.
Medical Research Ltd, Clinical Goniometer, http://www.mie-uk.com/Gonio, 1997, pp. 1 page.
Minimally Invasive TKA GENESIS II Anterior Cut First, Surgical Technique, Smith & Nephew, Nov. 2003, Memphis TN, in 16 pages.
Noble et al., "Computer Simulation: How Can it Help the Surgeon Optimize Implant Position?", Clinical Orthopaedics and Related Research, Dec. 2003, vol. 417, pp. 242-252.
Parratte, Sebastien, et al., "Validation and Usefulness of a Computer-Assisted Cup-Positioning System in Total Hip Arthroplasty. A Prospective, Randomized, Controlled Study", The Journal of Bone & Joint Surgery Am, 2007, vol. 89, pp. 494-499.
Partial Supplemental European Search Report issued in European Patent Application No. 13829614.0, dated Jun. 13, 2016, in 6 pages.
Perseus Intelligent Cutting Guide, Orthokey, Product Guide, in 8 pages.

(56) References Cited

OTHER PUBLICATIONS

Perseus Intelligent Cutting Guide, Smart Instruments for Knee Arthroplasty, Orthokey, in 2 pages.
Ritter, M.D., et al., Postoperative Alignment of Total Knee Replacement, Its Effect on Survival, Clinical Orthopaedics and Related Research, Feb. 1, 1994, Issue 299, pp. 153-156, Philadelphia.
Rocon, et al., Application of Inertial Sensors and Rehabilitation Robotics, Rehabilitation Robotics 2007, Jun. 1, 2007, pp. 145-150.
Sacks-Davis et. al., Atlas: A nested Relational Database System for Text Applications, IEEE Transations on Knowledge and Data Engineering, vol. 7, No. 3, Jun. 1995, pp. 454-470.
Schep, et al., "Computer assisted orthopaedic and trauma surgery State of the art and future perspectives", Injury Int. J. Care Injured 34, (website: www.elsevier.com/locate/injury), 2003 pp. 299-306.
Scott, M.S., et al., P.F.C. Sigma Knee System, Primary Surgical Technique Part 1 of 2, DePuy International Ltd., 2003, England, (up to p. 44), in 48 pages.
Scott, M.S., et al., P.F.C. Sigma Knee System, Primary Surgical Technique Part 2 of 2, DePuy International Ltd., 2003, England, Part A (up to p. 74), in 31 pages. (This reference was split in two due to size exceeding over 25MB).
Scott, M.S., et al., P.F.C. Sigma Knee System, Primary Surgical Technique Part 2 of 2, DePuy International Ltd., 2003, England, Part B (up to p. 104), in 31 pages. (This reference was split in two due to size exceeding over 25MB).
Sikorski et al., "Computer-Assisted Orthopaedic Surgery: Do We Need CAOS?", The Journal of Bone & Joint Surgery (Br), Apr. 2003, vol. 85-B, No. 3, pp. 319-323.
Slomczykowski, et al., "Novel Computer-Assisted Fluoroscopy System for Intraoperative Guidance: Feasibility Study for Distal Locking of Femoral Nails", Journal of Orthopaedic Trauma, 2001, vol. 15, No. 2, pp. 122-131, Lippincott Williams & Wilkins, Inc., Philadelphia.
Stulberg, et al., Computer-Assisted Total Knee Replacement Arthroplasty, Operative Techniques in Orthopaedics, Jan. 2000, vol. 10, Issue 1, pp. 25-39.
Supplementary European Search Report issued in European Patent Application No. 13829614.0, dated Sep. 22, 2016, in 8 pages.
The Academy of Orthopaedic Surgeons, Academy News, http://www.aaos.org/wordhtml/2001news/b6-01.htm, Mar. 1, 2001, pp. 1 page.
Tilt Sensors: High Accuracy, Digital Series, Crossbow Technology, Inc., pp. 32-35.
Upadhyay et al., "Medical Malpractice in Hip and Knee Arthroplasty", The Journal of Arthroplasty, 2007, vol. 22, No. 6, Suppl. 2, pp. 2-7.
Visser, et al., 3D Analysis of Upper Body Movements in Bilateral Amputee Gait Using Inertial Sensors, Journal of Biomechanics, Jan. 1, 2007, vol. 40, Issue S509.
Wentzensen et al., "Image-based hip navigation", International Orthopaedics (SICOT), 2003, vol. 27 (Suppl. 1), pp. S43-S46.
Wolfstadt et al., "An intelligent instrument for improved leg length and hip offset accuracy in total hip arthroplasty", Abstract Only.
Written Opinion for International Application No. PCT/US2009/051769, dated Nov. 19, 2009, in 7 pages.
Written Opinion for International Application No. PCT/US2011/022162, dated Jun. 16, 2011, in 9 pages.
Written Opinion of the ISR for Application No. PCT/US2004/018244, received Mar. 14, 2005, in 10 pages.
Wylde et al., "Prevalence and functional impact of patient-perceived leg length discrepancy after hip replacement", International Orthopaedics, 2009, vol. 33, pp. 905-909.
Wylde et al., "Patient-perceived leg length discrepancy after total hip replacement: prevalence and impact on functional outcome", International Orthopaedics, 2008, vol. 24, No. 2, pp. 210-216.
Zheng et al., "Technical Principles of Computer Assisted Orthopaedic Surgery", Suomen Ortopedia ja Traumatologia, Feb. 2008, vol. 31, pp. 135-147.
Zhou, et al., Use of Multiple Wearable Inertial Sensors in Upper Limb Motion Tracking, Medical Engineering & Physics, Jan. 1, 2008, vol. 30, pp. 123-133.
Zimmer NexGen Flexion Balancing Instruments, Surgical Technique, 2007, www.zimmer.com, in 44 pages.
Zorman, David, et al., "Computer-assisted total knee arthroplasty: comparative results in a preliminary series of 72 cases", ActaOrthop. Belg., 2005, 71, pp. 696-702.
International Search Report and Written Opinion issued in PCT Application No. PCT/US2018/022233, dated Jul. 17, 2018, in 19 pages.

* cited by examiner

DETAIL A

DETAIL B

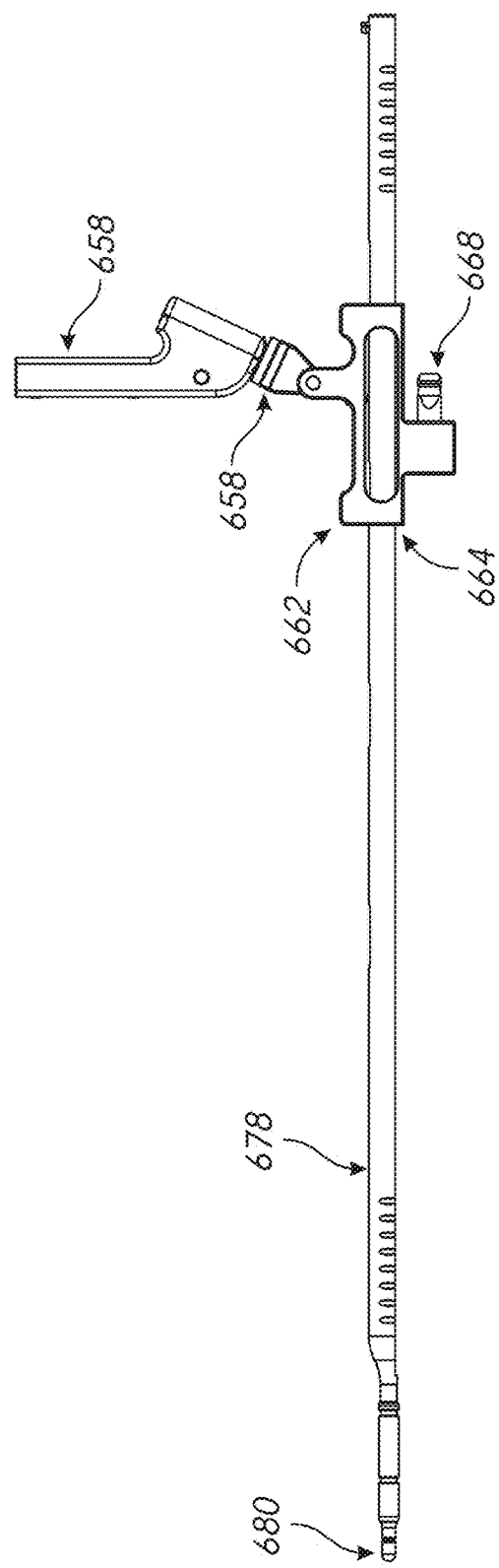
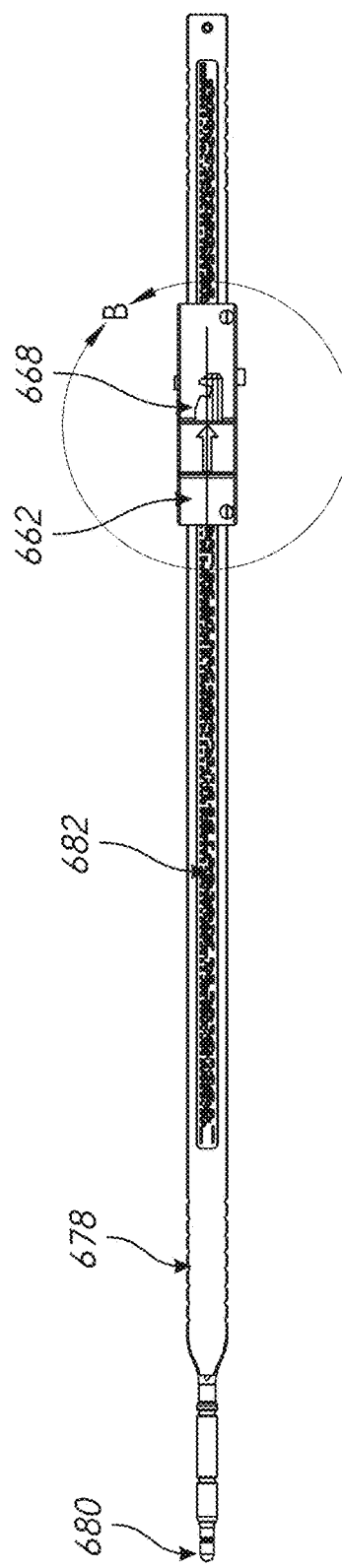

DETAIL A

DETAIL B

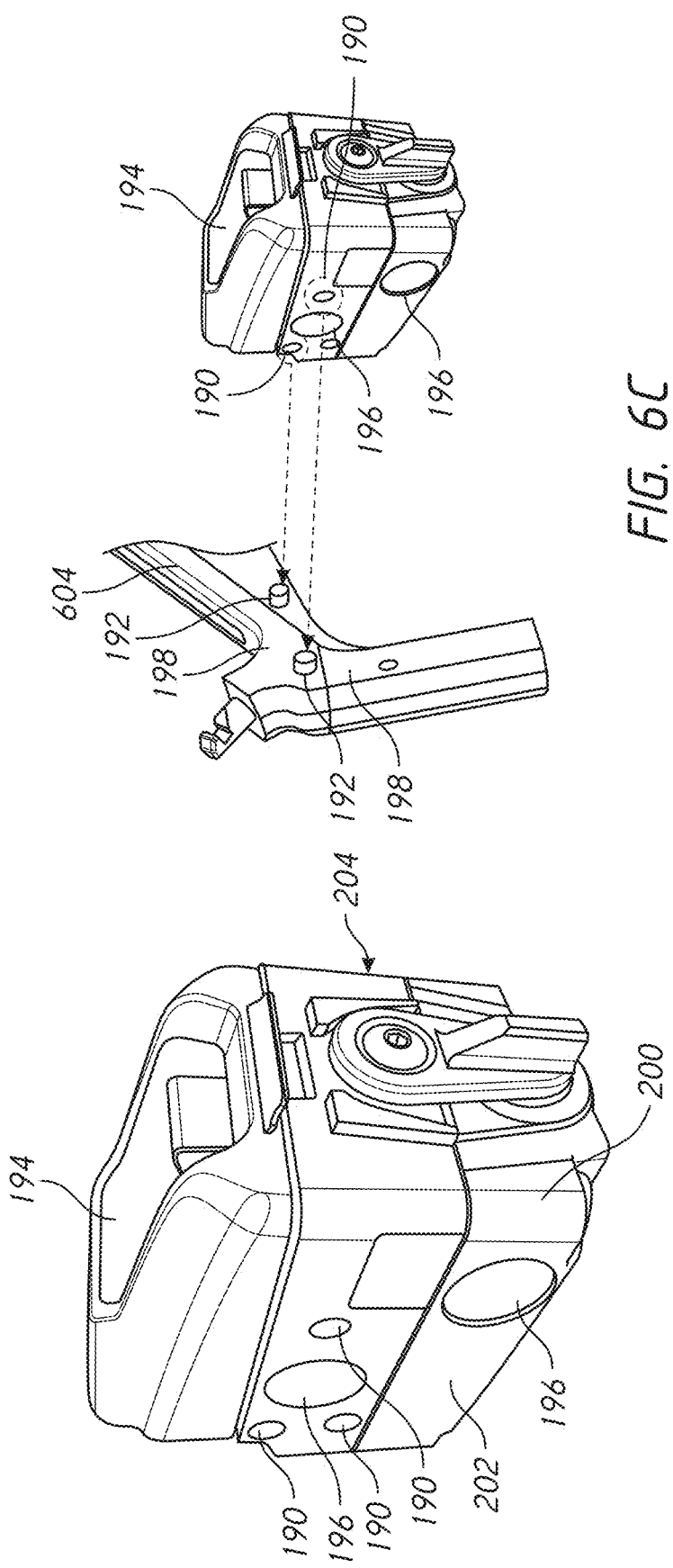

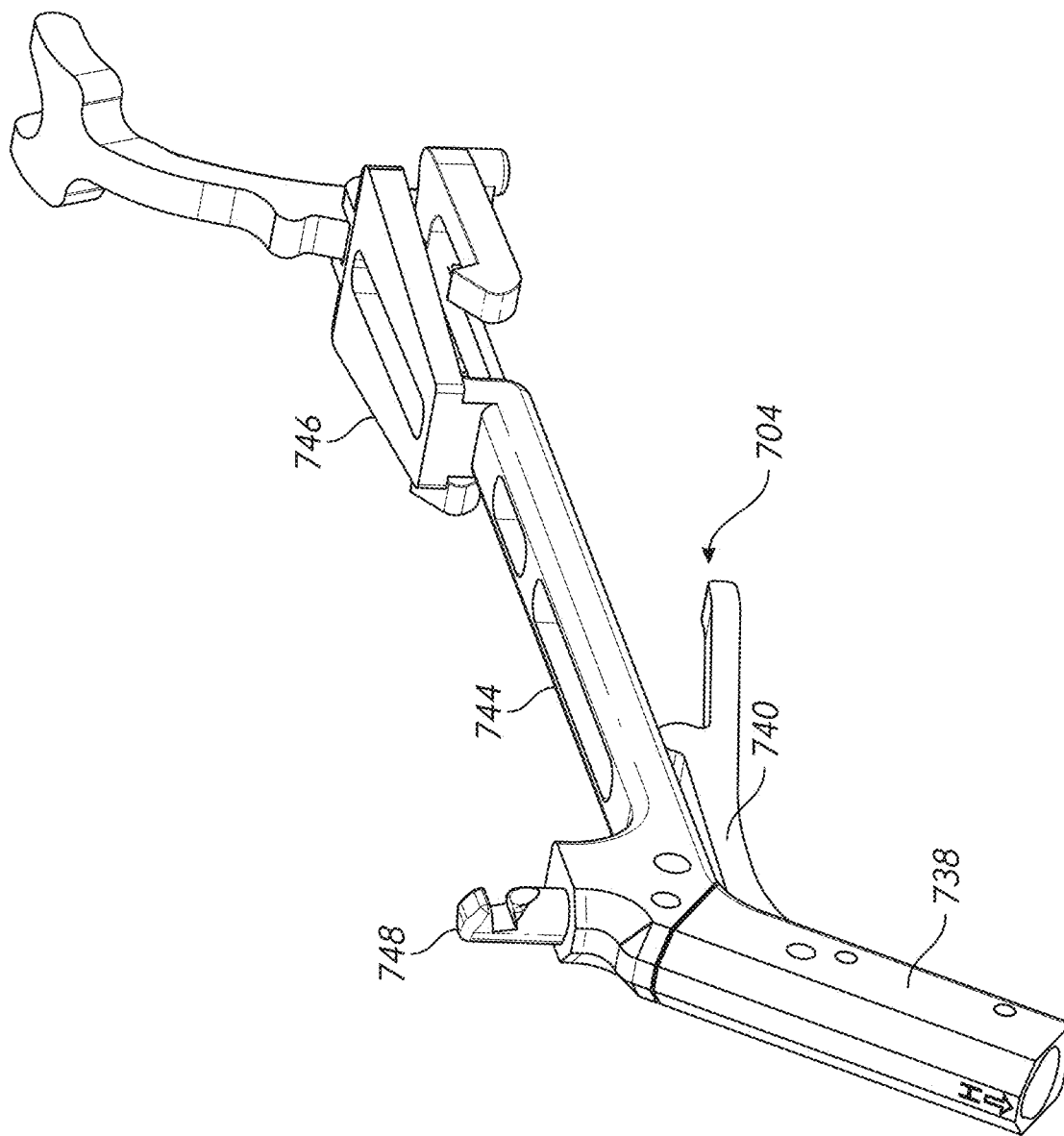

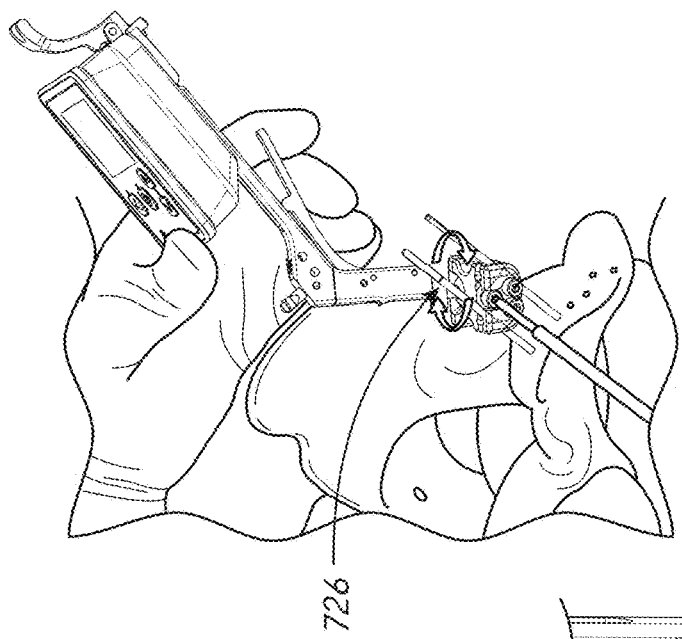
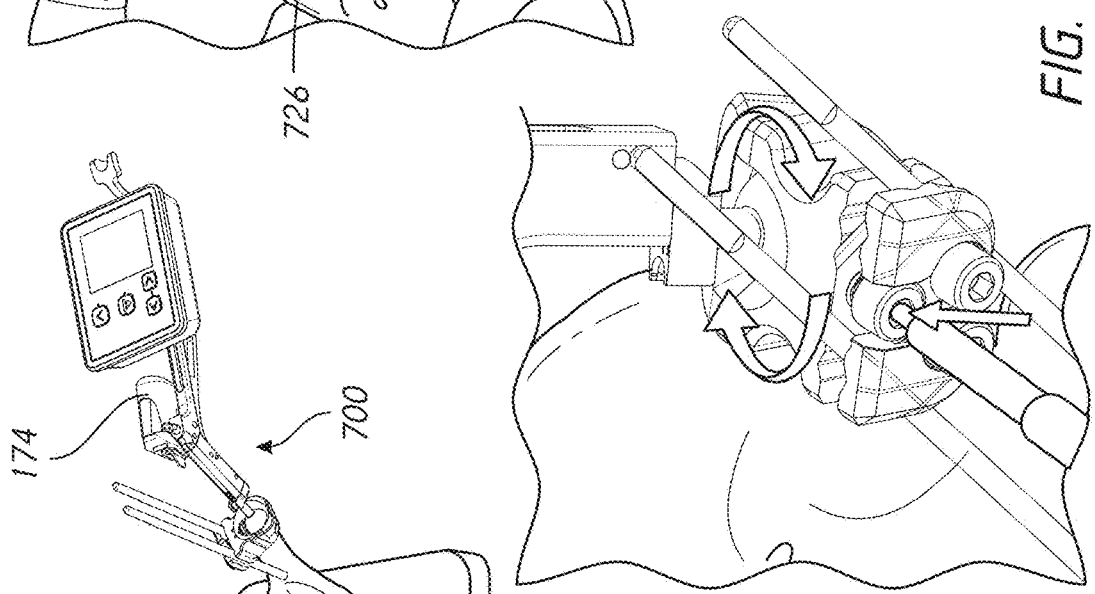
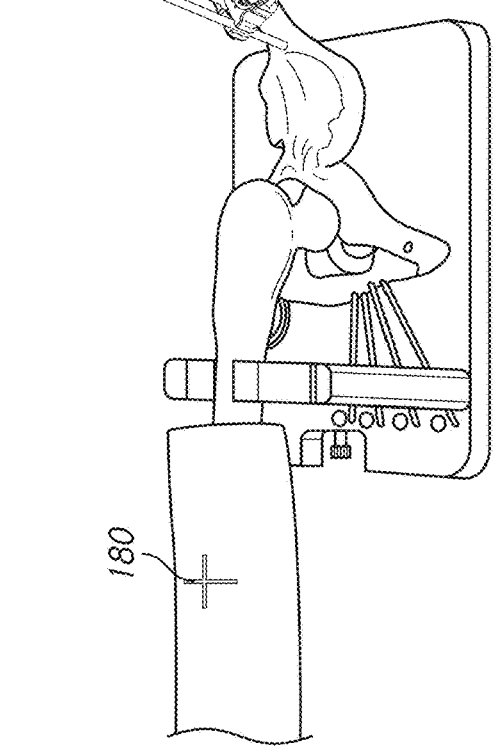
FIG. 15B
FIG. 15C
FIG. 15A

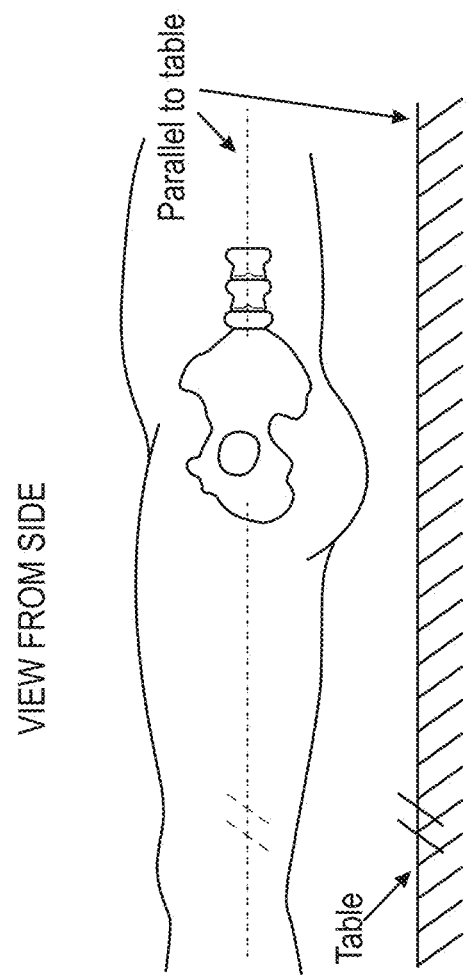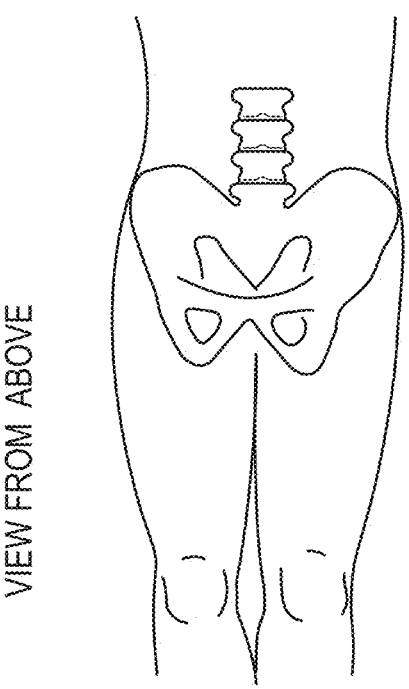
FIG. 22

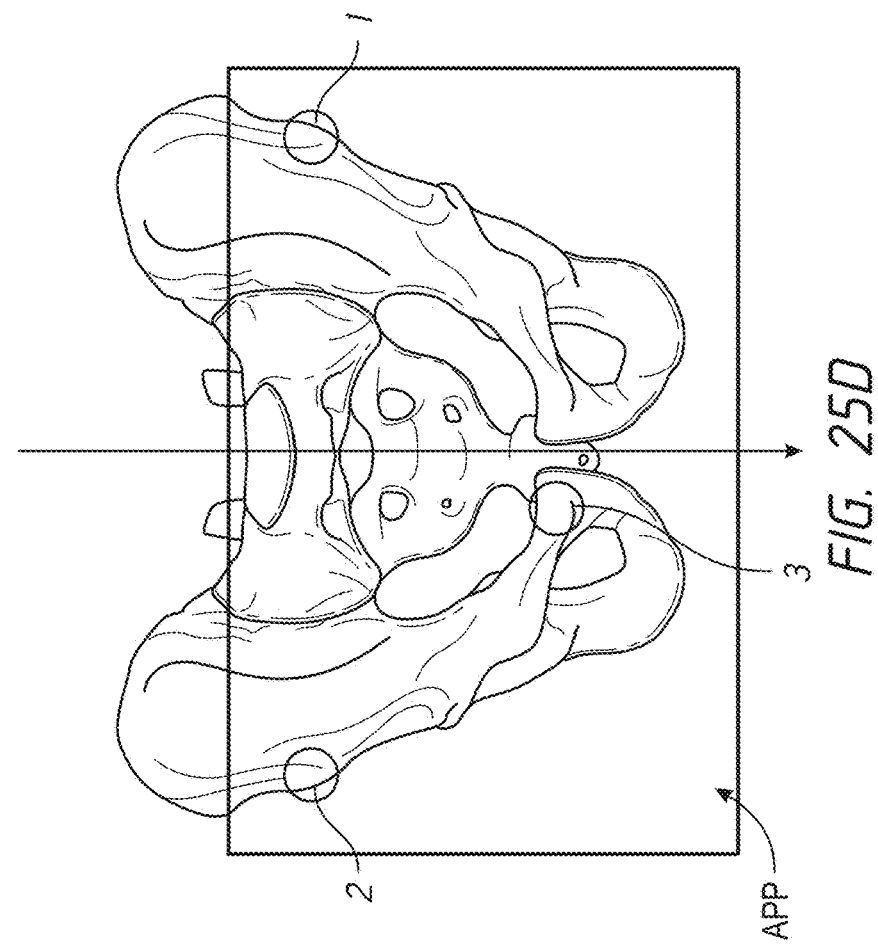
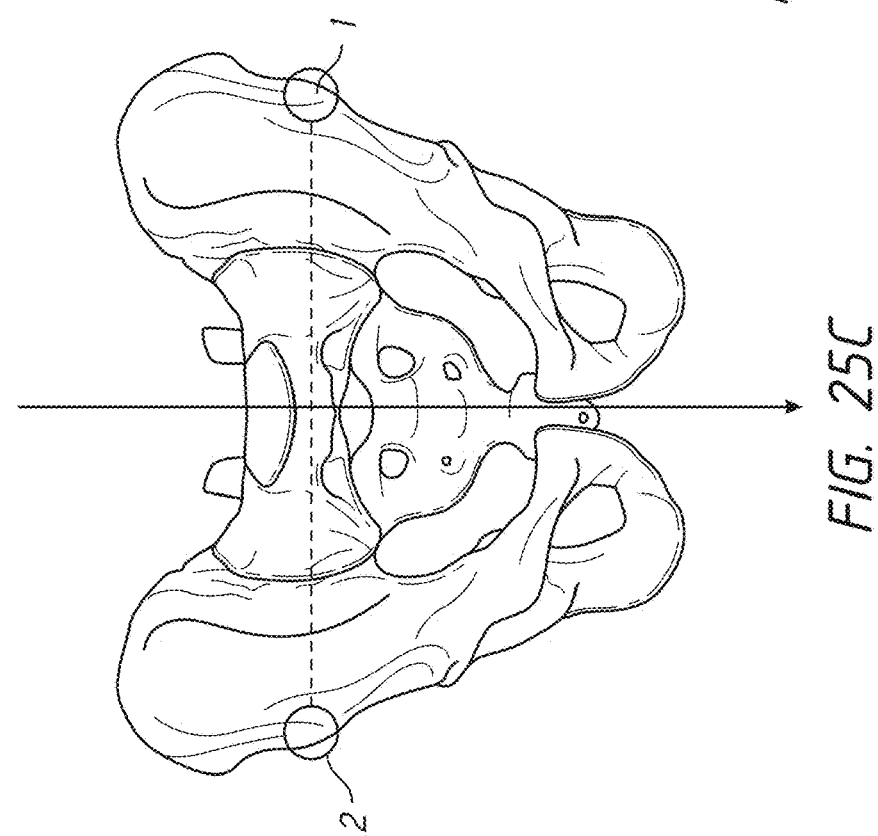
FIG. 25D
FIG. 25C

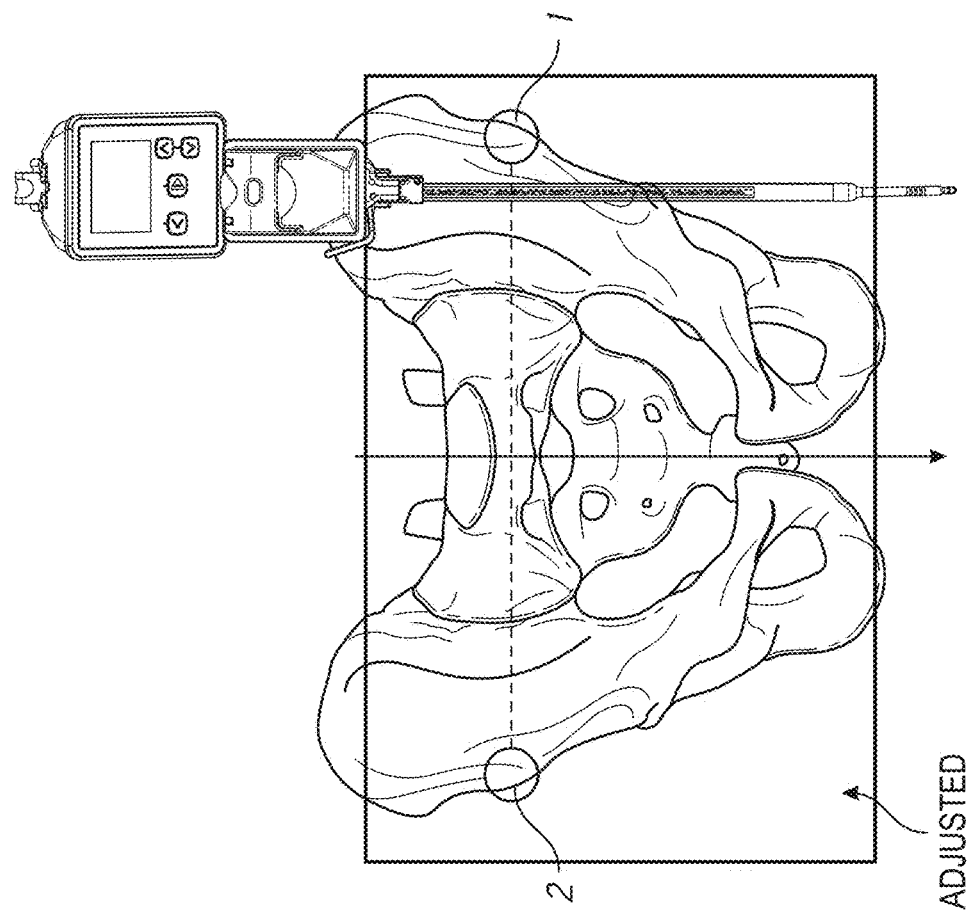
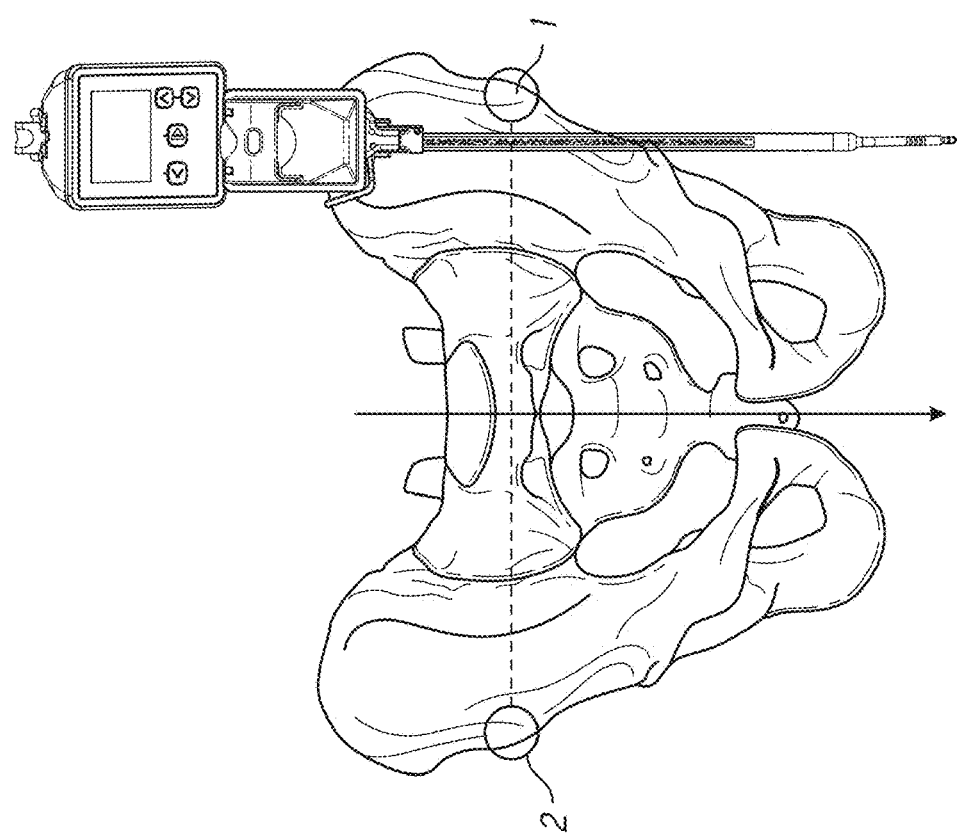
FIG. 27D
FIG. 27C

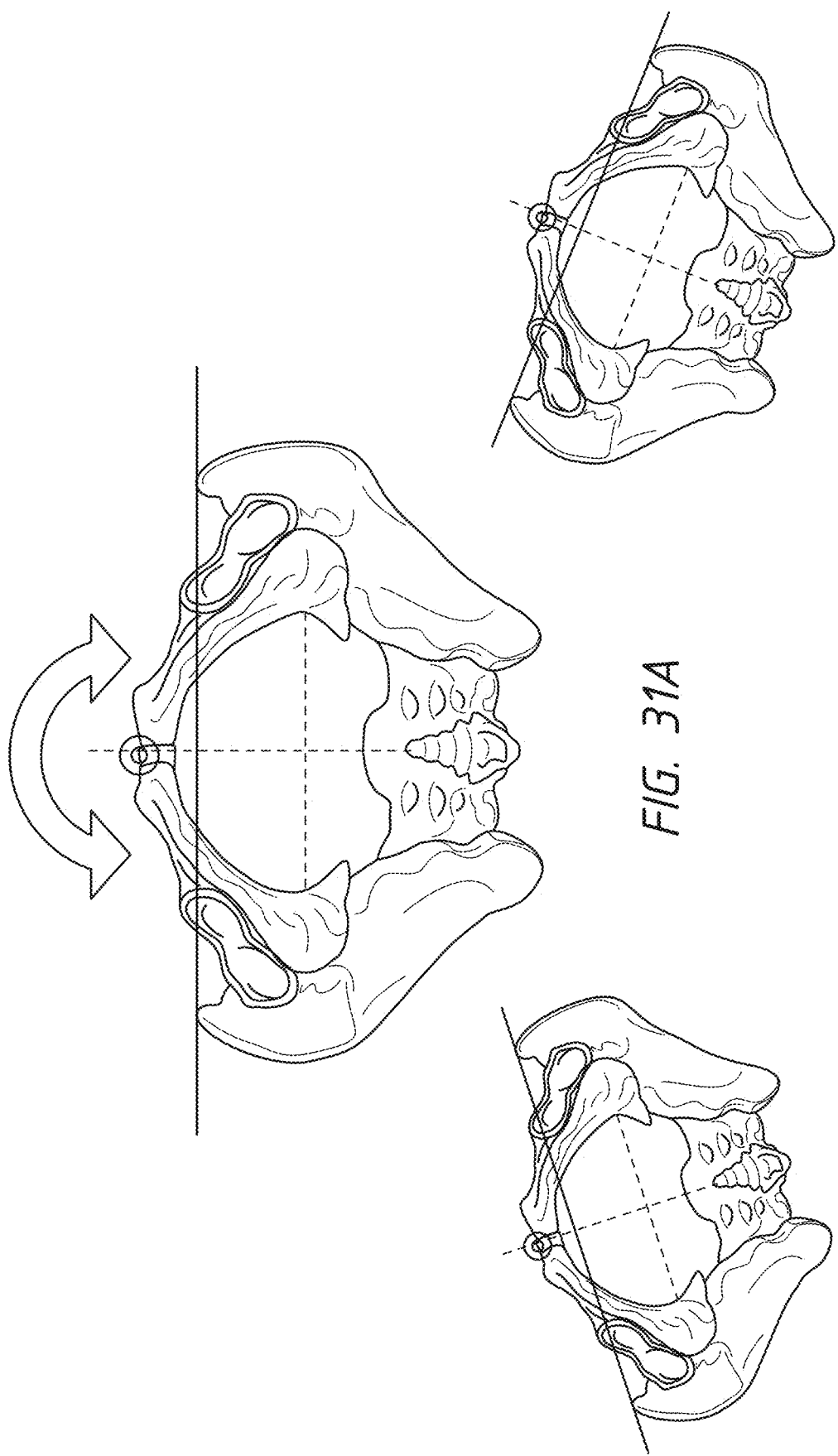

HIP REPLACEMENT NAVIGATION SYSTEMS AND METHODS

INCORPORATION BY REFERENCE TO ANY PRIORITY APPLICATIONS

Any and all applications for which a foreign or domestic priority claim is identified in the Application Data Sheet as filed with the present application including U.S. provisional application No. 62/471,185, filed Mar. 14, 2017 and U.S. provisional application No. 62/521,097, filed Jun. 16, 2017, each are hereby incorporated by reference in its entirety under 37 CFR 1.57.

BACKGROUND

Field

This application is directed to the field of hip replacement, and particularly to surgical tools and methods for establishing a reference plane. This application is also directed surgical tools and methods for calculating leg length and joint offset.

Description of the Related Art

Hip replacement surgery is common and getting more common by the year. One persistent issue with hip replacement is poor placement of the cup and ball components of the prosthetic hip joint. For example, the cup is optimally placed in a specific abduction and anteversion orientations. While an acceptable window of deviation from the optimal abduction and anteversion angles has been observed in clinical practice for several reasons an unacceptably high percentage of patients have the cup of the artificial hip joint out of this window.

Unfortunately, misalignment can lead to dislocation of the hip as soon as within one year of the implantation procedure. This is particularly problematic because recovery from a hip procedure can take many months. Patients undergoing a revision so soon after the initial implantation will certainly be dissatisfied with their care, being subject to addition redundant surgery. Of course, all surgery carries some degree of risk. These poor outcomes are unsatisfactory for patients and surgeons and are inefficient for the healthcare system as a whole.

SUMMARY

There is a need for improved systems and methods for providing for proper alignment of hip components with a patient's anatomy during a hip replacement procedure. This can involve use of a table reference frame. This can involve use of a vertical reference plane. This can involve use of a reference plane that approximates the Anterior Pelvic Plane. This can involve providing the user with additional information related to the anatomy including leg length and joint offset.

In some embodiments, a method of positioning a medical prosthesis is provided. The method can include establishing a vertical plane with a measuring device. The method can include positioning a probe to contact a point. The method can include recording a position of the probe when the probe is contacting the point before replacing a joint. The method can include recording a second position of the probe when the probe is contacting the point after replacing the joint. In some embodiments, a comparison between the first position and the second position indicates a change in leg length or joint offset.

In some embodiments, the method can include coupling the measuring device and the probe to a patient. In some embodiments, the point is a structure. In some embodiments, the point is a burr. In some embodiments, the point is an anatomical landmark. In some embodiments, the method can include determining cup angles relative to the vertical plane. In some embodiments, the method can include positioning a medical prosthesis at an angle relative to the vertical plane. In some embodiments, the method can include manually repositioning the femur after replacing the joint. In some embodiments, the method can include establishing a horizontal plane with a measuring device, wherein the vertical plane and the horizontal plane define a reference frame.

In some embodiments, a method of positioning a medical prosthesis is provided. The method can include establishing a vertical plane with a measuring device. The method can include projecting a pattern of light onto the leg of a patient. The method can include recording the incidence of light on the leg of a patient. The method can include replacing the joint by inserting a cup, wherein angles of the cup are measured relative to the vertical plane. The method can include projecting the pattern light onto the leg of the patient after replacing the joint. The method can include repositioning the leg to align the recording of the incidence of light with the pattern of light.

In some embodiments, the method can include recording a position of a probe when contacting a point pre-dislocation. In some embodiments, the method can include recording a position of a probe when contacting a point post-instrumentation. In some embodiments, the method can include determining a change in leg length. In some embodiments, the method can include determining a change in leg length in the vertical plane. In some embodiments, the method can include determining a change in joint offset. In some embodiments, the method can include determining a change in joint offset in a plane perpendicular to the vertical plane. In some embodiments, the method can include establishing a horizontal plane with a measuring device, wherein the vertical plane and the horizontal plane define a reference frame. In some embodiments, the method can include recording a point in the reference frame. In some embodiments, the method can include recording a point pre-operatively in the reference frame. In some embodiments, the method can include recording a point post-operatively in the reference frame.

In some embodiments, a surgical system for assisting a surgeon in obtaining correct orientation of an acetabular prosthetic socket in a patient's acetabulum in provided. In some embodiments, the instrument can include a support device. The instrument can include a first electronic orientation device having a coupler for releasably coupling the first electronic orientation device to the support device. In some embodiments, the first electronic orientation device comprises at least one inertial sensor. In some embodiments, the first electronic orientation device and the second electronic orientation device are adapted to establish a reference plane based upon a direction of gravity.

In some embodiments, the system can include a probe assembly comprising a base portion and an elongate member configured to pivot and translate relative to the base portion, the probe assembly comprising an second electronic orientation device, wherein the second electronic orientation device comprises at least one inertial sensor. In some embodiments, the first electronic orientation device and the second electronic orientation device are adapted to record a point when the probe contacts a point. In some embodiments, the first electronic orientation device and the second electronic orientation device are adapted to record a point when the probe contacts a point pre-operatively and post-operatively. In some embodiments, the at least one inertial sensor of the first electronic orientation device or the at least one inertial sensor of the second electronic orientation device comprises an accelerometer. In some embodiments, the reference plane comprises a vertical plane. In some embodiments, the first electronic orientation device includes a display configured to provide an indication of the change in angular position of the second electronic orientation device relative to the reference plane. In some embodiments, the system can include an optical component configured to project a pattern of light.

In some embodiments, a hip joint navigation system is provided. The system can include a jig assembly. The system can include a first inertial navigation device configured to be immovably coupled to the jig assembly. The system can include an optical component configured to project a pattern of light, wherein incidence of the pattern of light can be record to assist the user in realigning the femur to a pre-operative position. The system can include a second inertial navigation device configured to determine the orientation of a probe when the probe is moved to touch a point.

In some embodiments, the pattern of light is a cross-hair. In some embodiments, the pattern of light is two lines. In some embodiments, the pattern of light is three points.

There is a need for improved systems and methods for providing for proper alignment of hip components with a patient's anatomy during a hip replacement procedure. This can involve use of the Anterior Pelvic Plane. This can involve the use of a table plane. This can involve the use of an Adjusted Plane. This can involve providing the user with additional information related to the anatomy including pelvic tilt and rotation.

In some embodiments, a method of positioning a medical prosthesis is provided. The method can include coupling a measuring device and probe to a patient. The method can include positioning the probe to contact a first point. The method can include recording the position of the probe when the probe is contacting the first point. The method can include positioning the probe to contact a second point. The method can include recording the position of the probe when the probe is contacting the second point. The method can include positioning the probe to contact a third point. The method can include recording the position of the probe when the probe is contacting the third point. In some embodiments, the first point, the second point, and the third point define a plane, the plane can be rotated by the direction of gravity define an adjusted plane.

The method can include coupling the measuring device with a second measuring device, wherein the second measuring device includes a digital display to provide an indication of positional changes of the probe. In some embodiments, the first point is the ipsilateral ASIS. In some embodiments, the second point is the contralateral ASIS. The method can include positioning the probe horizontally to measure the direction of gravity. The method can include determining cup angles relative to the reference plane. The method can include positioning a medical prosthesis at an angle relative to the adjusted plane. In some embodiments, the first point and the second point define the inter-ASIS line. In some embodiments, the first point, the second point, and the third point define the anterior pelvic plane. In some embodiments, the third point is the anterior surface of the pubic symphysis.

In some embodiments, a surgical system for assisting a surgeon in obtaining correct orientation of an acetabular prosthetic socket in a patient's acetabulum is provided. The instrument can include a support device. The instrument can include a first electronic orientation device having a coupler for releasably coupling the first electronic orientation device to the support device, wherein the first electronic orientation device comprises at least one inertial sensor. The instrument can include a probe assembly comprising a base portion and an elongate member configured to pivot and translate relative to the base portion, wherein the elongate member has a length sufficient to enable a tip thereof to contact anatomy disposed about the pelvis at a plurality of discrete, spaced apart locations, the probe assembly comprising an second electronic orientation device, wherein the second electronic orientation device comprises at least one inertial sensor. In some embodiments, the first electronic orientation device and the second electronic orientation device are adapted to establish a reference plane based upon a direction of gravity and based upon the position of the at least one inertial sensor when the tip contacts the plurality of spaced apart locations.

In some embodiments, the at least one inertial sensor of the first electronic orientation device or the at least one inertial sensor of the second electronic orientation device comprises an accelerometer. In some embodiments, the reference plane comprises the inter-ASIS line. In some embodiments, the first electronic orientation device includes a display configured to provide an indication of the change in angular position of the second electronic orientation device relative to the reference plane.

In some embodiments, a hip joint navigation system is provided. The system can include a jig assembly. The system can include a first inertial navigation device configured to be immovably coupled to the jig assembly. The system can include a landmark acquisition probe configured to be movably coupled to the jig assembly, the landmark acquisition probe configured to move in a plurality of degrees of freedom relative to the jig assembly. The system can include a second inertial navigation device configured to determine the orientation of the landmark acquisition probe when the landmark acquisition probe is moved to touch an anatomical landmark. In some embodiments, the first inertial navigation device, the second inertial navigation device, or the first inertial navigation device and the second inertial navigation device are configured to adjusts for tilt by rotating the Anterior Pelvic Plane about the inter-ASIS line to determine a reference plane.

In some embodiments, the second inertial device comprises a mount device configured to detachably connect the second inertial device to the landmark acquisition probe. In some embodiments, the second inertial device comprises a camera. In some embodiments, the first inertial navigation device comprises a display.

In some embodiments, a method of positioning a medical prosthesis is provided. The method can include establishing a vertical plane with a measuring device. The method can include positioning a probe to contact a point. The method can include recording a position of the probe when the probe is contacting the point before replacing a joint. The method can include recording a second position of the probe when the probe is contacting the point after replacing the joint. In some embodiments, a comparison between the first position and the second position indicates a change in leg length or joint offset.

The method can include coupling the measuring device and the probe to a patient. In some embodiments, the point is a structure. In some embodiments, the point is a burr. In some embodiments, the point is an anatomical landmark. The method can include determining cup angles relative to the vertical plane. The method can include positioning a medical prosthesis at an angle relative to the vertical plane. The method can include manually repositioning the femur after replacing the joint. The method of claim 1, further comprising establishing a horizontal plane with a measuring device, wherein the vertical plane and the horizontal plane define a reference frame.

In some embodiments, a method of positioning a medical prosthesis is provided. The method can include establishing a vertical plane with a measuring device. The method can include projecting a pattern of light onto the leg of a patient. The method can include recording the incidence of light on the leg of a patient. The method can include replacing the joint by inserting a cup, wherein one or more angles of the cup are measured relative to the vertical plane. The method can include projecting the pattern light onto the leg of the patient after replacing the joint. The method can include repositioning the leg to align the recording of the incidence of light with the pattern of light. The method can include recording a position of a probe when contacting a point pre-dislocation. The method can include recording a position of a probe when contacting a point post-instrumentation. The method can include determining a change in leg length. The method can include determining a change in leg length in the vertical plane. The method can include determining a change in joint offset. The method can include determining a change in joint offset in a plane perpendicular to the vertical plane. The method can include establishing a horizontal plane with a measuring device, wherein the vertical plane and the horizontal plane define a reference frame. The method can include recording a point in the reference frame. The method can include recording a point pre-operatively in the reference frame. The method can include recording a point post-operatively in the reference frame.

In some embodiments, a surgical system for assisting a surgeon in obtaining correct orientation of an acetabular prosthetic socket in a patient's acetabulum is provided. The surgical system can include a support device. The surgical system can include a first electronic orientation device having a coupler for releasably coupling the first electronic orientation device to the support device. In some embodiments, the first electronic orientation device comprises at least one inertial sensor. In some embodiments, the first electronic orientation device and the second electronic orientation device are adapted to establish a reference plane based upon a direction of gravity.

The surgical system can include a probe assembly comprising a base portion and an elongate member configured to pivot and translate relative to the base portion. In some embodiments, the probe assembly comprises an second electronic orientation device. In some embodiments, the second electronic orientation device comprises at least one inertial sensor. In some embodiments, the first electronic orientation device and the second electronic orientation device are adapted to record a point when the probe contacts a point. In some embodiments, the first electronic orientation device and the second electronic orientation device are adapted to record a point when the probe contacts a point pre-operatively and post-operatively. In some embodiments, the at least one inertial sensor of the first electronic orientation device or the at least one inertial sensor of the second electronic orientation device comprises an accelerometer. In some embodiments, the reference plane comprises a vertical plane. In some embodiments, the first electronic orientation device includes a display configured to provide an indication of the change in angular position of the second electronic orientation device relative to the reference plane. The surgical system can include an optical component configured to project a pattern of light.

In some embodiments, a hip joint navigation system is provided. The hip joint navigation system can include a jig assembly. The hip joint navigation system can include a first inertial navigation device configured to be immovably coupled to the jig assembly. The hip joint navigation system can include an optical component configured to project a pattern of light. In some embodiments, incidence of the pattern of light can be record to assist the user in realigning the femur to a pre-operative position. The hip joint navigation system can include a second inertial navigation device configured to determine the orientation of a probe when the probe is moved to touch a point.

In some embodiments, the pattern of light is a cross-hair. In some embodiments, the pattern of light is two lines. In some embodiments, the pattern of light is three points. In some embodiments, the optical component is configured to couple to the jig assembly with one or more magnets. The hip joint navigation system can include a target probe for recording or displaying the pattern of light, wherein the target probe comprises an anatomical contact portion and a target portion. In some embodiments, the anatomical contact portion and a target portion are separate component. In some embodiments, the anatomical contact portion comprises an incision drape.

In some embodiments, a hip joint navigation system is provided. The hip joint navigation system can include an impactor. The hip joint navigation system can include a coupler configured to be immovably coupled with and to be decoupled from the impactor. The hip joint navigation system can include an inertial navigation device configured to be immovably coupled to the coupler. In some embodiments, the inertial navigation device is configured to determine the orientation of the impactor as the impactor is moved.

The hip joint navigation system can include a universal impactor adaptor comprising the coupler. In some embodiments, the universal impactor adaptor is configured to be removably coupled to the impactor. In some embodiments, the universal impactor adaptor comprises a clamp. In some embodiments, the universal impactor adaptor comprises a magnet.

In some embodiments, a method of positioning a medical prosthesis is provided. The method can include coupling a measuring device and probe to a patient. The method can include positioning the probe to contact a first point. The method can include recording the position of the probe when the probe is contacting the first point. The method can include positioning the probe to contact a second point. The method can include recording the position of the probe when the probe is contacting the second point. The method can include positioning the probe to contact a third point. The method can include recording the position of the probe when the probe is contacting the third point. In some embodiments, the first point, the second point, and the third point define a plane, the plane can be rotated by the direction of gravity define an adjusted plane.

The method can include coupling the measuring device with a second measuring device, wherein the second measuring device includes a digital display to provide an indication of positional changes of the probe. In some embodiments, the first point is the ipsilateral ASIS. In some embodiments, the second point is the contralateral ASIS. The method can include positioning the probe horizontally to measure the direction of gravity. The method can include determining cup angles relative to the reference plane. The method can include positioning a medical prosthesis at an angle relative to the adjusted plane. In some embodiments, the first point and the second point define the inter-ASIS line. In some embodiments, the first point, the second point, and the third point define the anterior pelvic plane. In some embodiments, the third point is the anterior surface of the pubic symphysis.

In some embodiments, a surgical system for assisting a surgeon in obtaining correct orientation of an acetabular prosthetic socket in a patient's acetabulum is provided. The surgical system can include a support device. The surgical system can include a first electronic orientation device having a coupler for releasably coupling the first electronic orientation device to the support device. In some embodiments, the first electronic orientation device comprises at least one inertial sensor. The surgical system can include a probe assembly comprising a base portion and an elongate member configured to pivot and translate relative to the base portion. In some embodiments, the elongate member has a length sufficient to enable a tip thereof to contact anatomy disposed about the pelvis at a plurality of discrete, spaced apart locations. In some embodiments, the probe assembly comprises an second electronic orientation device. In some embodiments, the second electronic orientation device comprises at least one inertial sensor. In some embodiments, the first electronic orientation device and the second electronic orientation device are adapted to establish a reference plane based upon a direction of gravity and based upon the position of the at least one inertial sensor when the tip contacts the plurality of spaced apart locations.

In some embodiments, the at least one inertial sensor of the first electronic orientation device or the at least one inertial sensor of the second electronic orientation device comprises an accelerometer. In some embodiments, the reference plane comprises the inter-ASIS line. In some embodiments, the first electronic orientation device includes a display configured to provide an indication of the change in angular position of the second electronic orientation device relative to the reference plane.

In some embodiments, a hip joint navigation system is provided. The hip joint navigation system can include a jig assembly. The hip joint navigation system can include a first inertial navigation device configured to be immovably coupled to the jig assembly. The hip joint navigation system can include a landmark acquisition probe configured to be movably coupled to the jig assembly. In some embodiments, the landmark acquisition probe is configured to move in a plurality of degrees of freedom relative to the jig assembly. The hip joint navigation system can include a second inertial navigation device configured to determine the orientation of the landmark acquisition probe when the landmark acquisition probe is moved to touch an anatomical landmark. In some embodiments, the first inertial navigation device, the second inertial navigation device, or the first inertial navigation device and the second inertial navigation device are configured to adjust for tilt by rotating the Anterior Pelvic Plane about the inter-ASIS line to determine a reference plane.

In some embodiments, the second inertial device comprises a mount device configured to detachably connect the second inertial device to the landmark acquisition probe. In some embodiments, the second inertial device comprises a camera. In some embodiments, the first inertial navigation device comprises a display. In some embodiments, the second inertial navigation is configured to couple to an impactor. The hip joint navigation system can include a universal impactor adaptor comprising a coupler, wherein the second inertial navigation is configured to couple to an impactor with the adaptor. In some embodiments, the universal impactor adaptor comprises a clamp. In some embodiments, the universal impactor adaptor comprises one or more magnets. The hip joint navigation system can include an optical component. In some embodiments, the optical component is configured to couple to the jig assembly with one or more magnets.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments.

FIGS. 4A-4F illustrate various view of embodiments of a second assembly of the system of FIG. 1.

FIGS. 6B-6C illustrate an embodiment of an optical component.

FIG. 9 illustrates an embodiment of a first assembly of the system of FIG. 7.

FIGS. 15A-15C illustrates the adjustment of the system of FIG. 7 including the optical component of FIG. 6A.

FIG. 18A illustrates a hip prosthesis placement system.

FIG. 22 illustrates the positioning of a patient prior to connection of the system of FIG. 1 in an anterior approach.

FIGS. 25A-25D illustrates method steps to identify the Anterior Pelvic Plane.

FIGS. 27A-27D illustrates method steps to calculate an Adjusted Plane.

FIGS. 28A-1 and 28B-1 are alternative views.

FIGS. 31A-31C illustrate a neutral and two rotation positions of the pelvis.

DETAILED DESCRIPTION

A variety of systems and methods are discussed below that can be used to improve outcomes for patients by increasing the likelihood of proper placement of a medical prosthesis. These systems can be focused on inertial navigation techniques to establish a reference plane. These systems can be focused on inertial navigation techniques to measure leg length and/or joint offset.

A. Systems for Anterior and Poster Approach

1. Hip Navigation System

Figure 1:
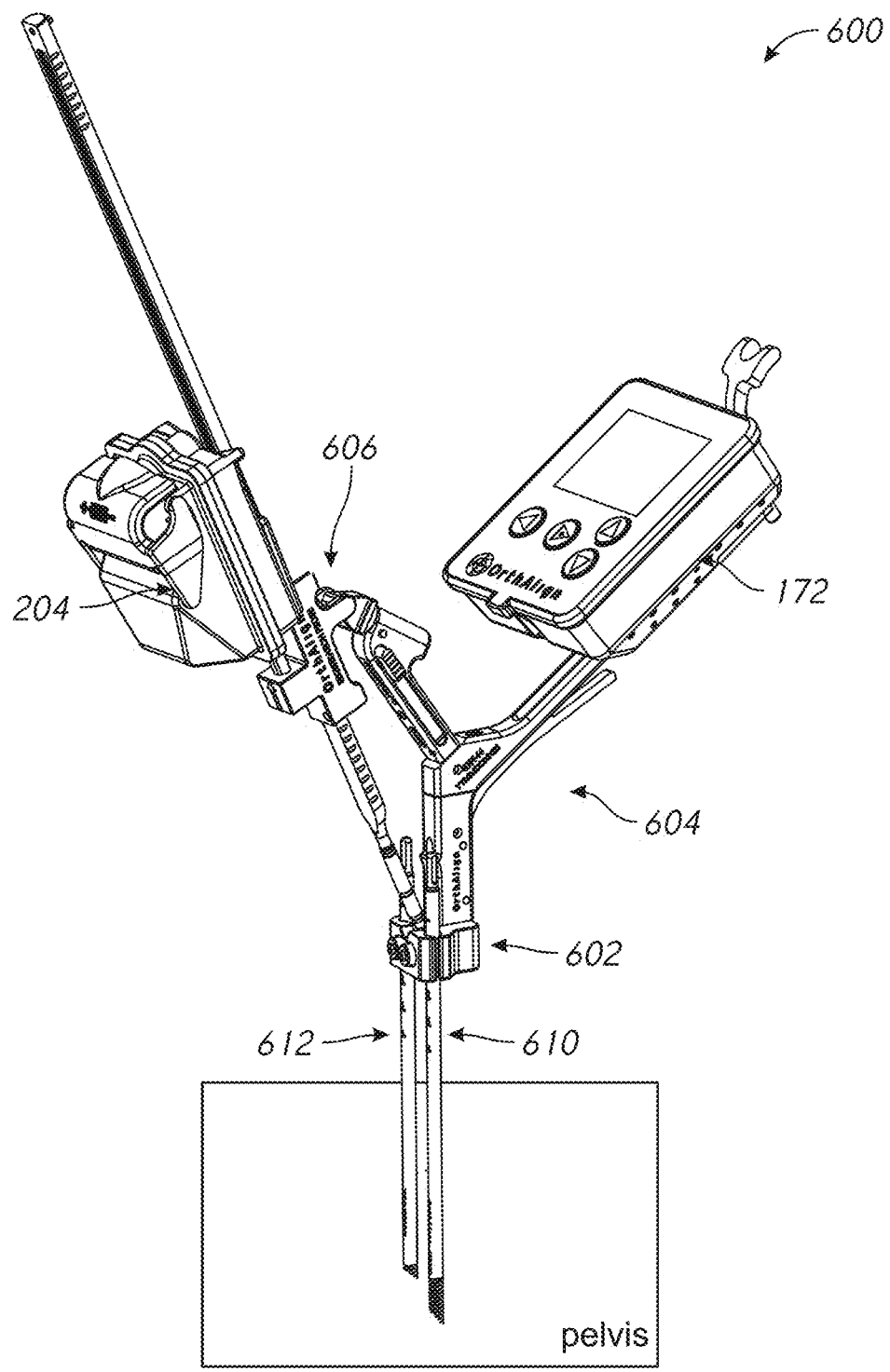
FIG. 1 is a perspective view of a hip navigation system applied to a patient.

FIG. 1 shows a hip navigation system 600 adapted to navigate a hip joint procedure with reference to anatomical landmarks. The system 600 is shown mounted on a pelvis in FIG. 1, which is shown as a box for simplicity. The system 600 can be mounted on a pelvis for a posterior approach as described herein. The system 600 can be mounted on a pelvis for an anterior approach as described herein The system 600 can include a fixation base 602, a first assembly 604, and a second assembly 606. The first assembly 604 is rigidly connected to the hip or pelvis in the illustrated configuration so that motion of the pelvis causes corresponding motion of sensor(s) in the first assembly 604 as discussed herein. Sensing this motion enables the system 600 to eliminate movement of the patient as a source of error in the navigation. The second assembly 606 provides a full range of controlled motion and sensor(s) that are able to track the motion, in concert with sensor(s) in the first assembly 604. Additional details of systems, devices, sensors, and methods are set forth in U.S. application Ser. No. 10/864,085 filed Jun. 9, 2004, U.S. application Ser. No. 11/182,528 filed Jul. 15, 2009 and related to U.S. Pat. No. 8,057,479, U.S. application Ser. No. 12/557,051 filed Sep. 10, 2009 and related to U.S. publication no. 2010/0076505, U.S. application Ser. No. 12/509,388 filed Jul. 24, 2009, U.S. application Ser. No. 13/011,815 filed Jan. 21, 2011, U.S. application Ser. No. 13/115,065, filed May 24, 2011 and issued as U.S. Pat. No. 8,118,815; U.S. application Ser. No. 14/399,046 filed Nov. 5, 2014, U.S. application Ser. No. 14/401,274 filed Nov. 14, 2014, U.S. application Ser. No. 13/800,620 filed Mar. 13, 2013, U.S. application Ser. No. 14/643,864 filed Mar. 10, 2015 and U.S. application Ser. No. 15/550,564 filed Aug. 11, 2017, which are all incorporated by reference herein in their entireties for all purposes. The sensors in assemblies 604, 606 preferably transfer data among themselves and in some cases with external devices and monitors wirelessly, using Bluetooth, Wifi® or other standard wireless telemetry protocol. The system 600 can include one or more fixation pins 610, 612. The system 600 can also include a surgical orientation device 172 and an orientation sensing device 204, as described herein.

Figure 2:
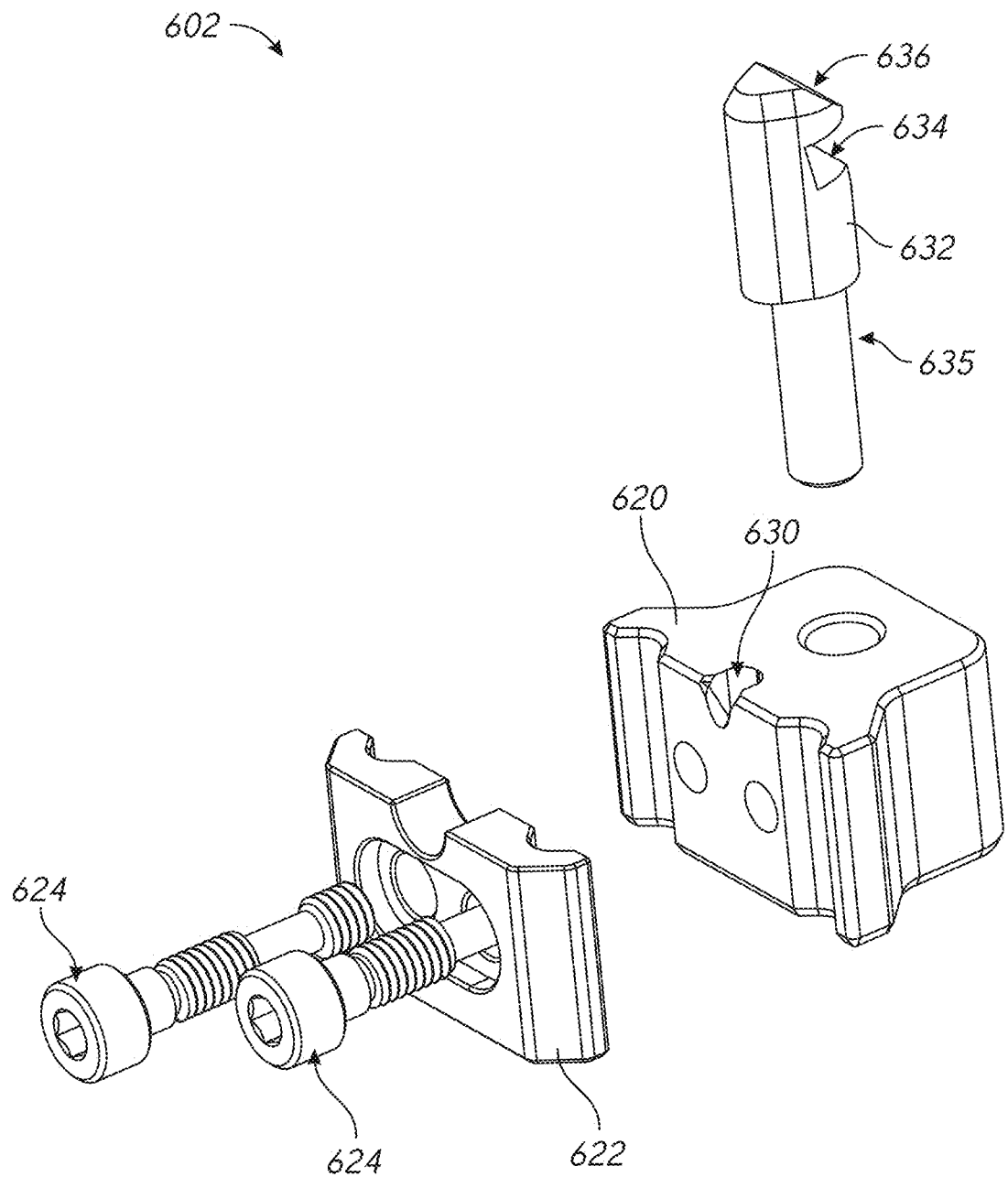
FIG. 2 illustrates an exploded view of embodiments of a fixation base of the system of FIG. 1.
Figure 3A:
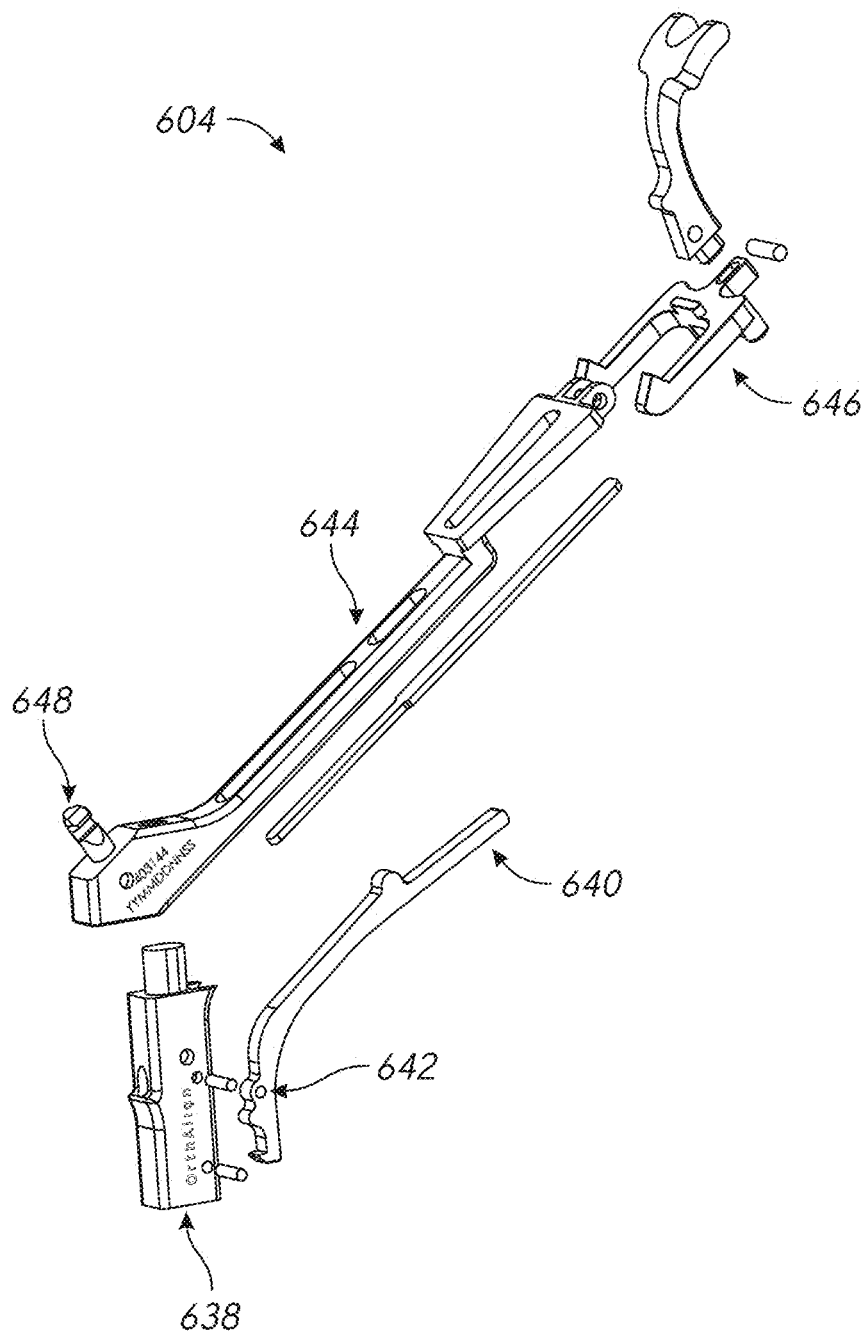
FIGS. 3A-3G illustrate various view of embodiments of a first assembly of the system of FIG. 1.
Figure 3B:
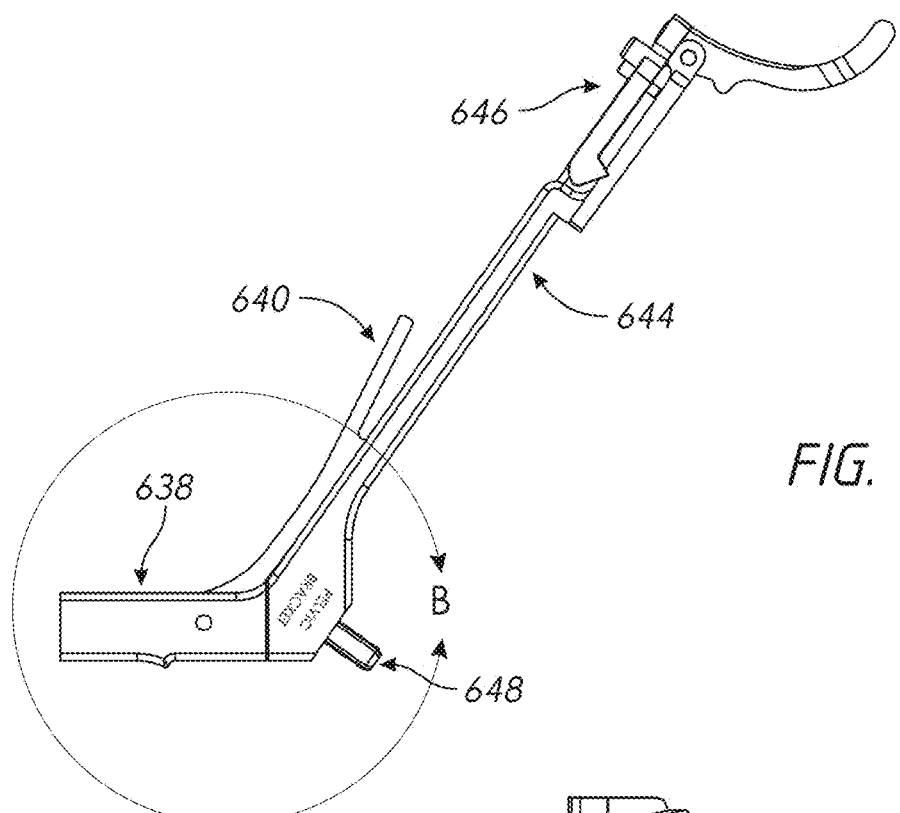
Figure 3C:
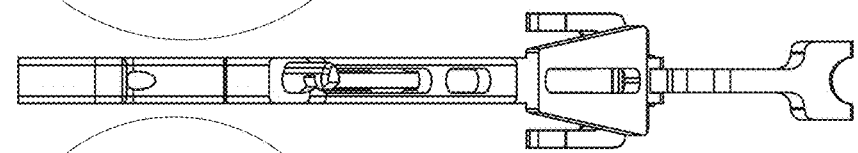
Figure 3D:
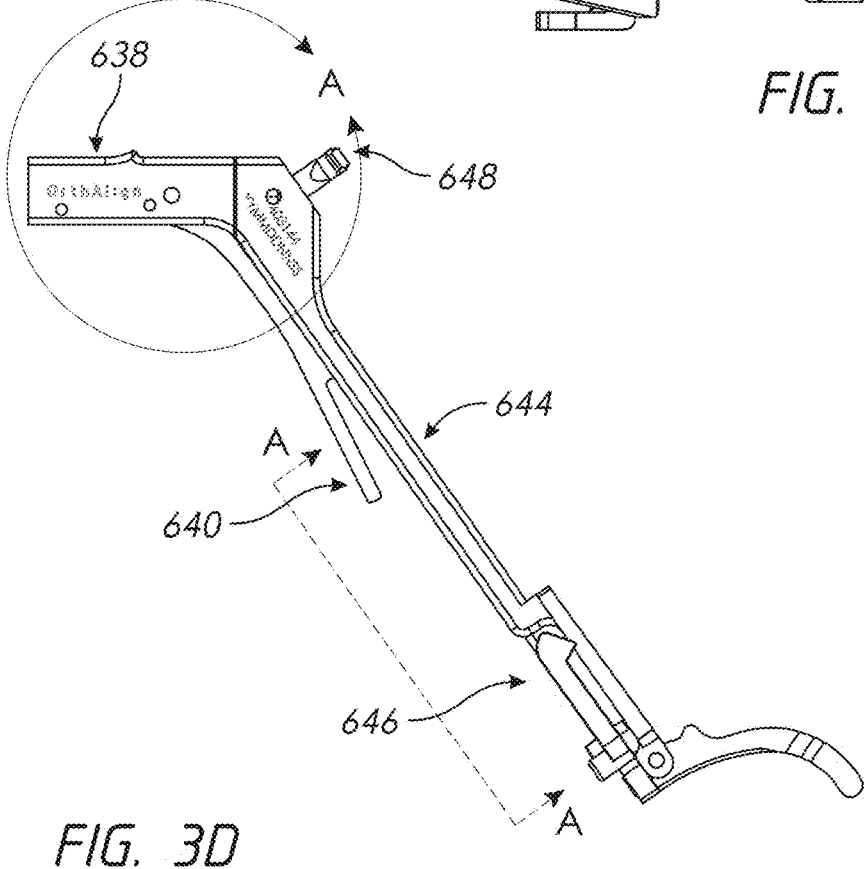
Figure 3E:
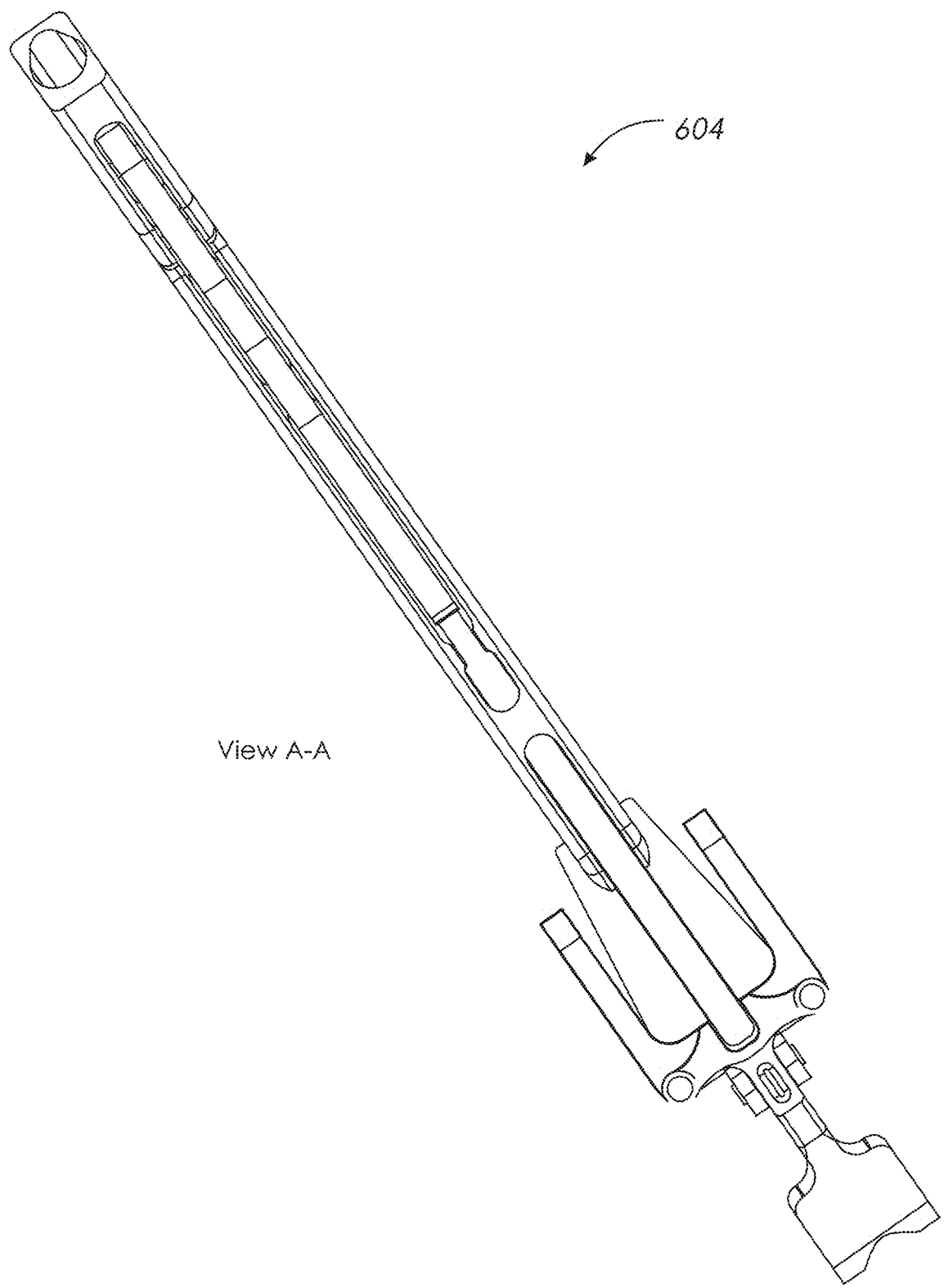
Figure 3F:
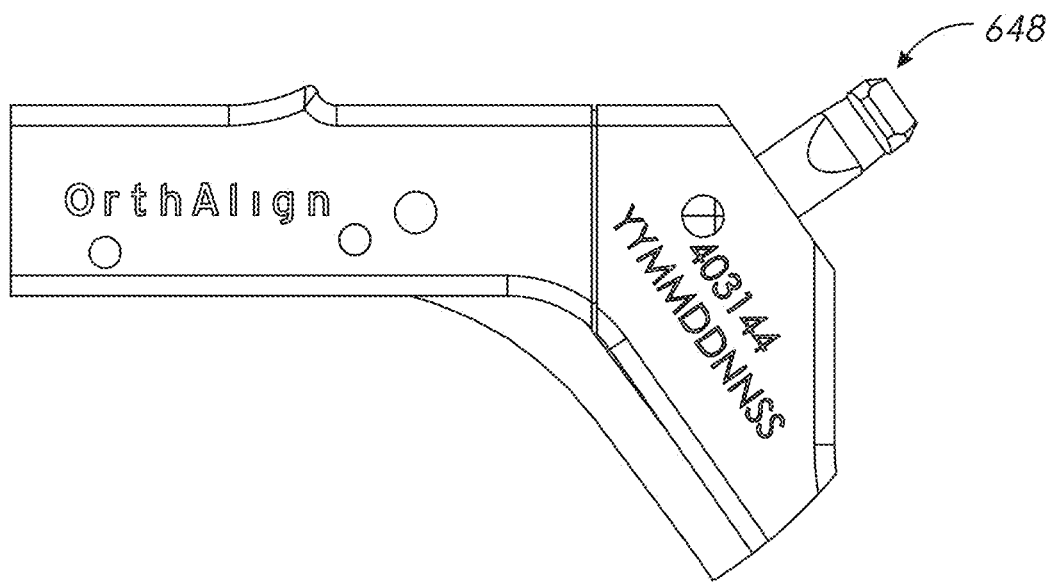
Figure 3G:
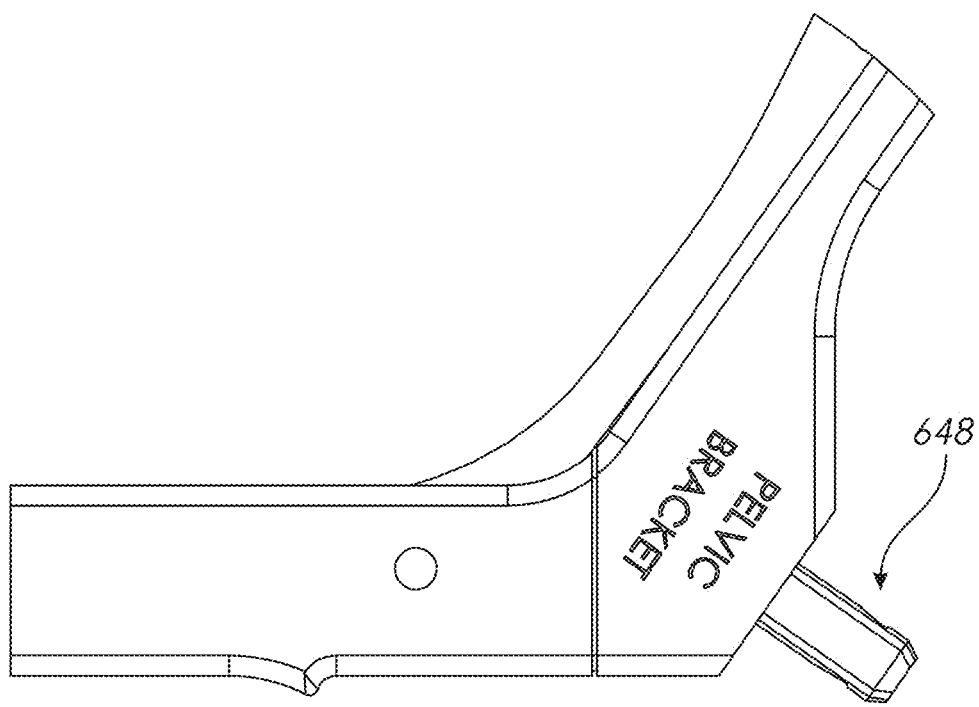

The system 600 can include the fixation base 602 shown in FIG. 2. FIG. 2 shows an exploded view of the fixation base 602. The fixation base 602 can include a platform 620 and a support 622. The platform 620 can interact with the support 622 to function as a clamp. In the illustrated embodiment, the fixation base 602 can include one or more fixation devices 624 such as screws. The fixation devices 624 can pass through the support 622 and engage corresponding holes in the platform 620.

The platform 620 and the support 622 form one or more channels therebetween. The number of channels can correspond to the number of fixation pins. Upon rotation of the fixation devices 624, each fixation pin 610, 612 is retained between the platform 620 and the support 622. The fixation base 602 can include a divot 630. The divot 630 can be associated with a parked configuration or home position, as described herein.

The fixation base 602 can include a first coupler 632. The first coupler 632 can couple to one or more components of the system 600. The first coupler 632 can include an elongate post 635. The first coupler 632 can include a slot 634. The slot 634 can be designed to interact with detents of other components of the system 600, as described herein. The first coupler 632 can include a tapered surface 636. The tapered surface 636 can facilitate entry of the first coupler 632 within other components of the system 600. In some embodiments, the first coupler 632 can have a regular shape (e.g., cylindrical). In some embodiments, the first coupler 632 can have an irregular shape (e.g., triangular, teardrop, elliptical, rectangular). The irregular shape may facilitate alignment of other components of the system 600 with the platform 620 of the fixation base 602. In the illustrated embodiment, the other components of the system 600 can mate with the first coupler 632 in a single orientation.

The system 600 can include the first assembly 604 shown in FIGS. 3A-3G. The first assembly 604 can include a pelvic bracket 638. In the illustrated embodiment, the pelvic bracket 638 can be substantially vertical in use, as shown in FIG. 1. The first assembly 604 can be designed to couple with the fixation base 602. The first assembly 604 can include a lock lever 640 to couple the first assembly 604 with the fixation base 602. In some embodiments, the tapered surface 636 of the first coupler 632 causes the pivoting of the lock lever 640. In some embodiment, the surgeon causes the pivoting of the lock lever 640. The lock lever 640 can include a detent 642. The detent 642 is sized and shaped to be received within the slot 634. The engagement of the detent 642 and the slot 634 can rigidly couple the first assembly 604 with the fixation base 602.

The first assembly 604 can include an extension 644. The extension 644 can be coupled to the pelvic bracket 638. The extension 644 can include a second coupler 648. The second coupler 648 can be designed to couple with the second assembly 606. The second coupler 648 provides a stable manner to position the second assembly 606 relative to the first assembly 604.

The extension 644 can include a mount 646 designed to couple with a surgical orientation device 172. The surgical orientation device 172 is rigidly coupled to the extension 644 when engaged with the mount 646. The surgical orientation device 172 can be angled when coupled to the first assembly 604, as shown in FIG. 1. The surgical orientation device 172 can be angled approximately 35° from the horizontal axis. Other angles from the horizontal axis are contemplated, (e.g., 5°, 10°, 15°, 20°, 25°, 30°, 40°, 45°, 50°, 55°, 60°, 65°, 70°, 75°, 80°, or 85°, between 30°-40°, between 25°-45°). In some embodiments, the angle of the surgical orientation device 172 improves visibility. The angle is a compromise between tilting the surgical orientation device 172 up toward the surgeon and allowing another surgeon or surgical assistant on the other side of the patient to still see the display. One reason for angling the surgical orientation device 172 is that in an anterior approach, the surgeon stands toward the patient's feet while impacting the acetabular implant and a horizontal display may be difficult to see.

The surgical orientation device 172 detects orientation and rotation of the device 172 relative to a reference frame. The surgical orientation device 172 preferably comprises at least one sourceless sensor, such as an accelerometer, a gyroscope, or a combination of these sensors and other sensors. In some embodiments, the surgical orientation device 172 includes a three axis accelerometer to detect orientation relative to gravity and a plurality of gyroscopes to detect rotation. Other sensors could be used in various modifications. Examples of specific sensor combinations include Analog Devices ADIS 16445 and Invensense MPU-6050 or MPU-9150 among others. In some approaches, the surgical orientation device 172 can be disposable and so the sensors preferably are less expensive sensors. In some embodiments, the surgical orientation device 172 is disposable.

The surgical orientation device 172 includes one or more sensors that together form an inertial measurement unit (IMU). In particular, the IMU can include a first sensor for determining acceleration and a second sensor for determining gyroscopic positioning. As discussed herein, the first sensor can be an accelerometer and the second sensor can be a gyroscopic sensor. In some embodiments, the sensors can comprise a three-axis gyroscopic sensor and a three-axis accelerometer sensor. The surgical orientation device 172 can include a transmitter for sending data or receiving data from one or more sensors of the system 600, such as one or more sensors of the orientation sensing device 204. The information received from the orientation sensing device 204 can be fed to an input port, or alternatively, the electronic control unit can itself receive the information (e.g., wirelessly). The information from the orientation sensing device 204 can correspond, for example, to the position and/or orientation of the orientation sensing device 204 and can be used by the surgical orientation device 172 to determine an aggregate, or overall, position and/or orientation of the surgical orientation device 172.

The system 600 can include the second assembly 606 shown in FIG. 4A-4F. The second assembly 606 can include a probe bracket 652. In the illustrated embodiment, the probe bracket 652 can be substantially angled with respect to the pelvic bracket 638 when in use, as shown in FIG. 1. The second assembly 606 can be designed to couple with the second coupler 648 of the first assembly 604. The second assembly 606 can include a lock lever 654. The lock lever 654 can be coupled to the probe bracket 652 with pivot pins. The lock lever 654 can be pivoted relative to the probe bracket 652. In some embodiments, the tapered surface of the second coupler 648 causes the pivoting of the lock lever 654. In some embodiments, the surgeon causes the pivoting of the lock lever 654. The lock lever 654 can include a detent 656. The detent 656 is sized and shaped to be received within the slot of the second coupler 648. The engagement of the detent 656 and the slot can rigidly couple the second assembly 606 with the first assembly 604.

In the illustrated embodiment, the second assembly 606 includes a mount 658. The mount 658 can be coupled to the probe bracket 652 to allow relative movement therebetween. The mount 658 can be received within an opening in the probe bracket 652. The mount 658 can permit rotation about a longitudinal axis of the mount 658 relative to the probe bracket 652.

Figure 4A:
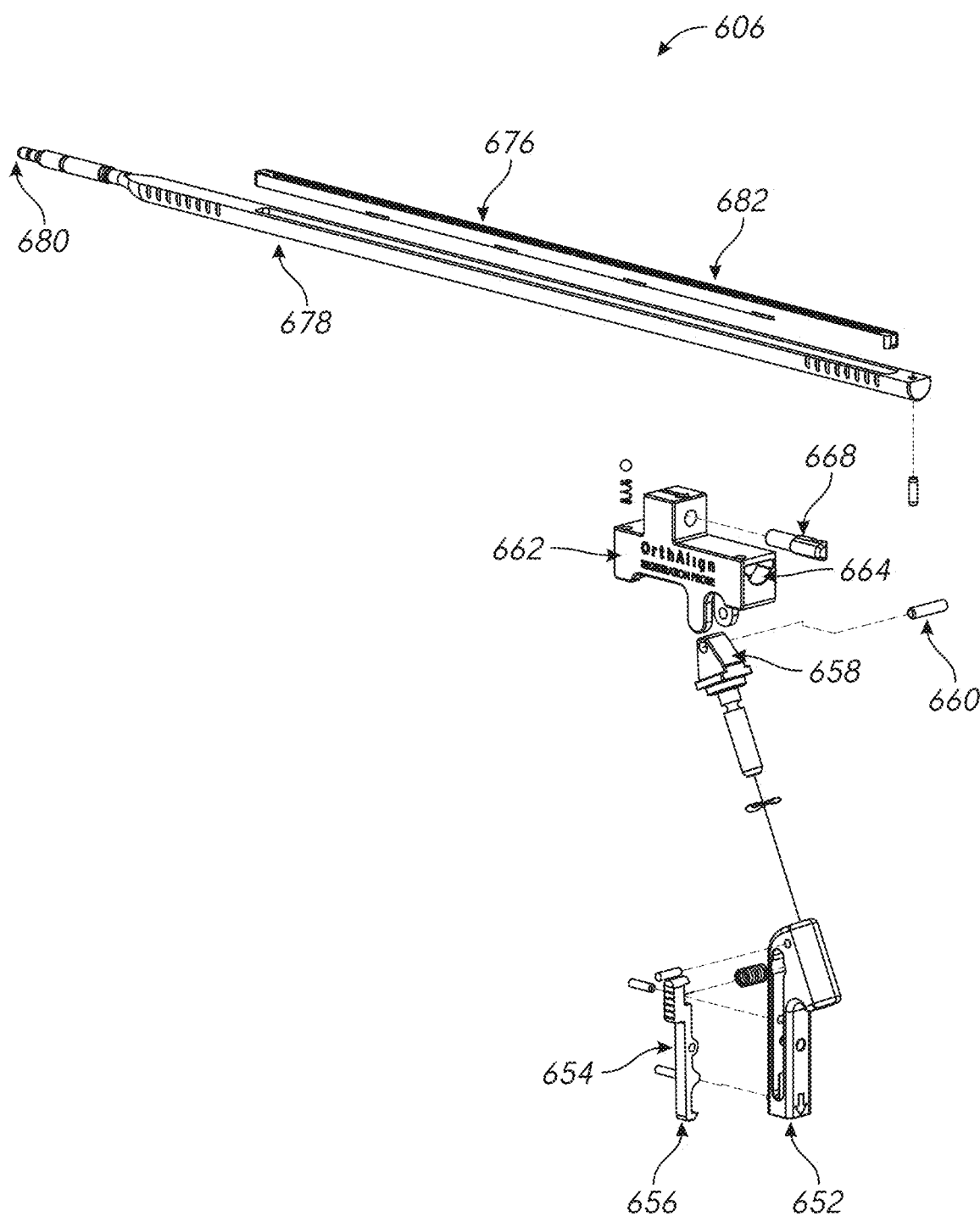
Figure 4D:
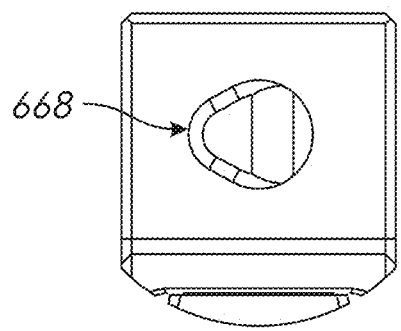
Figure 4E:
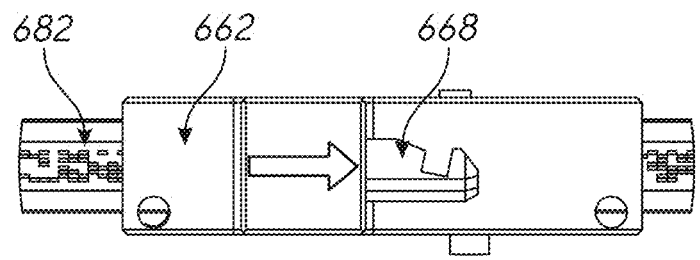
Figure 4F:
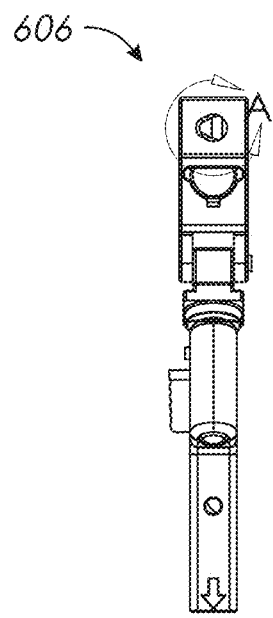

The second assembly 606 can include a dock 662. The dock 662 can be coupled to the mount 658 to allow relative movement therebetween. The dock 662 can be coupled to the mount 658 with one or more pivot pins 660. The dock 662 can have two degrees of freedom relative to the probe bracket 652 (e.g., rotational motion and pivoting motion). The dock 662 can include a sliding support with a through lumen 664. The through lumen 664 is sized to accept a probe 678. The probe 678 has a distal end 680 designed to touch a point or a location or locations, as described herein. The distal end 680 can be straight as shown in FIG. 4A. In other embodiments, the distal end 680 is slanted or curved.

The through lumen 664 of the dock 662 permits slideable extension of the probe 678. The dock 662 is movable relative to the probe bracket 652 (e.g., via rotation of the mount 658 and pivoting of the pivot pin 660). The dock 662 can be rotated about a longitudinal axis of the mount 658 to different rotational positions relative to the attachment location of the fixation pins 610, 612. This may require movement of the mount 658 in a rotational manner relative to the probe bracket 652. The dock 662 can be pivoted about the longitudinal axis of the pivot pins 660 to different positions relative to the attachment location of the fixation pins 610, 612. This may require movement of the dock 662 in a pivoting manner relative to the mount 658.

The probe 678 can be coupled to the dock 662 such that the probe 678 is movable relative to the probe bracket 652 (e.g., via rotation of the mount 658 and pivoting of the pivot pin 660). This maneuverability enables the distal end 680 of the probe 678 to pivot or rotate to contact anatomical landmarks, as discussed herein. The probe 678 can be slid relative to the dock 662 to different translational positions relative to the attachment location of the fixation pins 610, 612. The slideability of the probe 678 within the dock 662 enables the distal end 680 to move to reach a point or anatomical landmarks in the same plane of the probe 678 but closer to or farther from the distal end 680.

The second assembly 606 permits a range of motion of a distal end 680 of the probe 678 to facilitate acquiring a point that that is spaced apart from the attachment location of the fixation pins 610, 612. The second assembly 606 permits a range of motion of a distal end 680 of the probe 678 to facilitate acquiring a plurality of landmarks that are different distances from the attachment location of the fixation pins 610, 612. In other words, the distal end 680 of the probe 678 can be extended away from the axis of the sliding support of the dock 662 or can be retracted to a position closer to the axis of the sliding support of the dock 662.

Figure 5A:
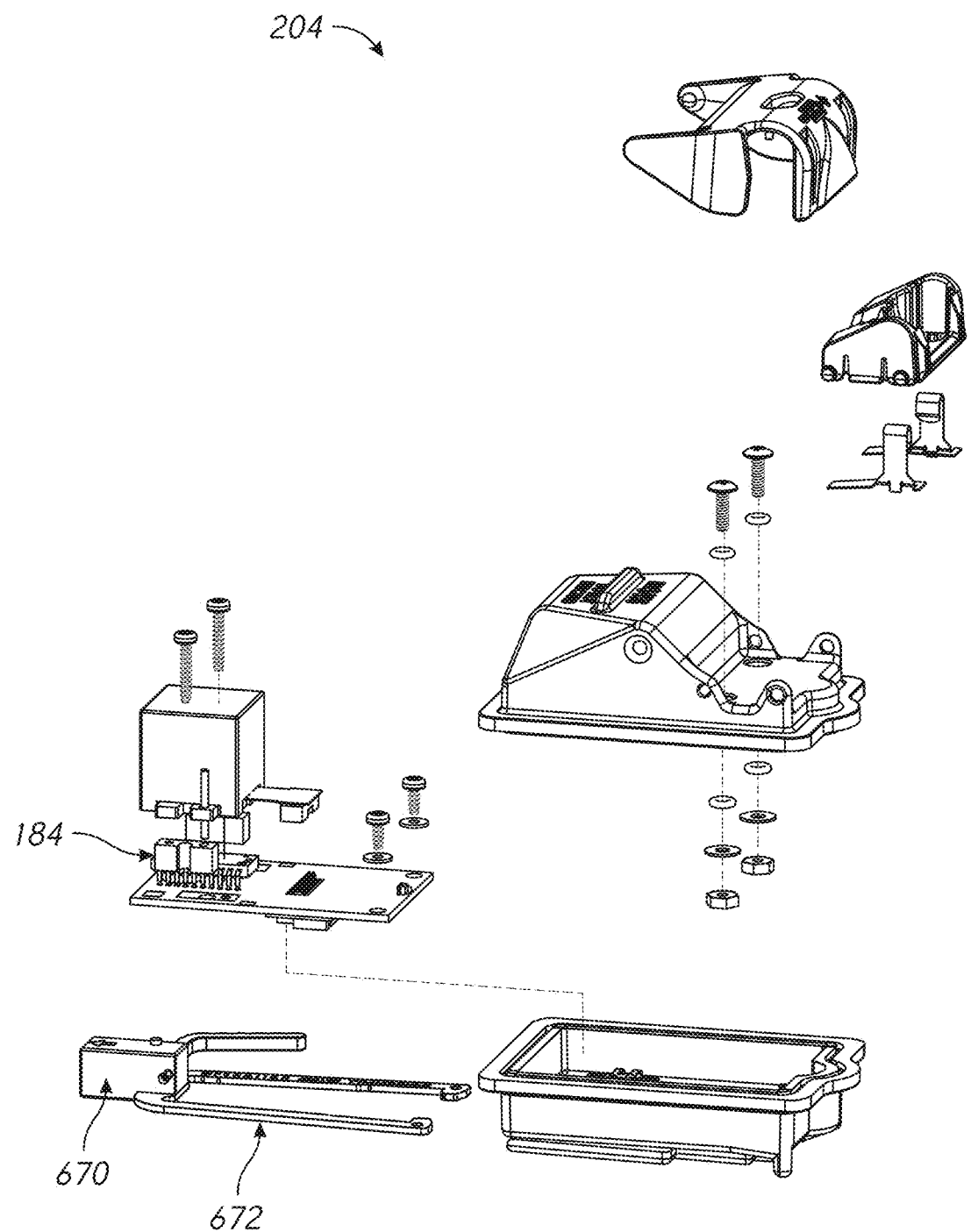
FIGS. 5A-5C illustrate various view of embodiments of an orientation sensing device of the system of FIG. 1.
Figure 5B:
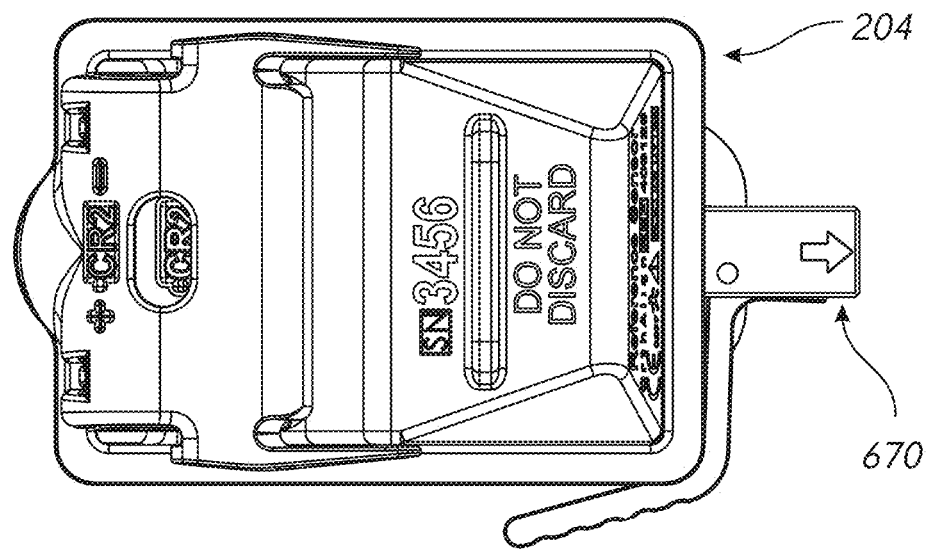
Figure 5C:
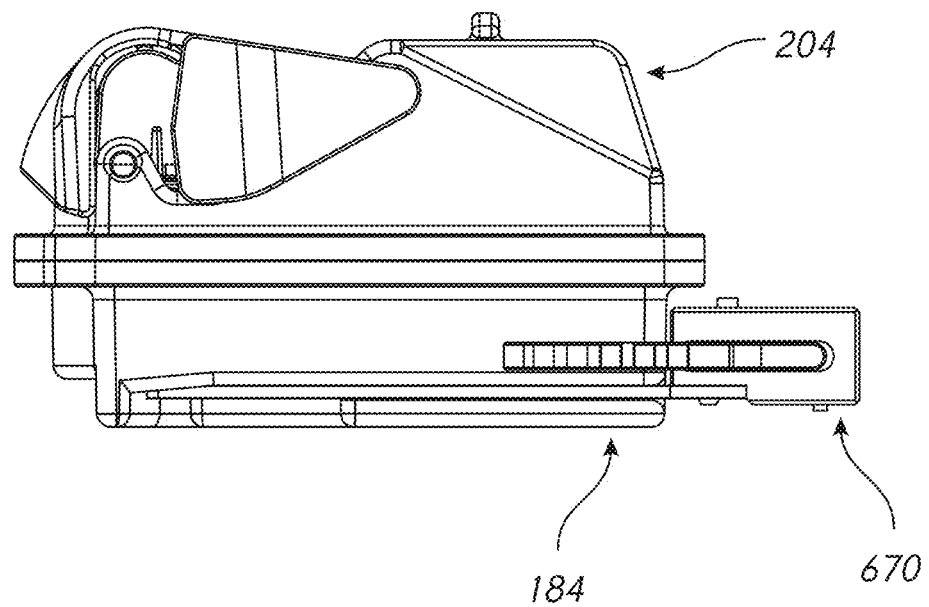

The dock 662 can include a third coupler 668. In some embodiments, the third coupler 668 is a universal coupler. In some embodiments, the third coupler 668 is identical or substantially similar to the second coupler 648. This permits the orientation sensing device 204 to couple to either the second coupler 648 or the third coupler 668, as described herein. In some embodiments, the third coupler 668 can be substantially similar to the first coupler 632 described herein. The third coupler 668 can be designed to couple with the orientation sensing device 204. FIG. 5A-5C illustrate an embodiment of the orientation sensing device 204. The second assembly 606 can include an extension 670. The extension 670 can couple to the third coupler 668 of the dock 662. The engagement between the third coupler 668 and the extension 670 minimizes or prevents relative movement therebetween to avoid any mechanical relative movement during navigation procedures. The extension 670 can include a mount 672 designed to couple with the orientation sensing device 204. In the illustrated embodiment, the mount 672 includes a lock and release lever that can pivot relative to the extension 670. The orientation sensing device 204 can include features to mate with the lock and release lever. Other configurations are contemplated. The orientation sensing device 204 is rigidly coupled to the extension 670 when engaged with the mount 672.

The orientation sensing device 204 can be angled when coupled to the second assembly 606, as shown in FIG. 1. The orientation sensing device 204 can be angled approximately 35° from the horizontal axis. Other angles from the horizontal axis are contemplated, (e.g., 5°, 10°, 15°, 20°, 25°, 30°, 40°, 45°, 50°, 55°, 60°, 65°, 70°, 75°, 80°, or 85°, between 30°-40°, between 25°-45°). In some embodiments, the angle of the orientation sensing device 204 improves visibility.

The orientation sensing device 204 detects orientation and rotation of the probe 678, as described herein. The orientation sensing device 204 preferably comprises at least one sourceless sensor, such as an accelerometer, a gyroscope, or a combination of these sensors and other sensors. In some embodiments, the orientation sensing device 204 includes a three axis accelerometer to detect orientation relative to gravity and a plurality of gyroscopes to detect rotation. Other sensors could be used in various modifications. In some embodiments, the orientation sensing device 204 is reusable.

Referring back to FIGS. 4A and 4C, the probe 678 can include a marking 682. The marking 682 can indicate length or extension of the probe 678 relative to the dock 662. The marking 682 can include a scale. In some embodiments, the marking 682 can be over a range of from about 8 inches, 10 inches, 12 inches, approximately 8-12 inches, etc. The marking 682 can be printed on the probe 678. In some embodiments, the marking 682 can be on a separate component such as a probe inlay 676. The probe inlay 676 can be received within a portion of the probe 678. In some embodiments, the probe inlay 676 is separated a distance from the distal end 680 of the probe 678.

Referring to FIG. 5A-5C, the orientation sensing device 204 can include a camera 184. The camera 184 can capture images of the marking 682. In some embodiments, the dock 662 includes a window to permit the camera 184 to capture images. The camera 184 can read the marking 682 to provide accurate determination of the translational position of the probe 678 relative to the dock 662. In another embodiment, camera data derived from the marking 682 can be used to confirm the data from sensors in the orientation sensing device 204.

2. Optical Component

Figure 6A:
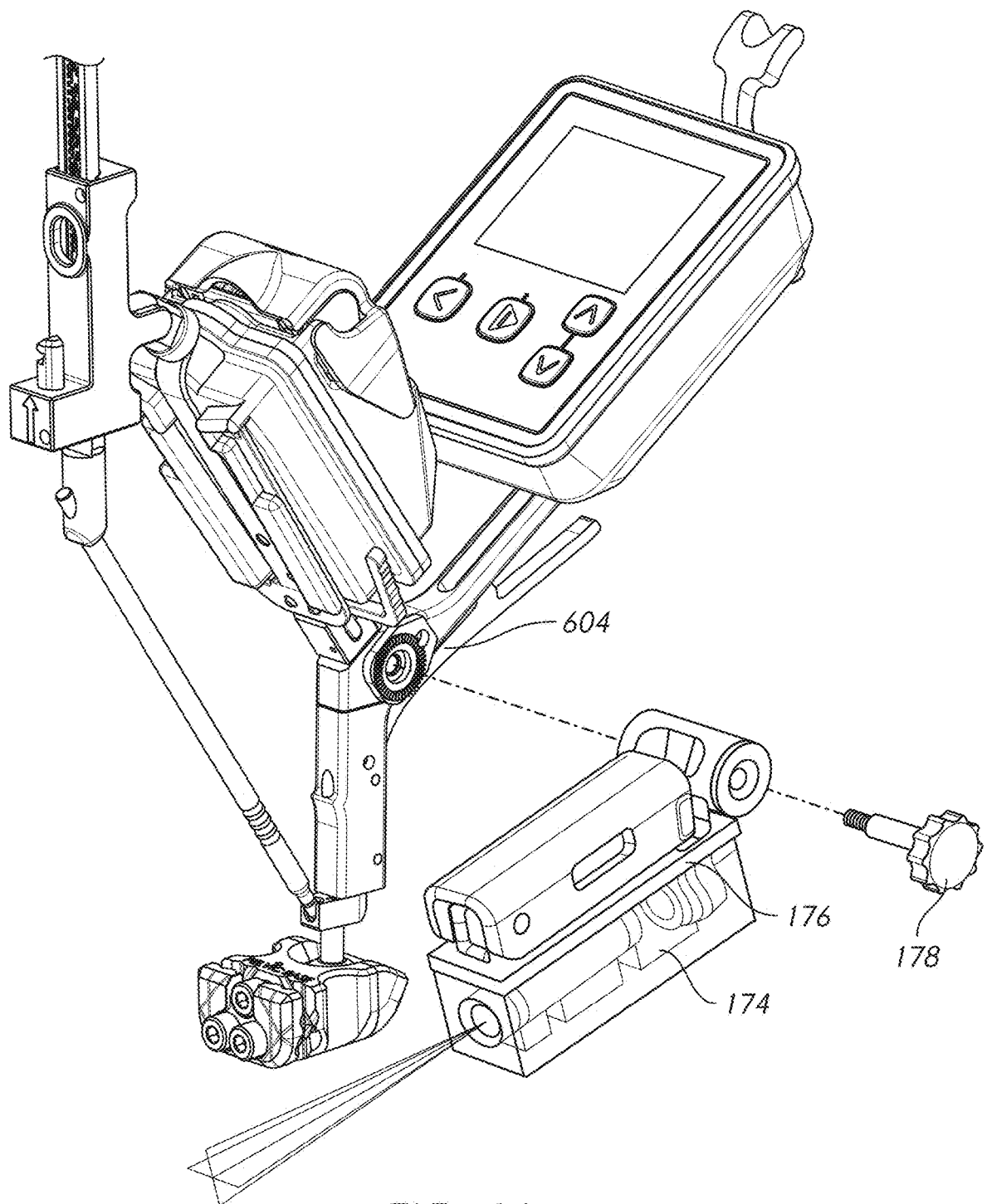
FIG. 6A illustrates an embodiment of an optical component.

In some methods of use, the system 600 includes an optical component 174 shown in FIG. 6A. In some embodiments, the optical component 174 is integrated into the surgical orientation device. In some embodiments, the optical component 174 can be a separate component from the surgical orientation device 172. The optical component 174 can be located below the surgical orientation device 172 adjacent to a fixture to be coupled with a patient, e.g., closer to the pelvis of the patient. The optical component 174 can be located beside or adjacent to or above the surgical orientation device 172. The display of the surgical orientation device 172 can include instructions related to the method of using the optical component 174.

In some embodiments, the optical component 174 can include a housing. The optical component 174 can include one or more light sources within the housing of the optical component 174. The optical component 174 can include one or more windows which allow light to project outward from the optical component 174. The optical component 174 can include one or more additional optical components such as one or more lens, one or more reflectors, one or more filters, one or more diffractor, and/or one or more diffusors. The optical component 174 can include one or energy sources to supply energy to the light source. The optical component 174 can include any features of the surgical orientation device 172 and/or the orientation sensing device 204 described herein.

In some embodiments, the optical component 174 is coupled to the system 600. In some embodiments, the optical component 174 is coupled to the first assembly 604. In some embodiments, the optical component 174 can be rotated, pivoted, or otherwise moved relative to the first assembly 604. The system 600 can include additional features to facilitate positioning of the optical component 174 relative to the first assembly 604. The optical component 174 can include a bracket 176. The bracket 176 can facilitate connection between the optical component 174 and another component of the system 600. In some embodiments, the bracket 176 can be a housing for the laser or other light source, described herein. The optical component 174 can include one or more features to allow the independent adjustment of the optical component 174. The optical component 174 can include an adjustment feature 178. The adjustment feature 178 can cause the rotation of the optical component 174 relative to the first assembly 604. The adjustment feature 178 can cause the rotation of the optical component 174 relative to the second assembly 606. The adjustment feature 178 can cause the rotation of the optical component 174 relative to the fixation base 602. The adjustment feature 178 can cause the rotation of the optical component 174 relative to the pelvis. The adjustment feature 178 can be a knob. The adjustment feature 178 can be coupled to an axle to cause rotation of the optical component 174 about the axle. The adjustment feature 178 can be coupled to the bracket 176 to cause rotation of the bracket 176. The bracket 176 can include a sleeve or tubular portion designed to fit around an axle of the adjustment feature 178. In some embodiments, the optical component 174 is coupled independently to the bone of the patient. The optical component 174 can be coupled to the pelvis. Other configurations of the optical component are contemplated, see FIG. 12C.

FIGS. 6B-6C illustrate another embodiment of an optical component 194. The optical component 194 can include one or more magnets 196. The one or more magnets 196 can be located on a surface of the optical component 194. The one or more magnets 196 can be disposed in or on a housing 200 of the optical component 194. In some embodiments, the optical component 194 can include one magnet, two magnets, three magnets, four magnets, etc. In some embodiments, the optical component 194 can include one or more magnets on a first surface 202 and one or more magnets on a second surface 204. The first surface 202 can be located on an opposite side as the second surface. In some embodiments, the optical component 194 can include one or more magnets on opposite sides of the optical component 194. In some embodiments, the one or more magnets 196 on opposite sides of the optical component 194 can allow the optical component 194 to be coupled with another component of any of the systems disclosed herein on either side of the optical component 194.

In some embodiments, the optical component 194 is coupled to the system 600. In some embodiments, the optical component 194 is coupled to the first assembly 604. In some embodiments, the first assembly 604 can include one or more magnets 198. The one or more magnets 198 can be located on a surface of the first assembly 604. The one or more magnets 198 can be disposed in or on an outer flat surface of the first assembly 604. In some embodiments, the first assembly 604 can include one magnet, two magnets, three magnets, four magnets, etc. In some embodiments, the first assembly 604 includes one or more magnets 198 on a first surface and one or more magnets 198 on a second surface. In some embodiments, the first assembly 604 can include one or more magnets on opposite sides of the first assembly 604. In some embodiments, the optical component 194 can couple to either side of the first assembly 604. The one or more magnets 198 of the first assembly 604 can correspond in number, size, shape and/or pattern to the one or more magnets 196 of the optical component 194. The one or more magnets 196 of the optical component 194 can be configured to attract and couple to the one or more magnets 198 of the first assembly 604. In some embodiments, the first assembly 604, or a portion thereof, comprises a magnetic material. In some embodiments, the entire first assembly 604 is magnetic. In some embodiments one or more magnets 198 can be configured to attract a magnetic material disposed on or in the housing of the optical component 194. Accordingly, magnets may be positioned in or on the optical component 194, in or on the first assembly 604, or on or in both the component 194 and the assembly 604.

In some embodiments, the optical component 194 can be held in position relative to the first assembly 604 with the one or more magnets 196, 198. In some embodiments, the optical component 194 can be removably coupled and decoupled from the system 600. In some embodiments, the optical component 194 can allow for independent rotational adjustment of the optical component 194 relative to the system 600. In some embodiments, the optical component 194 can connect to the system 600 in a single orientation. In some embodiments, the optical component 194 can connect to the system 600 in one of a plurality of orientations. In some embodiments, the optical component 194 can connect to the system 600 on either side of the first assembly 604. As described herein, the optical component 194 can include one or more magnets 196 on opposite sides of the optical component 194. The first assembly 604 can include one or more magnets 198 or magnetic surfaces on opposite sides of the first assembly 604.

In some embodiments, the optical component 194 and the first assembly 604 can include one or more mounting features 190, 192. The mounting features 190, 192 can include one or more recesses 190 and one or more protrusions 192. In some embodiments, the first assembly 604 can include one or more protrusions 192 and the optical component 194 can include one or more corresponding recesses 190. In some embodiments, the first assembly 604 can include two protrusions 192 and the optical component 194 can include two or more recesses 190. In the illustrated embodiment, the first assembly 604 includes two protrusions 192 and the optical component 194 includes three recesses 190. The two protrusions 192 can engage two of the recesses 190 in a first configuration and two of the recesses in a second configuration. In embodiments, including three recesses 190 and two protrusions 192, one of the recesses 190 is engaged in both the first and second configurations. The first configuration and the second configuration can tilt the optical component 194 relative to the first assembly 604. Other configurations are contemplated (e.g., one protrusion, two protrusions, three protrusions, four protrusions, etc.) and (e.g., one recess, two recesses, three recesses, four recesses, five recesses, six recesses, etc.). In some embodiments, there are more recesses 190 than protrusions 192. The mounting features 190, 192 can reduce or limit rotation between the optical component 194 and the first assembly 604. The mounting features 190, 192 can facilitate alignment between the optical component 194 and the first assembly 604. The mounting features 190, 192 can facilitate the connection between the optical component 194 and the first assembly 604. The one or more magnets 196 of the optical component 194 can allow for quicker and simpler attachment to the system 600. The one or more magnets 196 of the optical component 194 can allow for a magnetic snap-on connection. In other embodiments the polarity of the magnets 196 and/or the magnets 198 can be configured such that only one or only two relative positions of the optical component 194 and the assembly 604 result in attraction and magnetic securement therebetween. Other types of connections between the optical components and the systems described herein are contemplated.

In some embodiments, the optical component 174, 194 can be positioned at any one of a plurality of discrete positions relative to the first assembly 604. For instance, the system 600 can include a plurality of splines between the optical component 174, 194 and an adjacent structure. The plurality of splines can be a serrated plate. The adjacent structure can be coupled to the first assembly 604. The plurality of splines can retain the position of the optical component 174, 194 relative to the first assembly 604. In some embodiments, the optical component 174, 194 can be oriented at an infinite number of positions relative to the first assembly 604. In some embodiments, the optical component 174, 194 can be oriented at a select position along a continuum of motion. In some embodiments, the optical component 174, 194 can be oriented at one discrete position or orientation relative to the first assembly 604. In some embodiments, the optical component 174, 194 can be oriented at two discrete positions or orientations relative to the first assembly 604. In some embodiments, the optical component 174, 194 can be oriented at one discrete position or orientation on each side of the first assembly 604. In some embodiments, the optical component 174, 194 can be oriented at a plurality of discrete positions or orientations relative to the first assembly 604. The connection between the optical component 174, 194 and the first assembly 604 is sufficiently rigid to maintain the position of the optical component 174, 194 relative to the first assembly 604 once moved into position.

As described herein, in some methods of use, the optical component 174, 194 is mounted to the pelvis of the patient. In some embodiments, the optical component 174, 194 can be mounted to any component of the system 600. In some embodiments, the optical component 174, 194 can be mounted to the platform 602. In some embodiments, the optical component 174, 194 can be mounted to the first assembly 604. In some embodiments, the optical component 174, 194 can be separately mounted to the pelvis. In some methods of use, the optical component 174, 194 can be independently mounted to the pelvis of the patient. In some methods of use, the optical component 174, 194 can be spaced apart from the system 600. In some methods of use, the optical component 174, 194 can be fixed in position relative to the pelvis during the surgical procedure. In some methods of use, the optical component 174, 194 can project light from the same position during the surgical procedure. The rigidity of the system 600 can secure the position of the optical component 174, 194 once moved into position. In some methods of use, the optical component 174, 194 can be positioned and/or moved until the optical component 174, 194 projects light on a selected portion of the anatomy. In some methods of use, the optical component 174, 194 can be positioned and/or moved until the optical component 174, 194 projects light on a target probe, as described herein. In some methods of use, the optical component 174, 194 can be positioned and/or moved until the optical component 174, 194 projects light on sterile wrap, medical drape, bandage, tape, and/or other instruments. In some methods of use, the optical component 174, 194 can be positioned and/or moved until the optical component 174, 194 projects light on a device coupled to the anatomy. In some methods of use, the optical component 174, 194 can be positioned and/or moved until the optical component 174, 194 projects light on a device placed near the anatomy, as described herein.

The optical component 174, 194 can emit a pattern of light. Examples of patterns of lights include one or more lines, one or more points, one or more plane, or one or more shapes. The optical component 174, 194 can be moved until the light is projected on at least one anatomical region. In some methods of use, the light is projected onto at least one anatomical region with little soft tissue. The soft tissue may move relative to the underlying bone. The surgeon can select locations to illuminate where the skin is close to the underlying bone. In some methods of use, the optical component 174, 194 can project a pattern onto a portion of the anatomy. In some methods of use, the optical component 174, 194 can project a pattern onto a target coupled to the anatomy. The surgeon can complete any method steps described herein. Thereafter, the optical component 174, 194 can project the same pattern on the selected portion of the anatomy.

In some embodiments, the optical component 174, 194 can project light onto an anatomical surface. In some embodiments, the optical component 174, 194 can project light onto an anatomical feature or landmark. The light can illuminate a portion of the femur. The light can illuminate a portion of the knee joint. The light can illuminate a portion of the tibia. The light can illuminate can illuminate a portion of the ankle. The light can illuminate a portion of the foot. The light can illuminate a portion of the foot constrained within a positioning boot. In some embodiments, the light can be projected onto a flat or substantially flat local area. In some embodiments, the light can be projected onto a curved or substantially curved local area. In some methods of use, the shape of the surface does alter the projection of light, e.g., changes in angle, tilt, shape, etc. In some methods of use, the shape of the surface does not alter the projection of light. In some methods of use, the shape of the surface does not alter the utility of the approach, as described herein.

In this context, optical component is a broad term. The optical component 174, 194 can be any device designed to project light including visible, ultraviolet, and infrared light. The optical component 174, 194 can comprise one or more lasers, which can be configured to project laser light. The laser can emit light with a very narrow spectrum, for instance a single color of light. The optical component 174, 194 can focus light on a single location, such as a point. The optical component 174, 194 can focus light along a line. The optical component 174, 194 can project one or more points, one or more lines, one or more planes, one or more shapes, one or more colors, and/or one or more patterns. In some embodiments, the projection of light when incident on a surface is visible as two intersecting lines, the pattern may be referred to herein as a cross-hair.

The optical component 174, 194 can be positioned to project light toward a desired location. The optical component 174, 194 can provide a visual guide to replicate an original position of an anatomical feature relative to another anatomical feature, as described herein. In methods wherein the optical component 174, 194 is mounted to the pelvis, the optical component 174, 194 can provide a visual guide to replicate the original position of the leg or a portion thereof relative to the hip. In some embodiments, the optical component 174, 194 can provide a visual guide to replicate the original position of the femur relative to the pelvis as described herein. The optical component 174, 194 can provide alternative or additional orientation information to a surgeon regarding the position on the pelvis relative to the femur. In methods wherein the optical component 174, 194 is mounted to the pelvis, the optical component 174, 194 can provide a visual guide to replicate the original orientation of the leg or a portion thereof relative to the hip. In some embodiments, the optical component 174, 194 can provide a visual guide to replicate the original orientation of the femur relative to the pelvis as described herein. The optical component 174, 194 can provide alternative or additional orientation information to a surgeon regarding the orientation on the pelvis relative to the femur.

The optical component 174, 194 can be used to perform one or more methods or method steps. In some methods of use, the optical component 174, 194 can project the pattern of light pre-operatively. In some methods of use, the optical component 174, 194 can project the pattern of light before cup placement. In some methods of use, the optical component 174, 194 can project the pattern of light before joint replacement. In some methods of use, the optical component 174, 194 can project the pattern of light before joint dislocation. In some methods of use, the optical component 174, 194 can project the pattern of light that can be traced. In some methods of use, the optical component 174, 194 can project the pattern of light after cup placement. In some methods of use, the optical component 174, 194 can project the pattern of light post-instrumentation. In some methods of use, the optical component 174, 194 can project the pattern of light that can align with a marking as the femur is moved. In some methods of use, the optical component 174, 194 can project the pattern of light onto the same surface before and after the cup is replaced. In some methods of use, the optical component 174, 194 can project the pattern of light onto the same surface intra-operatively. In some methods of use, the optical component 174, 194 can project the pattern of light onto the same surface intra-operatively at two or more times during the procedure.

3. Alternative Hip Navigation System

Figure 7:
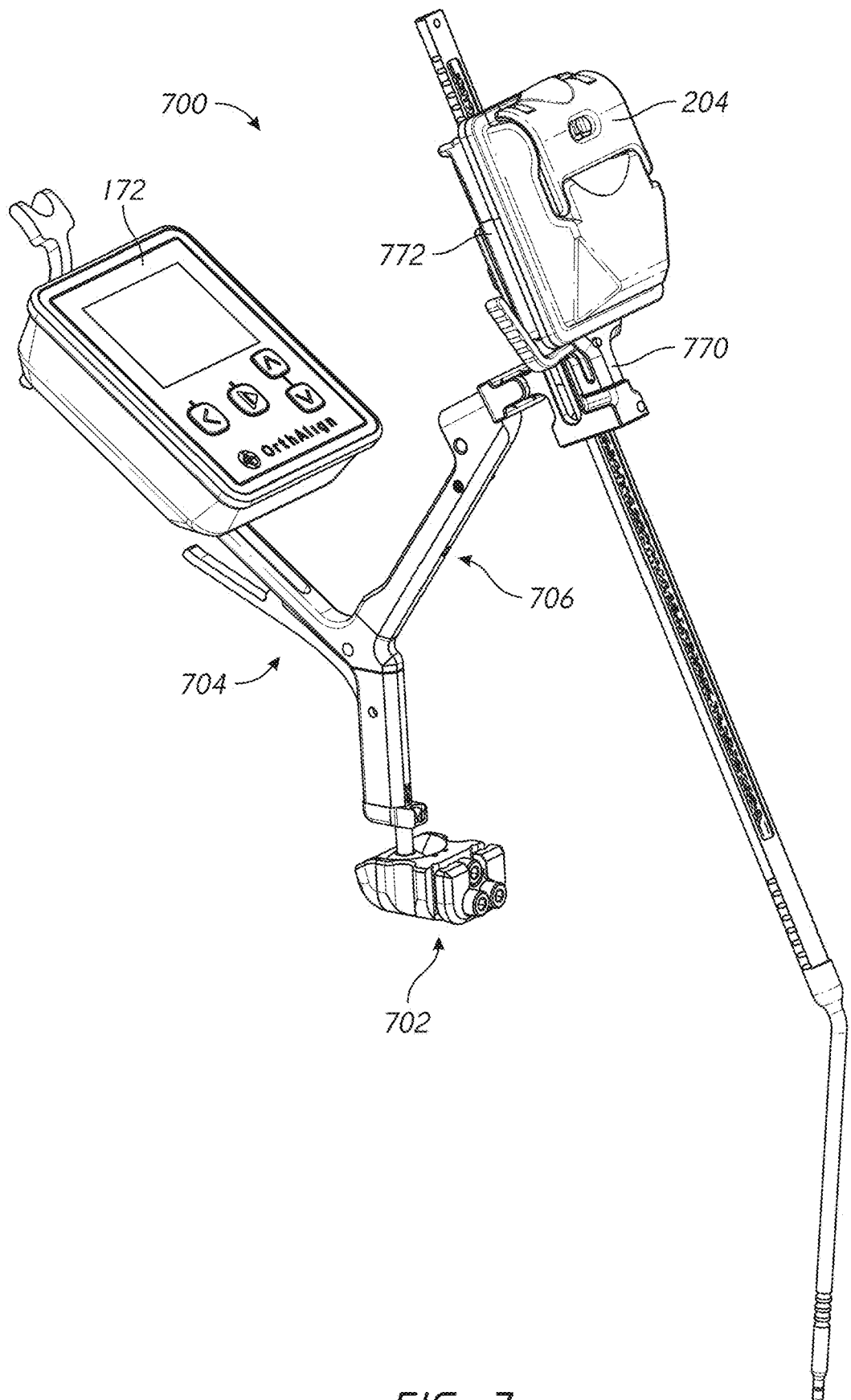
FIG. 7 illustrates a hip navigation system.
Figure 8A:
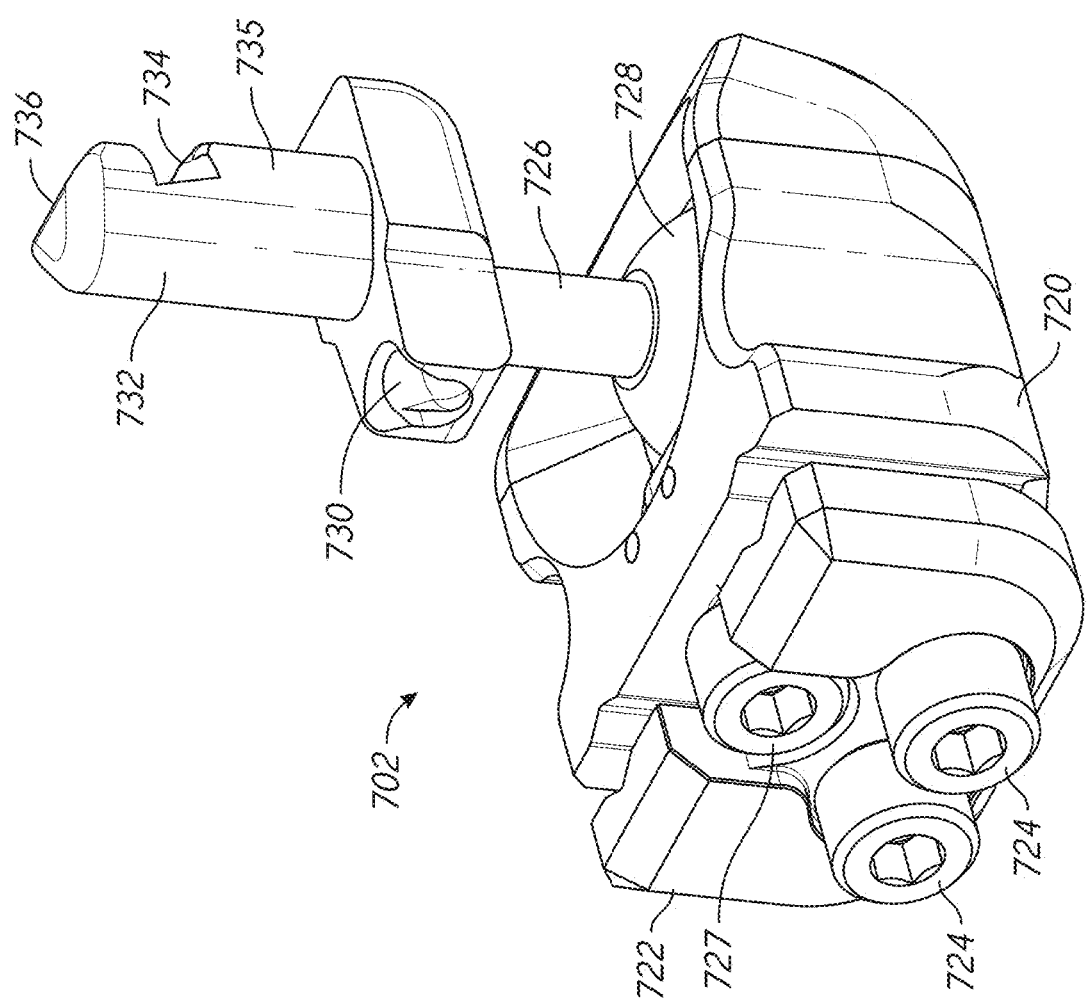
FIGS. 8A-8B illustrate an embodiment of a fixation base of the system of FIG. 7.
Figure 8B:
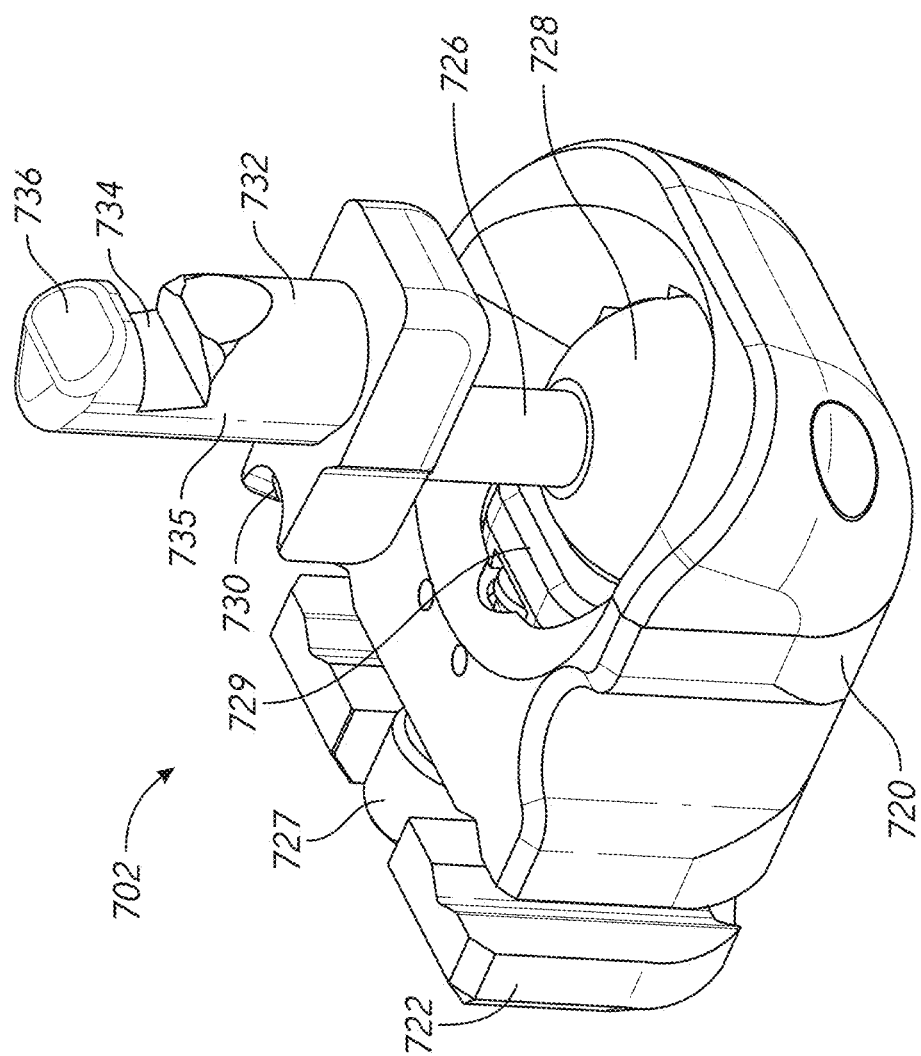

FIG. 7 illustrates a hip navigation system 700. FIGS. 8A-8B illustrate an embodiment of a fixation base 702 of the system 700 of FIG. 7. FIG. 9 illustrates an embodiment of a first assembly 704 of the system 700 of FIG. 7. FIGS. 10A-10D illustrate an embodiment of a second assembly 706 of the system 700 of FIG. 7.

The system 700 can include any of the features described herein with respect to system 600. Similar elements are provided with similar reference numbers. The system 700 can include a fixation base 702, a first assembly 704, and a second assembly 706. The system 700 can include the surgical orientation device 172 and the orientation sensing device 204. The orientation sensing device 204 can include a camera 184 as shown in FIG. 5A. The system 700 can include an optical component 174 as shown in FIG. 6A and/or the optical component 194 shown in FIGS. 6B-6C. The optical component 174 can include one or more of the following features: a bracket 176 and an adjustment feature 178 (see FIG. 6A). The optical component 194 can include one or more of the following features: one or more magnets 196 and one or more mounting features 190, 192 (see FIGS. 6B-6C).

Referring to FIGS. 8A-8B, the fixation base 702 can include one or more of the following: a platform 720, a support 722, one or more fixation devices 724, a divot 730, and a first coupler 732 with a slot 734 and a tapered surface 736. The system 700 can include one or more fixation pins, such as a fixation pin 710 and a fixation pin 712 (see FIGS. 13A-13C).

Referring to FIG. 9, the first assembly 704 can include one or more of the following: a pelvic bracket 738, a lock lever 740, a detent 742 sized and shaped to be received within the slot 734 (see FIG. 3A for similar detent 642), an extension 744, a second coupler 748 and a mount 746 designed to couple with a surgical orientation device 172.

Figure 10A:
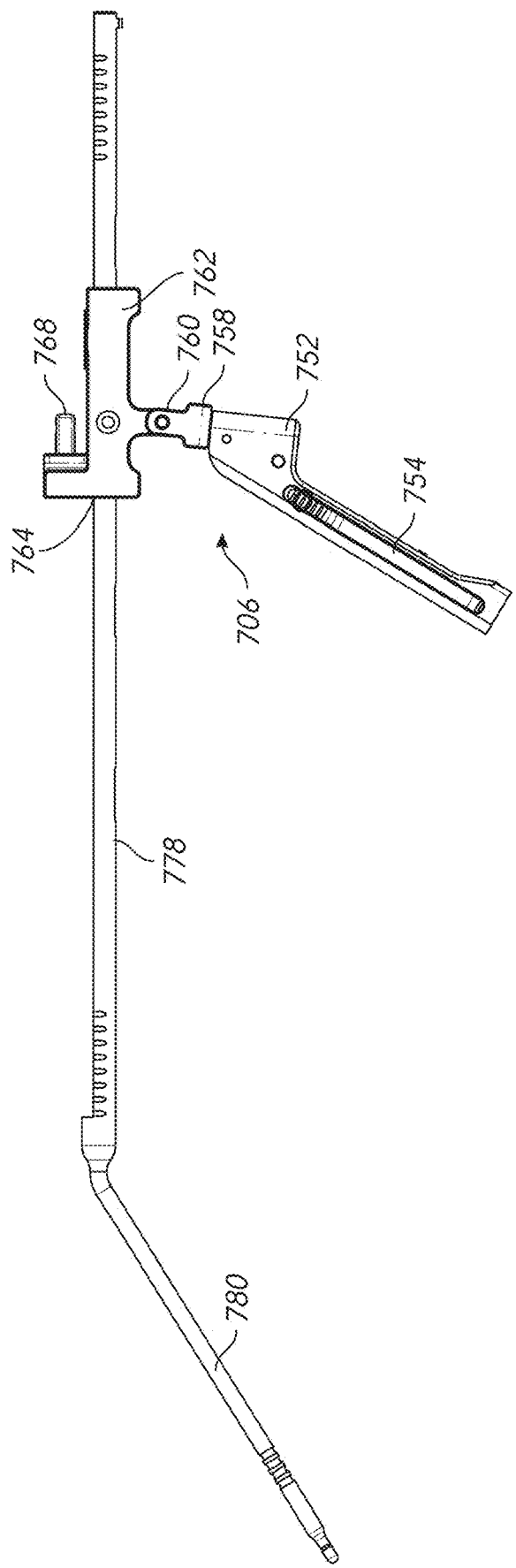
FIGS. 10A-10D illustrate an embodiment of a second assembly of the system of FIG. 7.
Figure 10B:
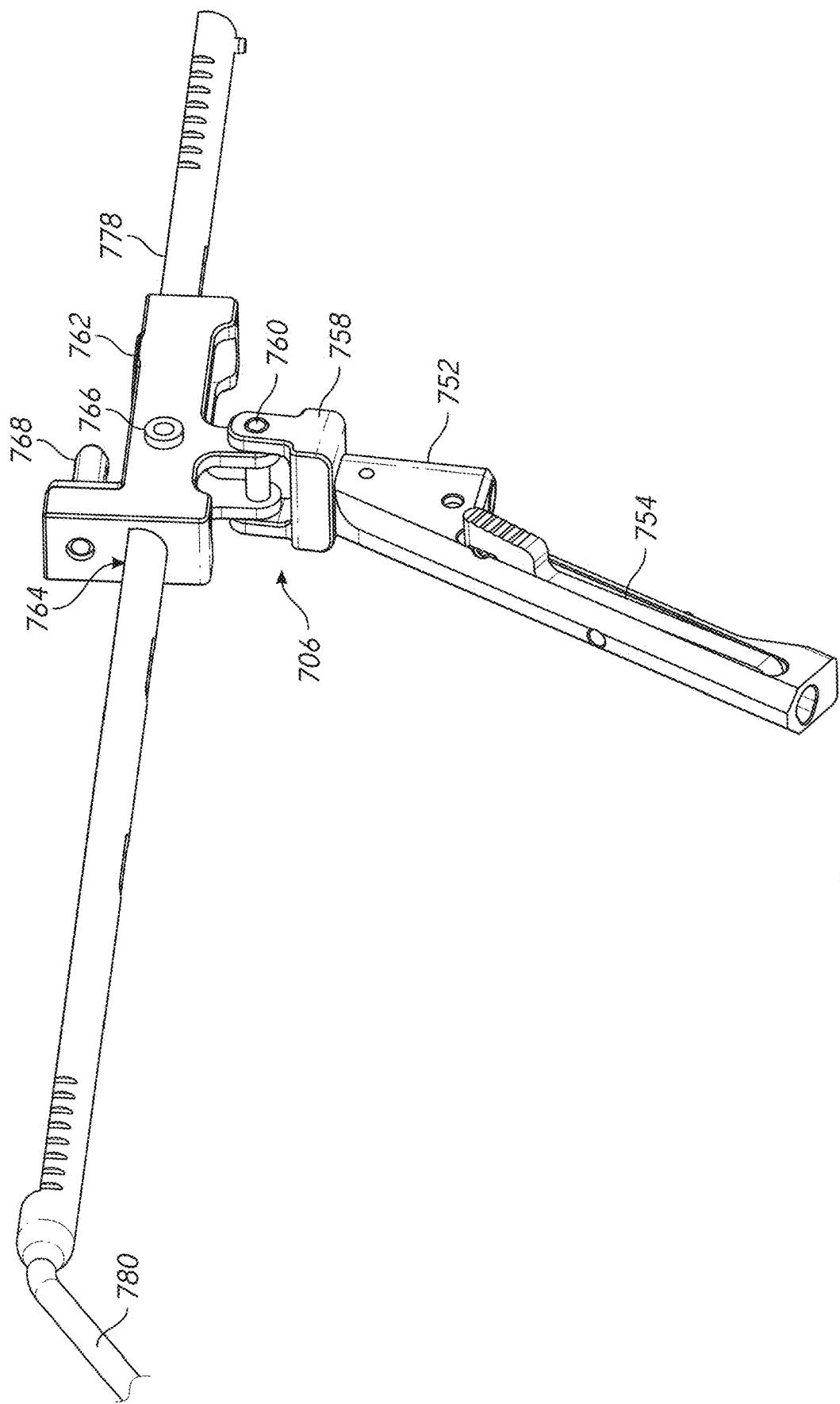
Figure 10C:
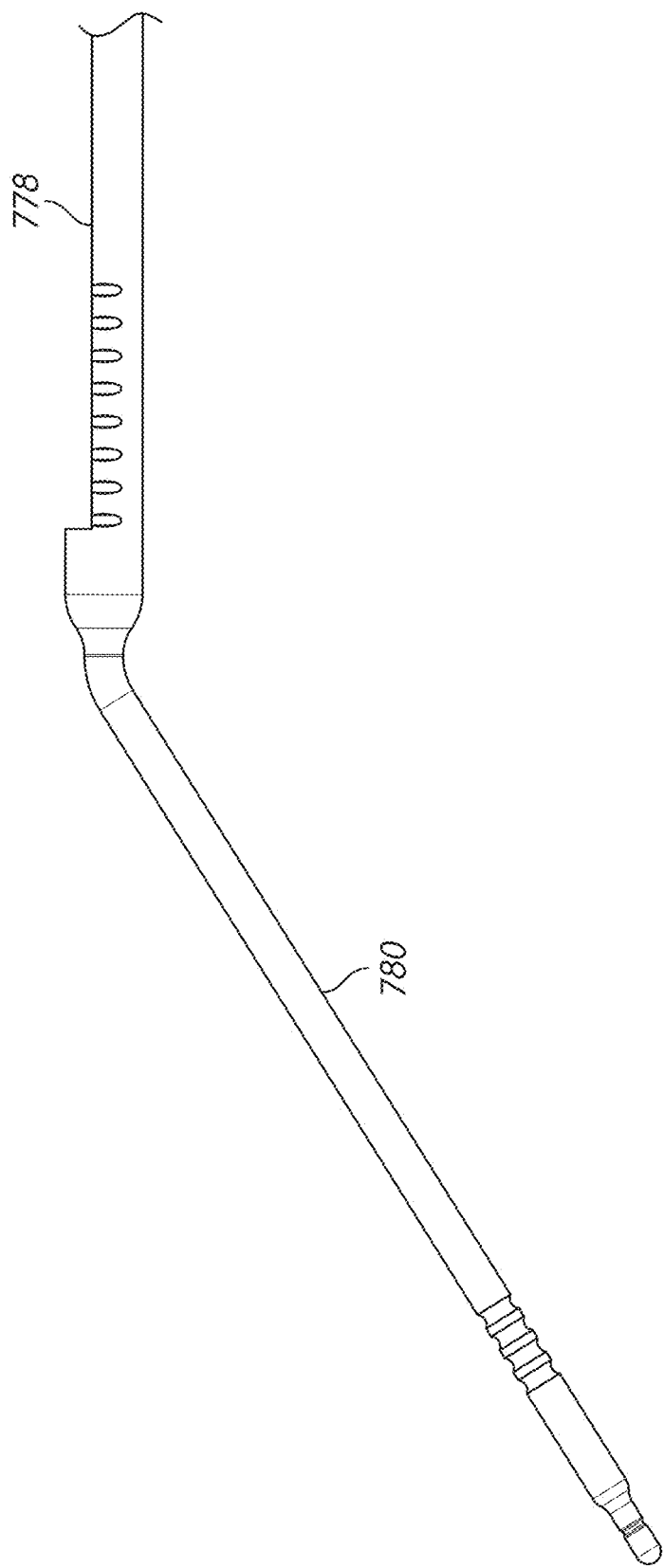
Figure 10D:
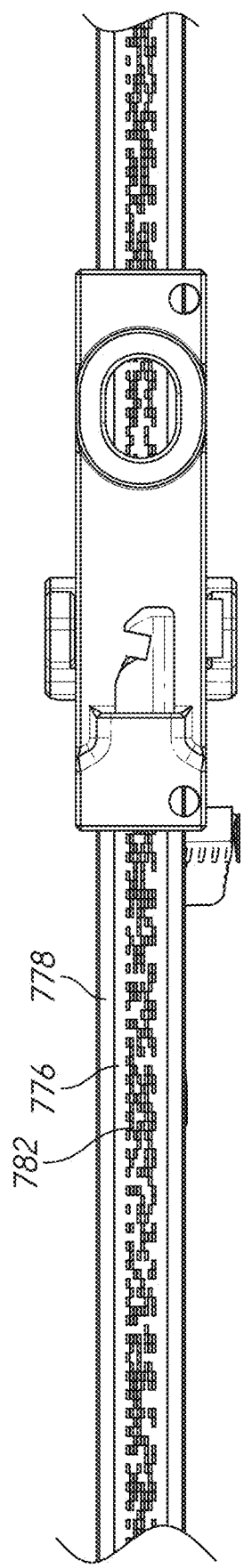

Referring to FIGS. 10A-10B, the second assembly 706 can include one or more of the following: a probe bracket 752, a lock lever 754, a detent 756 (see FIG. 4A for similar detent 656), a mount 758 to permit rotation about a longitudinal axis of the mount 758 relative to the probe bracket 752, a dock 762 coupled to the mount 758, a through lumen 764 sized to accept a probe 778, a third coupler 768, an extension 770 (see FIG. 7), and a mount 772 (see FIG. 7). The orientation sensing device 204 can couple to either the second coupler 748 or the third coupler 768. Referring to FIGS. 10C-10D, the system 700 can include the probe 778. The probe 778 can include one or more of the following: a distal end 780 designed to touch a point, a marking 782, and a probe inlay 776.

The system 700 can include additional features from the system 600 described herein. The system 600 can include one or more of these additional features. Referring back to FIGS. 8A-8B, the platform 720 can include an articulation 726. The articulation 726 can allow movement between the platform 720 and the first assembly 704. The articulation 726 can form a ball and socket joint with the platform 720. The articulation 726 can include a head 728. The head 728 can interact with the platform 720 to form a joint. In the illustrated embodiment, the platform 720 includes the socket.

The articulation 726 can include the first coupler 732. The first coupler 732 can couple to one or more components of the system 700. In some embodiments, the first coupler 732 is a universal coupler. The first coupler 732 can include an elongate post 735. In some embodiments, the first coupler 732 can have a regular shape (e.g., cylindrical). In some embodiments, the first coupler 732 can have an irregular shape (e.g., triangular, teardrop, elliptical, rectangular). The irregular shape may facilitate alignment of other components of the system 700 with the platform 720 of the fixation base 702. In the illustrated embodiment, the other components of the system 700 can mate with the first coupler 732 in a single orientation. The articulation 726 can include the divot 730. The divot 730 can be associated with a parked configuration or home position, as described herein.

The fixation base 702 can include the platform 720 and the support 722. The platform 720 can interact with the support 722 to function as a clamp. In the illustrated embodiment, the fixation base 702 can include one or more fixation devices 724. In the illustrated embodiment, fixation base 702 includes two fixation devices 724. The fixation devices 724 can pass through the support 722 and engage corresponding holes in the platform 720. Upon advancement of the fixation devices 724, each fixation pin 710, 712 is clamped between the platform 720 and the support 722. In some embodiments, the fixation devices 724 are screws, but other configurations are contemplated to clamp the platform 720 and the support 722.

The articulation 726 can be locked in position. The fixation base 702 can include a lock 727. The lock 727 can be advanced against the head 728 to reduce, limit, or prevent movement of the articulation 726. The lock 727 can include fastener such as a screw. In some embodiments, the lock 727 can include a contacting surface 729. The fastener can be rotated or translated to advance the contacting surface 729 relative to the platform 720. The contacting surface 729 can be moved away from the head 728 to enable the head 728 to articulate with the platform 720. The contacting surface 729 can be moved toward the head 728 to apply a force or pressure on the head 728. The contacting surface 729 can be moved toward the head 728 push the head 728 against a surface of the platform 720. The force or pressure of the contacting surface of the lock 727 against the head 728 can reduce movement of the head 728. Other configuration to reduce or prevent movement of the joint are contemplated.

The articulation 726 is illustrated as a ball and socket joint. The articulation 726 can be any joint known in the art. The articulation 726 can include an axle, a sleeve, a bearing, a bushing, and/or a swivel. The articulation 726 can be any joint or connection that allows motion about one or more planes or axes. The articulation 726 can be sufficiently rigid to maintain the position of the first assembly 704 relative to the platform 720 once moved into position. Other configurations are contemplated.

In some methods of use, the fixation base 702 is mounted to the pelvis, as described herein. The position of the pelvic bracket 738 of the first assembly 704 can be adjusted via the articulation 726. The position of the extension 744 of the first assembly 604 can be adjusted via the articulation 726. The optical component 174, 194 can be coupled to the first assembly 604 as described herein. The position of the optical component 174, 194 can be adjusted via the articulation 726. In some embodiments, the position of the optical component 174, 194 is determined in part by the position of the articulation 726. The system 700 can have additional features to position of the optical component 174, 194, as described herein. In other embodiments, the position of the optical component 174, 194 is determined entirely by the position of the articulation 726.

Referring now to FIGS. 10A-10D, the second assembly 706, or a portion thereof such as the probe 778, can be easily removed when not in use. The distal end 780 of the probe 778 can be angled, bent or curved to facilitate acquiring a point. The distal end 780 of the probe 778 can be bent or curved to reach the home position. The shape of the probe 778 can facilitate the touching of a point or structure in the posterior approach. In some embodiments, the probe 778 comprises two or more components. In some embodiments, the distal end 680 is removable.

The second assembly 706 can include a dock 762. The dock 762 can be coupled to the mount 758 to allow relative pivotal movement therebetween. For instance, the dock 662 can be coupled to the mount 758 with one or more pivot pins 760. The dock 762 can have two degrees of freedom relative to the probe bracket 752 (e.g., rotational motion and pivoting motion). The dock 762 can include a sliding support with a through lumen 764. The through lumen 764 is sized to accept a probe 778. The probe 778 has a distal end 780 designed to touch a point, as described herein. The distal end 780 can be slanted or curved. This maneuverability enables the distal end 780 of the probe 778 to pivot, rotate, or slide to contact a point, as discussed herein.

The through lumen 764 of the dock 762 permits slideable extension of the probe 778. The probe 778 can slide relative to the dock 762 to different translational positions relative to the attachment location of the fixation pins 710, 712. The slideability of the probe 778 within the dock 762 enables the distal end 780 to move to reach a point in the which is offset from the plane of the probe 778 but closer to or farther from the distal end 780.

The second assembly 706 can include a lock 766. The lock 766 can be advanced against the probe 778 to reduce, limit, or prevent movement of the probe 778. The lock 766 can include fastener such as a screw. In some embodiments, the lock 766 includes a contacting surface 767. In some embodiments, the contacting surface 767 can be the end of the fastener. The fastener can be rotated or translated to advance the contacting surface 767 relative to the dock 762. The contacting surface 767 can be moved away from the probe 778 to enable the probe 778 to slide within the dock 762. The contacting surface 767 can be moved toward the probe 778 to apply a force or pressure on the probe 778. The contacting surface 767 can be moved toward the probe 778 push the probe 778 against a surface of the dock 762. The force or pressure of the contacting surface 767 of the lock 766 against the probe 778 can reduce movement of the probe 778. The lock 766 can limit or reduce slidablility of the probe 778 relative to the dock 762. In some methods of use, the probe 778 can still pivot (e.g., pivotal motion between the dock 762 and the mount 758). In some methods of use, the probe 778 can still rotate (e.g., rotational motion between the mount 758 and the probe bracket 752). The lock 766 can reduce slidability when the point is registered, as described herein.

The system 700 can be utilized in the posterior approach as described herein. The system 700 can be utilized in the anterior approach as described herein.

B. Navigation for Cup Placement with Posterior Approach

1. Methods for Posterior Approach

FIGS. 1-10D illustrate hip navigation systems 600, 700 adapted to navigate a hip joint procedure from a posterior approach. While the method is described with respect to system 700, any systems described herein or in the following publications can be utilized: U.S. Pat. Pub. No. 2016/0242934, filed Mar. 10, 2015; U.S. Pat. Pub. No. 2014/0052149 filed Mar. 13, 2013; U.S. Pat. Pub. No. 2010/0137871 filed Sep. 10, 2009, all of which are incorporated by reference in their entirety.

In some methods of cup placement in total hip arthroplasty, the inclination and anteversion angles are with respect to the Anterior Pelvic Plane (defined as a plane created by the two anterior superior iliac spines (ASIS) and the pubic symphysis). While these anatomical features are visible/palpable while the patient is in a supine position, the majority of total hip replacements are accomplished via a posterolateral approach with the patient in some variation of a lateral position, in which most of these landmarks are not accessible or visible. Historically, navigation for posterior approach hip replacement has been accomplished by registering the anatomical features of the Anterior Pelvic Plane with the patient first in a supine position and, once this plane is recorded by the navigation computer, moving the patient to a lateral position in order to perform hip surgery—with navigation performed with respect to the directly registered Anterior Pelvic Plane. This approach to hip navigation is sub-optimal for surgical workflow because the extra movement of the patient from supine to lateral position takes more surgeon and staff time and requires breaking sterility and re-draping. This is one of the key reasons why hip navigation has failed to be adopted by most of the market.

Additionally, altered leg length is a common patient complaint arising from hip replacement surgery and has been a common cause of medical malpractice lawsuits that arise from hip replacement. Because part of the hip replacement procedure requires precise measurements of patient leg length and joint off-set that are frequently difficult to visualize utilizing conventional instrumentation, there are opportunities to improve the surgeon's performance of these measurements using computer technology.

Most hip replacement procedures presently are performed from a posterior approach. In this approach, the patient is positioned on his/her side and the anterior pelvic plane is oriented vertically, e.g., perpendicular to the plane of the table on which the patient is positioned. Most surgeons performing hip replacement are very familiar with this approach and will immediately recognize the benefit of enhanced certainty about the orientation of the relevant anatomy when the patient is in this position.

As discussed herein, the method of use can include using the probe 778 and the sensor 204 to estimate a horizontal plane of the surgical table upon which the patient is resting. As discussed herein, the method of use can include using the probe 778 and the sensor 204 to estimate a vertical plane utilizing a measurement of gravity. The system 700 can establish a reference frame for guiding the placement of the cup without registering landmarks. The system 700 can measure leg length and/or joint offset within the established reference frame.

Figure 11:
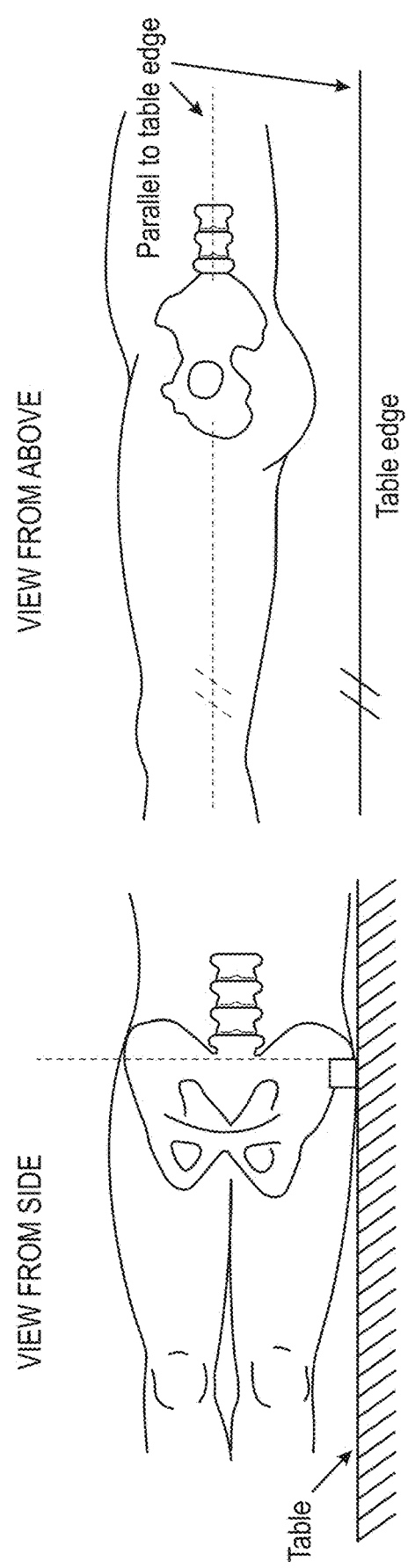
FIG. 11 illustrates a configuration of positioning of a patient in a posterior approach.

FIG. 11 shows an embodiment of the patient positioning for the posterior hip approach. In the posterior hip approach, the patient can be placed on their side. In some methods of use, the patient can be placed in the lateral decubitus position. When positioning patient prior to surgery, the surgeon can align the anterior pelvic landmarks (both ASIS's and pubic tubercle) in a vertical plane parallel to the long edge of the operating table. In some methods of use, when positioning patient prior to surgery, the surgeon can align the anterior pelvic landmarks (both ASIS's and pubic tubercle) in a vertical plane perpendicular to a surface of the table. In some methods of use, when positioning patient prior to surgery, the surgeon can align the anterior pelvic landmarks (both ASIS's and pubic tubercle) in a vertical plane parallel to gravity. In some methods of use, when positioning patient prior to surgery, the surgeon can align Anterior Pelvic Plane parallel to gravity. In some methods of use, when positioning patient prior to surgery, the surgeon can align Anterior Pelvic Plane vertically. The surgeon can ensure that pelvis is securely held by an appropriate positioning device such as a peg board or vise-type patient positioner. The surgeon can verify that patient is positioned in an appropriate position for the posterior approach. Correct patient positioning is important for accurate navigation. In some methods of use, the system 700 calculates cup angles based on the assumption that the pelvis is accurately positioned during table registration. In some methods of use, the system 700 calculates cup angles based on the assumption that the Anterior Pelvic Plane is vertical during the posterior procedure.

The surgical orientation device 172 and the orientation sensing device 204 can be turned on before the procedure begins. If the system can be used in a knee or hip procedure, one method can involve a surgeon selecting a module corresponding to the hip. If the system can be used in a posterior or anterior approach, one method can involve a surgeon selecting a module corresponding to the posterior approach. The surgical orientation device 172 can include a display screen. The surgical orientation device 172 can include a user interface, such as buttons which can be depressed by the user. The display screen can confirm the communication between the surgical orientation device 172 and the orientation sensing device 204.

Figure 12A:
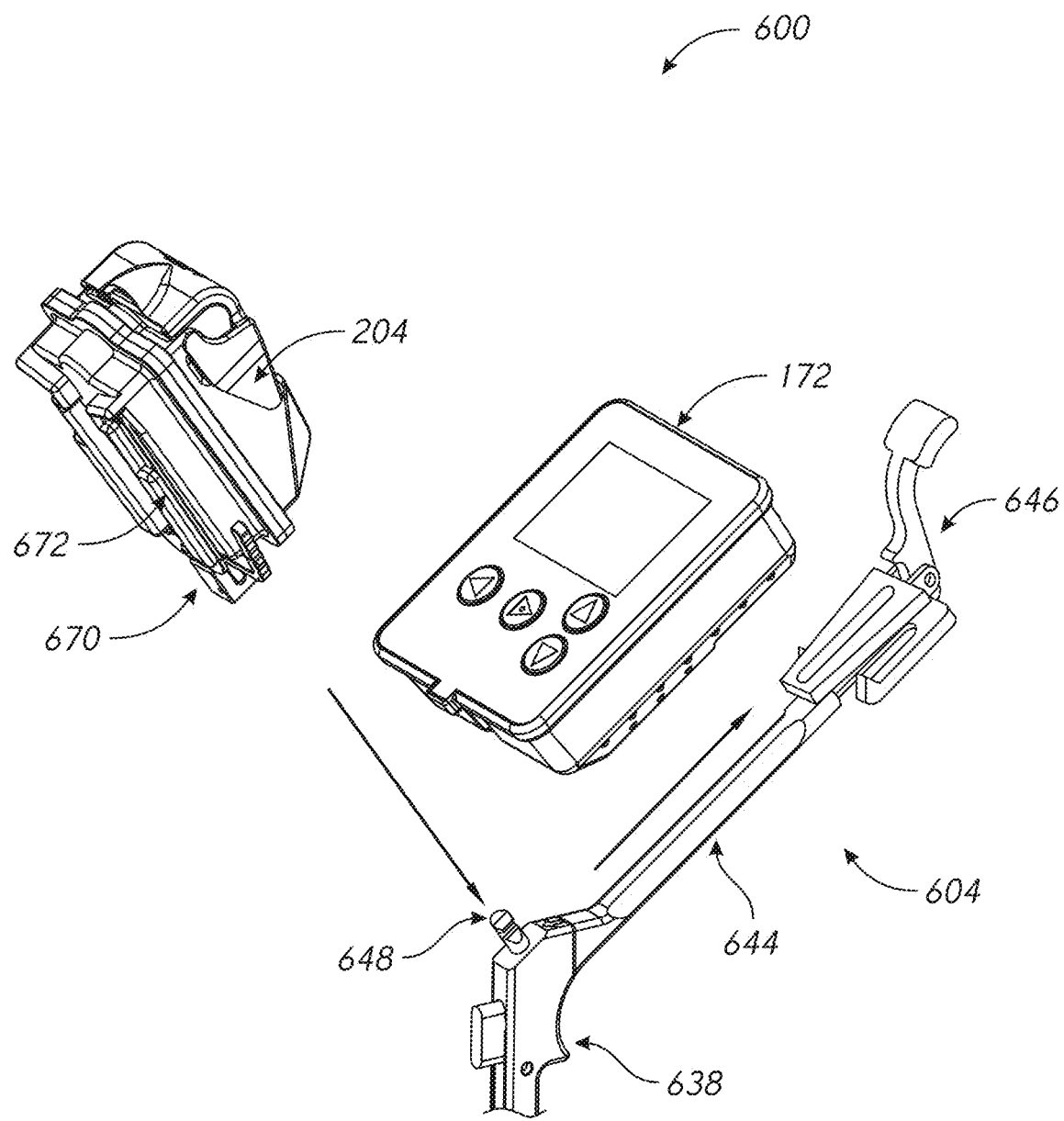
FIG. 12A illustrates a configuration of and a manner of coupling of components of the system.

The system 700 can be partially assembled for calibration. While the system 600 is shown in FIG. 12A, the system 700 can be similarly coupled. In some embodiments, the first assembly 604, 704 can be assembled. The pelvic bracket 638, 738 can be coupled to the extension 644, 744, if separate components. The surgical orientation device 172 can be coupled to the mount 646, 746. In some techniques, the extension 670, 770 can be coupled to the second coupler 648, 748. The orientation sensing device 204 can be coupled to the mount 672, 772. The surgical orientation device 172 and the orientation sensing device 204 form a general V-shaped configuration, similar to the orientation shown in FIG. 12A. The orientation sensing device 204 can be fixed in position relative to the surgical orientation device 172.

Figure 12B:
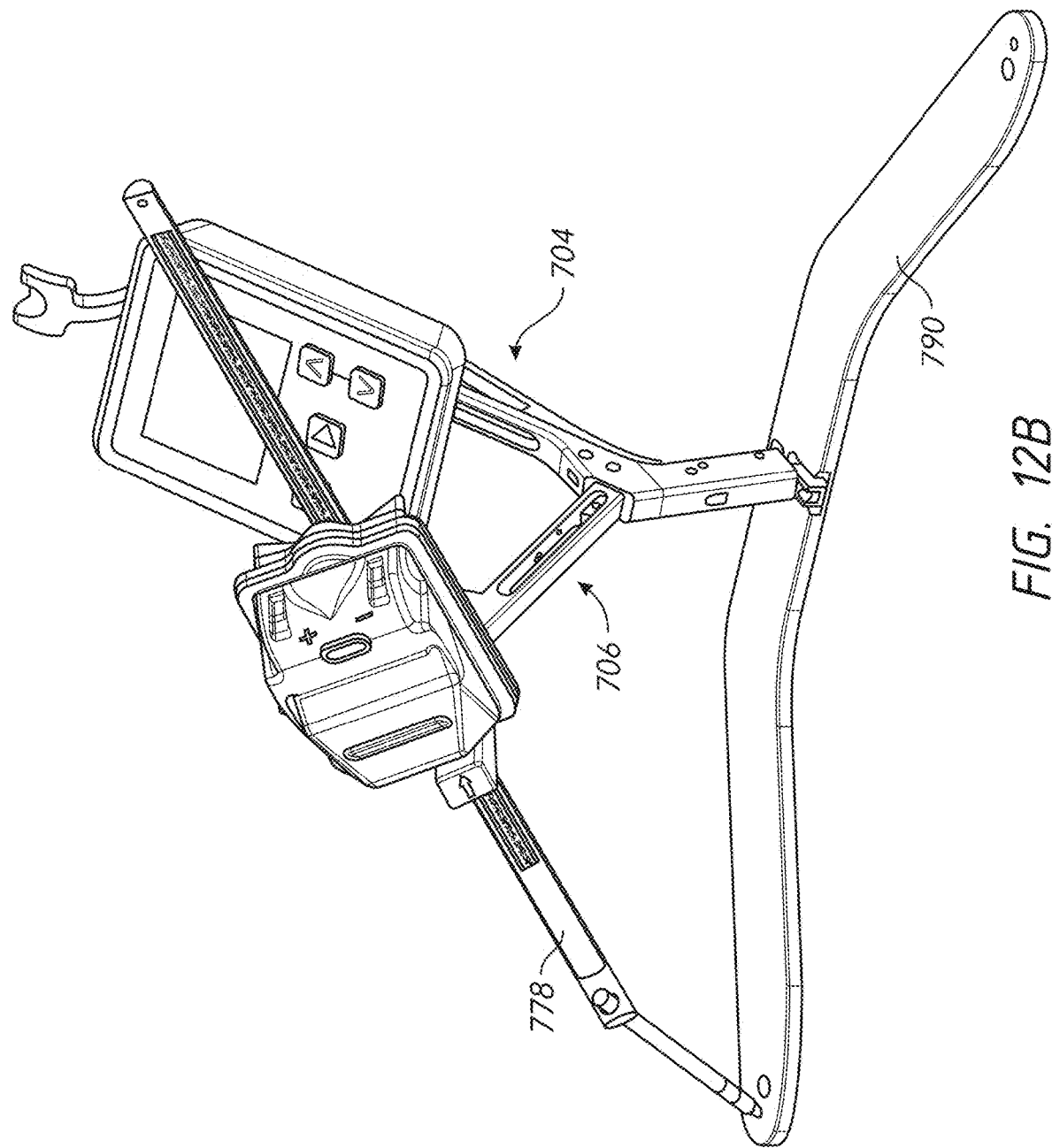
FIG. 12B illustrates a configuration of the system with a calibration fixture.

In some methods of use, the probe 778 can be calibrated. The extension 770 can be decoupled from the second coupler 748. The second assembly 706 can be assembled as shown in FIG. 12B. The first assembly 704 can be coupled to the second assembly 706 as shown in FIG. 12B. In some methods of use, the system 700 can include a calibration fixture 790. The first assembly 704 and the second assembly 706 can be mounted to the calibration fixture 790. The calibration fixture can include a plurality of points for the probe 778 to contact.

In some methods of use, the probe 778 can contact a center hole at the base of the calibration fixture 790 to calibrate a center point. The user can depress a button when the probe 778 is placed. In some methods of use, the probe 778 can contact a left hole at the base of the calibration fixture 790 to calibrate a left point. The user can depress a button when the probe 778 is placed. In some methods of use, the probe 778 can contact a right hole at the base of the calibration fixture 790 to calibrate a right point. The user can depress a button when the probe 778 is placed. The calibration fixture 790 can be utilized prior to the procedure. The calibration fixture 790 can be located away from the patient, for instance on a back table. Other calibration fixtures and jigs are contemplated.

The surgical orientation device 172 and the orientation sensing device 204 can be calibrated. The surgical orientation device 172 can be rested on a level horizontal surface with the display horizontal (facing up). The surgeon can hold the assemblies 704, 706 steady until the surgical orientation device 172 indicates completion. The orientation sensing device 204 can be rested on a level horizontal surface with the display vertical (facing user). The surgeon can hold the assemblies 704, 706 steady until the surgical orientation device 172 indicates completion. The surgical orientation device 172 can be rested on a level horizontal surface with the display pointed sideways (left side). The surgeon can hold the assemblies 704, 706 steady until the surgical orientation device 172 indicates completion. The surgical orientation device 172 can be rested on a level horizontal surface with the display horizontal (facing up) again. The surgeon can hold the assemblies 704, 706 steady until the surgical orientation device 172 indicates completion. Other orientations of the surgical orientation device 172 and the orientation sensing device 204 are contemplated for calibration.

Figure 12C:
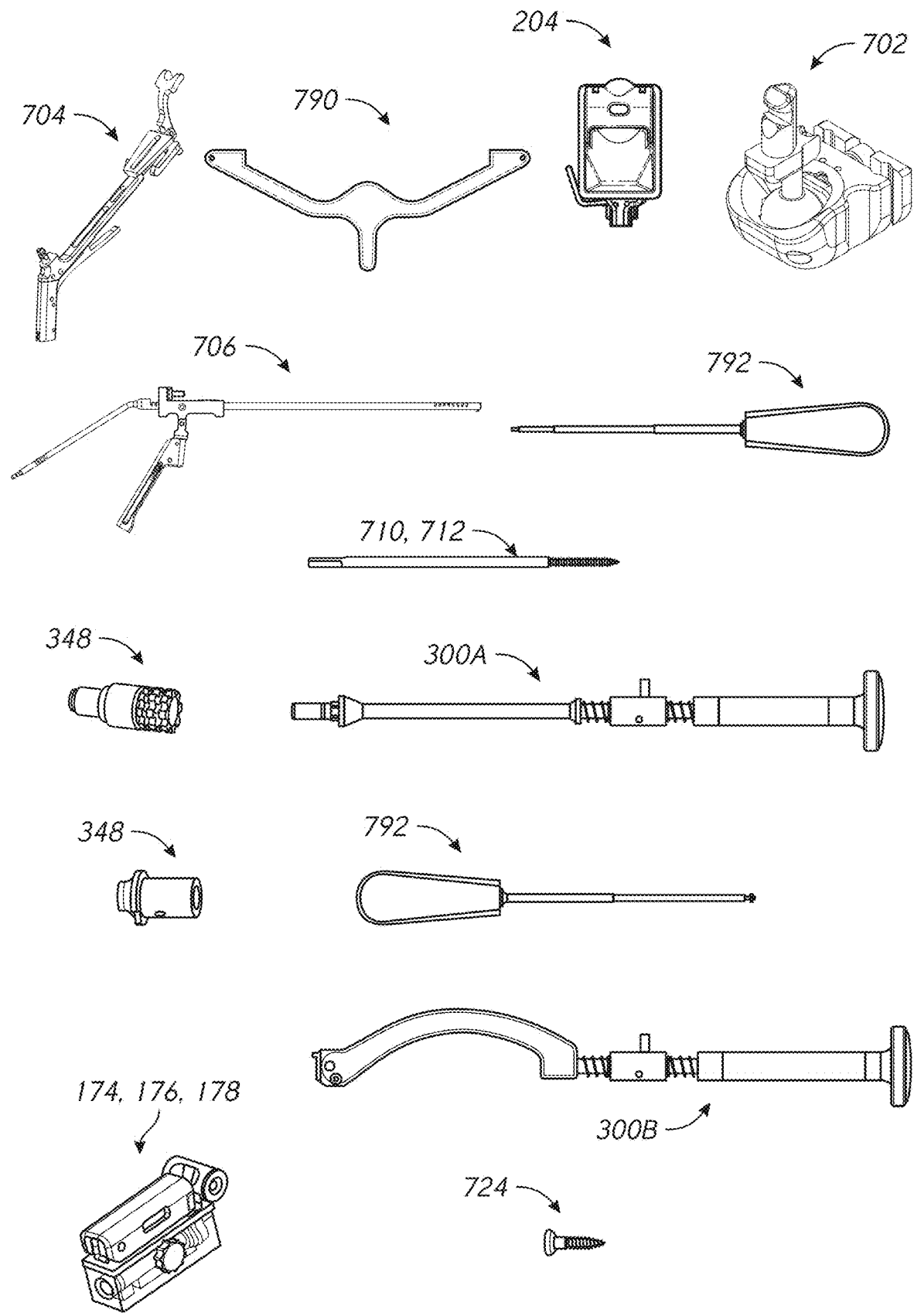
FIG. 12C illustrates embodiments of components described herein.

The user can remove the required instruments and prepare the instruments for use. FIG. 12C illustrates examples of components described herein. The optical component 174, 194 can be activated. In some embodiments, the optical component 174, 194 can include a movable cover or screen, such as a shutter. The user can close the shutter and insert a battery into the optical component 174, 194. In some embodiments, the optical component 174, 194 can be coupled to the first assembly 704 using one or more fasteners. In some embodiments, the fastener is the adjustment feature 178. In some embodiments, the fastener can be secured using a driver 792, see FIG. 12C. In some embodiments, the optical component 174, 194 is affixed to the first assembly 704 using a hex driver. In some embodiments, the optical component 174, 194 is affixed to the first assembly 704 using a ball driver. In some embodiments, the optical component 174, 194 can be affixed to the first assembly 704 using one or more magnets as described in relation to FIGS. 6B-6C. In some embodiments, the optical component 174, 194 can be affixed to the first assembly 704 using one or more removable coupling devices such as clips, straps, bayonet connection, etc., and/or non-removable coupling devices such as adhesive, integrally formed, monolithically formed, etc. The surgeon can ensure that the optical component 174, 194 is securely attached and does not rotate on the first assembly 704. In some embodiments, the bracket 176 facilitates the coupling of the optical component and the first assembly 704. In some embodiments, the adjustment feature 178 facilitates the coupling of the optical component and the first assembly 704. In some embodiments, the optical component 174, 194 is coupled to the fixation base 702. In some embodiments, the optical component is coupled to the fixation pins 710, 712. In some embodiments, the optical component is coupled to the second assembly 606, 706. In some embodiments, the optical component 174, 194 is coupled directly to the pelvis. In some embodiments, the optical component 174, 194 remains on as long as the battery is installed. The laser or other light emission is shown or hidden through the movement of the shutter. The optical component 174, 194 can include a marking to indicate the direction of the emission. In some embodiments, the optical component 174, 194 can include an arrow to indicate the direction of the laser.

The user can interact with the surgical orientation device 172. If the system 700 can be used in either hip procedure, one method can involve a surgeon selecting a module corresponding to the right hip or the left hip. In some methods of use, the user can input a target cup abduction angle. This is the Radiographic Abduction angle defined as the coronal plane projection of the angle between the acetabular axis and the longitudinal axis of the body. Abduction and adduction are also used to describe movement of the limb within the coronal plane. In some methods of use, the user can input a target cup anteversion angle. This is the Radiographic Anteversion angle defined as the angle between the acetabular axis and the coronal plane. The user can input target angles which can be stored by the surgical orientation device 172. In some methods of use, these target angles are utilized by the surgical orientation device 172 during cup placement.

Figure 13C:
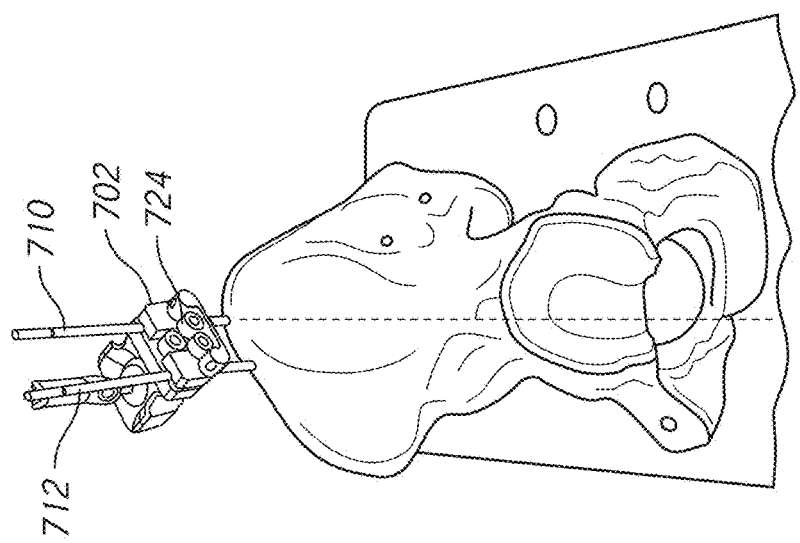
FIGS. 13A-13C illustrates the fixation base and fixation pins of the system of FIG. 7 coupled to the pelvis.
Figure 13B:
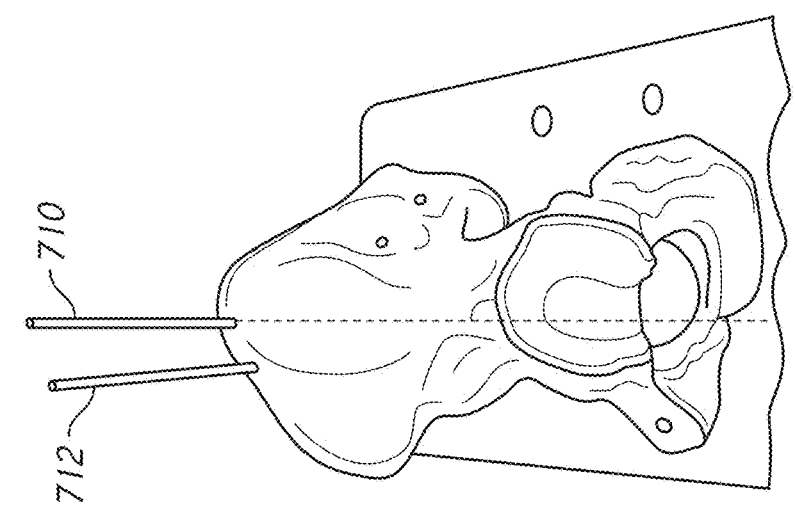
Figure 13A:
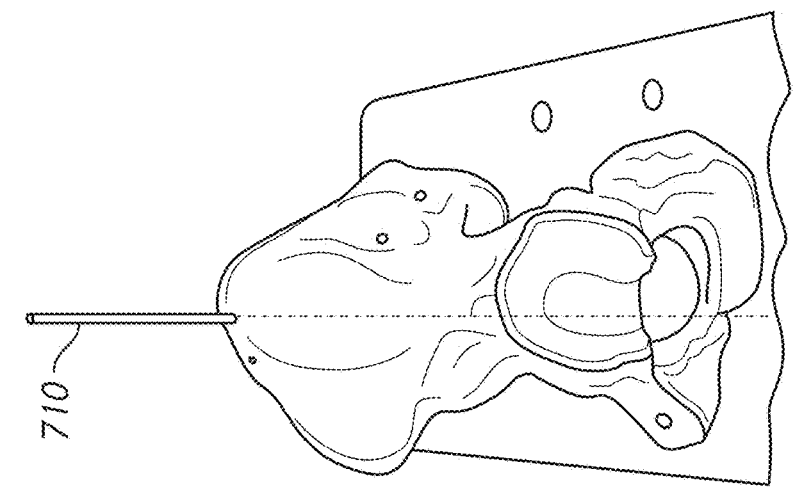

The system 700 can be attached to the pelvis as shown in FIGS. 13A-13C. The user can position the system 700 such that the system 700 has solid and stable mount for attachment of the instrumentation to the pelvis. In some methods of use, all measurements and references are based off the initial registration process and any movement of the first assembly 704 after will result in error in the resulting readouts of cup position, leg length, and/or joint offset. In some methods, the fixation pins 710, 712 are placed in the ipsilateral iliac crest. Referring to FIG. 13A, for the first fixation pin 710, the surgeon can make a stab incision over the ipsilateral iliac crest, directly superior to the greater trochanter. The surgeon can insert the fixation pin 710. In some embodiments, the fixation pin 710 is a 4.0 mm threaded fixation pin. The fixation pin 710 can be inserted vertically using a wire driver. Referring to FIG. 13B, the surgeon can make a second stab incision, and insert the second fixation pin 710 in the iliac crest 2 cm anterior parallel to the first pin 712. The surgeon can use the fixation base 702 as a guide for spacing between the pins 710, 712. Referring to FIG. 13C, the surgeon can slide the fixation base 702 over both pins to the level of the skin. The surgeon can use a driver to tighten the two fixation devices 724 to secure fixation base 702 to the fixation pins 710, 712. In some methods of use, the fixation pins 710, 712 are placed in a similar fashion to placement of pins for pelvic external fixation. In some methods of use, the fixation pins 710, 712 enter the iliac wing at its most superior surface and travel between the tables of the inner and outer bone of the iliac wing. In some methods of use, the fixation base 702 is attached prior to dislocating the hip to ensure correct patient positioning and navigation accuracy. The surgeon can take steps to avoid plunging through the medial wall of the iliac wing. The surgeon can verify that fixation base 702 is securely mounted to the bone. The surgeon can minimize divergence or bending of fixation pins 710, 712.

Figure 14C:
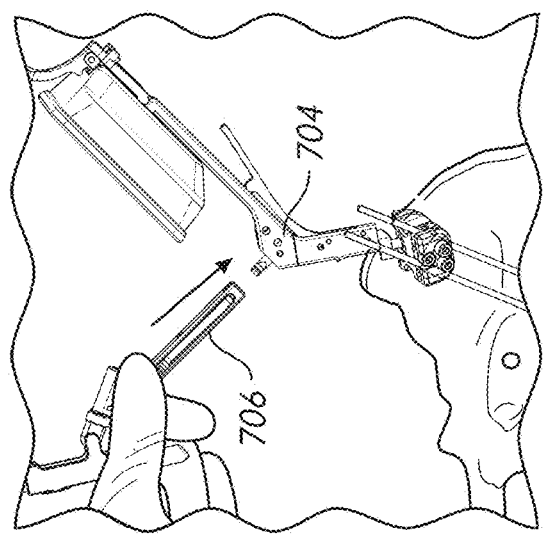
FIGS. 14A-14C illustrates the assembly of the system of FIG. 7.
Figure 14B:
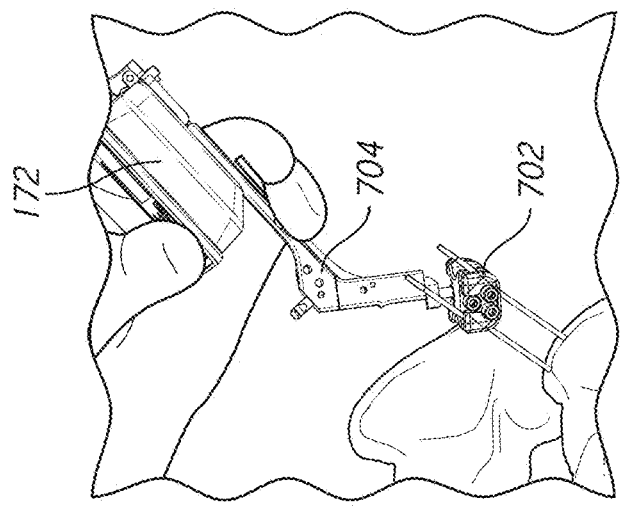
Figure 14A:
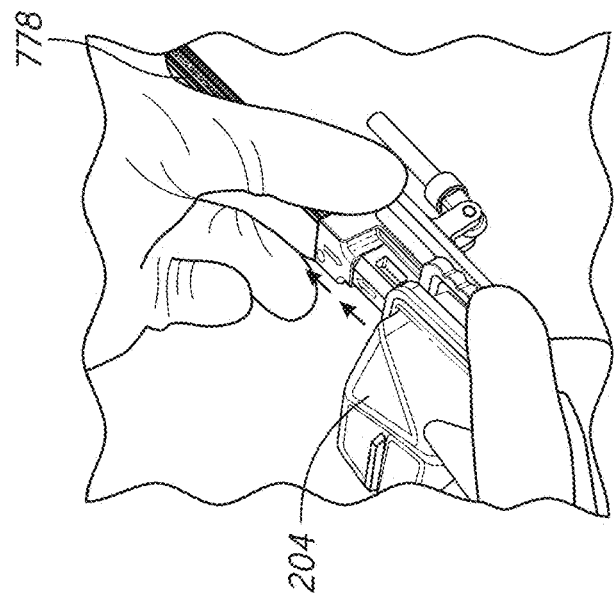

The system 700 can be assembled as shown in FIG. 14A-14C. Referring to FIG. 14A, the orientation sensing device 204 can be coupled to the probe 778. In some embodiments, the orientation sensing device 204 and/or the probe 778 can include indicia such as arrows to facilitate alignment. Referring to FIG. 14B, the first assembly 704 can be secured to the fixation base 702 with the surgical orientation device 172 attached. The first assembly 704 can be secured by pushing on the lock lever 740, as described herein. Referring to FIG. 14C, the second assembly 706 can be secured to the fixation base 702 with the orientation sensing device 204 attached. In some embodiments, the second assembly 706 and/or the fixation base 702 can include indicia such as arrows to facilitate alignment. The second assembly 706 can be secured by pushing on the lock lever 754, as described herein. The optical component 174, 194 can be secured to the first assembly 704. In some embodiments, the optical component 174, 194 and/or the first assembly 704 can include indicia such as arrows to facilitate alignment.

The system 700 can be aligned as shown in FIG. 15A. The surgeon can place the leg on the operative side in a neutral position. The surgeon can open the shutter on the optical component 174, 194. The surgeon can align the optical component 174, 194 so that the laser projects a pattern of light. One example of the incidence of light is shown as 180. In some embodiments, the pattern of light includes two lines. In some embodiments, the pattern of light includes two intersecting lines. In some embodiments, the pattern of light includes two perpendicular lines. In some embodiments, the pattern of light includes two parallel lines. In some embodiments, the pattern of light includes three points. In some embodiments, the pattern of light includes three points that form a triangle. In some embodiments, the pattern of light includes three points which do not lie on the same line. In some embodiments, the pattern of light is projected onto the leg. In some embodiments, the pattern of light is projected onto the knee. In some embodiments, the pattern of light is projected onto the distal foot. In some embodiments, the pattern of light is projected onto the distal thigh. In some embodiments, the pattern of light is projected onto a portion of the leg including a sterile wrap.

The system 700 can be adjusted as shown in FIGS. 15B-15C. To adjust the projection of the optical component 174, 194, the user can adjust the articulation 726. To adjust the projection of the optical component 174, 194, the user can adjust the adjustment feature 178 (see FIG. 6A). To adjust the projection of the optical component 174, 194, the user can adjust the re-position of the fixation base 702. The surgeon can loosen the fixation devices 724 to adjust the fixation base 702 as desired. The surgeon can adjust the articulation 726 to position the articulation 726 as desired. The surgeon can adjust the bracket 176 and/or adjustment feature 178 to position the optical component as desired. The surgeon can reposition any component of the system 700 as desired.

Once the system 700 is in the desired position, components of the system 700 can be immobilized. The surgeon can tighten the fixation devices 724 to secure the fixation base 702. The fixation base 702 can be secured to the fixation pins 710, 712. In some methods of use, the fixation base 702 remains in this position for the procedure. The articulation 726 can be locked in position. The fixation base 702 can include the lock 727. The surgeon can advance the lock 727 against head 728 to prevent movement of the articulation 726. In some methods of use, the surgeon can use a driver to rotate the lock 727. The driver can be a 3.5 mm hex driver to advance the contact surface 729 against the head 728 of the articulation 726. In some methods of use, the articulation 726 remains in this position for the procedure. The surgeon can adjust the lock 727 to reduce or prevent movement of the articulation 726. The optical component 174, 194 can be secured to the first assembly 704 and/or the fixation base 702. In some embodiments, the adjustment feature 178 can be self-locking. The adjustment feature 178 can include a plurality of discrete location. The adjustment feature 178 can lock when moved to one of the plurality of discrete location. In some methods of use, the optical component 174, 194 can remain immobilized during the rest of the procedure. In some methods of use, the first assembly 604 can remain immobilized during the rest of the procedure.

Referring to back to FIG. 15A, the method can include recording the incidence of the light 180. The surgeon can record the shape of the projection. The surgeon can record the incidence of light from the optical component onto a surface. The incidence of light can be the intersection of the light with an anatomical surface of the patient. The anatomical surface can be any surface of the patient. The anatomical surface can be any surface on the leg. The method can include marking the position of the light. The method can include the step of marking two or more points along a line of light. The method can include drawing a line along the line of light. The method can include capturing an image of the incidence of light. The method of use can include the step of utilizing a camera to capture the incidence of light. In some embodiments, the surgeon traces the pattern of light. In some embodiments, the surgeon can make a mark on the femur, such as a bovie mark, a pen mark, a stitch or other durable indication.

In some embodiments, the surgeon can mark the incidence of light 180. In some embodiments, the surgeon can mark two lines. In some embodiments, the surgeon can mark two intersecting lines. In some embodiments, the surgeon can mark two perpendicular lines. In some embodiments, the surgeon can mark two parallel lines. In some embodiments, the surgeon can mark a cross-hair. In some embodiments, the surgeon can mark the incidence of light from a projected pattern of light. In some embodiments, the surgeon can mark three points In some embodiments, the surgeon can mark three points which do not lie on the same line. In some embodiments, the surgeon can mark three points which are localized on a region of the leg. In some embodiments, the surgeon can mark three points which are projected onto femur. In some embodiments, the surgeon can mark three points, one or more points lie on the femur. In some embodiments, the surgeon can mark three points, one or more points lie on the femur, tibia, knee, ankle, or foot, or any combination thereof. In some embodiments, the surgeon can mark onto the leg. In some embodiments, the surgeon can mark onto the knee. In some embodiments, the surgeon can mark onto the distal foot. In some embodiments, the surgeon can mark onto the distal thigh. In some embodiments, the surgeon can trace the pattern with a marker. In some embodiments, the surgeon can trace the pattern onto the leg directly.

In some embodiments, the surgeon can trace the pattern on the sterile wrap. In some embodiments, the pattern of light is projected onto a portion of the leg including a sterile wrap. In some embodiments, the surgeon traces the pattern of light on the sterile wrap. In some embodiments, the surgeon marks the two lines on the sterile wrap. In some embodiments, the surgeon marks the three points on the sterile wrap.

Figure 20A:
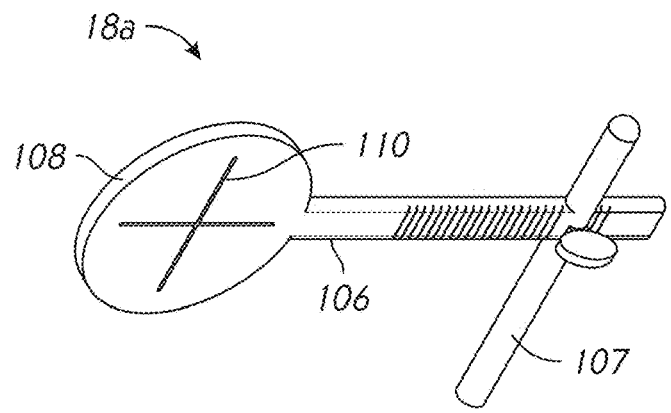
FIGS. 20A-20I illustrate embodiments of target probes.
Figure 20B:
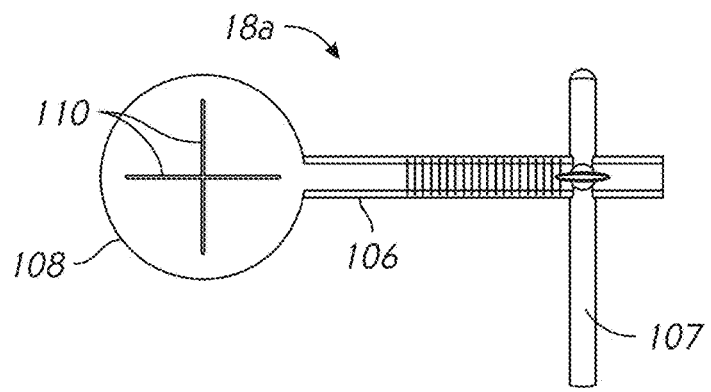
Figure 20C:
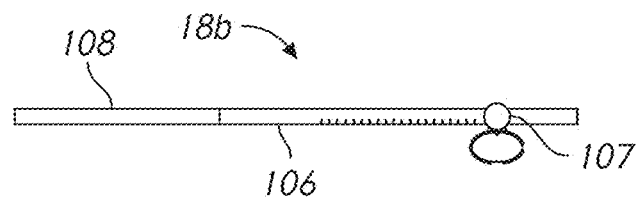
Figure 20D:
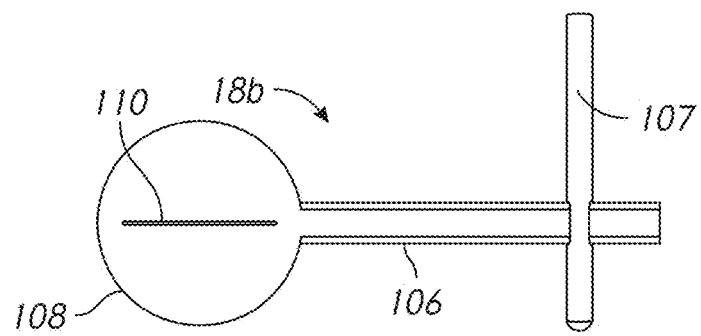

In some embodiments, target probes can be provided for recording the incidence of light. FIGS. 20A-20I illustrates examples of target probes. FIGS. 20A-20B illustrate target probe 18a and FIG. 20C-20D illustrates target probe 18b. At least one target probe 18a, 18b, or other targets or devices, can comprise a structure for contacting the anatomy of a patient and serving as a target for an emitted light from the optical component 174, 194. For example, in some embodiments, the at least one target probe 18a, 18b can comprise an elongate member 106 with an anatomical contact portion 107 and a target portion 108. The anatomical contact portion 107 can comprise an end of the elongate member 106 or other structure configured to contact an anatomical feature or surface. In some embodiments, the anatomical contact portion 107 contacts the femur. In some embodiments, the anatomical contact portion 107 contacts the knee. In some embodiments, the anatomical contact portion 107 contacts the upper thigh. In some embodiments, the anatomical contact portion 107 can be held against the anatomical feature. In some embodiments, the anatomical contact portion 107 can be drilled into the anatomical feature. In some embodiments, the anatomical contact portion 107 coupled with the anatomical feature.

The anatomical contact portion 107 can be connected to or integrally formed with the target portion 108. The target portion 108 can comprise a surface which can be marked by the surgeon. The target portion 108 can comprise a surface which can record the incidence of light. The target portion 108 is configured to assist in recording the incidence of light. Aligning the incidence of light on the target portion 108 before and after cup placement can assist in aligning the underlying anatomy before and after cup placement.

In some embodiments, the target portion 108 can comprise one or more target shapes 110, in the form of markings, slits, or other structures. In some methods of use, the target shapes 110 can be marked before placement of the target 18a, 18b on the anatomy. In some methods of use, the target shapes 110 are marked by the surgeon after placement of the target 18a, 18b on the anatomy. In some methods of use, the target shapes 110 are marked by the surgeon before cup placement. In some methods of use, the target shapes 110, if for example in the form of slots, can be wide enough to allow a beam of laser light, such as for example a beam in the form of a plane or a cross-hair beam, to pass through the target shapes 110. FIG. 20 illustrates an embodiment of a target probe 18b with a target shape 110 in the form of a single slot, and a target probe 18a with two slots in the form of a cross, for example formed as two perpendicular lines or slots. FIG. 20 can illustrate opposite sides of the same target probe. For example, one side of the target probe can have a cross-hair target 110, and the other side of the target probe can have a single slot target 110.

In some embodiments, the optical component 174, 194 is adjusted to align the incidence of light with the target 18a, 18b. In some embodiments, the system 700 is adjusted to align the incidence of light with the target 18a, 18b. For instance, the articulation 726 can be adjusted. In some embodiments, the target 18a, 18b is adjusted to align the incidence of light with the target portion 108 of the target 18a, 18b. The target portion 108 can be adjustable, such that as the anatomical contact portion 107 is held in place against the anatomical landmark, the target portion 108 can be moved relative to the anatomical landmark. For example, the target portion 108 can comprise a screw or other element which can be adjusted in order to change the length of the target probe 18a, 18b. In one embodiment, a device is provided to enable the position of the target portion 108 on the elongate member 106 to be adjusted. The device enables the target portion 108 to be moved closer to or away from the contact portion 106. Such adjustment provides one technique for aligning the incidence of light with the target 18a, 18b. The target probes 18a, 18b can further include a marking or markings which indicate a current length of the target probe 18a, 18b, and/or indicate the degree or amount of adjustment which has been made to the target probe 18a, 18b. For example, the target portion 108 can comprise millimeter markings or other visual indicia corresponding to lengthwise offset along a length of the target portion 108, indicating adjustments in the length of millimeters.

Figure 20F:
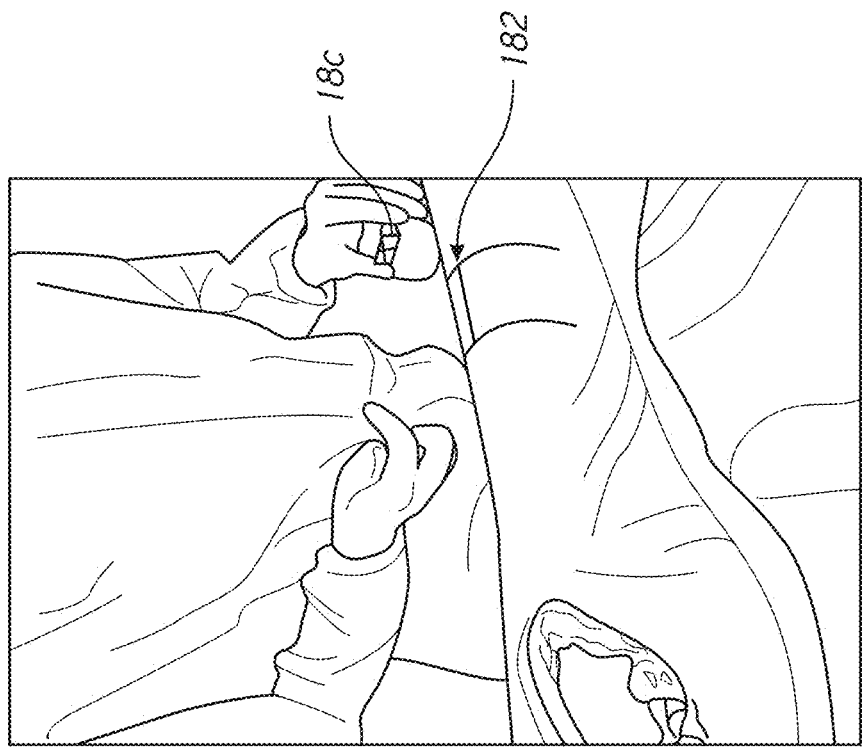
Figure 20E:
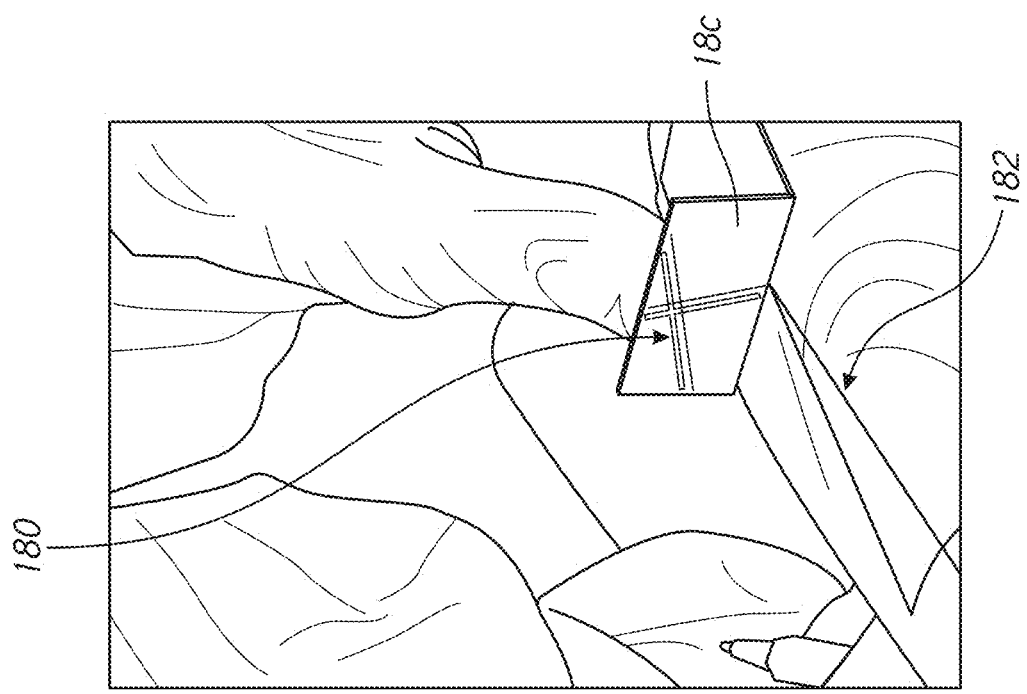

FIGS. 20E-20F illustrate an embodiment of target probe 18c. In some embodiments, the target probe 18c is not attached rigidly to the leg. In some embodiments, the target probe 18c is held in position by the user. FIG. 20E illustrates the target probe 18c in position against the anatomy of the patient, and FIG. 20F illustrates the target probe 18c being removed by the surgeon. In the illustrated embodiment, the leg is wrapped with an incise drape. The incise drape can be marked by the user. The user has marked the longitudinal axis of the bone, as well as a home position for the target probe 18c. These markings on the drape can be performed when the surgeon marks the incidence of light on the target probe 18c. The target probe 18c can be oriented within the home position and the incidence of light can be marked. During the procedure, the user can align the marking with the marked longitudinal axis. The surgeon can adjust the anatomy until the incidence of light aligns with the marking on the target 18*c*. The target 18*c* can be any shape to allow the marking of the incidence of light. In the illustrated embodiment, the target 18*c* is generally L-shaped. In some embodiments, the target probe 18*c* is removable during the surgery. The target probe 18*c* can be positioned on the leg. In some methods of use, one or more markings on the thigh 182 can aid in re-positioning of the target 18*c*. The markings can include one or more lines, points, shapes, symbols, etc. In the illustrated embodiment, the markings on the thigh 182 can include a cross-hair or other pattern related to the incidence of light 180. In some methods of use, the surgeon can position the target 18*c* before and after cup replacement. In some methods of use, the surgeon can mark the incidence of light before joint dislocation. In some methods of use, the surgeon can reposition the femur after cup placement such that the incidence of light aligns with the markings.

Figure 20G:
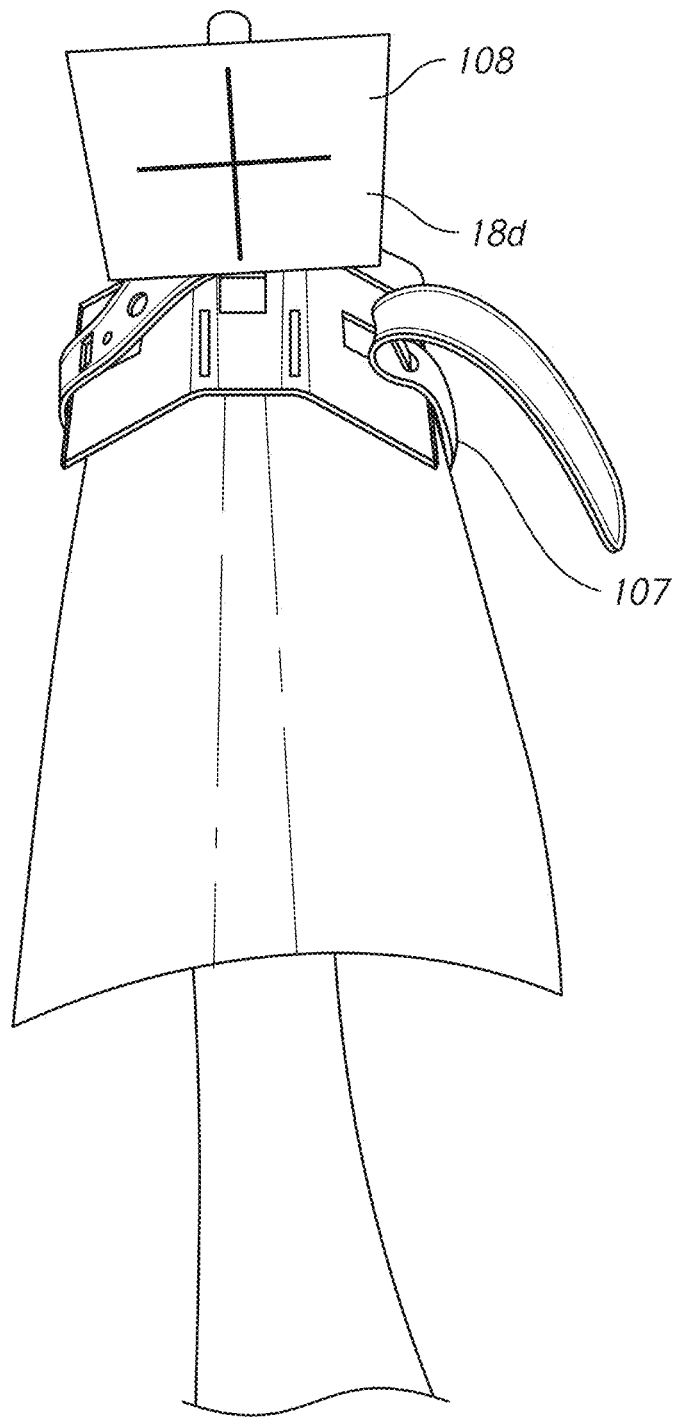

FIG. 20G illustrates an embodiment of target probe 18*d*. The target probe 18*d* can comprise an anatomical contact portion 107 and a target portion 108. The anatomical contact portion 107 can comprise a strap, clip, bracket, zip-tie or other structure configured to wrap around an anatomical feature or surface. In some embodiments, the anatomical contact portion 107 contacts the thigh. In some embodiments, the anatomical contact portion 107 contacts the knee. In some embodiments, the anatomical contact portion 107 contacts the shin. In some embodiments, the target portion 108 can be moved relative to the anatomical contact portion 107. The target portion 108 can be rotated, pivoted, and/or translated to position the target portion 108 relative to the anatomical contact portion 107. In some embodiments, the target portion 108 is fixed relative to the anatomical contact portion 107. The target portion 108 can include one or more surfaces to mark the incidence of light.

Figure 20I:
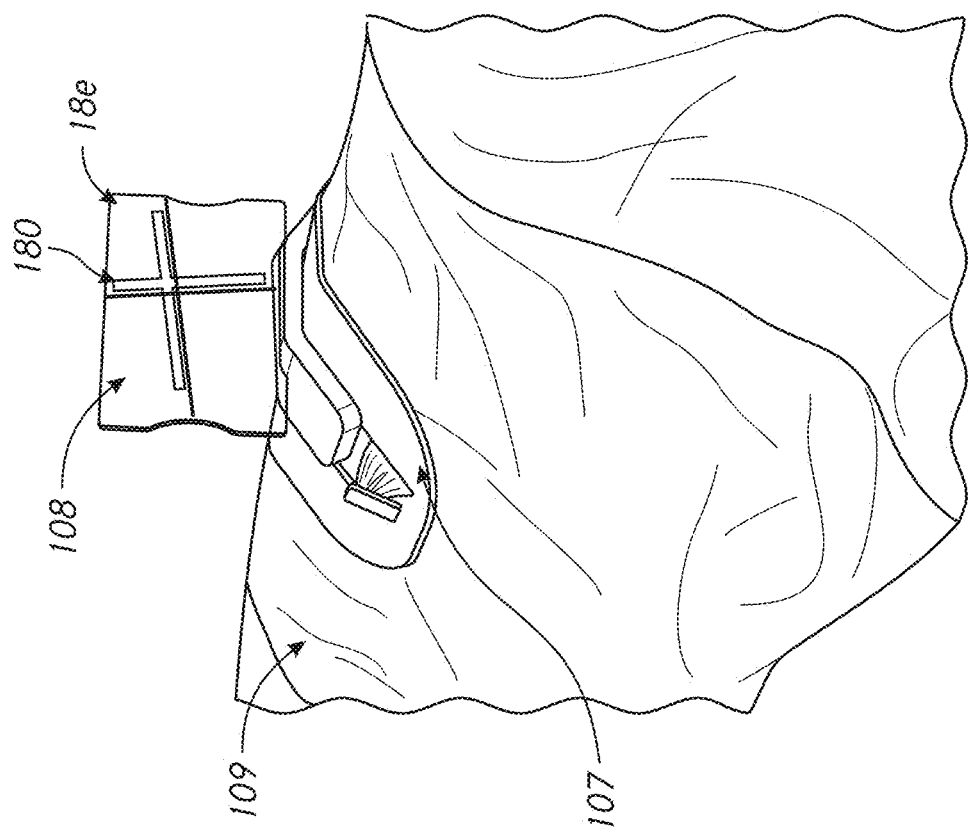
Figure 20H:
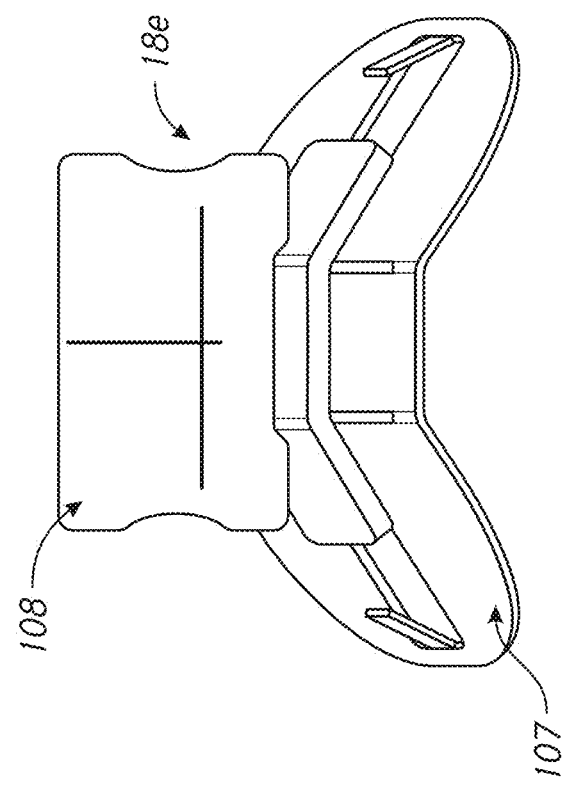

FIGS. 20H-20I illustrate an embodiment of a target probe 18*e*. The target probe 18*e* can comprise an anatomical contact portion 107 and a target portion 108. The anatomical contact portion 107 can comprise a bendable surface configured to adapt to and directly contact or indirectly couple with the anatomy of the patient. The contact portion 107 can create a tri-fold shape or can be formed to a continuous curve. The contact portion 107 can include a portion to wrap around the anatomical feature or surface of the patient. In some embodiments the wrap is a separate component that is stretched or wrapped around the contact portion 107. The contact portion 107 can include or be wrapped by an incise drape 109, such as an iodine-impregnated incision drape (Ioban® manufactured by 3M®). The incise drape 109 can provide strong adhesion to the surface of the skin. In some embodiments, the incise drape 109 can provide antimicrobial properties for the reduction of post-operative wound infections. The contact portion 107 can be adhered or otherwise coupled to the incise drape 109 or to the leg prior to wrapping the drape 109. The contact portion 107 can be integrally formed with the incise drape 109. The target portion 108 can be integrally formed with the contact portion 107. The target portion 108 can be integrally formed with the incise drape 109. Other wraps or drapes are contemplated. The contact portion 107 can by connected to the anatomy of the patient through any means. In some embodiments, the contact portion 107 includes an adhesive. In some embodiments, the contact portion 107 is adjustable, such as through the use of an adjustable adhesive or putty. In some embodiments, the contact portion 107 includes a tape or other medical wrap. In some embodiments, the contact portion 107 includes one or more fixation pins.

In some embodiments, the incise drape 109 wraps around the thigh of the patient. In some embodiments, the incise drape 109 wraps around the knee of the patient. In some embodiments, the incise drape 109 wraps around the shin of the patient. In some embodiments, the target portion 108 is fixed relative to the anatomical contact portion 107 and/or the incise drape 109. In some embodiments, the target portion 108 can be moved relative to the anatomical contact portion 107 and/or the incise drape 109. The target portion 108 can be rotated, pivoted, and/or translated to position the target portion 108 relative to the anatomical contact portion 107. The target portion 108 can include one or more surfaces to mark the incidence of light. The target probe 18*e* can be a vertical laser target. The target portion 108 can extend from the skin of a patient in a vertical direction. The target portion 108 can extend from the skin of a patient in a horizontal direction.

The target probe 18*e* can be formed of two pieces. The contact portion 107 and the target portion 108 can be separate component. The contact portion 107 and the incise drape 109 can be separate components. The target portion 108 and the incise drape 109 can be separate component. The contact portion 107 and/or the incise drape 109 can be rigidly affixed to the body of the patient. In some embodiments, the contact portion 107 and/or the incise drape 109 can be permanently fixed, or at least permanently fixed during the duration of the procedure. The contact portion 107 and/or the incise drape 109 can be affixed to the thigh to form a self-supporting structure with the thigh. The target portion 108 can be removably attached to the contact portion 107. The target portion 108 and the contact portion 107 can couple via any mechanical connection such as a snap-fit, one or more hooks, pinch tab or button, slide pin, bayonet, and/or one or more magnets.

In some methods, the incise drape 109 is removed from a protective covering to expose an adhesive. In some methods, the surgeon can couple the contact portion 107 with the incise drape 109. In some methods, the incise drape 109 and the contact portion 107 are provide to the surgeon coupled. The surgeon can position the contact portion 107 relative to the anatomy. The contact portion 107 can be positioned such that the contact portion 107 is aligned with the optical component 174, 184. The contact portion 107 can be positioned against a portion of the anatomy with little or no soft tissue. The contact portion 107 can be positioned adjacent to the bone. In some embodiments, the contact portion 107 contacts the skin of the patient. In some embodiments, the contact portion 107 is spaced from the skin of the patient In some methods, the incise drape 109 can be coupled to the contact portion 107 prior to positioning the contact portion 107. In some methods, the incise drape 109 can provide an adhesive to couple the contact portion 107 to the patient. In some methods, the surgeon positions both the contact portion 107 and the incise drape 109 simultaneously. In some methods, the incise drape 109 can be coupled to the contact portion 107 after to positioning the contact portion 107 on the leg of the patient. In some methods, the incise drape 109 can be coupled to the patient after positioning the contact portion 107. In some methods, the surgeon positions the contact portion and the incise drape 109 independently. The surgeon can cover the anatomy with the incise drape 109. In some methods, the surgeon can wrap the anatomy with the incise drape 109 forming one or more closed loops around the anatomy.

In some methods, the target portion 108 can be coupled to the contact portion 107 prior to positioning the contact portion 107. In some methods, the target portion 108 can be coupled to the contact portion 107 after to positioning the contact portion 107. In some methods, the target portion 108 can be coupled to the contact portion 107 by a snap fit connection. In some methods, the incise drape 109 is positioned over the contact portion 107. In some methods, the target portion 108 can couple to the contact portion 107 even if the incise drape 109 is positioned over the contact portion 107. The target portion 108 can couple to the contact portion 107 to form a rigid connection. The target portion 108 can couple to the contact portion 107 to form a releasable connection. In some embodiments, the target portion 108 cannot be removed from the contact portion 107 once coupled.

The surgeon can activate the optical component 174, 194 to project light. The surgeon can align the optical component 174, 194 to project a pattern of light on the target portion 108. One example of the incidence of light is shown as 180. In some embodiments, the pattern of light includes two lines. In some embodiments, the pattern of light includes two intersecting lines. The surgeon can adjust the optical component 174, 194 such that the incidence of light 180 is located on the target portion 108. In some embodiments, the optical component 174, 194 emits light before or as the surgeon positions one or more of the contact portion 107, the target portion 108, and/or the incise drape 109. In some embodiments, the optical component 174, 194 emits light after the surgeon positions one or more of the contact portion 107, the target portion 108, and/or the incise drape 109. The surgeon can mark the incidence of light 180 on the target portion 108. The target portion 108 can include a markable, flat surface to facilitate the marking of the incidence of light 180. The surgeon can perform one or more methods or method steps described herein.

The surgeon can activate the optical component 174, 194 to project light again. The surgeon can move the anatomy of the patient connected to the target probe 18e. In some methods, the target probe 18e is coupled to the thigh and the surgeon moves the thigh. In some methods, the target probe 18e is coupled to the upper leg (e.g., femur) and the surgeon moves the upper leg (e.g., femur). In some methods, the target probe 18e is coupled to the lower leg (e.g., tibia) and the surgeon moves the lower leg (e.g., tibia). In some methods, the target probe 18e is coupled to the foot and the surgeon moves the foot. The surgeon can realign a portion of the anatomy such that the incidence of light 180 aligns with the mark on the target portion 108. The surgeon can manually realign a portion of the anatomy with the position of the anatomy when the incidence of light 180 was recorded. The surgeon can realign a portion of the anatomy in order to measure joint offset. The surgeon can realign a portion of the anatomy in order to measure changes in leg length. The surgeon can realign a portion of the anatomy in order to compare a measurement before and after joint replacement.

The surgeon can register a parked configuration or home position. In some techniques, the distal end 780 of the probe 778 can be engaged with a point on the fixation base 702, such as the divot 730. The probe 778 can be vertical in the home position. The orientation sensing device 204 can be vertical in the home position. The distal end of the probe 778 can be curved or bent to facilitate registering the home position.

When registering the home position, the user can hold the probe 778 close to the distal end 780 to maximize accuracy of the measurement of the point. When interacting with the surgical orientation device 172, the user can support the back of the surgical orientation device 172 to avoid flexing the fixation pins 710, 712 and/or the fixation base 702. The user can register the home position by pressing a button of the surgical orientation device 172. If the registration is not accepted, the user can keep the probe 778 stationary and press the button again.

Figure 16:
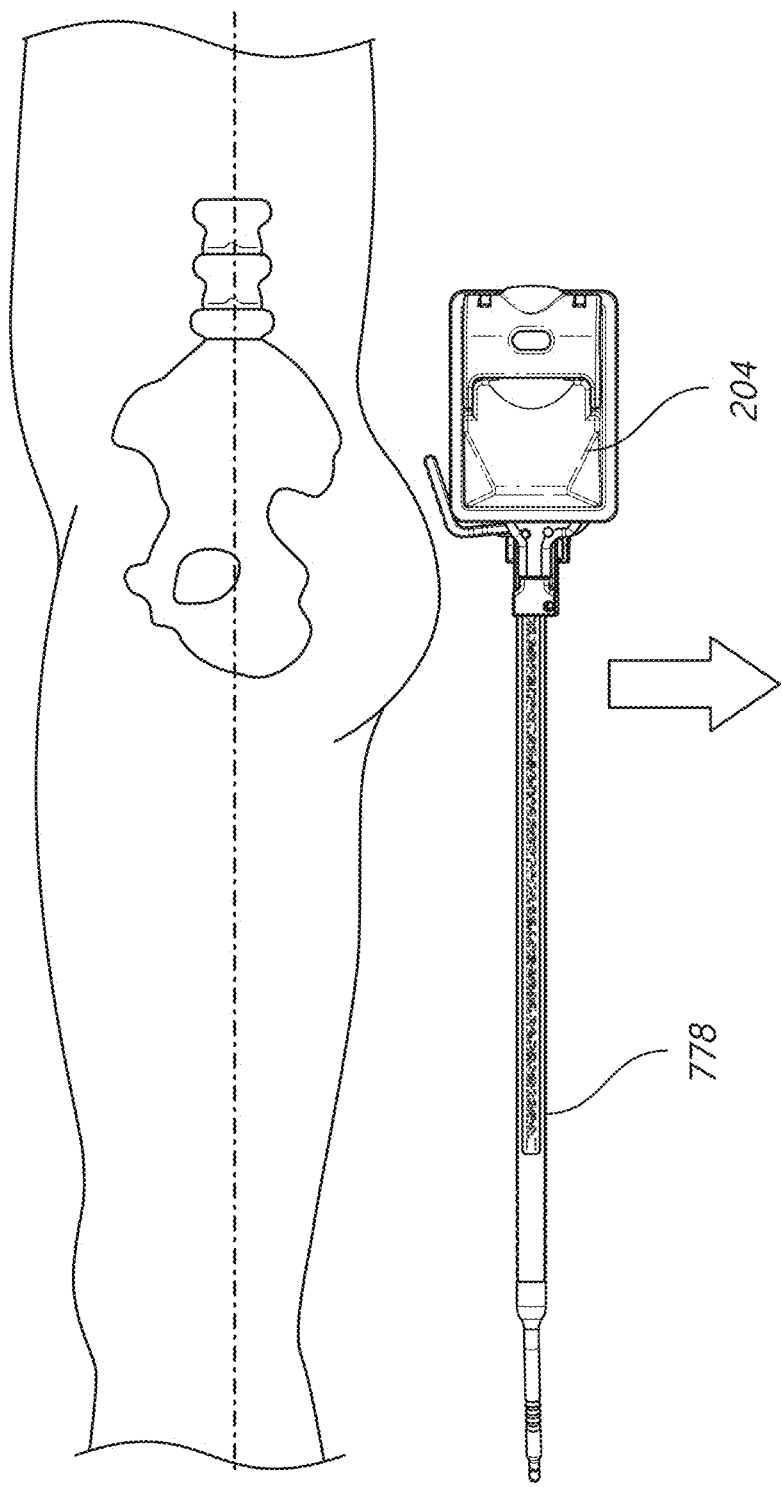
FIG. 16 illustrates an embodiment of table registration.

FIG. 16 illustrates one embodiment of registering the table. FIG. 16 is a top view with the patient in the lateral decubitus position of the posterior approach. The surgeon can verify the sagittal plane of pelvis is level. During positioning of the patient, the Anterior Pelvic Plane is positioned vertically. The Anterior Pelvic Plane can be defined as a plane created by the two anterior superior iliac spines (ASIS) and the anterior surface of the pubic symphysis.

The Anterior Pelvic Plane can be oriented vertically when the patient is in the lateral decubitus position of the posterior approach. The top surface of the operating table upon which the patient is positioned is positioned horizontally. The patient can be positioned so that the Anterior Pelvic Plane is perpendicular to the table. In some embodiments, the surgeon can visually verify the Anterior Pelvic Plane is vertical. In some embodiments, the surgeon can use devices to position the patient's body to align the Anterior Pelvic Plane perpendicular to the plane of the top surface of the table.

If not already horizontal, the surgeon can position operating table horizontally. The table plane can be a horizontal or generally horizontal plane. In some techniques, the operating table is horizontal and the table plane approximates the plane of the table. In some techniques, the table plane can be oriented relative to other surface in the operating room. In some techniques, the floor is horizontal and the table plane approximates the plane of the floor. In some techniques, the wall is vertical and the table plane approximately a plane perpendicular to the wall. In some techniques, the ceiling is horizontal and the table plane approximates the ceiling. Other surfaces may be use to approximate a horizontal plane.

During table registration, the probe 778 is coupled with the orientation sensing device 204. In some methods of use, the probe 778 and the orientation sensing device 204 are constrained. As one example, the probe 778 can be coupled with other components of the first assembly 704 and/or the second assembly 706. In some methods of use, the system 700 is assembled, such that the first assembly 704 and the second assembly 706 are coupled to the patient via the fixation pins 710, 712. There may be mechanical constraints imposed by the configuration of the system 700.

FIG. 16 illustrates one position of the probe 778 to calculate the direction of gravity when the probe 778 is generally horizontal. The probe 778 is rotated and/or pivoted by the mount 758. The probe 778 can be extended toward the patient's foot. The probe 778 can be aligned with the long axis of the body. The probe 778 can be held substantially parallel to the plane of the table. In some embodiments, the user can align the probe 778 with the horizontal. The user can visually inspect the probe 778 from one or more locations. For instance, the user can inspect the probe 778 from a top view and a side view. In some embodiments, the user can align the probe 778 with the sagittal plane. The probe 778 can be parallel with the sagittal plane or a para-sagittal plane. The sagittal plane divides the body into right and left parts. As described herein, the orientation sensing device 204 can be positioned horizontally to measure gravity. As described herein, the probe 778 coupled to the orientation sensing device 204 can be positioned horizontally or substantially horizontally to measure gravity. Referring back to FIG. 11, the side view of the patient illustrates one dashed line which is parallel to the table. During table registration, the probe 778 can be parallel to the table as viewed from the side.

The probe 778 can be held in position or immobilized. The probe 778 can be held steady during table registration. The second assembly 706 can include the lock 766. The lock 766 can limit or reduce slidablility of the probe 778 relative to the dock 762. In some methods of use, the probe 778 can still pivot (e.g., pivotal motion between the dock 762 and the mount 758). In some methods of use, the probe 778 can still rotate (e.g., rotational motion between the mount 758 and the probe bracket 752). The lock 766 can reduce slidability when the table is registered. The lock 766 limits or reduces one degree of freedom during table registration.

The position and/or orientation of the orientation sensing device 204 can be recorded by the surgical orientation device 172. The user can enter an input to register the table (e.g., depress a button on the surgical orientation device 172). The user can interact with a user interface on the surgical orientation device 172 to signal to the surgical orientation device 172 to capture data of the orientation sensing device 204. The surgical orientation device 172 can indicate that data was recorded. In some methods of use, the table registration can be taken at any point during the procedure. The table registration can be taken during pre-operative calibration. The table registration can be taken during intra-operative calibration. The table reference frame can be calculated in addition or as an alternative to the table plane. The surgical orientation device 172 can store the table plane and/or the table reference frame.

In some techniques, the table registration can be completed prior to dislocating the hip. The torque applied during dislocation can move pelvis away from the correct initial alignment. In some techniques, the fixation base 702 cannot be adjusted by the user after table registration. For instance, the user cannot adjust the fixation base 702 relative to the pins 710, 712. The fixation base 702 remains in position for the rest of the procedure. In some techniques, the pelvic bracket 738 cannot be adjusted by the user after table registration. The pelvic bracket 738 remains in position for the rest of the procedure. In some techniques, angle of the pelvic bracket 738 relative to the fixation base 702 cannot be changed after table registration.

In some embodiments, information from one or more inertial sensors is used during table registration. As described herein, the orientation sensing device 204 and the surgical orientation device 172 can include one or more inertial sensors. In some embodiments, the position and/or the orientation of one or more inertial sensors can provide data related to the table plane. The one or more inertial sensors can detect gravity and provide a vector for the down direction.

The table registration can utilize a measurement of gravity. As described herein surgical orientation device 172 comprise one or more inertial sensors. As described herein orientation sensing device 204 comprise one or more inertial sensors. In some embodiments, inertial data from one or more inertial sensors is used to calculate the vertical plane and/or horizontal plane. In some embodiments, the position and/or the orientation data of one or more inertial sensors is used to calculate the table plane or table reference frame. The surgical orientation device 172 and/or the orientation sensing device 204 can comprise an accelerometer, which can provide a measurement of the direction of gravity. In some embodiments, the surgical orientation device 172 and/or the orientation sensing device 204 includes a sensor to detect the direction of gravity. The surgical orientation device 172 and/or the orientation sensing device 204 can be sensitive to the direction of gravity. The one or more inertial sensors can provide a vector aligned with vertical, e.g., for the down direction. In some embodiments, the surgical orientation device 172 and/or the orientation sensing device 204 includes a three axis accelerometer to detect orientation relative to or of gravity.

In some embodiments, the surgical orientation device 172 includes an accelerometer. In some embodiments, the orientation sensing device 204 includes an accelerometer. The accelerometer at rest can measure the acceleration due to Earth's gravity. The accelerometer can measure the acceleration from gravity straight downward or vertically. In some embodiments, the accelerometer can detect the magnitude and direction of the force of gravity. The accelerometer can produce a vertical vector. The accelerometer can produce a horizontal vector by transforming the vertical vector (e.g., by rotation of 90 degrees). The accelerometer can provide orientation and/or position data such that the table plane is perpendicular to the force of gravity.

In some embodiments, the orientation sensing device 204 measures gravity. In some embodiments, the surgical orientation device 172 measures gravity. The surgical orientation device 172 and/or the orientation sensing device 204 can provide an indication of the upward/downwards or vertical direction. The orientation sensing device 204 and/or the surgical orientation device 172 can produce a vertical vector. The surgical orientation device 172 and/or the orientation sensing device 204 can produce a horizontal vector by transforming the vertical vector of gravity (e.g., by rotation of 90 degrees). In some embodiments, the surgical orientation device 172 remains stationary when measuring gravity. In some embodiments, the surgical orientation device 172 is coupled or affixed to the pelvis of the patient when measuring gravity. In some methods of use, the surgical orientation device 172 is coupled to the patient via the fixation pins 710, 712 when measuring gravity. In some methods of use, the surgical orientation device 172 is constrained when measuring gravity. As one example, the surgical orientation device 172 can be coupled with other components of the first assembly 704 and/or the second assembly 706. In some methods of use, the orientation sensing device 204 is constrained when measuring gravity. As one example, the orientation sensing device 204 can be coupled with other components of the first assembly 704 and/or the second assembly 706. In some embodiments, the orientation sensing device 204 and the surgical orientation device 172 both determine the direction of gravity. In some embodiments, inertial data from two or more sensors are used to measure gravity.

The surgical orientation device 172 and/or the orientation sensing device 204 can provide a reference to gravitational zero. Gravitational zero, as referred to herein, refers generally to an orientation in which an axis of a sensor is perpendicular to the force of gravity, and thereby experiences no angular offset, for example tilt, pitch, roll, or yaw, relative to a gravitational force vector. The surgical orientation device 172 can store gravitational zero for calculations related to the table plane. In some methods, gravitational zero is registered only once and utilized throughout the procedure. The table registration can include recording a measurement of gravitational zero.

In some methods of use, the orientation sensing device 204 can be positioned in other ways than horizontally to measure the direction of gravity. In some methods of use, the orientation sensing device 204 can measure gravity when in the home position. In some methods of use, the orientation sensing device 204 can be positioned vertically or substantially vertically to measure gravity. In some methods of use, the orientation sensing device 204 can measure gravity when contacting a point or anatomical landmark. In some methods of use, the orientation sensing device 204 can measure gravity when contacting the point before cup placement. In some methods of use, the orientation sensing device 204 can measure gravity when contacting the tracker 784. In some methods of use, the orientation sensing device 204 can measure gravity when contacting the point on the femur. The point on the femur can be a mark, such as Fm described herein. The point on the femur can be an anatomical landmark. In some methods of use, the orientation sensing device 204 can measure the force of gravity at any angular orientation. In some methods of use, the orientation sensing device 204 determine a vertical vector of gravity when held at any position.

The table reference frame can include two perpendicular planes. The two perpendicular planes can include a vertical plane and a horizontal plane. The table registration generates two planes, a plane including a vector for the force of gravity and a plane perpendicular to said plane. The table plane is considered a horizontal plane. In some methods of use, the vector for the down direction can be used by the system to verify that the table plane is a horizontal plane. Plane. The horizontal plane may be recorded and stored by the surgical orientation device 172 and/or the orientation sensing device 204.

In some methods of use, the vector for the down direction can be used by the system to establish a vertical plane. In some methods of use, the vector for the down direction can be used by the system to establish true vertical and true horizontal. The vertical plane can approximate the Anterior Pelvic Plane. For instance, abduction and anteversion angles can be calculated relative to the vertical plane. The vertical plane provides an estimation of the orientation of the Anterior Pelvic Plane. The vertical plane may be recorded and stored by the surgical orientation device 172 and/or the orientation sensing device 204. The system 700 can calculate cup angles based on the vertical plane based on the assumption that the pelvis of the patient is correctly positioned such that the Anterior Pelvic Plane is vertical. In some methods of use, the abduction and anteversion angles in cup placement in total hip arthroplasty can be with respect to the vertical plane determined during table registration.

The orientation of the vertical plane can be a baseline for placement of the cup portion of a hip prosthesis. The surgical orientation device 172 can display information with respect to the vertical plane. In some methods of use, the abduction and anteversion angles in cup placement in total hip arthroplasty can be with respect to the vertical plane. In some embodiments, the vertical plane is determined by the surgical orientation device 172 and/or the orientation sensing device 204. In some embodiments, the surgical orientation device 172 and/or the orientation sensing device 204 can provide orientation and/or position data related to the table reference frame. In some embodiments, the surgical orientation device 172 and/or the orientation sensing device 204 can provide orientation and/or position data related to vertical plane. In some embodiments, the surgical orientation device 172 and/or the orientation sensing device 204 can provide orientation and/or position data related to horizontal plane.

In some embodiments, the table plane is determined completely independently of any anatomical landmarks. The table plane provides a reference plane that is unaffected by pelvic tilt. The table plane provides a reference plane that is unaffected by errors in landmark registration due to soft tissue. The table plane also appears in large console navigation which might be familiar to the surgeon. In some methods of use, the horizontal plane is calculated based on aligning the probe 778. In some methods of use, the vertical plane is calculated based on a measurement of gravity. In some methods of use, target cup angles are relative to the Anterior Pelvic Plane. In some methods of use, navigated cup angles are relative to the vertical plane which approximates the Anterior Pelvic Plane. The pre-operative and/or post-operative images, such as x-rays, are captured within a reference plane similar to the Anterior Pelvic Plane. The table registration may provide a reference plane that approximates the reference plane of imaging techniques. The table registration may provide a reference plane that approximates the Anterior Pelvic Plane.

Figures 17A, 17B:
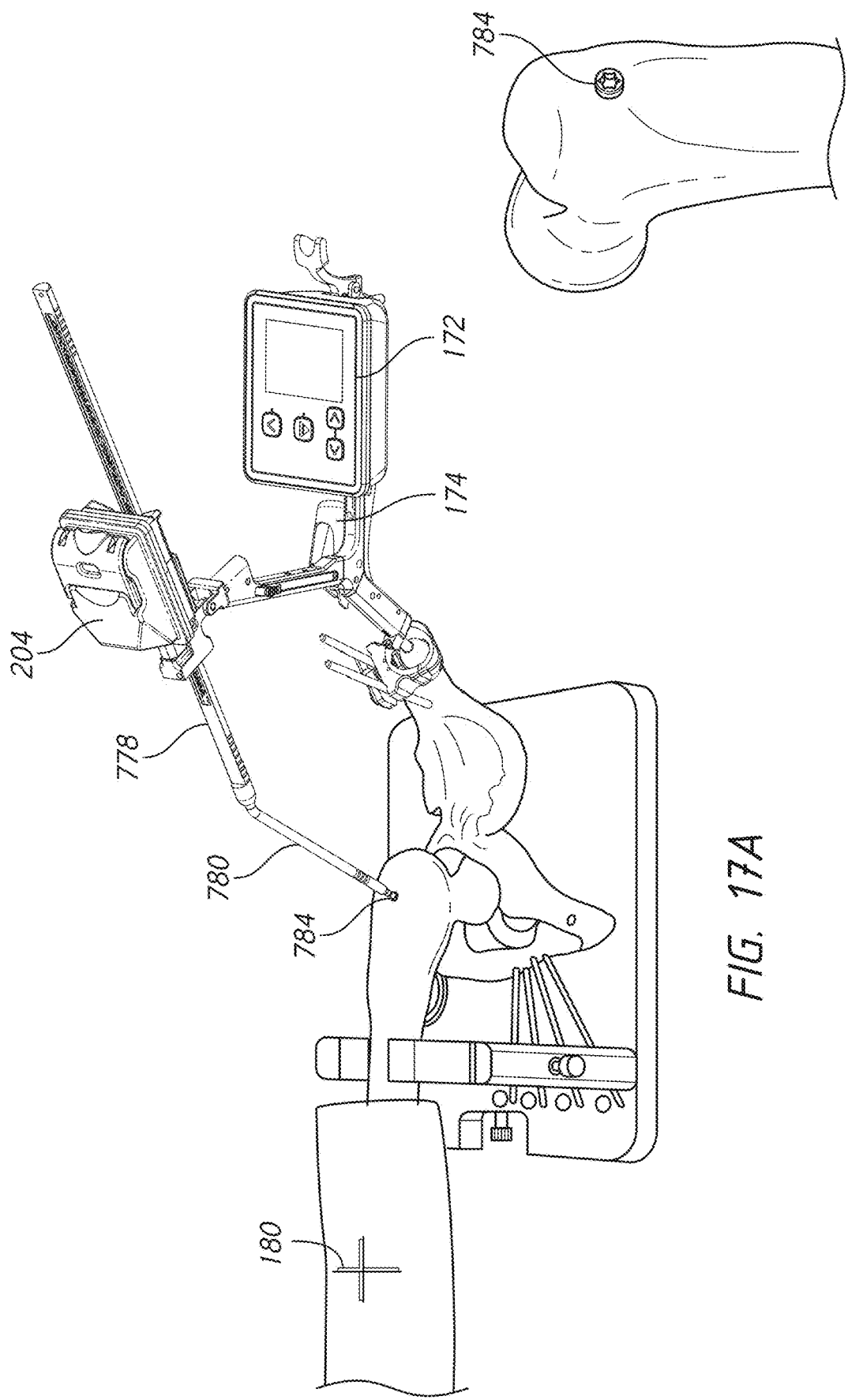
FIGS. 17A-17B illustrate an embodiment of point registration before cup placement.

Referring to FIGS. 17A-17B, in some methods of use, the surgeon can register a point. In some methods of use, the surgeon can register only one point. In some methods of use, the surgeon registers a single point on the femur. In some methods of use, the surgeon registers a single anatomical landmark during the procedure. The point can be located on femur of the joint being operated on. For some procedures on a patient's left hip, the point is on the left femur. For some procedures on a patient's right hip, the point is on the right femur. In some methods of use, the surgeon can make the standard incision. In some methods of use, the surgeon can identify a point along the transtrochanteric line on the proximal femur. In some methods of use, the point is the located on the greater trochanter.

The surgeon can position the distal end 780 of the probe 778 at the point. In some methods of use, the distal end 780 of the probe 778 is placed on the point on the greater trochanter. In some methods of use, the tip of the distal end 780 is brought into contact with a part of the greater trochanter or elsewhere on the proximal femur. In some methods of use, the tip of the distal end 780 is brought into contact with any point on the anatomy of the patient.

In some methods of use, after a point is found and/or contacted, the clinician can make a mark on the femur. In some methods of use, the surgeon can make a mark using a bovie mark, a pen mark, a stitch or other durable indication. In some methods of use, the surgeon can couple tracker 784. The tracker 784 can be fastener such as a screw, bolt, pin, plate, or other durable structure. In some methods of use, the surgeon can insert 20 mm screw into the femur. In some embodiments, the tracker 784 can be secured to the femur. The tracker 784 can be rotated to be secured into the femur. The tracker 784 can be advanced into the femur with a driver. The surgeon should ensure that the tracker 784 is lateral enough so as not to interfere with the stem. The point can be located on the tracker 784. In some methods of use, the surgeon can make a divot or burr into a bone or other portion of the anatomy of the patient. In some embodiments, the divot or burr is in the femur. The point can be located on the divot or burr. In some methods of use, the surgeon can alter the femur to provide a reliable indication of the point that is registered.

The probe 778 can be immobilized to register the point. In some embodiments, the surgeon can hold the tip of the probe 778 at the point. In some embodiments, the surgeon can hold the tip of the probe 778 in a divot or burr. In some embodiments, the surgeon can hold the tip of the probe 778 in a hole of the tracker 784. In some embodiments, the surgeon can hold the tip of the probe 778 at an anatomic landmark. In some embodiments, the surgeon can hold the tip of the probe 778 at the marked point Fm.

As described herein, the second assembly 706 can include a lock 766. The lock can limit or reduce slidablility of the probe 778 relative to the dock 762. In some methods of use, the probe 778 can still pivot (e.g., pivotal motion between the dock 762 and the mount 758). In some methods of use, the probe 778 can still rotate (e.g., rotational motion between the mount 758 and the probe bracket 752). The lock 766 can reduce slidability when the point is registered. In some embodiments, the lock 766 is advanced before the point is registered. In some methods of use, the lock 766 limits or reduces one degree of freedom during point registration.

Once the tip of the distal end 780 is in contact with the desired point, the system 700 processes data from and stores the orientation of one or more sensor(s) in the orientation sensing device 204. During registration, the position of the orientation sensing device 204 can be recorded by the surgical orientation device 172. During registration, the orientation of the orientation sensing device 204 can be recorded by the surgical orientation device 172. During registration, the extension of the orientation sensing device 204 can be recorded by the surgical orientation device 172.

The distance related to the extension of the probe 778 can be used in conjunction with the positional and/or orientation data from the orientation sensing device 204. Additionally, in some embodiments, the probe 778 is provided with a marking 782 indicating position of the tip of the probe 778, e.g., relative to the dock 762 or some other relevant fixed feature of the patient or the system 700. The marking 782 can be read by the clinician or the camera 184. In some embodiments, the camera 184 records the marking 782 indicating the extension of the probe 778. The distance that the probe 778 is extended, as captured by the camera 184, to contact the point can be recorded by the orientation device 172. In some methods, the orientation sensing device 204 or the surgical orientation device 172 can converts the image of the camera 184 into an extension measurement of the probe 778. When registering the anatomical points, the camera 184 captures an image of the marking 782. The camera 184 can read the marking 782 to provide accurate determination of the translational position of the probe 778 relative to the dock 762. The camera 184 can be directly above the marking 782. In some methods, the camera 184 can read a binary code of the marking 782. The surgical orientation device 172 can use the length measurement from the camera 184 and the data from the orientation sensing device 204 to determine the location of the distal end 780 of the probe 778.

In some embodiments, the surgeon will enter an input (e.g., depress a button) to collect data from the orientation sensing device 204. In some methods, the surgeon will enter an input (e.g., depress a button) to collect data from the camera 184. In some embodiments, the surgeon will enter an input (e.g., depress a button) to collect data from the orientation sensing device 204 and the camera 184 simultaneously. In some methods, the orientation sensing device 204 and/or the camera 184 will only send data if the orientation sensing device 204 is stable or non-moving. In some embodiments, the surgeon can press a button on the surgical orientation device 172 to register the point. The surgeon can enter an input to register the point. Other ways of entering an input include interacting with a touchscreen, using a verbal command, touching an icon, holding the probe 778 steady for a period of time, and/or reaching the end of a countdown clock, etc. The surgical orientation device 172 can indicate that the point was recorded.

In some methods, the surgeon marks the incidence of light before registering the point. In some methods, the surgeon marks the incidence of light after registering the point. In some methods, the surgeon marks the incidence of light simultaneously with registering the point. In some methods, the surgeon marks the incidence of light but does not register the point. In some methods, the surgeon registers the point but does not mark the incidence of light. In some methods, the surgeon marks the incidence of light independently of registering the point. In some methods, the surgeon marks the incidence of light and registers the point after the leg is secured. In some methods, the surgeon marks the incidence of light and registers the point when the leg is in the same orientation.

The surgical orientation device 172 can record a point in the table reference frame. The table reference frame can form a coordinate system. The table reference frame can include the vertical plane and the horizontal plane. In some methods of use, the registered point is located at the origin of the table reference frame. In some methods of use, the center of rotation of the femur is located at the origin of the table reference frame. The user can record a point in the table reference frame before cup placement. The user can record the same point in the table reference frame after cup placement. The system 700 can compare the measurement of the same point before and after cup placement. The comparison can relate to leg length. The comparison can relate to joint offset. In some embodiments, changes in the registered point along the vertical plane indicate a change in leg length. In some embodiments, changes in the registered point along the horizontal plane indicate a change in joint offset.

In some techniques, the table registration is completed prior to dislocating the hip. In some techniques, the point is registered prior to dislocating the hip. In some techniques, the incidence of light is marked prior to dislocating the hip. Once registration is complete, the surgeon can proceed to dislocate the hip, resect the femoral head, and prepare the acetabulum as per the implant manufacturer's technique. The torque applied during dislocation can move pelvis away from the correct initial alignment.

In some techniques, the fixation base 702 cannot be adjusted by the user after table registration, home registration, recording the incidence of light, and/or point registration. For instance, the user cannot adjust the fixation base 702 relative to the pins 710, 712. The fixation base 702 remains in position for the rest of the procedure. In some techniques, the pelvic bracket 738 cannot be adjusted or removed. The pelvic bracket 738 remains in position for the rest of the procedure. In some techniques, angle of the pelvic bracket 738 relative to the fixation base 702 cannot be changed. In some techniques, the probe 778 cannot be replaced with a different probe. The same probe 778 is used for the remainder of the procedure.

In some methods of use, the surgical orientation device 172 can provide options to the user regarding how to proceed. In some methods of use, the surgeon can set anteversion and/or abduction cup angles. In some methods of use, the surgical orientation device 172 can store target cup angles. In some methods of use, the surgeon can input anteversion and/or abduction cup angles into the surgical orientation device 172. In some methods of use, the surgeon set the target angle of the cup. In some methods of use, the surgical orientation device 172 can allow the surgeon to check the target angles after the surgeon sets the target angle of the cup.

In some methods of use, the surgical orientation device 172 can provide options related to leg length and joint offset. In some methods of use, the surgical orientation device 172 can measure leg length from a pre-operative state. In some methods of use, the surgical orientation device 172 can measure offset from a pre-operative state. In some methods of use, the surgical orientation device 172 can measure leg length before cup placement. In some methods of use, the surgical orientation device 172 can measure joint offset before cup placement. In some methods of use, the surgical orientation device 172 can measure changes in the registered point. In some methods of use, the surgical orientation device 172 can measure changes in the registered point in the table reference frame. In some methods of use, the surgical orientation device 172 can measure changes in the registered point in the table reference frame comprising the vertical plane. In some methods of use, the surgical orientation device 172 can measure changes in the registered point in the table reference frame comprising the horizontal plane. In some methods of use, the surgical orientation device 172 can measure changes in the registered point in the table reference frame comprising the vertical plane and the horizontal plane.

In some methods of use, the surgical orientation device 172 can provide options related to the home position. In some methods of use, the surgeon can position the probe 778 at the home position during the procedure. In some methods of use, the surgeon can position the probe 778 at the home position to verify that one or more components of the system 700 remain fixed. In some methods of use, the surgical orientation device 172 can repeat the registration of a point. In some methods of use, the surgical orientation device 172 can repeat the acquisition of the point used. The surgical orientation device 172 can repeat acquisition of the point before the joint is dislocated. The surgical orientation device 172 can repeat acquisition of the point after insertion of a medical prosthesis. In some methods of use, the surgical orientation device 172 can indicate the end of the procedure. In some methods of use, the surgeon can end the procedure to select the other hip for a bi-lateral procedure.

Once registration is complete, the user can proceed to proceed to dislocate the hip, resect the femoral head, and prepare the acetabulum. The user can prepare the impactor and shell. The user can remove the second assembly 706 from the first assembly 704. The user can remove the orientation sensing device 204 from the probe 778. The user can dock the orientation sensing device 204 to the first assembly 704. The surgical orientation device 172 and the orientation sensing device 204 form a general V-shaped configuration, similar to the orientation shown in FIG. 12. The user can set the cup angle. In some methods of use, the surgeon can hold the hip stable until the surgical orientation device 172 provides an indication to proceed.

The user can remove the orientation sensing device 204 from the first assembly 704. The orientation sensing device 204 and the surgical orientation device 172 can at this point be used to guide placement of the cup in the prescribed orientation. The surgeon can remove the extension 770 from the third coupler 768. The surgeon can couple the extension 770 to an impactor. In some embodiments, if the orientation sensing device 204 is moved too quickly, an error message will appear on the surgical orientation device 172. In some embodiments, if the orientation sensing device 204 is moved too quickly, the orientation sensing device 204 can be coupled to the first assembly 704 as shown in FIG. 12.

Figure 18A:
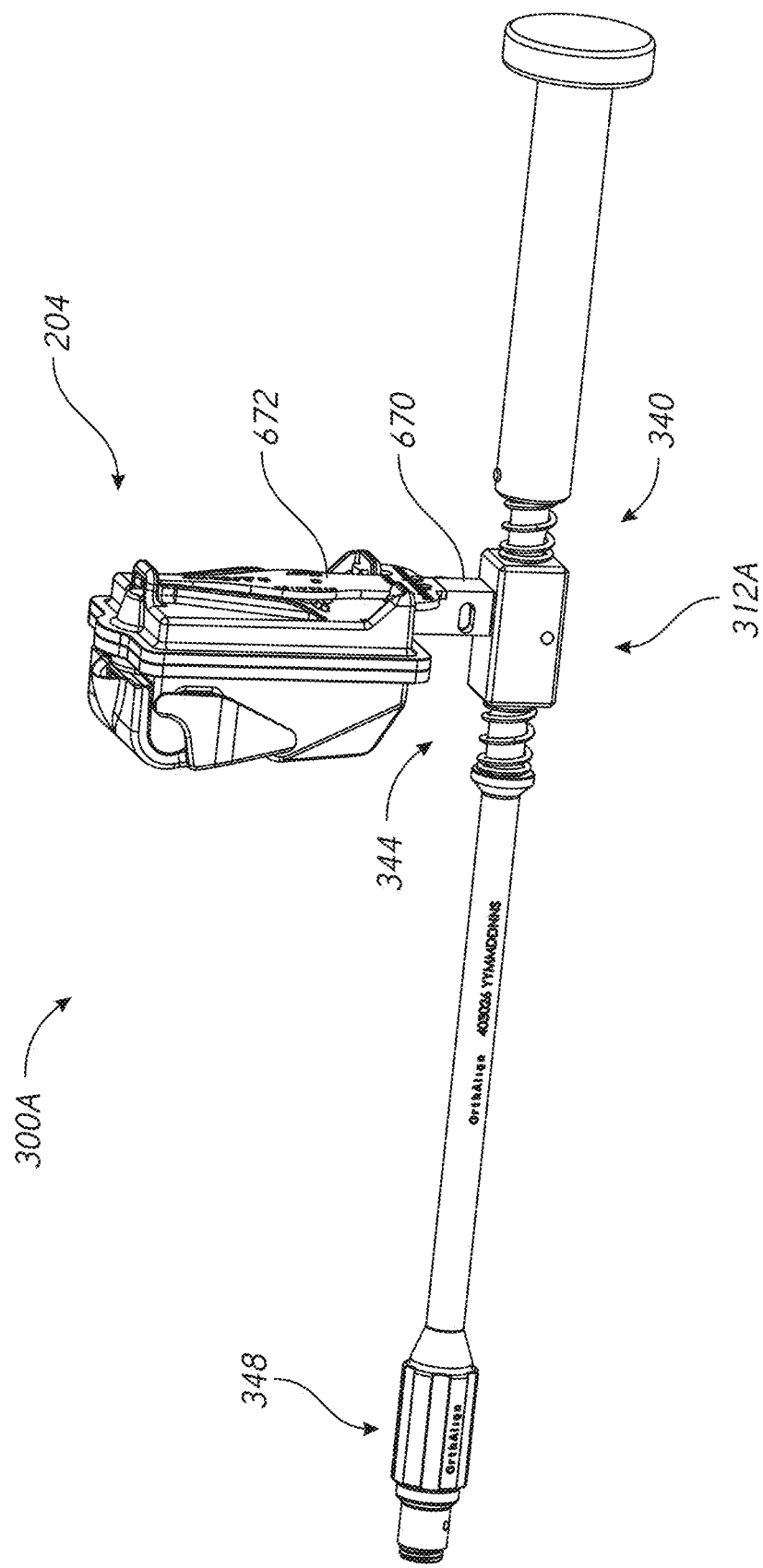
FIG. 18A illustrates an embodiment of an impactor including the orientation sensing device of FIGS. 5A-5C.

FIG. 18A illustrates an embodiment of an impactor 300A. In some methods of use, the orientation sensing device 204 can be coupled to the impactor 300A. The orientation sensing device 204 can determine cup angles relative to a reference plane as the impactor 300A is moved. The impactor 300A can include a shell 312A. The movement of the shell 312A is cushioned by a plurality of spring members 340, 344 which are configured to absorb at least some of the shock of the impact on the impactor 300A. The shell 312A can include a fourth coupler 342 (see FIGS. 18B-18D). This fourth coupler 342 permits the orientation sensing device 204 to couple to the shell 312A. The orientation sensing device 204 can be removably coupled to the fourth coupler 342. The orientation sensing device 204 can be coupled to the impactor 300A in order to navigate cup angles, as described herein.

In some embodiments, the fourth coupler 342 can be a universal coupler. This permits the fourth coupler 342 couple to any other device or subsystem, as described herein. In some embodiments, the fourth coupler 342 is identical or substantially similar to the first coupler 632, second coupler 648, and/or the third coupler 668. The fourth coupler 342 can couple to one or more components of the system 600, such as the orientation sensing device 204. The fourth coupler 342 can include an elongate post. The fourth coupler 342 can include a slot. The slot can be designed to lock with the orientation sensing device 204, or a component thereof such as the extension 670. The extension 670 can include a detent. The detent can be sized and shaped to be received within the slot of the fourth coupler 342. The engagement of the detent and the slot can rigidly couple the orientation sensing device 204 with the fourth coupler 342. The engagement between the fourth coupler 342 and the extension 670 of the orientation sensing device 204 minimizes or prevents relative movement therebetween to avoid any mechanical relative movement during navigation procedures.

The fourth coupler 342 can include a tapered surface. The tapered surface can facilitate entry of the fourth coupler 342 into the extension 670. In some embodiments, the fourth coupler 342 can have a regular shape (e.g., cylindrical). In some, the orientation sensing device 204 can mate with the fourth coupler 342 in a plurality of orientations. In some embodiments, the fourth coupler 342 can have an irregular shape (e.g., triangular, teardrop, elliptical, rectangular). The irregular shape can facilitate alignment of the orientation sensing device 204 relative to the fourth coupler. In some, the orientation sensing device 204 can mate with the fourth coupler 342 in a single orientation.

The orientation sensing device 204 can be releasbly coupled to the extension 670. The extension 670 can include a mount 672 designed to couple with the orientation sensing device 204. In the illustrated embodiment, the mount 672 includes a lock and release lever that can pivot relative to the extension 670. The orientation sensing device 204 can include features to mate with the lock and release lever. Other configurations are contemplated. The orientation sensing device 204 is rigidly coupled to the extension 670 when engaged by the mount 672.

Figure 18B:
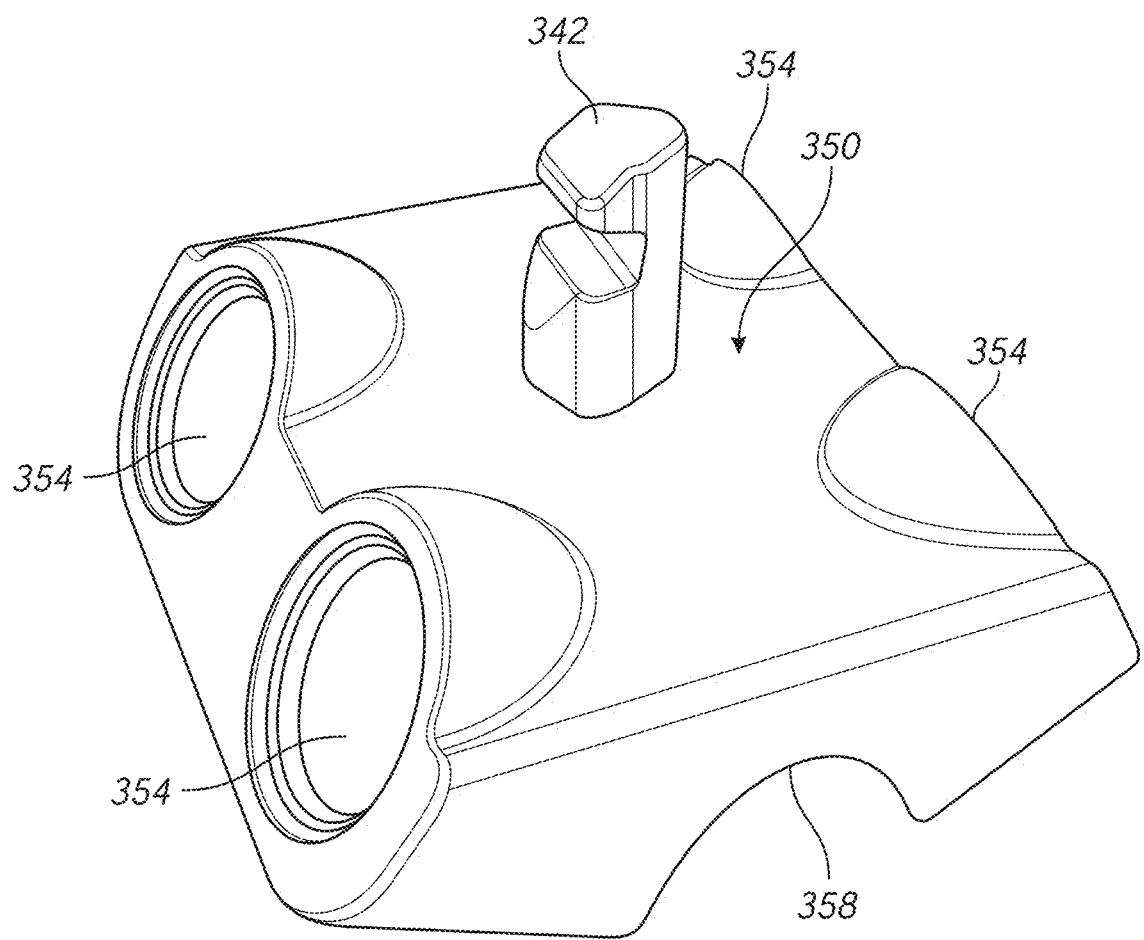
FIGS. 18B-18D illustrate embodiments of a universal impactor adapter.
Figure 18D:
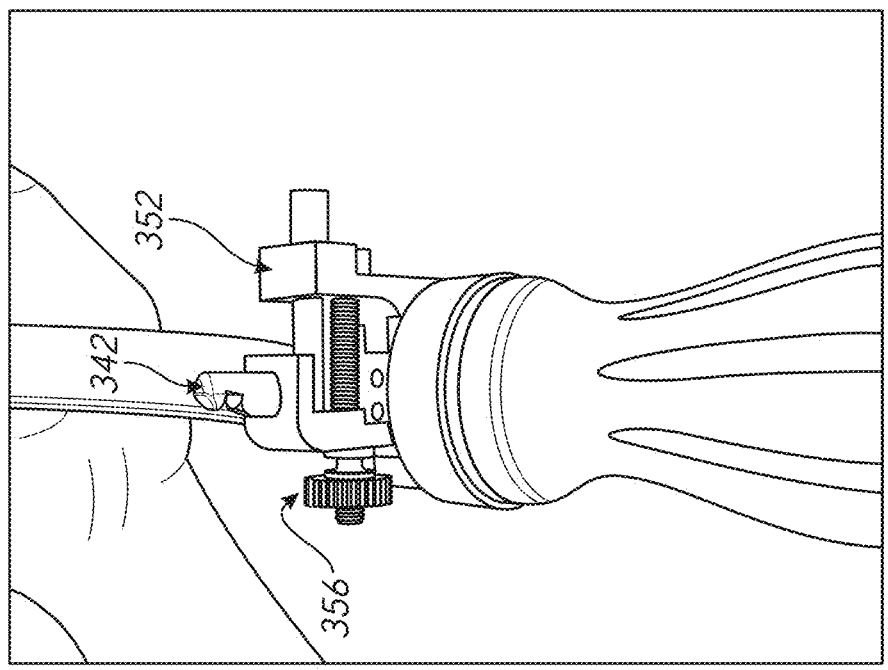
Figure 18C:
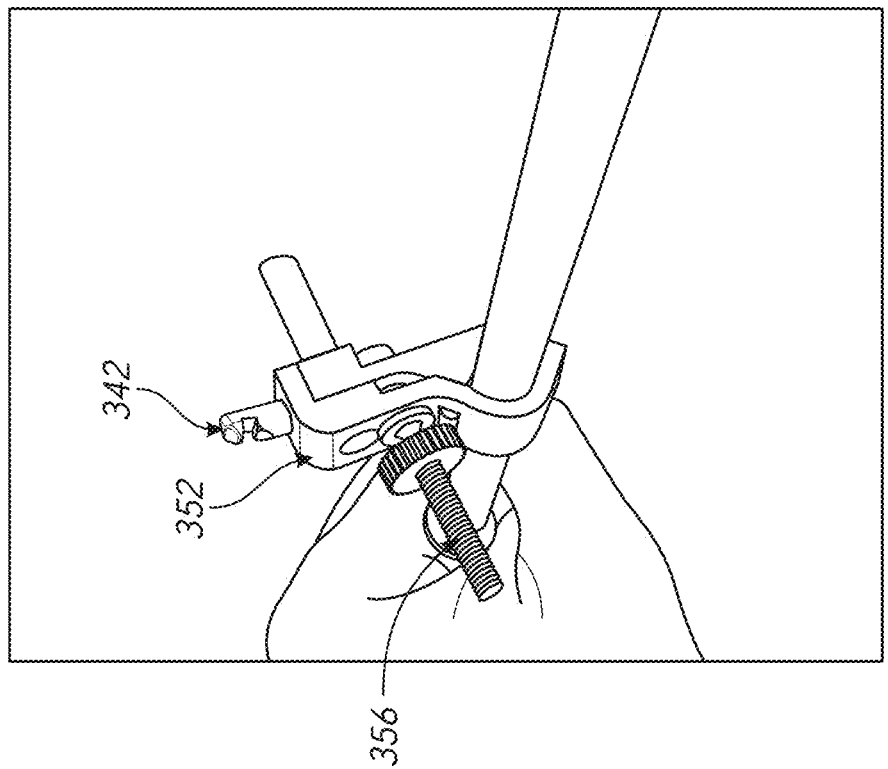

In some embodiments, impactor 300A is provided which includes the shell 312A with the fourth coupler 342. The impactor 300A can be provided by the manufacturer of other components of the systems described herein. The impactor 300A can include the forth coupler 342 to allow the impactor 300A to interface with the orientation sensing device 204. In some embodiments, an impactor is provided which does not include the fourth coupler 342. FIGS. 18B-18D illustrate embodiments of a universal impactor adapter. The universal impactor adapter can allow any impactor to be used with the systems described herein. The universal impactor adapter can allow the orientation sensing device 204 to couple with any impactor. In some embodiments, the universal impactor adapter can be an attachment which provides the fourth coupler 342 to allow the orientation sensing device 204 to mount thereon. The orientation sensing device 204 can mount on a large array of impactors, not only impactor 300A. The universal impactor adapter can be coupled to any impactor to provide the fourth coupler 342. The universal impactor adapter can provide a means to rigidly couple the fourth coupler 342 to the impactor. The universal impactor adapter can provide a means to rigidly couple the orientation sensing device 204 to the impactor.

FIG. 18B is an embodiment of a universal impactor adapter 350. FIGS. 18C-18D is an embodiment of a universal impactor adapter 352. The universal impactor adapter 350, 352 can be designed to couple to a plurality of impactors. The universal impactor adapter 350, 352 can be designed to couple to impactors having a certain range of sizes of shafts or coupling portions. The universal impactor adapter 350, 352 can be designed to couple to impactors having a different shapes or configurations. The universal impactor adapter 350, 352 can include the fourth coupler 342. The universal impactor adapter 350, 352 can include any coupler designed to couple to the orientation sensing device 204. The universal impactor adapter 350, 352 can couple to a shaft of an impactor by any manner of connections. The universal impactor adapter 350 can connect to a shaft of an impactor with one or more magnets 354. The one or more magnets 354 of the universal impactor adapter 350 can be configured to attract and couple to the one or more magnets (not shown) of an impactor. The impactor is configured to be inserted within the recess 358. The recess 354 is an arcuate channel for receiving a shaft of an impactor within a range of impactor shaft sizes. While four magnets 354 are shown in FIG. 18B, other configurations are contemplated (e.g., one magnet, two magnets, three magnets, four magnets, five magnets, six magnets, etc.). The four magnets can be angled downward toward the recess 358. This orientation is to concentrate the magnetic force in the recess 358 to enhance the attraction of the adaptor 350 to a shaft of an impactor that is fitted in the recess 358. The four magnets can be angled downward relative to the fourth coupler 342. While two magnets are shown on one side of the universal impactor adapter 350, two additional magnets 354 have a mirror image configuration on the other side of the device in the illustrated embodiment. The magnets are directed toward the recess 358 are configured to interact with corresponding magnets of the impactor in one embodiment. The one or more magnets 354 of universal impactor adapter 350 can be configured to attract and couple to the one or more magnets of the impactor. In some embodiments, one or more magnets 354 can be configured to attract a magnetic material disposed on or in the shaft of the impactor. In some embodiments, the impactor, or a portion thereof, comprises a magnetic material. In some embodiments, the entire impactor is magnetic. The one or more magnets 354 of the universal impactor adapter 350 can allow the universal impactor adapter 350 and the forth coupler 342 to form a self-supporting structure with the impactor when assembled. The forth coupler 342 can be rigidly coupled such that any movement of the impactor causes correcting movement of the fourth coupler and the reference sensor device 204 coupled thereto. The one or more magnets 354 of the universal impactor adapter 350 can reduce or prevent unwanted movement between the impactor and the orientation sensing device 204.

The universal impactor adapter 352 can connect to a shaft of an impactor with one or more clamps 356. FIG. 18C illustrates the clamp 356 when tightened and FIG. 18D illustrates the clamp 356 when loosened. The clamp is an example of a mechanical connection between the universal impactor adapter 352 and any impactor. The clamp 356 can include a round inner surface to connect to a round outer surface an impactor.

The clamp 356 of the universal impactor adapter 352 can allow the universal impactor adapter 352 and the forth coupler 342 to form self-supporting structure with the impactor. The clamp 356 of the universal impactor adapter 352 can reduce or prevent unwanted movement between the impactor and the orientation sensing device 204. The clamp 356 can apply a force necessary to rigidly couple to the exterior surface of the impactor. Other configurations of the universal impactor adapter are contemplated.

The impactor 300A or any impactor with the universal impactor adapter 350, 352 can be modified to suit any of a plurality of hip prostheses. For example, a plurality of tip components 348 can be provided in a kit where each tip component is attachable to and detachable from a distal end of the shaft of the impactor. Two types of tip adapters are shown in FIG. 12C. In some embodiments, the tip adapter 348 can be offset. The plurality of tip adaptors is optional.

The acetabular shell can be threaded onto a tip component 348. The user can select the appropriate shell adapter for the desired impactor. The impactor 300A or any impactor with the universal impactor adapter 350, 352 also is configured to be modified to suit any of a plurality of hip prostheses. In some methods of use, the surgeon can thread acetabular shell onto tip component 348. In some methods of use, the surgeon can snap the tip component 348 onto end of impactor shaft. In some embodiments, the tip component 348 can be rotated to multiple angles relative to impactor to align the screw holes of shell as desired. In some embodiments, if none of available tip component 348 fit on selected shell, then the impactor 300A cannot be navigated. In some embodiments, if none of available tip component 348 fit on selected shell, then another impactor is selected based on the selected shell. The impactor can be outfitted with the universal impactor adapter 350, 352 to be able to couple with the orientation sensing device 204. In some embodiments, prior to impacting, the surgeon can verify shell is fully seated on shoulder of impactor. In some embodiments, prior to impacting, the surgeon can verify that threads do not protrude beyond outer face of shell. Another embodiment of an impactor is shown in FIG. 12C. The impactor 300B can have any of the features of the impactor 300A described herein. The impactor 300B is an offset shell impactor. The impactor 300A is a straight shell impactor. The plurality of impactors is optional.

In some methods of use, the impactor is not navigated as described herein. In some embodiments, the cup angle can be checked after insertion by registering the hip center. In some methods of use, the surgeon can register three points on the outer rim of the cup. These three points define the hip center. In some embodiments, the point which is equidistant from all three points is the hip center. Additionally, these three points define the plane of the cup. The cup angle is defined as the angle of an axis which is perpendicular to this plane. Note that the impactor is perpendicular to this axis. Additional information regarding the registration of points and identification of the hip center can be found in U.S. application Ser. No. 14/639,758 filed Mar. 5, 2015; Ser. No. 14/639,784 filed Mar. 5, 2015; Ser. No. 13/800,620, filed Mar. 13, 2013; and Ser. No. 14/643,864 filed Mar. 10, 2015, the disclosures of which are incorporated by reference in their entirety. In some methods of use, there is no registration of the hip center. In some methods of use, only a single point is registered. In some methods of use, the point is registered before and after cup placement for leg length and/or joint offset. In some methods of use, no points are registered. In some methods of use, the surgeon does not calculate leg length and/or joint offset using point registration.

The acetabular shell can be inserted into the acetabulum and positioned at the desired angle. As described herein, the surgeon can store target angles with the surgical orientation device 172. The surgical orientation device 172 can guide the surgeon in placing the cup relative to the target angles. As described herein, the target abduction and anteversion angles can be cup angles entered by the surgeon into the surgical orientation device 172. The target abduction and anteversion angles can be an input into the system 700.

In some methods of use, once the orientation sensing device 204 is attached to impactor 300A or any other impactor with the universal impactor adapter 350, 352, the surgical orientation device 172 can display radiographic inclination and anteversion angles of impactor. In some methods of use, once the orientation sensing device 204 is attached to impactor, the surgical orientation device 172 can display radiographic inclination and anteversion angles of impactor relative to frontal pelvic plane. In some methods of use, once the orientation sensing device 204 is attached to impactor, the surgical orientation device 172 can display radiographic inclination and anteversion angles of impactor relative to the vertical plane. In some methods of use, once the orientation sensing device 204 is attached to impactor, the surgical orientation device 172 can display radiographic inclination and anteversion angles of impactor relative to a plane that approximates the Anterior Pelvic Plane. The angle of the impactor can be calculated in real-time.

The surgical orientation device 172 can graphically display when the orientation sensing device 204 is navigated to the target abduction and anteversion angles. The surgical orientation device 172 can include indicia such as a target or bullseye to indicate the pre-determined abduction and anteversion angles. The surgical orientation device 172 can include indicia such as a dot or cross-hair to indicate movement of the impactor. Aligning the indicia in the center of the target or bullseye can indicate that the impactor is aligned with the predetermined cup angles. In some methods of use, the surgeon aligns cross-hairs in a center of a bull's eye. In some methods of use, the surgeon aligns a bubble level. In some methods of use, the surgeon aligns two indicia. In some methods of use, the surgeon substantially aligns a moving indicia with a fixed indicia. In some methods of use, the surgeon moves an indicia on the user interface of the surgical orientation device 172 by moving the impactor. In some methods of use, the surgeon moves an indicia on the user interface of the surgical orientation device 172 by moving the orientation sensing device 204. Aligning a visual indicator displayed on the surgical orientation device 172 can guide the user to position the impactor at the desired cup angles. The indicia can move in real-time.

The surgical orientation device 172 can graphically display the abduction and anteversion angles as the orientation sensing device 204 is moved. In some methods of use, the indicia align when the impactor is positioned at the target anteversion angle. In some methods of use, the indicia align when the impactor is positioned at the target abduction angle. In some methods of use, the surgeon enters the target anteversion angle and/or the target abduction angle into the surgical orientation device 172.

In some methods of use, the surgical orientation device 172 displays a target angle. The target abduction and anteversion angles can be displayed statically. The surgical orientation device 172 can include a readout of the abduction and anteversion angles. The readout of the abduction and anteversion angles can change as the impactor is moved. The readout of the abduction and anteversion angles can be in real-time. In some methods of use, the surgeon compares readout and the target angle to position a cup at the target angle. In some methods of use, the surgical orientation device 172 provides a graphical display to assist the surgeon in aligning the cup with the target angles. In some methods of use, the surgical orientation device 172 provides a user interface to assist the surgeon in aligning the cup with the target angles. In some methods of use, the surgical orientation device 172 provides visual feedback when the impactor is aligned with one or more target angles. As described herein, angles displayed can be calculated according to their radiographic definitions. In some methods of use, the surgical orientation device 172 can provide the readout of angles dynamically.

The user can enter an input once the desired cup angles are reached. The user can have a set amount of time to align the impactor with the desired cup angles. In some methods of use, the surgeon must align the impactor at the desired target angle within a period of time. In some methods of use, the surgeon must align the impactor at the desired target angle within 30 seconds, 25 second, 20 seconds, less than a minute, less than 30 seconds, etc. The user can align impactor at desired cup angle. In some methods, after the impactor is positioned relative to the desired cup angles, the cup angles can be displayed statically. The cup angles can be checked after impacting by repeating one or more of the proceeding steps.

In some methods of use, the surgical orientation device 172 proceeds to the next step if the timer expires (e.g., 30 second timer, 25 second timer, 20 second timer, 1 minute timer, etc.). In some methods of use, the surgical orientation device 172 proceeds to the next step if a button of the surgical orientation device 172 is pressed. In some methods of use, the surgical orientation device 172 proceeds to the next step if the orientation sensing device 204 detects an impact strong enough to disrupt navigation. In some methods of use, the surgical orientation device 172 displays abduction and/or anteversion cup angles statically. In some methods of use, the surgical orientation device 172 displays abduction and/or anteversion cup angles statically after impaction. In some methods of use, the surgical orientation device 172 displays abduction and/or anteversion cup angles after the timer expires. In some methods of use, the surgical orientation device 172 displays abduction and/or anteversion cup angles after the user enters an input, such as depressing a button. In some methods of use, the surgical orientation device 172 displays abduction and/or anteversion cup angles after navigation has ended.

The surgical orientation device 172 can provide cup angles relative to any reference plane, including those described herein. The surgical orientation device 172 can provide cup angles relative to the vertical plane. The surgical orientation device 172 can provide cup angles relative to a plane that approximates the Anterior Pelvic Plane. The surgical orientation device 172 can provide cup angles relative to a plane acquired during table registration. The surgical orientation device 172 can provide cup angles relative to a plane that includes a vector for gravity.

In some embodiments, the surgeon can check cup angle after impacting as cup angle will change during impaction. In some embodiments, the cup angle is displayed up to the beginning of impaction, typically after the first mallet strike. In some methods of use, the surgeon will typically strike the impactor several times during cup placement. In some methods of use, these strikes may change the orientation of the cup. In some embodiments, the surgical orientation device 172 displays only the cup angle from prior to impaction. In some methods of use, the surgeon will repeat the cup navigation procedure by coupling the orientation sensing device 204 to the first assembly 704 such that it is in a fixed orientation with the surgical orientation device 172. In some methods of use, the configuration can be similar to the configuration shown in FIG. 12A. In some methods of use, the surgeon can interact with the orientation sensing device 204 and/or surgical orientation device 172 using one or more of the method steps described herein. Then the surgeon will move the orientation sensing device 204 to the impactor. The system 700 will now display the current cup angle. In some embodiments, the surgeon can check cup angle after impacting to improve accuracy. In some embodiments, the surgeon can verify the position of orientation sensing device 204 and the surgical orientation device 172 after impacting before checking angles. In some embodiments, the surgeon can visually confirm cup angles before proceeding.

After positioning the cup, the user can attach the second system 706 to the first system 704, similar to the configuration shown in FIG. 7. In some methods of use, the user can measure for leg length and/or joint offset. At the surgeon's discretion, the system 700 can be used to navigate a condition, location and/or orientation of the femur prior to hip replacement. At the surgeon's discretion, the system 700 can be used to navigate a condition, location and/or orientation of the femur after hip replacement.

Figure 19C:
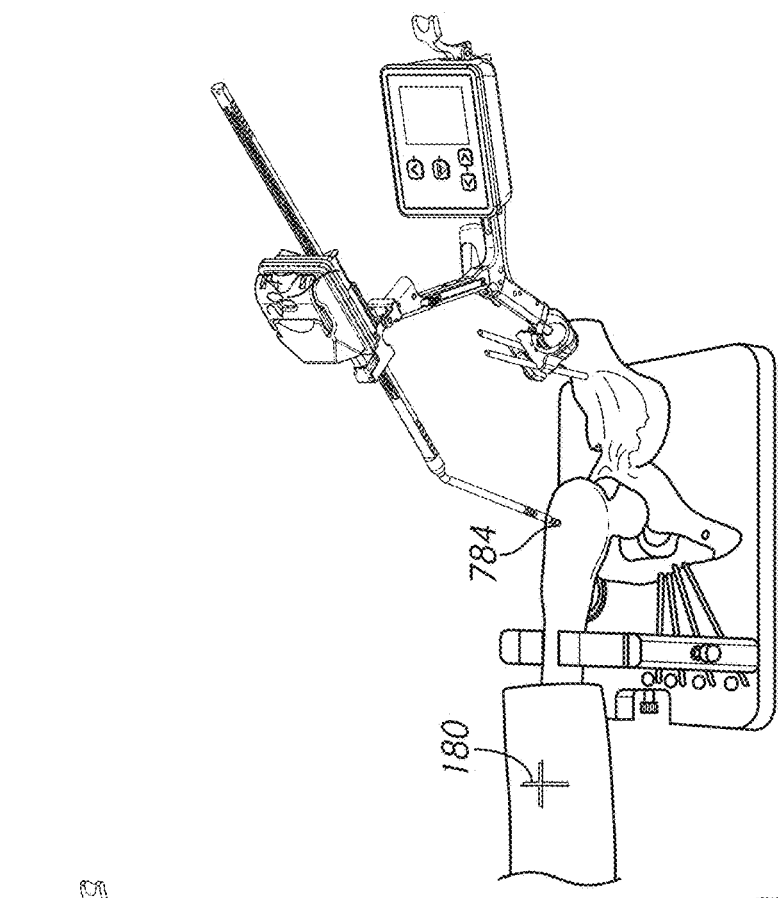
FIGS. 19A-19C illustrate an embodiment of point registration after cup placement.
Figure 19A:
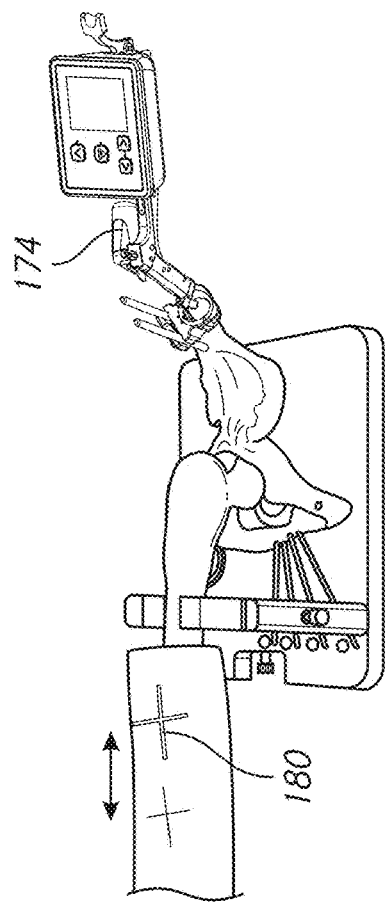
Figure 19B:
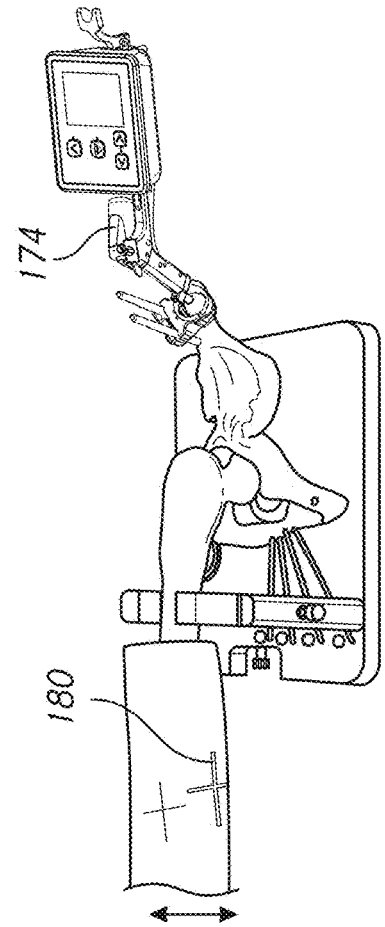

Referring to FIG. 19A-19B, the surgeon can manually re-position the femur. In some embodiments, the surgeon can manually re-position the femur in the orientation in which the point was recorded. In some embodiments, the surgeon can manually re-position the femur in the orientation prior to cup placement. In some embodiments, the surgeon can manually re-position the femur in the orientation prior to joint replacement. In some methods, the surgeon opens the shutter of the optical component 174, 194. The method can include projecting light from the optical component 174, 194. In some methods of use, the incidence of light may not align with the marking. In some methods of use, the femur has moved from the orientation when the point was registered. In some methods of use, the femur has moved from a previously recorded orientation. In some methods, the surgeon positions the leg so that the optical component 174, 194 projects a light onto the leg. In some embodiments, the optical component 174, 194 projects onto the femur. In some embodiments, the optical component 174, 194 projects onto the sterile wrap. In some embodiments, the optical component 174, 194 projects light onto the distal thigh.

Referring to FIGS. 19A-19B, the method can include aligning incidence of light with the prior marking or recording of the incidence of the light. In some embodiments, the surgeon can manually position the femur by moving the femur. The femur can be moved in anterior-posterior direction. The femur can be moved in varus-vulgas direction. The femur can be rotated about the head of the femur. In some embodiments, the surgeon can manually position the femur after the joint is replaced, such as after a cup is placed within the joint. In some embodiments, the surgeon can realign the femur such that the femur is in same position before and after cup placement. In some embodiments, the surgeon can realign the femur such that the femur is in same position before and after joint replacement. In some embodiments, the surgeon can position the femur to be in the same position as when the surgeon traced the incidence of light. In some embodiments, the surgeon can position the femur to be in the same position as when the surgeon recorded the point. The surgeon can extend and/or rotate the femur to position the femur.

In some embodiments, the surgeon positions the leg such that the incidence of light from the optical component 174, 194 aligns with the traced pattern. In some embodiments, the surgeon positions the femur relative to the pelvis. In some embodiments, the surgeon positions the femur such that the incidence of light from the optical component 174, 194 aligns with one or more marks. In some embodiments, the surgeon positions the femur such that the incidence of light aligns with two lines. In some embodiments, the surgeon positions the femur such that the incidence of light aligns with a marked cross-hair. In some embodiments, the surgeon positions the femur such that the incidence of light aligns with three marked points. In some embodiments, the surgeon positions the femur such that the incidence of light aligns with a marking on the sterile wrap. In some embodiments, the surgeon positions the femur such that the incidence of light aligns with a marking on the target probe 18a, 18b. In some embodiments, the surgeon positions the femur such that the incidence of light passes through one or more slots of the target probe 18a, 18b. In some embodiments, the surgeon discontinues use of the optical component if the cross-hair pattern is obscured.

Referring to FIG. 19C, in some methods of use, the surgeon can register the point after positioning the femur. In FIG. 19C, the incidence of light 180 aligns with the marking. While a cross-hair pattern is shown in FIG. 19C, the incidence of light 180 and the marking can be any pattern. By aligning the incidence of light 180 and the marking, the femur is in the same position before and after cup placement.

In some methods of use, the surgeon can register the point after cup placement. In some methods of use, the surgeon can register the same point intra-operatively. In some embodiments, the surgeon can register the point after the cup is placed at one or more desired target angles. In some embodiments, the surgeon can register the point after joint replacement. The surgeon can position the distal end 780 of the probe 778 at the point. In some methods of use, the distal end 780 of the probe 778 is placed on part of the greater trochanter or elsewhere on the proximal femur. In some methods of use, the distal end 780 of the probe 778 is placed on the mark on the femur. In some methods of use, the distal end 780 of the probe 778 is placed on the tracker 784. In some methods of use, the distal end 780 of the probe 778 is placed on a divot or burr on the femur.

The probe 778 can be immobilized to register the point. In some embodiments, the surgeon can hold the tip of the probe 778 at the point. The second assembly 706 can include a lock 766. The lock 766 can limit or reduce slidablility of the probe 778 relative to the dock 762. The lock 766 limits or reduces one degree of freedom during point registration.

Once the tip of the distal end 780 is in contact with the desired point, the system 700 processes data from and stores the orientation of one or more sensor(s) in the orientation sensing device 204. During registration, the position of the orientation sensing device 204 can be recorded by the surgical orientation device 172. During registration, the orientation of the orientation sensing device 204 can be recorded by the surgical orientation device 172. During registration, the extension of the orientation sensing device 204 can be recorded by the surgical orientation device 172. In some embodiments, the surgical orientation device 172 can register the point. In some embodiments, the surgeon can press a button on the surgical orientation device 172 to register the point.

In some methods, the surgeon aligns the marking with the projection of light before registering the point. In some methods, the surgeon aligns the marking with the projection of light simultaneously with registering the point. In some methods, the surgeon aligns the marking with the projection of light but does not register the point. In some methods, the surgeon registers the point but does not align the marking with the projection of light. In some methods, the surgeon aligns the marking with the projection of light independently of registering the point. In some methods, the surgeon aligns the marking with the projection of light and registers the point after the leg is fixed. In some methods, the surgeon aligns the marking with the projection of light, secures the femur, and then registers the point after the femur is secured.

If the point is acquired in the procedure prior to separating the natural joint, the same point can be acquired after the prosthetic joint is placed to confirm that the replacement of the joint has not changed either the length of the leg, the off-set of the leg from the trunk of the patient, or both. After joint replacement, the distal end 780 of the probe 778 can be brought into contact with the same point acquired early in the procedure. The orientation of the orientation sensing device 204 and the extension of the probe 778 can be input into the surgical orientation device 172. These data enable the surgical orientation device 172 to output amounts of change in leg length and leg offset.

The system 700 can measure the orientation of the femur relative to pelvis during a baseline measurement of the point. The system 700 can measure the orientation of the femur relative to pelvis during one or more intra-operative measurements of the point. The system 700 can store the two-dimensional coordinates of the point in the table reference frame. In some methods of use, the surgeon can correct for changes in orientation by doing a rotation about the center of rotation of the femur. In some methods of use, the surgeon can correct for changes in orientation by aligning the incidence of light from the optical component 174, 194 with the marking on the femur. In some methods of use, the surgeon manually realigns the femur to take another measurement of the point. In some methods of use, the method can require obtaining a single point on the femur. The single point can be a mark. The single point can be a tracker 784 or other fixture such as a screw or pin. The single point can be an anatomical landmark. The single point can be a burr or divot in the femur. The point can be registered by the probe 778 intra-operatively each time the leg length and/or joint offset is to be measured.

Before navigation systems, such as system 700, surgeons did not take measurements intra-operatively. Rather, surgeons typically looked at the cup placement during a procedure and determined whether current cup placement looked like previous cup placements. The surgeon would visually confirm cup placements during surgery and past experience in viewing post-operative images. The surgeon would determine if the current cup placement was likely to correlate to the correct abduction and anteversion angles post-operatively. The surgeon would look at the cup placement and determine that the placement looks like 40 degrees×15 degrees based on their experience looking at post-operative images. The surgeon's confidence in the procedure would be based on their correlation of cup placement and post-operative images.

For the system 700, the user is provided with an output that assists a user to navigate to proper cup placement. The output can be abduction and anteversion angles displayed on the surgical orientation device 172. The user can navigate to the desired abduction and anteversion angles by moving components of the system 700, such as the impactor 300A or any impactor with the universal impactor adapter 350, 352. When the user places the cup at the desired abduction and anteversion angles, the user wants to see the same or similar angle on post-operative images. The user's confidence in the navigation of the system 700 increases if the abduction and anteversion angles produced by the system 700 match the post-operative images. The vertical plane, determined from gravity as described herein, can match the plane used in post-operative images. In some embodiments, the vertical plane may be similar to the reference plane of imaging techniques. In some methods of use, with some patients, the vertical plane provides abduction and anteversion angles that closely match post-operative images.

In some methods of use, as described herein, the method can include one or more of the following steps. The method can include recording the position of a probe 787 as the probe touches the point after replacing the hip joint. The method can include comparing the position of a probe as the probe touches the point to the position recorded before replacing the hip joint. In some embodiments, the surgical orientation device 172 compares two or more measurements of the point. In some embodiments, the surgical orientation device 172 compares measurements of the point before and after the cup is replaced. In some embodiments, the surgical orientation device 172 can provide a visual output of the change in leg length. In some embodiments, the surgical orientation device 172 can provide a visual output of the change in joint offset. In some embodiments, the surgical orientation device 172 can provide a visual output of the direction of change of leg length (e.g., longer or shorter). In some embodiments, the surgical orientation device 172 can provide a visual output of the direction of change of joint offset (e.g., lateral).

In some methods of use, as described herein, the method can include one or more of the following steps. The method can include confirming the leg length after replacing the hip joint. The method can include confirming joint offset after replacing the hip joint. When measuring changes in leg length and/or lateral joint offset, the apparent changes are sensitive to changes in the orientation of the femur relative to the pelvis. In some methods, the changes are particularly sensitive to the abduction angle. The changes are moderately sensitive to the rotation about the mechanical axis of the femur. The optical component 174, 194 can be used to verify the orientation of the femur relative to the pelvis before and after replacing the hip joint. In some methods, confirming the leg length and/or joint offset can include obtaining a single point of the femur. The method of use can include the step of manually realigning the femur about the center of rotation (COR) of the hip In some methods of use, as described herein, the method can include one or more of the following steps. The method can include projecting light after replacing the hip joint. The method can include comparing the position of the light before and after replacing the hip joint. The method can include comparing the incidence of light after replacing the hip joint with the one or more marks made before replacing the hip joint. The method can include the comparing the incidence of light after replacing the hip joint with the two or more marks made before replacing the hip joint. The method can include comparing the incidence of light after replacing the hip joint with a line made before replacing the hip joint.

In some methods of use, as described herein, the method can include one or more of the following steps. The method can include confirming the position of the leg relative to the pelvis after replacing the hip joint. The method can include confirming the position of the femur relative to the pelvis after replacing the hip joint. The optical component 174, 194 can be useful to measure the orientation of the leg relative to pelvis during preoperative baseline and postoperatively. The surgeon can correct for changes in orientation by repositioning the leg based on the incidence of light. These marks can guide the surgeon in replicating the orientation of the leg relative to the pelvis each time a leg length measurement or joint offset measurement is needed. The optical component 174, 194 can be used in conjunction with the posterior approach described herein.

In some embodiments, the surgeon can verify the home position after measuring leg length and/or joint offset. The second assembly 706 can be coupled to the first assembly 704. The first assembly 704 can be coupled to the fixation base 702. In some techniques, the distal end 780 of the probe 778 can be engaged with a point on the fixation base 702, such as the divot 730. The user can enter an input to record the home position. In some methods of use, the home position remains fixed relative to the pelvis throughout the procedure. In some embodiments, the surgical orientation device 172 can indicate a change in the home point. The number displayed may not be zero due to mechanical play and noise of the orientation sensing device 204. In some methods of use, if displayed number is greater than 3 mm, then the surgeon can verify all reference sensor attachments and jig connections are correct and secure before repeating. In some methods of use, if displayed number is greater than 3 mm, then surgeon can repeat registration of the point or alignment of the femur. In some methods of use, repeating registrations will result in a loss of all previous registrations. In some methods of use, the surgeon determines whether the fixation base 702 has moved. In some methods of use, the surgeon can end the procedure. In some methods of use, ending the procedure can result in loss of previous registrations. In some methods of use, ending the procedure can result in information being stored. In some methods of use, the leg length is stored. In some methods of use, the joint offset is stored. In some methods of use, the target angles are stored. In some methods of use, the fixation base 702 and the fixation pins 710, 712 are removed prior to closure. In some embodiments, the surgical orientation device 172 is discarded. In some embodiments, the orientation sensing device 204 is reusable. In some embodiments, the optical component 174, 194 is reusable.

The table plane can be an improvement over a landmark-based reference planes for some patients. In some embodiments, the landmark-based reference planes may differ from the vertical reference plane calculated herein due to patient specific factors. For instance, pelvic tilt may orient the landmark-based reference planes at an angle from the vertical reference plane. For instance, the patient's high body mass index may impact the ability to contact anatomical landmarks. For instance, the anatomical features of the reference points may not be visible and/or palpable while the patient is in the lateral decubitus position of the posterior approach. For instance, the ipsilateral ASIS, the contralateral ASIS, and/or the pubic symphysis may not be visible and/or palpable. The patient specific factors can results in differences between navigated cup angles from the landmark-based reference planes and angles measured post-operatively. In some methods of use, with some patients, the landmark-based reference planes may not provide abduction and anteversion angles that match post-operative images.

Systems and methods described herein can improve prosthetic hip joint placement using navigation. These hip procedures generally guide a prosthetic hip to an orientation within the acetabulum that minimizes the chance of dislocation due to impingement of the femoral neck on the cup or on bones around the acetabulum or other reasons related to suboptimal orientation of the prosthetic. Various techniques leverage population averages of proper placement while others are amenable to patient specific refinements.

C. Navigation Using One or More Reference Planes with Anterior Approach

1. Methods for Anterior Approach

FIGS. 1-5C illustrate a hip navigation system 600 adapted to navigate a hip joint procedure from an anterior approach. FIGS. 7-10D illustrate hip navigation system 700 adapted to navigate a hip joint procedure from an anterior approach. While the method is described with respect to system 600, any systems described herein or in the following publications can be utilized: U.S. Pat. Pub. No. 2016/0242934, filed Mar. 10, 2015; U.S. Pat. Pub. No. 2014/0052149 filed Mar. 13, 2013; U.S. Pat. Pub. No. 2010/0137871 filed Sep. 10, 2009, all of which are incorporated by reference in their entirety. Anterior approach to hip replacement advantageously can be less invasive than posterior approach. In particular, the anterior approach can enable smaller incisions, less soft tissue dissection, and shorten recovery time for patients.

Figure 21:
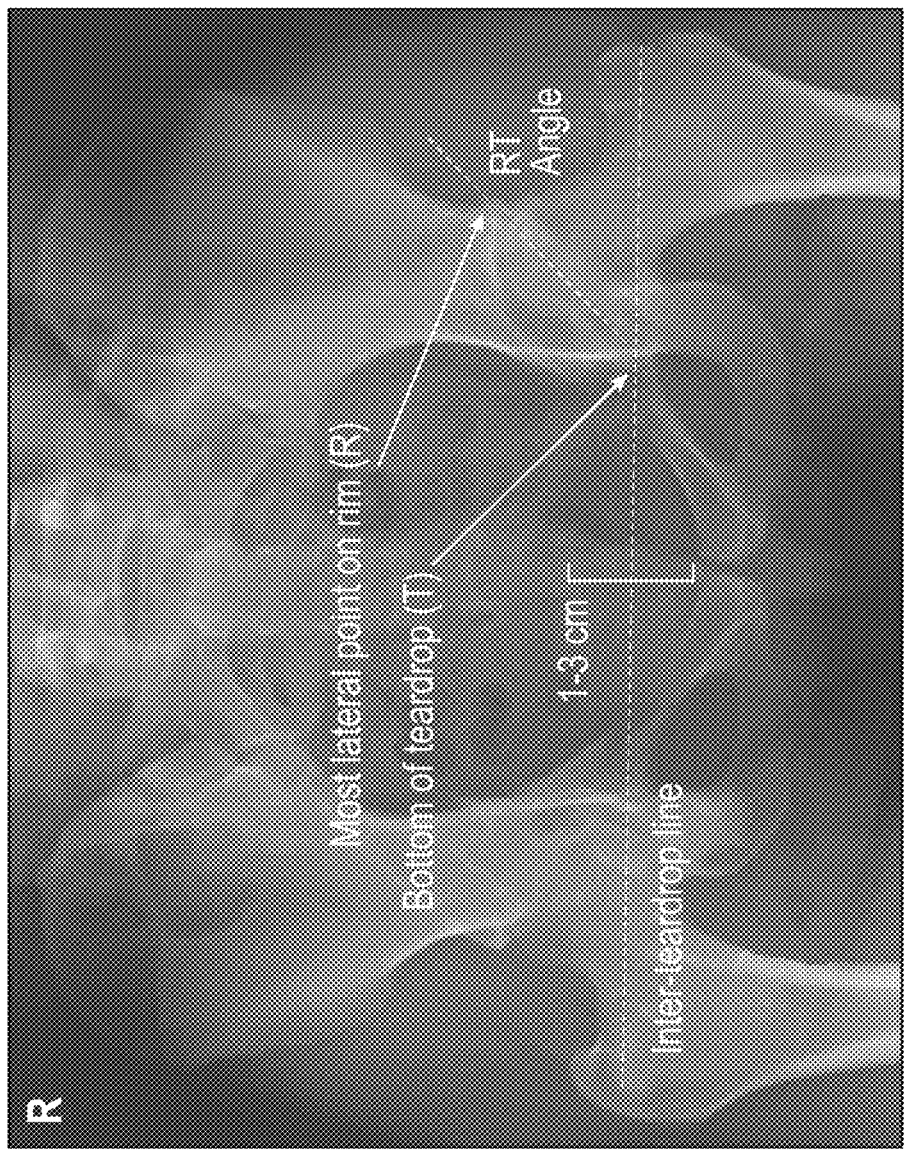
FIG. 21 is an example of an x-ray that can be taken pre-operatively.

In some embodiments, the navigation system 600 is configured to locate a relevant anatomical feature to aid in proper placement of a prosthetic hip joint. In some methods, pre-operative imaging techniques are used. In some methods of use, the surgeon can use a standing or supine anteroposterior (AP) pelvic x-ray. FIG. 21 shows standing AP radiograph taken with patient standing with feet in neutral rotation and shoulder width apart in stance. The x-ray tube-to-film distance should be 120 cm, with the crosshairs centered on the midpoint between the superior border of the pubic symphysis and a line drawn connecting the anterior superior iliac spines (ASIS). The coccyx should be centered in line with the pubic symphysis, and the iliac wings, obturator foramina and radiographic teardrops should be symmetrical in appearance. For appropriate pelvic inclination or abduction, a 1-3 cm gap should be seen between the tip of the coccyx and the superior border of the pubic symphysis. This positioning can be important for measuring the patient specific Rim Teardrop (RT) angle.

To obtain the patient specific Rim Teardrop (RT) angle from the AP pelvic x-ray the surgeon can complete one or more of the following steps. The surgeon can draw a line on the x-ray connecting the bottom of the teardrops. The surgeon can draw a line from the most lateral point on the rim of the acetabulum (R) on the operative side through the bottom of the teardrop (T) to the horizontal inter-teardrop line. If osteophytes are present on the rim (R), the surgeon can draw a line through the most lateral osteophyte. The surgeon can measure the angle between the inter-teardrop line and the RT line just drawn. This patient specific RT abduction angle can be an input for the system 600, 600A.

FIG. 22 shows the patient positioning for the anterior hip approach. In the anterior hip approach, the patient should be placed in the supine position. When positioning the patient prior to surgery, the surgeon should take care to align the spine and femur of a patient in a horizontal plane parallel to the long edge of the operating table. The surgeon can verify that patient is positioned in an appropriate position, e.g., in a supine position.

Figure 23:
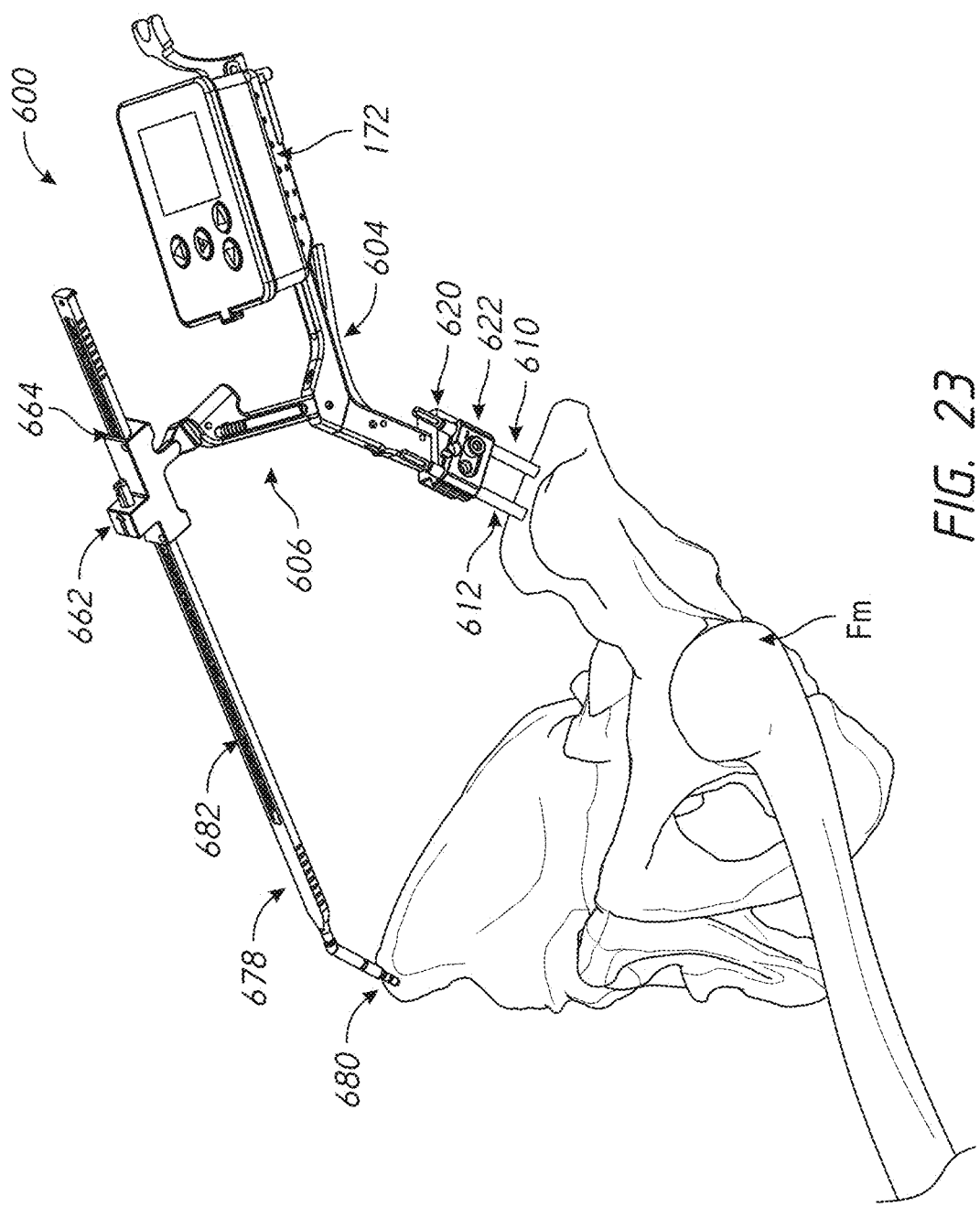
FIG. 23 illustrates a configuration of the system of FIG. 1 coupled with the pelvis.

FIG. 23 shows the system 600 adapted to navigate a hip joint procedure with reference to anatomical landmarks from an anterior approach. The system 600 can include the orientation sensing device 204, not shown in FIG. 23. The system 600 can be adapted for either a posterior approach or an anterior approach. In the anterior approach, the patient is in the supine position.

The surgical orientation device 172 and the orientation sensing device 204 can be turned on before the procedure begins. If the system can be used in a knee or hip procedure, one method can involve a surgeon selecting a module corresponding to the hip. If the system can be used in a posterior or anterior approach, one method can involve a surgeon selecting a module corresponding to the anterior approach. The surgical orientation device 172 can include a display screen. The surgical orientation device 172 can include a user interface, such as buttons which can be depressed by the user. The display screen can confirm the communication between the surgical orientation device 172 and the orientation sensing device 204.

The system 600 can be partially assembled for calibration as shown in FIG. 12A. In some embodiments, the first assembly 604 can be assembled. The pelvic bracket 638 can be coupled to the extension 644, if separate components. The surgical orientation device 172 can be coupled to the mount 646. In some techniques, the extension 670 can be coupled to the second coupler 648. The orientation sensing device 204 can be coupled to the mount 672. The surgical orientation device 172 and the orientation sensing device 204 form a general V-shaped configuration, similar to the orientation shown in FIG. 12A. The orientation sensing device 204 can be fixed in position relative to the surgical orientation device 172.

The surgical orientation device 172 and the orientation sensing device 204 can be calibrated. The surgical orientation device 172 can be rested on a level horizontal surface with the display horizontal (facing up). The surgeon can hold the assemblies 604, 606 steady until the surgical orientation device 172 indicates completion. The orientation sensing device 204 can be rested on a level horizontal surface with the display vertical (facing user). The surgeon can hold the assemblies 604, 606 steady until the surgical orientation device 172 indicates completion. The surgical orientation device 172 can be rested on a level horizontal surface with the display pointed sideways (left side). The surgeon can hold the assemblies 604, 606 steady until the surgical orientation device 172 indicates completion. The surgical orientation device 172 can be rested on a level horizontal surface with the display horizontal (facing up) again. The surgeon can hold the assemblies 604, 606 steady until the surgical orientation device 172 indicates completion. Other orientations of the surgical orientation device 172 and the orientation sensing device 204 are contemplated for calibration.

The user can remove the required instruments and prepare the instruments for use. FIG. 18A illustrates an impactor 300A. As described herein, the impactor 300A can include the fourth coupler 342 to couple the impactor 300A to the orientation sensing device 204. In some methods, any impactor can be used with the systems and methods described herein. The universal impactor adapter 350, 352 can provide the fourth coupler 342 to couple the impactor to the orientation sensing device 204. In some methods of use, the orientation sensing device 204 can be coupled to the impactor 300A. In some methods of use, the orientation sensing device 204 can be coupled to any impactor via the universal impactor adapter 350, 352. The orientation sensing device 204 can determine cup angles relative to a reference plane as the impactor is moved. As described herein, the impactor 300A can include a shell 312A. The movement of the shell 312A is cushioned by a plurality of spring members 340, 344 which are configured to absorb at least some of the shock of the impact on the impactor 300A. The shell 312A can include a fourth coupler 342. This permits the orientation sensing device 204 to couple to the shell 312A. The impactor 300A can be configured to be modified to suit any of a plurality of hip prostheses. For example, a plurality of tip components 348 can be provided in a kit where each tip component is attachable to and detachable from a distal end of the shaft of the impactor 300A. The acetabular shell can be threaded onto a tip component 348. The user can select the appropriate shell adapter for the desired impactor.

As described herein, any impactor can be utilized. The surgeon can utilize the universal impactor adapter 350, 352. The universal impactor adapter 350, 352 can include a fourth coupler 342. This permits the orientation sensing device 204 to couple to the impactor. The universal impactor adapter 350, 352 can form any rigid connection to the impactor. While magnets and clamps are described herein, any mechanical connection between the universal impactor adapter 350, 352 and the impactor is contemplated. The impactor can suit any of a plurality of hip prostheses. For example, a plurality of tip components 348 can be provided in a kit where each tip component is attachable to and detachable from a distal end of the shaft of the impactor. The impactor can suit a particular hip prosthesis. The tip of the impactor can be designed to interface with a single acetabular shell. The acetabular shell can be threaded onto the impactor. The universal impactor adapter 350, 352 can allow any impactor to be used with the orientation sensing device 204 as described herein.

The user can interact with the surgical orientation device 172. If the system can be used in either hip procedure, one method can involve a surgeon selecting a module corresponding to the right hip or the left hip. In some methods of use, the user can input a target cup abduction angle. This is the radiographic abduction angle defined as the coronal plane projection of the angle between the acetabular axis and the longitudinal axis of the body. Abduction and adduction are also used to describe movement of the limb within the coronal plane. In some methods of use, the user can input a target cup anteversion angle. This is the Radiographic Anteversion angle defined as the angle between the acetabular axis and the coronal plane.

The probe 678 can be calibrated. The extension 670 can be decoupled from the second coupler 648. The second assembly 606 can be assembled as shown in FIG. 12B. The first assembly 604 can be coupled to the second assembly 606 as shown in FIG. 12B. In some methods of use, the system 600 can include a calibration fixture 690. The first assembly 604 and the second assembly 606 can be mounted to the calibration fixture 690. The calibration fixture can include a plurality of points for the probe 678 to contact.

The probe 678 can contact a center hole at the base of the calibration fixture 690 to calibrate a center point. The user can depress a button when the probe 678 is placed. The probe 678 can contact a left hole at the base of the calibration fixture 690 to calibrate a left point. The user can depress a button when the probe 678 is placed. The probe 678 can contact a right hole at the base of the calibration fixture 690 to calibrate a right point. The user can depress a button when the probe 678 is placed. The calibration fixture 690 can be utilized prior to the procedure. The calibration fixture 690 can be located away from the patient, for instance on a back table. Other calibration fixtures and jigs are contemplated.

The system 600 can be attached to the pelvis as shown in FIG. 23. The user can position the system 600 such that the system 600 has solid and stable mount for attachment of the instrumentation to the pelvis. In some methods of use, all measurements and references are based off the initial registration process and any movement of the first assembly 604 after will result in error in the resulting readouts of cup position. In some methods, the fixation pins 610, 612 are placed in the ipsilateral iliac crest in a parallel fashion. The fixation pins 610, 612 are placed in a similar fashion to placement of pins for pelvic external fixation. The fixation pins 610, 612 enter the iliac wing at its most superior surface and travel between the tables of the inner and outer bone of the iliac wing.

In order to prevent obstruction of subsequent femoral exposure and broaching with the anterior approach, in some methods of use, the most anterior fixation pin should be placed 2-4 cm posterior to the ASIS. It is also helpful to evaluate the patients pre-operative x-rays to assess the relative angle that will allow for passage of the fixation pins 610, 612 within the bone. The most optimal position for the fixation pins 610, 612 is to enter at approximately a 45 degree angle from the anterior pelvic plane to allow the pins to enter into the thicker supra-acetabular bone along the anterior column. In some methods of use, fixation pins 610, 612 that are passed at an angle greater than 45 degrees are at risk for exiting the cortical bone where the ilium thins more posteriorly.

The fixation pins 610, 612 are designed with a pointed tip to allow for secure placement while starting through the thicker outer cortical bone. This decreases risk of pin slippage and aberrant placement. It is also important for the user feel for any significant resistance when passing the fixation pins 610, 612 to an appropriate depth to avoid perforating the cortical bone. If there is concern about pin location, the user may aim more to the outer iliac wall. In some methods of use, the fixation pins 610, 612 can be stabilized if they are placed at least half their length into the bone. This will provide a stable construct with the mount. The fixation base 602 has been designed to allow for parallel placement with the anterior pelvic plane if the pins are placed at 45 degrees.

The fixation pins 610, 612 can be inserted into the bone. In some techniques, one or more of the fixation pins 610, 612 are positioned as described herein. In some techniques, one or more of the fixation pins 610, 612 are positioned on the iliac crest. In some techniques, one the fixation pins 610, 612 is positioned on the iliac crest 2-4 cm posterior to ASIS. In some techniques, the other fixation pins 610, 612 is positioned 2 cm posterior to the first fixation pin. The fixation base 602 can be slid over the fixation pins 610, 612 to the level of the skin. The fixation devices 624 of the fixation base 602 can be tightened to secure the fixation base 602 to the fixation pins 610, 612. In some methods of use, the fixation base 602 must be attached prior to dislocating the hip.

The system 600 can be assembled as shown in FIG. 1. The orientation sensing device 204 can be coupled to the probe 678. In some embodiments, the orientation sensing device 204 and/or the probe 678 include indicia such as arrows to facilitate alignment. The first assembly 604 can be secured to the fixation base 602 with the surgical orientation device 172 attached. The first assembly 604 can be secured by pushing on the lock lever 640, as described herein. The second assembly 606 can be secured to the fixation base 602 with the orientation sensing device 204 attached. In some embodiments, the second assembly 606 and/or the fixation base 602 include indicia such as arrows to facilitate alignment.

The surgical orientation device 172 can be aligned with the sagittal plane. The system 600 can be placed such that the probe 678 can reach all required landmarks defining the Anterior Pelvic Plane. The fixation base 602 can be adjusted. In some methods of use, the fixation base 602 can be slid along the fixation pins 610, 612. In some methods of use, angle or tilt of the fixation base 602 can be adjusted. After adjustment, the screws on the fixation base 602 can be tightened to secure the fixation base 602 to the fixation pins 610, 612 for the remainder of the procedure.

The surgeon can register a parked configuration or home position. In some techniques, the distal end 680 of the probe 678 can be engaged with a point on the fixation base 602, such as the divot 630. The probe 678 can be vertical in the home position. The orientation sensing device 204 can be vertical in the home position. The distal end of the probe 678 can be curved or bent to facilitate locating anatomical landmarks or points.

When registering points, the user can hold the probe 678 close to the distal end 680 to maximize accuracy of the measurement of the point. When interacting with the surgical orientation device 172, the user can support the back of the surgical orientation device 172 to avoid flexing the fixation pins 610, 612 and/or the fixation base 602. The user can register a point by pressing a button of the surgical orientation device 172. If the registration is not accepted, the user can keep the probe 678 stationary and press the button again.

Figure 24:
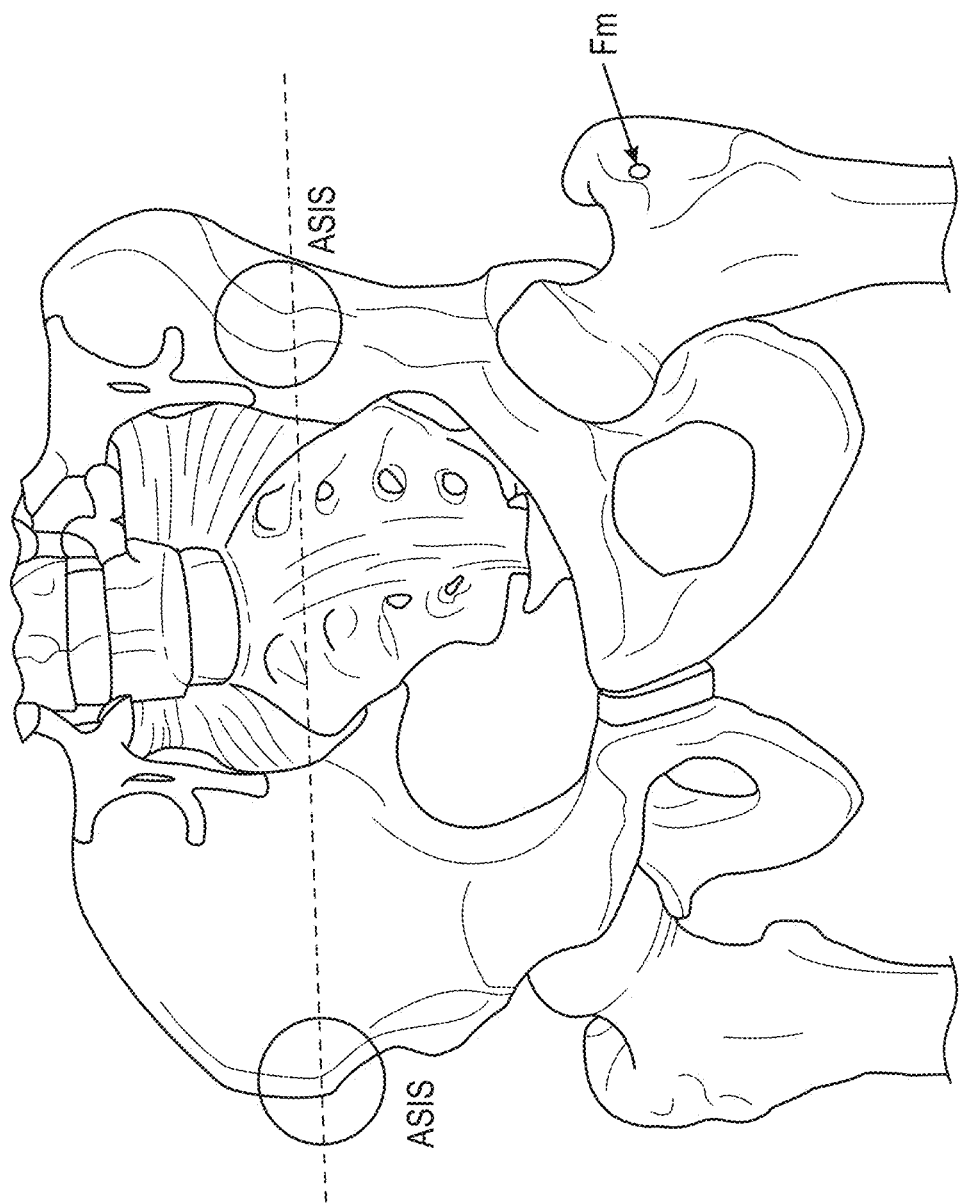
FIG. 24 illustrates anatomy of an anterior portion of the hip joint, including the pelvis and the proximal femur.

The surgeon can position the distal end 680 of the probe 678 at various anatomical landmarks or points. FIG. 24 illustrates the anatomy of the hip. As illustrated by FIG. 24, two landmarks are circled. The landmarks include the two anterior superior iliac spines (ASIS) which are bony projections of the iliac bone. The anterior superior iliac spines can be visualized and/or palpated by the user during surgery. The anterior superior iliac spine is the anterior extremity of the iliac crest of the pelvis. The inter-ASIS line extends between these landmarks. The inter-ASIS line extends between the ipsilateral ASIS and the contralateral ASIS. In other methods of use, other landmarks are used. Other landmarks that could be used include locations on the ilium, ischium, pubis, anterior insertion point of transacetabular ligament to the ischium, mid-point of the inferior aspect of the acetabular notch, the anterior superior iliac spine, anterior inferior iliac spine, convergence of the acetabulum and anterior inferior iliac spine, as well as the other landmarks known in the art.

The system 600 has one or more processors that receive(s) data and determines the relative position and/or orientation of these anatomical landmarks when the probe 678 contacts the anatomical landmark. The data can be generated by inertial sensors, as discussed elsewhere herein, or other types of sensors of the system 600. Preferably the sensors are small enough to be mounted on or in handheld housings or embedded in the instruments, such as the surgical orientation device 172 and the orientation sensing device 204. The system 600 preferably also has a memory device to at least temporarily store the position of these points. The system 600 preferably also has the ability to at least temporarily store the relevant position and/or orientation data when the probe 678 contacts the anatomic landmarks. In some methods of use, the system 600 records the position and/or orientation of the probe 678 when the probe 678 contacts each anatomic landmark or point. In some methods of use, the system 600 stores the recorded position and/or orientation of the probe 678 during the length of the procedure. In some methods of use, the system 600 stores the recorded position and/or orientation of the probe 678 until the system is powered off.

FIGS. 25A-25D illustrate method steps to calculate the Anterior Pelvic Plane. The Anterior Pelvic Plane can be defined as a plane created by the two anterior superior iliac spines (ASIS) and the anterior surface of the pubic symphysis. Three points provide adequate information to calculate a plane. The system 600 can generate the Anterior Pelvic Plane by registering Point 1, Point 2, and Point 3. These anatomical features are visible and/or palpable while the patient is in a supine position. In some methods, the probe 678 registers the Anterior Pelvic Plane with direct contact of anatomical landmarks when the patient is in the supine position. The system 600 is then able to provide the user navigation data of the orientation of a hip instrument (e.g., the impactor 300A or any impactor with universal impactor adapter 350, 352) with respect to the Anterior Pelvic Plane. In some embodiments, the system 600 is able to provide the user navigation data in real-time. In the anterior approach, the patient is positioned on his/her back and the Anterior Pelvic Plane is oriented substantially horizontally, e.g., substantially parallel to the plane of the table on which the patient is positioned.

Figure 25B:
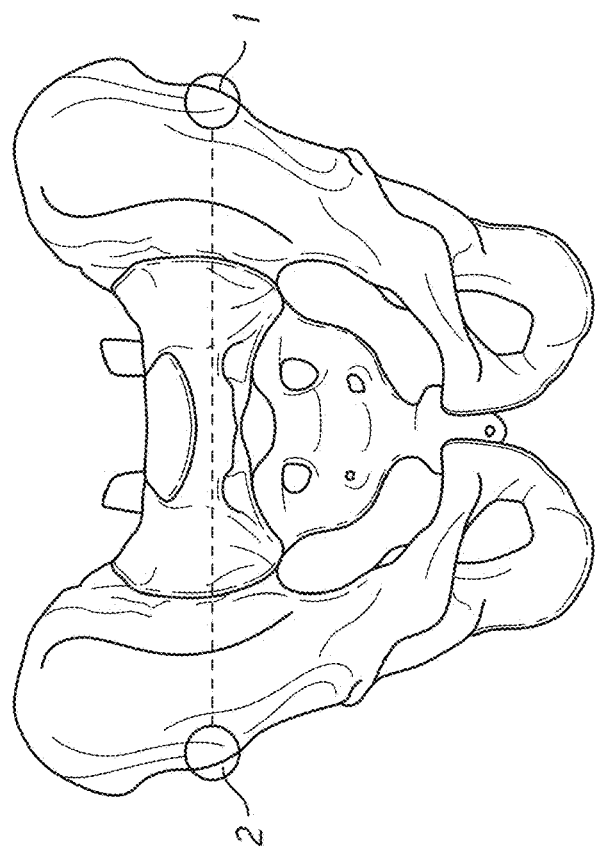
Figure 25A:
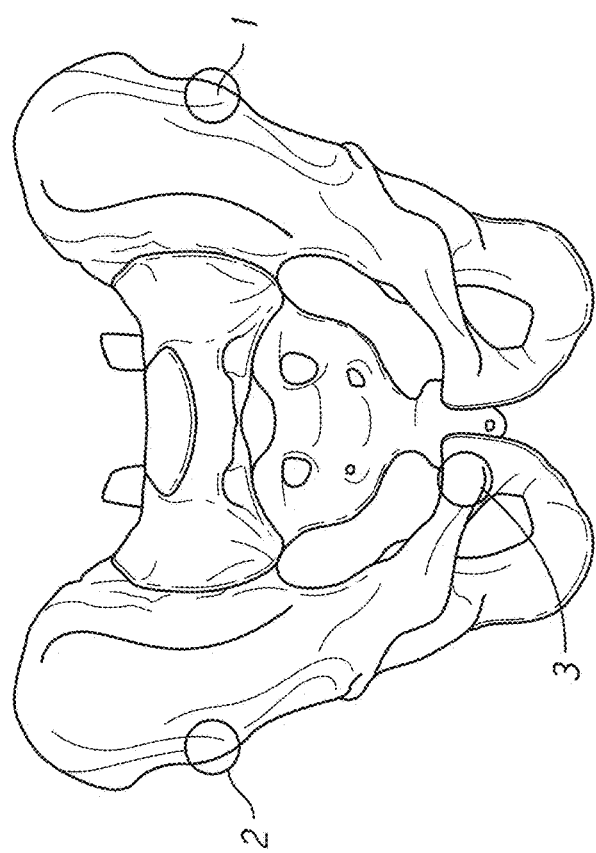

FIG. 25A illustrates the approximate location of three points of the Anterior Pelvic Plane. The surgeon can register Point 1, Point 2, and Point 3. The illustrated embodiment shows Point 1 on the left hip, Point 2 on the right hip, and Point 3 on the right hip. Other configurations are contemplated. For some procedures on a patient's left hip, Point 1 is on the left hip and Point 2 is on the right hip. For some procedure on a patient's right hip, Point 1 is on the right hip and Point 2 is on the left hip. Other methods are contemplated. In some methods, Point 1 is the ipsilateral ASIS. In some methods, the distal end 680 of the probe 678 is placed at the ipsilateral ASIS landmark. The probe 678 can be immobilized and the position and/or orientation of the orientation sensing device 204 can be recorded by the surgical orientation device 172. The surgeon can enter an input to register Point 1 (e.g., depress a button on the surgical orientation device 172). Other ways of entering an input include interacting with a touchscreen, using a verbal command, touching an icon, holding the probe 678 steady for a period of time, and/or reaching the end of a countdown clock, etc. The surgical orientation device 172 can indicate that Point 1 was recorded. Additionally, the distance that the probe 678 is extended, as captured by the camera 184, to contact the ipsilateral ASIS can be recorded by the orientation device 172. The process to record the ipsilateral ASIS can be repeated for one or more additional points.

In some methods, Point 2 is the contralateral ASIS. In some methods, the distal end 680 of the probe 678 is placed at the contralateral ASIS landmark. The probe 678 can be immobilized and the position and/or orientation of the orientation sensing device 204 can be recorded by the surgical orientation device 172. The surgeon can enter an input to register Point 2 (e.g., depress a button on the surgical orientation device 172). The surgical orientation device 172 can indicate that Point 2 was recorded. Additionally, the distance that the probe 678 is extended, as captured by the camera 184, to contact the contralateral ASIS can be recorded by the orientation device 172. The process to record the contralateral ASIS can be repeated for one or more additional points.

In some methods, Point 3 is the anterior surface of the pubic symphysis. In some methods, the distal end 680 of the probe 678 is placed at the pubis landmark. In some methods, either pubic tubercle may be used as Point 3. In some embodiments, the contralateral pubic tubercle is used as Point 3. The probe 678 can be immobilized and the position and/or orientation of the orientation sensing device 204 can be recorded by the surgical orientation device 172. The surgeon can enter an input to register Point 3 (e.g., depress a button on the surgical orientation device 172). The surgical orientation device 172 can indicate that Point 3 was recorded. Additionally, the distance that the probe 678 is extended, as captured by the camera 184, to contact the pubic symphysis can be recorded by the orientation device 172. The process to record the pubic symphysis can be repeated for one or more additional points.

The distance related to the extension of the probe 678 can be used in conjunction with the positional and/or orientation data from the orientation sensing device 204. In some methods, the orientation sensing device 204 converts the image of the camera 184 into an extension measurement of the probe 678. In some embodiments, the surgical orientation device 172 converts the image of the camera 184 into an extension measurement of the probe 678. When registering the anatomical points, the camera 184 captures an image of the marking 682. The camera 184 can read the marking 682 to provide accurate determination of the translational position of the probe 678 relative to the dock 662. The camera 184 can be directly above the marking 682. In some methods, the camera 184 can read a binary code of the marking 682.

The surgical orientation device 172 can use the length measurement from the camera 184 and the data from the orientation sensing device 204 to determine the location of the distal end 680 of the probe 678. In some embodiments, the surgeon will enter an input (e.g., depress a button) to collect data from the orientation sensing device 204. In some methods, the surgeon will enter an input (e.g., depress a button) to collect data from the camera 184. In some embodiments, the surgeon will enter an input (e.g., depress a button) to collect data from the orientation sensing device 204 and the camera 184 simultaneously. In some methods, the orientation sensing device 204 and/or the camera 184 will only send data if the orientation sensing device 204 is stable or non-moving.

Once the foregoing points of the pelvis have been navigated and the data recorded into the surgical orientation device 172, the Anterior Pelvic Plane can be calculated from data indicating the navigated points. The system 600 can calculate the Anterior Pelvic Plane from the three points recorded by the system 600. The three points are shown in FIG. 12A. FIG. 25B illustrates the inter-ASIS line. The inter-ASIS line connects Point 1 and Point 2. The inter-ASIS line provides a straight line between the ipsilateral ASIS and the contralateral ASIS. FIG. 25C illustrates the general horizontal direction of the Anterior Pelvic Plane. The Anterior Pelvic Plane can be considered a horizontal plane that pivots about the inter-ASIS axis depending on the location of Point 3. FIG. 25D illustrates the Anterior Pelvic Plane (APP) which is determined by Point 3. The Anterior Pelvic Plane includes the ipsilateral ASIS, the contralateral ASIS, and the anterior surface of the pubic symphysis.

As described herein, the system 600 can determine a reference plane. The plane can be uniquely determined by any of the following: three non-collinear points, a line and non-collinear point, two distinct but intersecting lines, or two parallel lines. In some methods of use, the Anterior Pelvic Plane is calculated based on three non-collinear points. In some methods of use, the Anterior Pelvic Plane is calculated based on ipsilateral ASIS, contralateral ASIS, and the anterior surface of the pubic symphysis. In some methods of use, the orientation of the Anterior Pelvic Plane can be a baseline for placement of the cup portion of a hip prosthesis. The surgical orientation device 172 can display information with respect to the Anterior Pelvic Plane. In some methods of use, the abduction and anteversion angles in cup placement in total hip arthroplasty can be with respect to the Anterior Pelvic Plane. The Anterior Pelvic Plane is cited in literature as a valid anatomical plane to guide cup placement. In some embodiments, the Anterior Pelvic Plane is determined by the surgical orientation device 172 and/or the orientation sensing device 204. In some embodiments, a reference frame is established by the Anterior Pelvic Plane. The Anterior Pelvic Plane reference frame is a three dimensional reference frame. The Anterior Pelvic Plane reference frame is a reference frame that contains the Anterior Pelvic Plane. In some embodiments, the surgical orientation device 172 and/or the orientation sensing device 204 can provide orientation and/or position data related to the Anterior Pelvic Plane reference frame. In some embodiments, the surgical orientation device 172 can display orientation and/or position data relative to the Anterior Pelvic Plane reference frame.

FIGS. 26A-26D illustrate method steps to calculate a table plane. Any method to establish the table plane described herein or incorporated by reference can be utilized. The table plane can be a horizontal or generally horizontal plane. In some techniques, the operating table is horizontal and the table plane approximates the plane of the table. In some techniques, the table plane can be oriented relative to other surface in the operating room. In some techniques, the floor is horizontal and the table plane approximates the plane of the floor. In some techniques, the wall is vertical and the table plane approximately a plane perpendicular to the wall. In some techniques, the ceiling is horizontal and the table plane approximates the ceiling. Other surfaces may be use to approximate a horizontal plane. The table registration estimates the coronal plane or frontal plane. The coronal plane is a plane that divides the body in anterior and posterior sections. The coronal plane is a horizontal reference plane when the patient is in the supine position of the anterior approach. The orientation sensing device 204 can register the operating table or perform table registration for the anterior approach. The top surface of the operating table upon which the patient is positioned is positioned horizontally. The patient can be positioned so that the coronal plane of the pelvis is level, e.g., parallel to the table and/or also horizontal. The user can visually verify the coronal plane is level or can use devices to position the patient's body to align the coronal plane with the plane of the top surface of the table. In some embodiment, a reference plane based on the plane of the top surface of the table can be input into the system 600.

The table plane provides clinical value. In some techniques, the table plane can provide a secondary reference plane to the Anterior Pelvic Plane. In some embodiments, the table plane is determined completely independently of any anatomical landmarks. The table plane provides a check against gross errors from the anatomical registrations. The table plane provides a reference plane that is unaffected by pelvic tilt. The table plane provides a reference plane that is unaffected by errors in registration due to soft tissue. The table plane appears in large console navigation. The table plane is calculated based on properly aligning the probe 678. In some methods of use, the alignment of the probe 678 can be done entirely by eye. The table plane provides a horizontal plane which may be useful for comparing the navigated cup angles to pre-operative and/or post-operative images. The pre-operative and/or post-operative images, such as x-rays, are captured within a horizontal reference plane. The table plane may provide a horizontal reference plane that approximates the horizontal reference plane of imaging techniques.

During table registration, the probe 678 is coupled with the orientation sensing device 204. In some methods of use, the probe 678 and the orientation sensing device 204 are constrained. As one example, the probe 678 can be coupled with other components of the first assembly 604 and/or the second assembly 606. In some methods of use, the system 600 is assembled, such that the first assembly 604 and the second assembly 606 are coupled to the patient via the fixation pins 610, 612. There may be mechanical constraints imposed by the pivot configuration of the system 600.

Figure 26B:
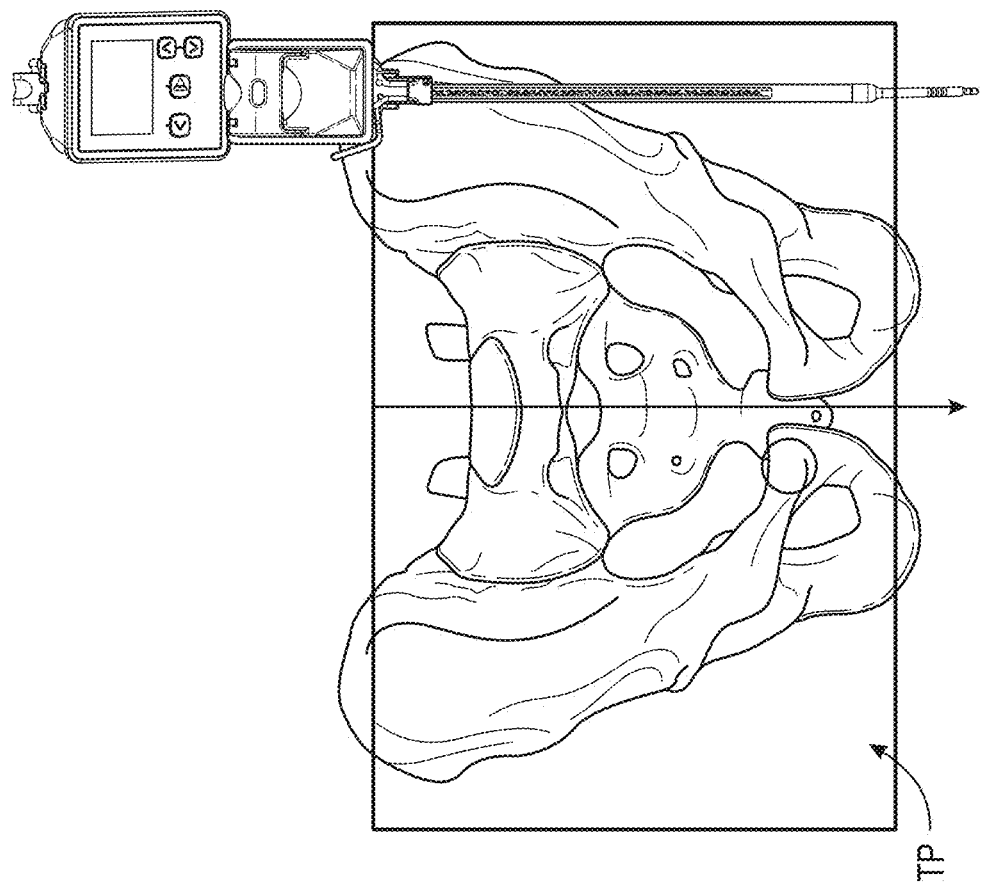
FIGS. 26A-26D illustrates method steps to identify a table or other horizontal plane.
Figure 26A:
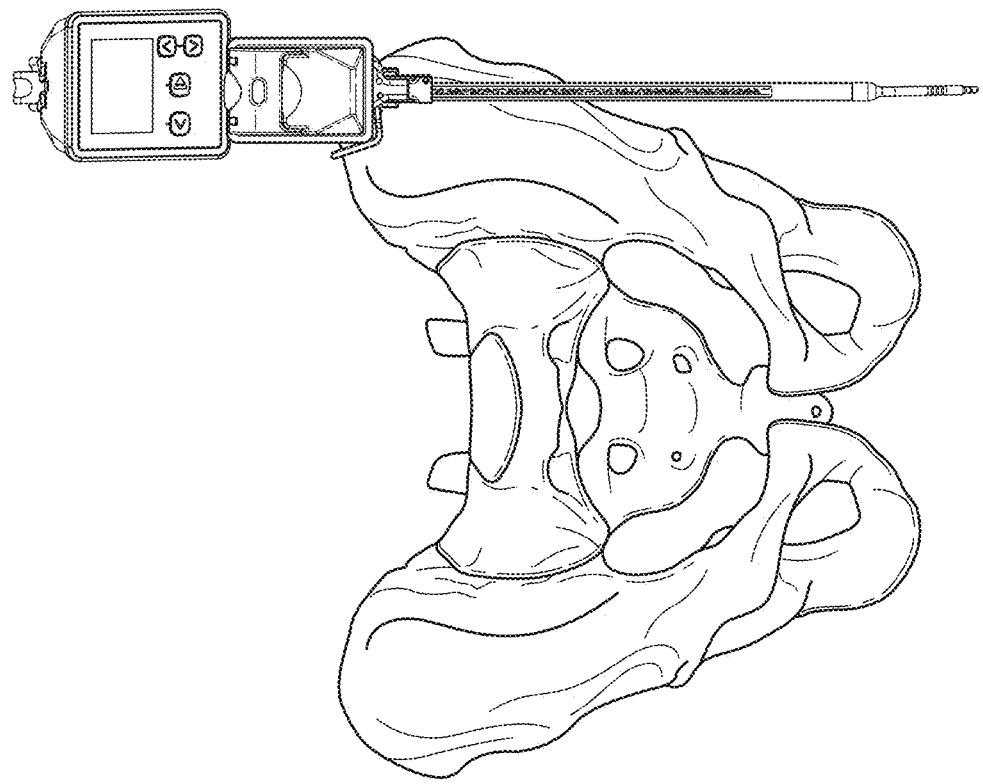

FIG. 26A illustrates the position of the probe 678 during table registration. The probe 678 is rotated and/or pivoted by the mount 658 such that the probe 678 points in a direction that is parallel to the patient's sagittal plane. The probe 678 can be extended toward the patient's foot. The probe 678 can be aligned with the long axis of the body. The probe 678 can be held substantially parallel to the plane of the table. Referring back to FIG. 22, the side view of the patient illustrates one line which is parallel to the table. During table registration, the probe 678 can be parallel to the table as viewed from the side. In some embodiments, the user can align the probe 678 with the horizontal. The user can visually inspect the probe 678 from one or more locations. For instance, the user can inspect the probe 678 from a top view and a side view. In some embodiments, the user can align the probe 678 with the sagittal plane. The probe 678 can be parallel with the sagittal plane or a para-sagittal plane. The sagittal plane divides the body into right and left parts.

FIG. 26B illustrates the table plane (TP) in a method of use. The probe 678 can be immobilized and the position and/or orientation of the orientation sensing device 204 can be recorded by the surgical orientation device 172. The user can enter an input to register the table (e.g., depress a button on the surgical orientation device 172). The user can interact with a user interface on the surgical orientation device 172 to signal to the surgical orientation device 172 to capture the position and/or orientation of the orientation sensing device 204. The surgical orientation device 172 can indicate that the table plane was recorded.

In some embodiments, information from one or more inertial sensors is used during table registration. As described herein, the orientation sensing device 204 and the surgical orientation device 172 can include one or more inertial sensors. In some embodiments, the position and/or the orientation of one or more inertial sensors can provide data related to the table plane. The one or more inertial sensors can detect gravity and provide a vector for the down direction. The table plane is considered a horizontal plane. In some methods of use, the vector for the down direction can be used by the system to verify that the table plane is a horizontal plane. In some embodiments, only the direction of the projection of the probe 678 onto a horizontal plane is used. In some embodiments, the table plane is determined by the surgical orientation device 172. In some embodiments, a reference frame is established by the table plane. The table reference frame is a three dimensional reference frame. The table reference frame can be determined by the orientation sensing device 204 and the surgical orientation device 172. The table reference frame can be determined in a different way for the anterior and posterior approach. For instance, different sensors of the orientation sensing device 204 and the surgical orientation device 172 can be utilized to determine the table reference frame for the anterior and posterior approach.

The table plane provides an estimation of the orientation of the coronal plane. The table plane may be recorded and stored in the system 600. The system 600 can calculate cup angles based on the table plane based on the assumption that the pelvis of the patient is correctly positioned during registration of the table plane. In some methods of use, the abduction and anteversion angles in cup placement in total hip arthroplasty can be with respect to the plane determined during table registration.

In some techniques, the table registration can be completed prior to dislocating the hip. The torque applied during dislocation can move pelvis away from the correct initial alignment. In some techniques, the fixation base 602 cannot be adjusted by the user after table registration. For instance, the user cannot adjust the fixation base 602 relative to the pins 610, 612. The fixation base 602 remains in position for the rest of the procedure. In some techniques, the pelvic bracket 638 cannot be adjusted by the user after table registration. The pelvic bracket 638 remains in position for the rest of the procedure. In some techniques, angle of the pelvic bracket 638 relative to the fixation base 602 cannot be changed after table registration. In some techniques, the probe 678 cannot be replaced with a different probe after table registration. The same probe 678 is used for the remainder of the procedure.

Figure 26D:
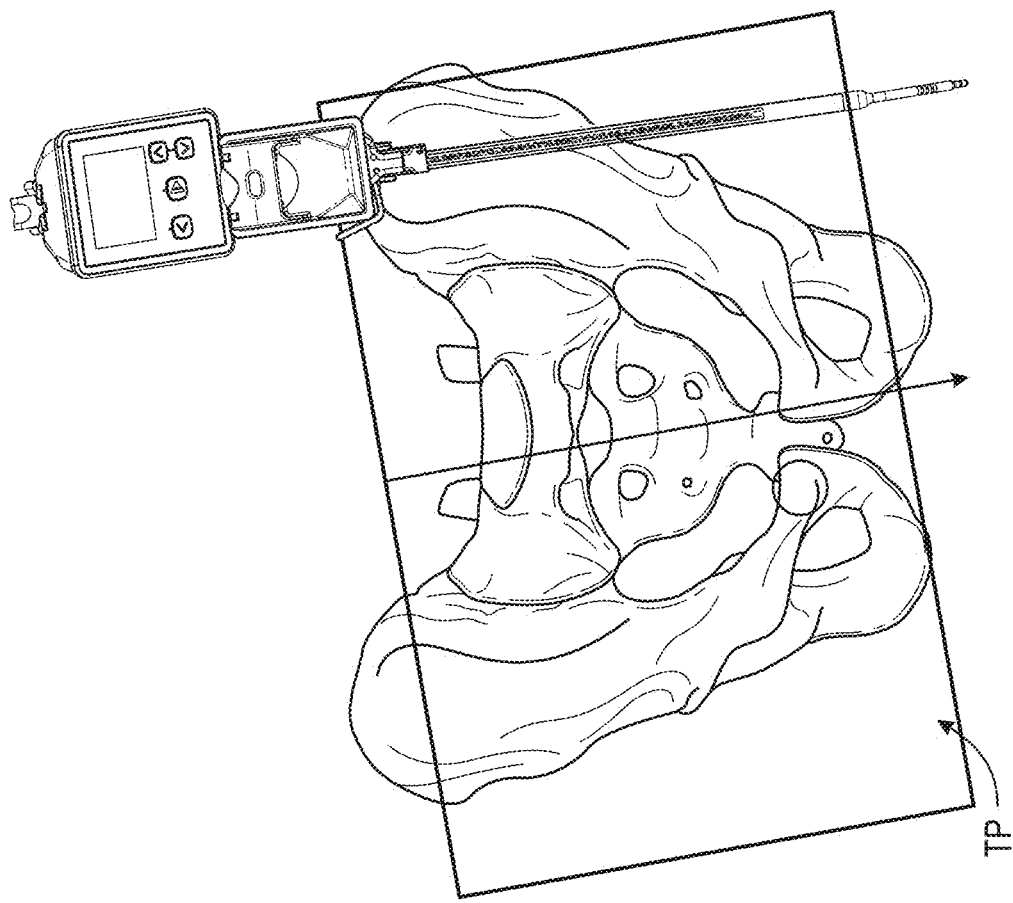
Figure 26C:
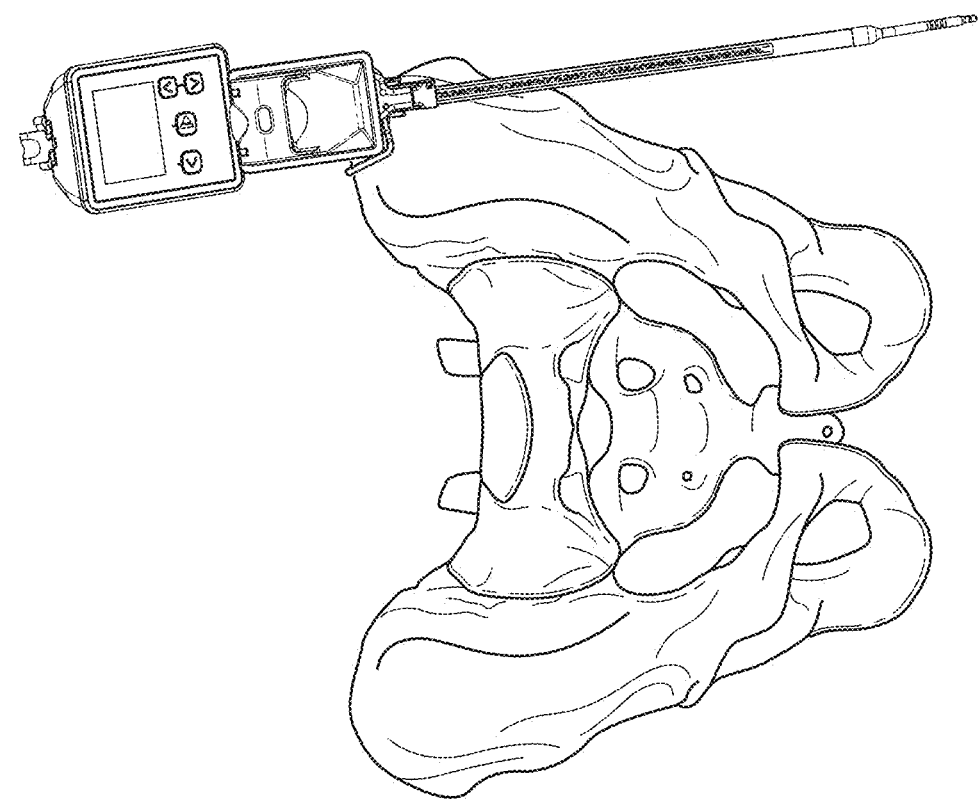

FIGS. 26C and 26D illustrate another outcome of table registration. In some methods of use, the probe 678 can be oriented at in an infinite number of angles from horizontal during table registration. For instance, when viewed from the side similar to the view of FIG. 22, the probe 678 may appear to be aligned with the coronal plane. However, the top view, shown in FIG. 26C, shows that the probe is angled relative to the sagittal plane. The user can introduce other errors based, in part, on the point of view of the user when probe 678 is positioned. FIG. 26D shows the resulting table plane (TP). FIGS. 13B and 26D show two different planes calculated during table registration. In both methods of use, the probe 678 is positioned parallel to the operating table. However, the two planes are angled based on the positioning of the probe 678. In some methods of use, there may be a potential for misalignment due to improper positioning of the probe 678.

Figure 27B:
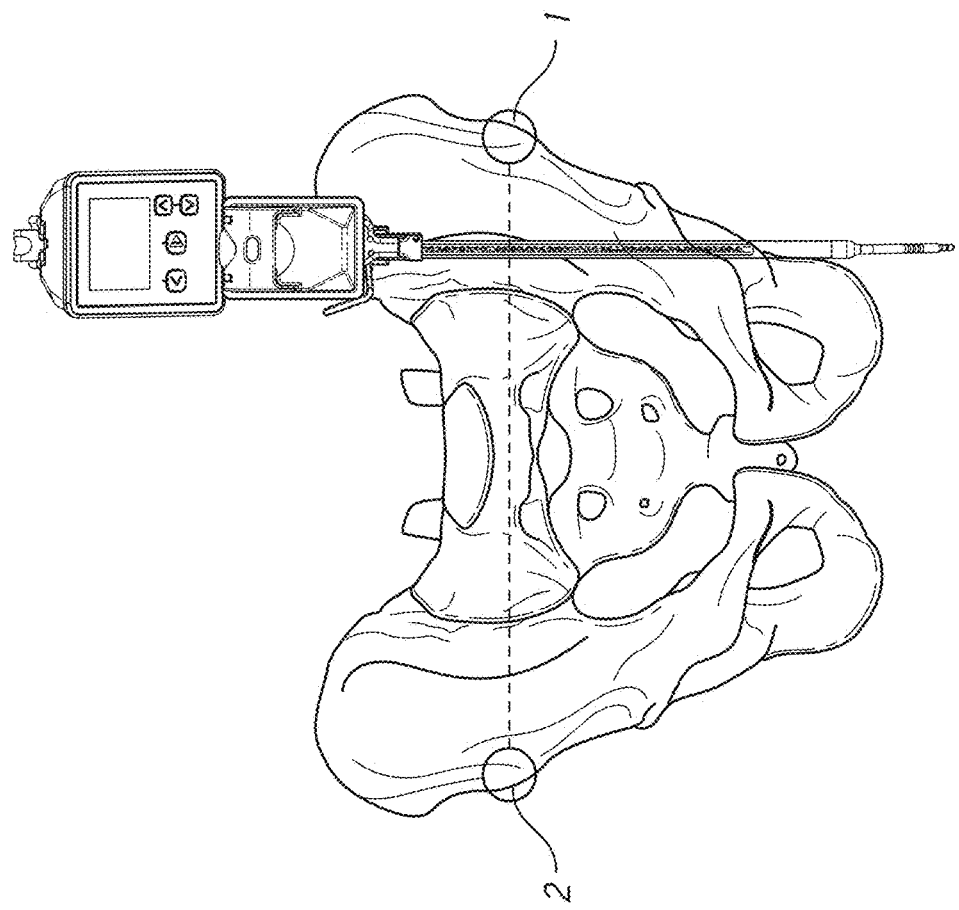
Figure 27A:
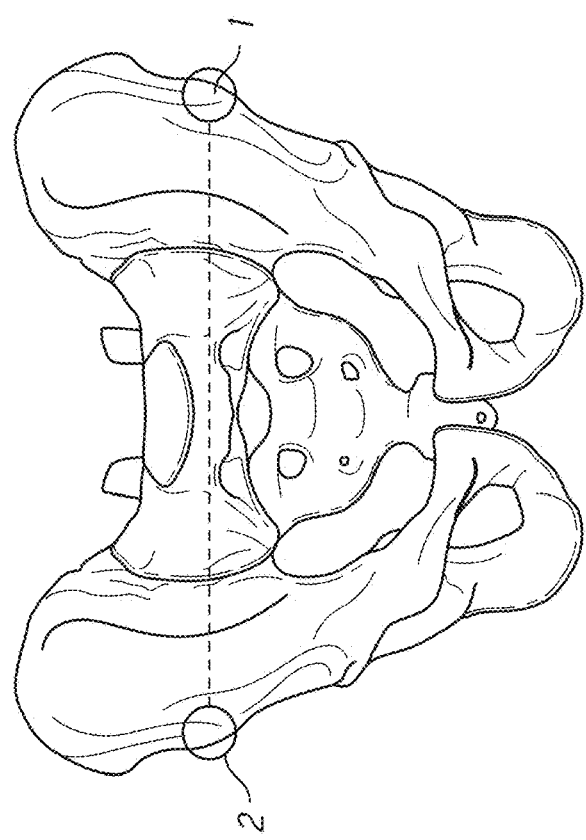

FIGS. 27A-27D illustrate method steps to calculate an Adjusted Plane (ADJUSTED). FIG. 27A illustrates the inter-ASIS line. The inter-ASIS line connects Point 1 and Point 2 discussed above in connection with FIG. 25A. The inter-ASIS line provides a straight line between the ipsilateral ASIS and the contralateral ASIS. As described herein, Point 1 and Point 2 can be recorded by the system 600. Point 1 and Point 2 can be recorded as part of a method to calculate the Anterior Pelvic Plane. Point 1 and Point 2 can be recorded independently from a method to calculate the Anterior Pelvic Plane. The Adjusted Plane can be calculated in addition or as an alternative to the Anterior Pelvic Plane. In some methods, Point 1 and Point 2 are used to calculate the Anterior Pelvic Plane and the Adjusted Plane. The system 200 can store Point 1 and Point 2 for the Anterior Pelvic Plane and the Adjusted Plane. In some methods, Point 1 and Point 2 are registered only once for the Anterior Pelvic Plane and the Adjusted Plane.

The system 600 can generate the Adjusted Plane by registering Point 1 and Point 2. These anatomical features are visible and/or palpable while the patient is in a supine position. The system 600 is then able to provide the user navigation data of the orientation of a hip instrument (e.g., the impactor 300A or any impactor with the universal impactor adapter 350, 352) with respect to the Adjusted Plane. In some methods of use, the navigation data is provided in real-time. In the anterior approach, the patient is positioned on his/her back and the Adjusted Plane is oriented horizontally, e.g., parallel to the plane of the table on which the patient is positioned.

FIG. 27A illustrates the approximate location of two points of the Adjusted Plane. The surgeon can register Point 1 and Point 2, as described herein. In some methods, Point 1 is the ipsilateral ASIS. In some methods, the distal end 680 of the probe 678 is positioned at the ipsilateral ASIS landmark. While the probe 678 is contacting the landmark, the position and/or orientation of the orientation sensing device 204 can be transmitted to the surgical orientation device 172. While the probe 678 is contacting the landmark, the distance that the probe 678 is extended, as measured by the camera 184, can be transmitted to the surgical orientation device 172. The user can enter an input to record Point 1 (e.g., depress a button on surgical orientation device 172). The surgical orientation device 172 can provide an indication that Point 1 was recorded, such as a visual or audial cue.

In some methods, Point 2 is the contralateral ASIS. In some methods, the distal end 680 of the probe 678 is placed at the contralateral ASIS landmark. In some methods, the distal end 680 of the probe 678 is positioned at the contralateral ASIS landmark. While the probe 678 is contacting the landmark, the position and/or orientation of the orientation sensing device 204 can be transmitted to the surgical orientation device 172. While the probe 678 is contacting the landmark, the distance that the probe 678 is extended, as measured by the camera 184, can be transmitted to the surgical orientation device 172. The user can enter an input to record Point 2 (e.g., depress a button on surgical orientation device 172). The surgical orientation device 172 can provide an indication that Point 2 was recorded, such as a visual or audial cue.

The Adjusted Plane is found by a rotation of the Anterior Pelvic Plane about the inter-ASIS line to be perpendicular to the force of gravity. The Adjusted Plane utilizes a measurement of gravity. As described herein surgical orientation device 172 comprise one or more inertial sensors. As described herein orientation sensing device 204 comprise one or more inertial sensors. In some embodiments, inertial data from one or more inertial sensors is used to calculate the Adjusted Plane. In some embodiments, the position and/or the orientation data of one or more inertial sensors is used to calculate the Adjusted Plane. The surgical orientation device 172 and/or the orientation sensing device 204 can comprise an accelerometer, which can provide a measurement of the direction of gravity. In some embodiments, the surgical orientation device 172 and/or the orientation sensing device 204 includes a sensor to detect the direction of gravity. The surgical orientation device 172 and/or the orientation sensing device 204 can be sensitive to the direction of gravity. The one or more inertial sensors can provide a vector aligned with vertical, e.g., for the down direction. In some embodiments, the surgical orientation device 172 and/or the orientation sensing device 204 includes a three axis accelerometer to detect orientation relative to or of gravity.

In some embodiments, the surgical orientation device 172 includes an accelerometer. In some embodiments, the orientation sensing device 204 includes an accelerometer. The accelerometer at rest can measure the acceleration due to Earth's gravity. The accelerometer can measure the acceleration from gravity straight downward or vertically. In some embodiments, the accelerometer can detect the magnitude and direction of the force of gravity. The accelerometer can produce a vertical vector. The accelerometer can produce a horizontal vector by transforming the vertical vector (e.g., by rotation of 90 degrees). The accelerometer can provide orientation and/or position data such that the Adjusted Plane is perpendicular to the force of gravity.

The surgical orientation device 172 and/or the orientation sensing device 204 can provide a reference to gravitational zero. Gravitational zero, as referred to herein, refers generally to an orientation in which an axis of a sensor is perpendicular to the force of gravity, and thereby experiences no angular offset, for example tilt, pitch, roll, or yaw, relative to a gravitational force vector.

In some methods of use, the measurement of gravity can be taken at any point during the procedure. The measurement of gravity can be taken during pre-operative calibration. The measurement of gravity can be taken during table registration. In some methods, the probe 678 is placed horizontally. The placement of the probe 678 can provide verification that the gravitational measurement is free from gross errors. FIG. 27B illustrates one position of the probe 678 to calculate the direction of gravity when the probe 678 is generally horizontal. The probe 678 is rotated and/or pivoted by the mount 658 such that the probe 678 points in a direction that is parallel to the patient's sagittal plane. The probe 678 can be extended toward the patient's foot. The probe 678 can be aligned with the long axis of the body. The probe 678 can be held substantially parallel to the plane of the table. In some embodiments, the user can align the probe 678 with the horizontal. The user can visually inspect the probe 678 from one or more locations. For instance, the user can inspect the probe 678 from a top view and a side view. In some embodiments, the user can align the probe 678 with the sagittal plane. The probe 678 can be parallel with the sagittal plane or a para-sagittal plane. The sagittal plane divides the body into right and left parts. As described herein, the orientation sensing device 204 can be positioned horizontally to measure gravity. As described herein, the probe 678 coupled to the orientation sensing device 204 can be positioned horizontally or substantially horizontally to measure gravity.

The probe 678 can be held in position or immobilized. The position and/or orientation of the orientation sensing device 204 can be recorded by the surgical orientation device 172. The user can enter an input when the probe 678 is positioned horizontally (e.g., depress a button on the surgical orientation device 172). The user can interact with a user interface on the surgical orientation device 172 to signal to the surgical orientation device 172 to capture data of the orientation sensing device 204 when the probe 678 is positioned horizontally. The surgical orientation device 172 can indicate that data was recorded. The Adjusted Plane can be calculated in addition or as an alternative to the table plane. The system 200 can store gravitational zero for calculations related to the Anterior Pelvic Plane. In some methods, gravitational zero is registered only once and utilized throughout the procedure.

In some methods of use, the orientation sensing device 204 can be positioned in other ways than horizontally to measure the direction of gravity. In some methods of use, the orientation sensing device 204 can measure gravity when in the home position. In some methods of use, the orientation sensing device 204 can be positioned vertically or substantially vertically to measure gravity. In some methods of use, the orientation sensing device 204 can measure gravity when contacting a point or anatomical landmark. In some methods of use, the orientation sensing device 204 can measure gravity when contacting Point 1. In some methods of use, the orientation sensing device 204 can measure gravity when contacting Point 2. In some methods of use, the orientation sensing device 204 can measure gravity when contacting a point on the femur. The point on the femur can be a mark, such as Fm described herein. The point on the femur can be a structure. The point on the femur can be an anatomical landmark. In some methods of use, the orientation sensing device 204 can measure the force of gravity at any angular orientation. In some methods of use, the orientation sensing device 204 determine a vertical vector of gravity when resting at any position.

In some embodiments, the surgical orientation device 172 measures gravity. The surgical orientation device 172 can provide an indication of the upward/downwards or vertical direction. The surgical orientation device 172 can produce a horizontal vector by transforming the vertical vector of gravity (e.g., by rotation of 90 degrees). In some embodiments, the surgical orientation device 172 remains stationary when measuring gravity. In some embodiments, the surgical orientation device 172 is coupled or affixed to the pelvis of the patient when measuring gravity. In some methods of use, the surgical orientation device 172 is coupled to the patient via the fixation pins 610, 612 when measuring gravity. In some methods of use, the surgical orientation device 172 is constrained when measuring gravity. As one example, the surgical orientation device 172 can be coupled with other components of the first assembly 604 and/or the second assembly 606. In some embodiments, the orientation sensing device 204 and the surgical orientation device 172 both determine the direction of gravity. In some embodiments, inertial data from two or more sensors are used to measure gravity.

FIG. 27C illustrates a horizontal direction of the Adjusted Plane. The Adjusted Plane can be considered a horizontal plane that pivots about the inter-ASIS line depending on the measurement of gravity. FIG. 27D illustrates the Adjusted Plane. Once the foregoing points of the pelvis have been navigated and the data recorded into the surgical orientation device 172, the Adjusted Plane can be calculated from data indicating the navigated points and the gravity measurement. The Adjusted Plane includes the ipsilateral ASIS and the contralateral ASIS. The Adjusted Plane includes the inter-ASIS line. The system 600 can combine the horizontal vector with Point 1 and Point 2 to calculate the Adjusted Plane. In some embodiments, the Adjusted Plane can be considered a horizontal plane determined by the direction of gravity. In some embodiments, the Adjusted Plane can be considered a horizontal plane containing the inter-ASIS line.

As described herein, three anatomical landmarks are registered for the Anterior Pelvic Plane. The ipsilateral ASIS, the contralateral ASIS, and the pubic symphysis, as registered by the probe 678, define the Anterior Pelvic Plane. As described herein, two anatomical landmarks are registered for the Adjusted Plane. The two landmarks define the inter-ASIS line.

In some embodiments, the surgical orientation device 172 can provide a corrected reference frame by transforming, e.g., by rotating the Anterior Pelvic Plane about the inter-ASIS line based on the direction of gravity. In some embodiments, the surgical orientation device 172 can rotate the Anterior Pelvic Plane about the inter-ASIS line to provide a corrected reference frame that is aligned with horizontal. The measurement of gravity enables the surgical orientation device 172 to rotate the Anterior Pelvic Plane. The measurement of gravity enables the surgical orientation device 172 to establish the Adjusted Plane. The measurement of gravity enables the surgical orientation device 172 to calculate the angle that the Anterior Pelvic Plane must rotate to be aligned with horizontal. In some embodiments, the orientation sensing device 204 can rotate the Anterior Pelvic Plane about the inter-ASIS line based on the direction of gravity. The surgical orientation device 172 and/or the orientation sensing device 204 can include hardware or software to enable the transformation of, e.g., the rotation of, the Anterior Pelvic Plane based on the direction of gravity. The one or more inertial sensors of the orientation sensing device 204 and/or the surgical orientation device 172 can provide data to determine how to transform, e.g., to rotate, a plane containing the inter-ASIS axis to be perpendicular to the force of gravity. In some methods of use, the vector for the down direction can be used by the orientation sensing device 204 and/or the surgical orientation device 172 to determine a horizontal plane containing the inter-ASIS axis. In some methods of use, inertial data related to gravity can be used by the system 600 to determine the degree in which to rotate the Anterior Pelvic Plane about the inter-ASIS axis to be horizontal.

The orientation of the Adjusted Plane can be a baseline for placement of the cup portion of a hip prosthesis. The surgical orientation device 172 can display information with respect to the Adjusted Plane. In some methods of use, the abduction and anteversion angles in cup placement in total hip arthroplasty can be with respect to the Adjusted Plane. In some embodiments, the Adjusted Plane is determined by the surgical orientation device 172 and/or the orientation sensing device 204. In some embodiments, a reference frame is established by the Adjusted Plane. The Adjusted Plane reference frame is a three dimensional reference frame. The Adjusted Plane reference frame is a reference frame that contains the Adjusted Plane. In some embodiments, the surgical orientation device 172 and/or the orientation sensing device 204 can provide orientation and/or position data related to the Adjusted Plane reference frame. In some embodiments, the surgical orientation device 172 can display orientation and/or position data relative to the Adjusted Plane reference frame.

Once registration is complete, the user can proceed to proceed to dislocate the hip, resect the femoral head, and prepare the acetabulum. The user can prepare the impactor and shell. The user can remove the second assembly 606 from the first assembly 604. The user can remove the orientation sensing device 204 from the probe 678. The user can dock the orientation sensing device 204 to the first assembly 604. The surgical orientation device 172 and the orientation sensing device 204 form a general V-shaped configuration, similar to the orientation shown in FIG. 12A.

The user can set the cup angle. The user can remove the orientation sensing device 204 from the first assembly 604. The orientation sensing device 204 and the surgical orientation device 172 can at this point be used to guide placement of the cup in the prescribed orientation. The surgeon can remove the extension 670 from the third coupler 668. The surgeon can couple the extension 670 to an impactor 300A, shown in FIG. 18A. The surgeon can couple the extension 670 to any of the universal impactor adapters 350, 352 described herein. The universal impactor adapter 350, 352 can be utilized to mount the fourth coupler 342 to any impactor. The fourth coupler 342 can allow the orientation sensing device 204 to couple to the impactor. The impactor can be configured to be modified to suit any of a plurality of hip prostheses or the impactor can be designed to suit a particular hip prosthesis.

The acetabular shell can be inserted into the acetabulum and positioned at the desired angle. The surgical orientation device 172 can guide the surgeon in setting the appropriate cup angle. The surgical orientation device 172 can graphically display when the orientation sensing device 204 is navigated to the desired abduction and anteversion angles. The desired abduction and anteversion angles can be preoperative cup angles entered by the surgeon during calibration. The surgical orientation device 172 can graphically display the abduction and anteversion angles as the orientation sensing device 204 is moved. The user can align impactor at desired cup angle. Aligning a visual indicator of the surgical orientation device 172 can guide the user to position the impactor at the desired cup angles. The abduction and anteversion angles can be displaced statically. The cup angles can be checked after impacting by repeating the proceeding steps.

The surgical orientation device can provide cup angles relative to any reference plane, including those described herein. The Adjusted Plane can provide several advantages over the table registration. The Adjusted Plane can increase the accuracy of the table registration. For instance, the Adjusted Plane provides a verification of the horizontal direction of the probe 678 via a measurement of gravity. For instance, the Adjusted Plane improves placement of the horizontal plane by including anatomical landmarks or points. For instance, the Adjusted Plane can include one or more anatomical locations. For instance, the Adjusted Plane can include an anatomical line. For instance, the Adjusted Plane can include the inter-ASIS line as described above. From a side view, the Adjusted Plane can look as though it is the same as the table plane. However, the Adjusted Plane includes the inter-ASIS line whereas the table plane may not always include this line. The table registration may introduce some errors in orientating the horizontal plane. There may be greater accuracy in the Adjusted Plane since it orients the plane based on anatomical landmarks and a measurement of gravity.

The surgical orientation device 172 can include indicia such as a target or bullseye to indicate the pre-determined abduction and anteversion angles. The surgical orientation device 172 can include indicia such as a dot or cross-hair to indicate movement of the impactor. Aligning the indicia in the center of the target or bullseye can indicate that the impactor is aligned with the predetermined cup angles. The indicia can move in real-time. The surgical orientation device 172 can include a readout of the abduction and anteversion angles. The angles can be calculated in real-time. The angles can change as the impactor is moved. The user can have a set amount of time to align the impactor with the desired cup angles. The user can enter an input once the desired cup angles are reached. In some methods, after the impactor is positioned relative to the desired cup angles, the cup angles can be displayed statically. The surgical orientation device 172 can provide information regarding the pelvis or other information dynamically.

After positioning the cup, the user can attach the second system 606 to the first system 604, similar to the configuration shown in FIG. 1. The user can verify the home position. In some techniques, a distal end of the probe 678 can be engaged with a point on the fixation base 602, such as divot. The probe 678 can be vertical in the home position. The orientation sensing device 204 can be vertical in the home position. The user can repeat registration if the home position has shifted. The user can end the procedure. The user can remove the system 600 prior to closure.

In some methods of use, the user can measure for leg length and joint offset. At the surgeon's discretion the system 600 can be used to navigate a condition, location and/or orientation of the femur prior to hip replacement. In some embodiments, a mark Fm as shown in FIG. 24 may be made on the proximal femur. In some embodiments, a structure is attached to the femur, such as a pin. In some embodiments, a burr or detent is made in the femur. Thereafter the orientation sensing device 204 can be initialized or zeroed such as by placing it back in the home position. Thereafter, the distal end 680 of the probe 678 can be brought into contact with the femur mark Fm. The surgical orientation device 172 can be signaled to record the orientation of the orientation sensing device 204. A distance from the point of attachment of the fixation pins 610, 612 to the marked position on the femur can then be recorded in the surgical orientation device 172. The position can be based on capturing the markings 682 the probe 678 or probe inlay 676 by the camera 184, in combination with inertial data from the orientation sensing device 204.

If femoral landmark Fm is acquired in the procedure prior to separating the natural joint, the same landmark can be acquired after the prosthetic joint is placed to confirm that the replacement of the joint has not changed either the length of the leg, the off-set of the leg from the trunk of the patient or both. Thereafter, the distal end 680 of the probe 678 can be brought into contact with the same landmark (e.g., Fm) acquired early in the procedure. The orientation of the orientation sensing device 204 and the extension of the probe 678 can be input into the surgical orientation device 172. These data enable the surgical orientation device 172 to output amounts of change in leg length and leg offset.

In some methods of use, the system 600 includes an optical component 174 shown in FIG. 6A and/or the optical component 194 shown in FIGS. 6B-6C. In some embodiments, the optical component 174, 194 is a separate component. In some embodiments, the optical component 174, 194 is coupled to the first assembly 604. In some embodiments, the optical component 174 can be rotated relative to the first assembly 604, for instance by a knob 176. The optical component 174, 194 can comprise one or more lasers, which can be configured to project laser light. The optical component 174, 194 can provide a visual guide to replicate the original position of the femur relative to the pelvis. The laser light can be used to project a point, a plane, and or a cross-hair onto a target or targets, including but not limited to an anatomical feature or landmark. The surgeon can mark one or more points along the line of the projection of the optical component 174, 194. The surgeon can complete any steps described herein. The surgeon, thereafter, can verify the one or more points are along the line of the projection of the optical component 174, 194. When measuring changes in leg length and lateral joint offset, the apparent changes are sensitive to changes in the orientation of the femur relative to the pelvis. The user can reposition the femur prior to measuring the change such that the orientation of the femur relative to the pelvis is the same as that when the preoperative baseline measurement was made.

Another method is to measure the orientation of the femur relative to pelvis during preoperative baseline and postoperatively and then correct for changes in orientation by doing a virtual rotation about the postoperative center of rotation of the femur. The method may require obtaining three points of the femur. The three points on the femur can be marks or anatomical landmarks. The three points can be on a femur plate. The three points on the femur or femur plate may be registered by the probe 678 to resolve for the femur orientation preoperatively and then postoperatively each time the leg length is to be measured.

2. Adjusted Plane and Anterior Pelvic Plane Comparison

Figure 28B:
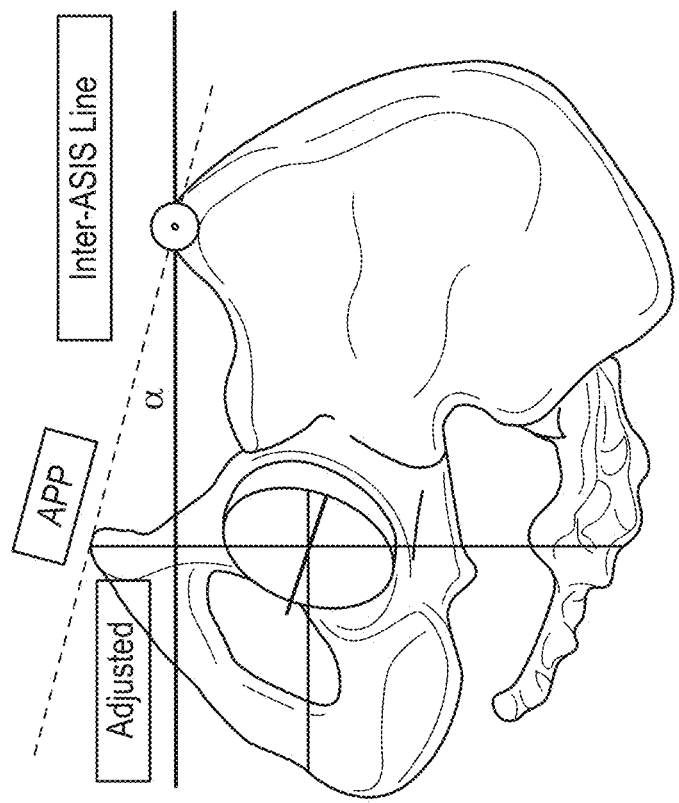
FIGS. 28A-28B illustrate side views of the pelvis and the Anterior Pelvic Plane and the Adjusted Plane thereof.
Figure 28A:
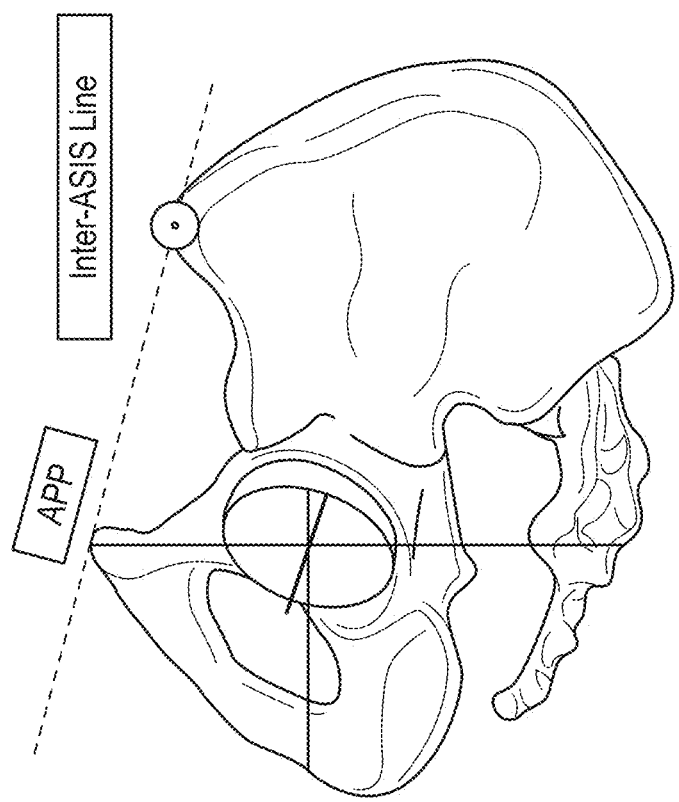
Figures 1, 28B:
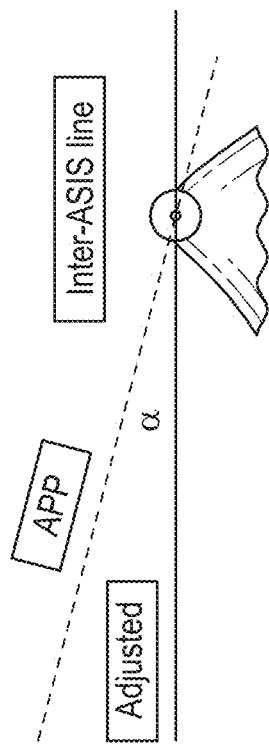
Figures 1, 28A:
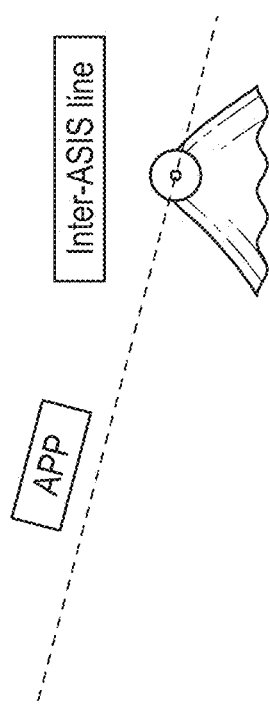
Figure 28C:
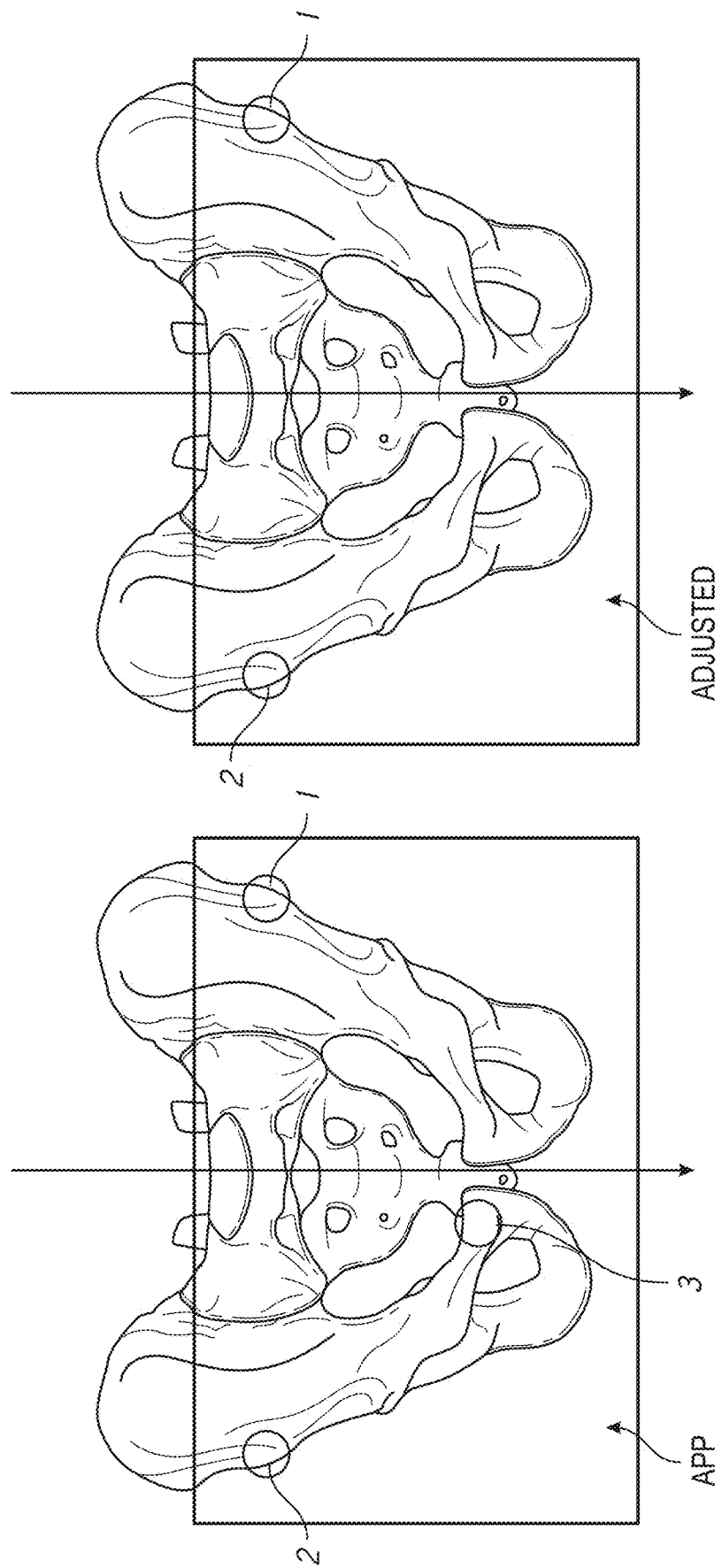
FIG. 28C illustrates a top view of these planes.

FIG. 28A illustrates a side view of the Anterior Pelvic Plane. The Anterior Pelvic Plane includes the inter-ASIS line as described herein. FIG. 28B illustrates a comparison between the Anterior Pelvic Plane and the Adjusted Plane. FIGS. 28A-1 and 28B-1 illustrate another side view of the system where in the ASIS are aligned. FIG. 28B illustrates a side view of the Anterior Pelvic Plane and the Adjusted Plane. FIG. 28C illustrates a top view of the Anterior Pelvic Plane and the Adjusted Plane. As described herein, the Anterior Pelvic Plane and the Adjusted Plane both contain the inter-ASIS line. The Anterior Pelvic Plane also contains Point 3 to define the plane. The Adjusted Plane utilizes the direction of gravity to define the plane. In some embodiments, the Anterior Pelvic Plane and the Adjusted Plane are coaxial about the inter-ASIS line as shown in FIGS. 28B and 28B-1. The Adjusted Plane is a rotation of the Anterior Pelvic Plane about the inter-ASIS line. The Adjusted Plane and the Anterior Pelvic Plane can form an angle alpha as shown in FIGS. 28B and 28B-1. The angle alpha can be a measurement of pelvic tilt. The angle alpha can measure the difference to horizontal from the Anterior Pelvic Plane. The angle alpha can adjust the Anterior Pelvic Plane such that the cup angles more closely match those shown in post-operative x-rays. In some embodiments, the Adjusted Plane adjusts for tilt. In some embodiments, the Adjusted Plane adjusts for tilt of the pubis relative to the inter-ASIS line.

The Adjusted Plane has clinical value. The pre-operative and post-operative x-rays produce two-dimensional images on a horizontal plane. The image receptor is positioned horizontally relative to the patient in the supine position. The image receptor captures the remnant beam as the beam exits the body of the patient. The anatomy of the patient is projected onto the horizontal plane of the image receptor. For pelvis x-rays, the routine projection is an anterior-posterior projection. The navigate angles can be correlated to the view of the post-operative x-ray via the Adjusted Plane. The Adjusted Plane may provide a horizontal reference plane that approximates the horizontal reference plane of imaging techniques. There is a clinical benefit in providing users with navigated cup angles during a procedure that will reflect those measured on post-operative x-rays. The navigated cup angles based on the Adjusted Plane can be provided in addition, or as a substitute to those based on the Anterior Pelvic Plane. The navigated cup angles based on the Adjusted Plane can be provided in addition, or as a substitute to those based on the table plane.

The adjustment from the Anterior Pelvic Plane to the Adjusted Plane can provide the user with cup angles that correlate to clinically expected cup angles. The adjustment from the Anterior Pelvic Plane to the Adjusted Plane can provide the user with cup angles that correlate to what they expect to see during surgery (e.g., a comparison between the image of the cup and the output of the system 600). The adjustment from the Anterior Pelvic Plane to the Adjusted Plane can provide the user with cup angles that correlate to what they expect to see on post-operative images (e.g., a comparison between the output of the system 600 and post-operative images). The user, such as a surgeon, correlates the output of the system 600 with numbers that correlate to clinical experience, e.g., calibrated to what they expect to see in post-operative images. The post-operative images can be 6 week post-operative supine films. The post-operative images are taken from a horizontal cross-section of the patient's body. The Adjusted Plane may be more similar to the plane of the post-operative images.

Before navigation systems, such as system 600, surgeons did not take measurements intra-operatively. Rather, surgeons typically looked at the cup placement during a procedure and determined whether current cup placement looked like previous cup placements. The surgeon would visually confirm cup placements during surgery and past experience in viewing post-operative images. The user would determine if the current cup placement was likely to correlate to the correct abduction and anteversion angles post-operatively. The surgeon would look at the cup placement and determine that the placement looks like 40 degrees×15 degrees based on their experience looking at post-operative images. The surgeon's confidence in the procedure would be based on their correlation of cup placement and post-operative images.

For the system 600, the user is provided with an output that assists a user to navigate to proper cup placement. The output can be abduction and anteversion angles displayed on the surgical orientation device 172. The user can navigate to the desired abduction and anteversion angles by moving components of the system 600, such as the impactor. When the user places the cup at the desired abduction and anteversion angles, the user wants to see the same or similar angle on post-operative images. The user's confidence in the navigation of the system 600 increases if the abduction and anteversion angles produced by the system 600 match the post-operative images.

The Adjusted Plane can be an improvement over a landmark-only reference plane, such as the Anterior Pelvic Plane, for some patients. In some embodiments, the Anterior Pelvic Plane may differ from the horizontal reference plane of imaging techniques due to patient specific factors. For instance, pelvic tilt may orient the Anterior Pelvic Plane at an angle from the horizontal reference plane of imaging techniques. For instance, the patient's high body mass index may impact the ability to contact anatomical landmarks. For instance, the anatomical features of the reference points may not be visible and/or palpable while the patient is in a supine position. For instance, the ipsilateral ASIS, the contralateral ASIS, and/or the pubic symphysis may not be visible and/or palpable. The patient specific factors can results in differences between navigated cup angles from the Anterior Pelvic Plane and angles measured post-operatively. In some methods of use, with some patients, the Anterior Pelvic Plane may not provide abduction and anteversion angles that match post-operative images.

The Adjusted Plane can be an improvement over a table plane-only reference frame for procedures. In some embodiments, the table plane may differ from the horizontal reference plane of imaging techniques. The user may introduce errors in the table plane by improper placement of the probe 678. In some methods of use, with some patients, the table plane may not provide abduction and anteversion angles that match post-operative images.

In some methods of use, two or more reference planes can be provided, e.g., any combination of the Adjusted Plane, the table plane, the horizontal plane and the Anterior Pelvic Plane. Any of the foregoing combinations of the reference planes provides redundancy that ensures that the angle information provided to the user is accurate and reliable such that the procedures performed will be better contained within an acetabular cup "safe zone".

Systems and methods described herein can improve prosthetic hip joint placement using navigation in combination of pre-operative imaging and landmark referencing. These hip procedures generally guide a prosthetic hip to an orientation within the acetabulum that minimizes the chance of dislocation due to impingement of the femoral neck on the cup or on bones around the acetabulum or other reasons related to suboptimal orientation of the prosthetic. Various techniques leverage population averages of proper placement while others are amenable to patient specific refinements.

3. Pelvis Tracking

Figure 29:
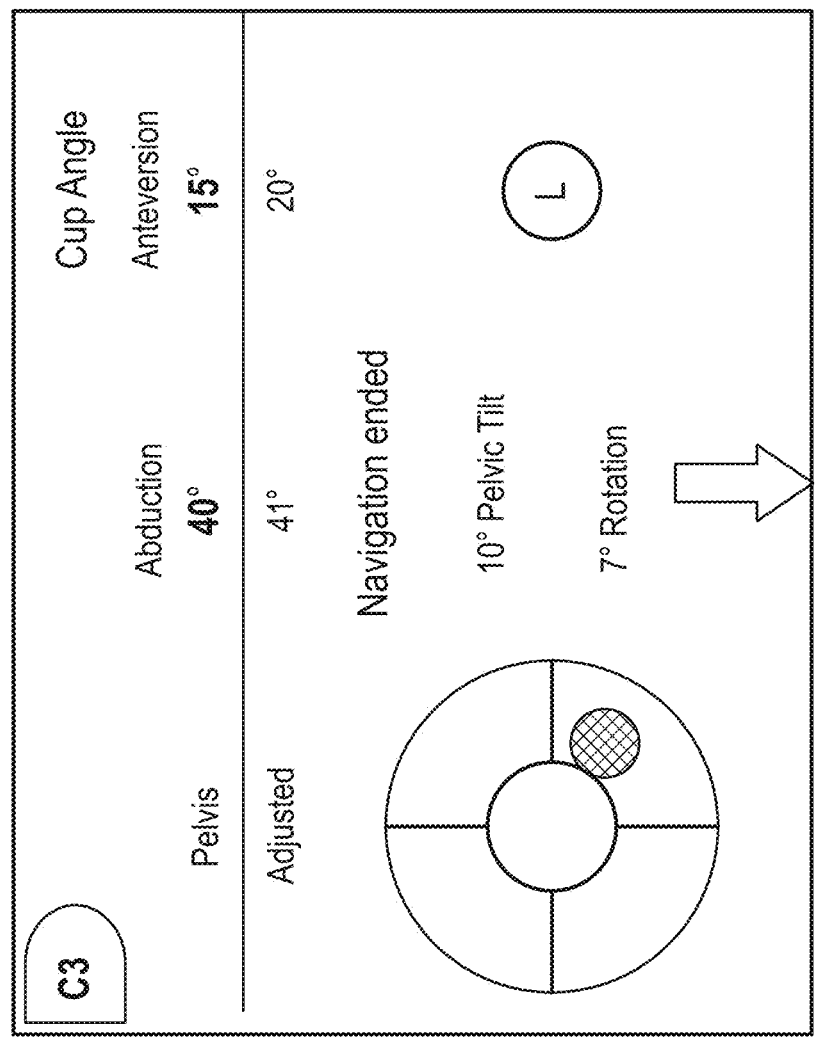
FIG. 29 illustrates a screen display of a surgical orientation device of the system of FIG. 1.

FIG. 29 shows a screen display for a hip method generated by one embodiment of the interactive user interface of the surgical orientation device 172. Once the orientation sensing device 204 is attached to the impactor 300A or any other impactor coupled to the universal impactor adapter 350, 352, the surgical orientation device 172 can display radiographic abduction and anteversion angles of impactor relative to a reference plane. The reference plane can be any plane including a frontal pelvic plane, the Anterior Pelvic Plane, the table plane, the Adjusted Plane, etc. The surgical orientation device 172 can display abduction and anteversion angles relative to two or more planes. In the illustrated embodiment, the surgical orientation device 172 can display radiographic abduction and anteversion angles relative to the Anterior Pelvic Plane. The surgical orientation device 172 displays "Pelvis" angles relative to the Anterior Pelvic Plane. The Anterior Pelvic Plane is based on inputs from the anatomic landmarks. In the illustrated embodiment, the surgical orientation device 172 can display radiographic abduction and anteversion angles relative to the Adjusted Plane. The surgical orientation device 172 displays "Adjusted" angles relative to the Adjusted Plane. The Adjusted Plane is a reference plane where the Anterior Pelvic Plane is rotated about the inter-ASIS axis until its superior-inferior axis is parallel to the level table. This effectively adjusts for pelvic tilt. The "Adjusted" angles may correlate with post-operative x-rays which use a horizontal plane.

The surgical orientation device 172 can display additional information for the user. For instance, the surgical orientation device 172 can display information related to the position and orientation of the pelvis. As described herein, the surgical orientation device 172 can be coupled to the pelvis such that the surgical orientation device 172 can measure changes in the pelvis. The surgical orientation device 172 can include one or more inertial sensors that can track the position of the pelvis during the procedure. The surgical orientation device 172 can display the change in positioning of the pelvis in real time. The surgical orientation device 172 can provide an indicia if the position of the pelvis has changed beyond a threshold, for instance by a visual or audial cue.

Figures 30A, 30B, 30C:
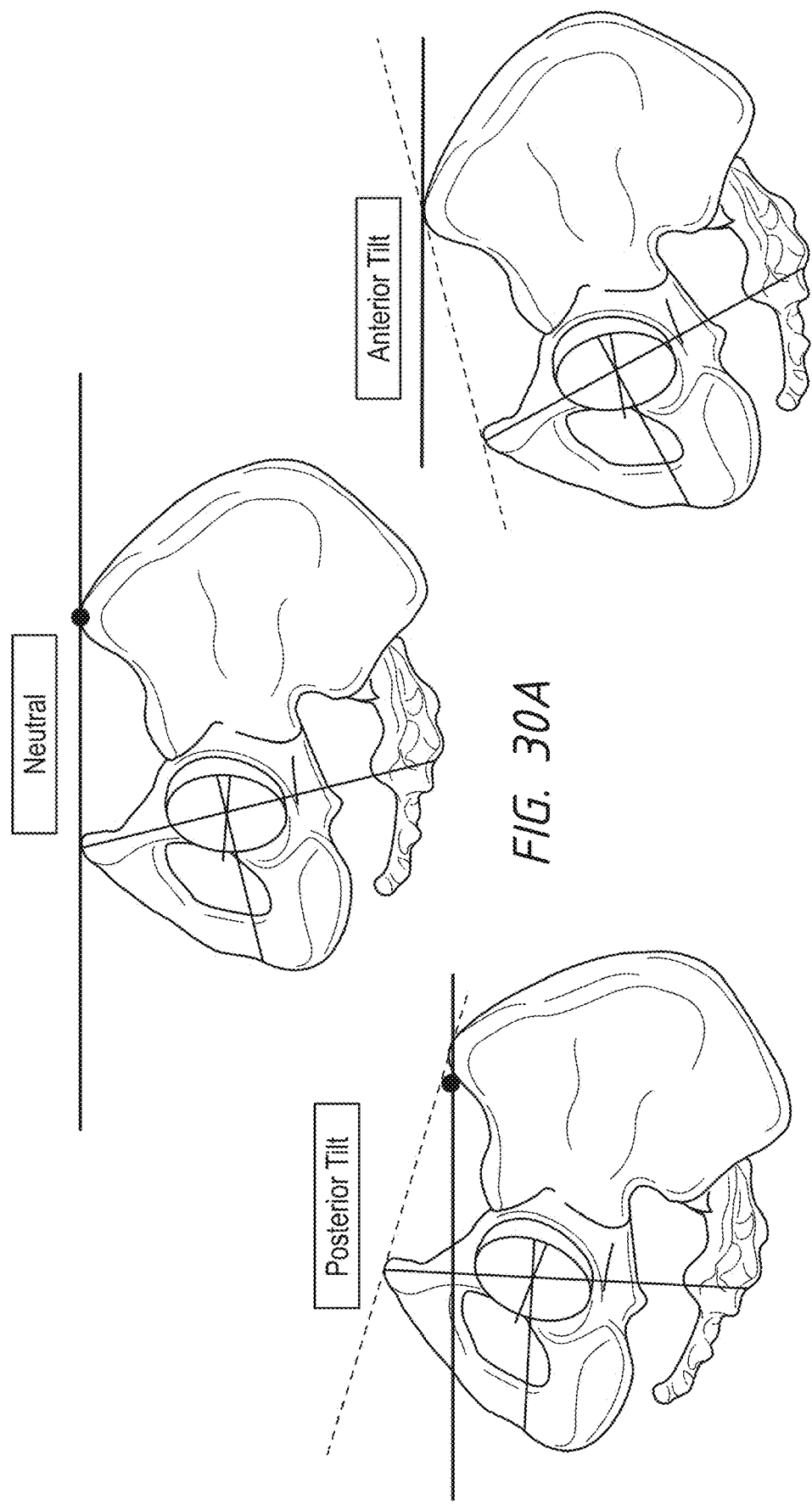
FIGS. 30A-30C illustrate a neutral and two tilt positions of the pelvis.

The surgical orientation device 172 can track pelvic tilt. The tilt of the pelvis can be displayed dynamically on the surgical orientation device 172. FIGS. 30A-30C illustrate the tilt of the pelvis. At the start of the procedure, the pelvis may be ideally positioned. However, the pelvis can shift through the rigors of the procedure. The surgical orientation device 172 can provide information about where the pelvis is relative to the rest of the body. The surgical orientation device 172 can indicate pelvic tilt from a neutral position. The surgical orientation device 172 can indicate a posterior tilt or an anterior tilt. The surgical orientation device 172 can track the pelvis throughout the surgical procedure.

The surgical orientation device 172 can track pelvic rotation. The rotation of the pelvis can be displayed dynamically on the surgical orientation device 172. FIGS. 31A-31C illustrate the rotation of the pelvis. The surgical orientation device 172 can indicate a pelvic rotation. The surgical orientation device 172 can include one or more sensors to provide an output. The surgical orientation device 172 can track the pelvis at the pelvis moves during the procedure. The surgical orientation device 172 can graphically display when the pelvis is located at neutral rotation. For instance, the neutral rotation can be recorded by the surgical orientation device 172 at the beginning of a procedure when the pelvis is ideally placed.

Referring back to FIG. 29, the screen display of the surgical orientation device 172 can indicate pelvic tilt. In the illustrated embodiment, pelvic tilt is shown as a measurement of an angle. The screen display of the surgical orientation device 172 can indicate pelvic rotation. In the illustrated embodiment, pelvic tilt is shown as a measurement of an angle.

The surgical orientation device 172 can include indicia such as a target or bullseye to indicate when the pelvic tilt and pelvic rotation are neutral. In the illustrated embodiment, pelvic tilt can be along the Y-axis or vertical axis of the bullseye. In the illustrated embodiment, pelvic rotation can be along the X-axis or horizontal axis of the bullseye. The surgical orientation device 172 can include indicia such as a dot to indicate the degree of pelvic tilt and rotation. The indicia can move in real-time. As the degree of pelvic tilt increases, the indicia can move further away from the origin or center of the bullseye. As the degree of pelvic tilt decrease, the indicia can move closer to the origin or center of the bullseye. As the degree of pelvic rotation increases, the indicia can move further away from the origin or center of the bullseye. As the degree of pelvic rotation decrease, the indicia can move closer to the origin or center of the bullseye. The indicia can assist the user in understanding the alignment of the pelvis. The indicia can assist the user in positioning the pelvis. For instance, the user can reposition the pelvis during surgery to a neutral position, such as a position having neutral tilt and/or neutral rotation.

Referring back to FIG. 28C, the Adjusted Plane can be provided by transforming, e.g., by rotating the Anterior Pelvic Plane to correct for pelvic tilt. The Adjusted Plane can rotate the Anterior Pelvic Plane about the inter-ASIS line to correct for anterior tilt or posterior tilt. The transformation between the Anterior Pelvic Plane and the Adjusted Plane accounts for tilt of the patient's pelvis. The transformation between the Anterior Pelvic Plane and the Adjusted Plane accounts for pelvic tilt due to the location of the pubic symphysis. The Adjusted Plane rotates a location corresponding to the pubic symphysis in the Anterior Pelvic Plane from the position in which the pubic symphysis was probed to a horizontal location.

Referring to FIGS. 31A-31C, pelvic rotation corresponds to the relative location of the ipsilateral ASIS and the contralateral ASIS. Regardless of pelvic rotation, the inter-ASIS line connects the ipsilateral ASIS and the contralateral ASIS. The Adjusted Plane and the Anterior Pelvic Plane both contain the inter-ASIS line.

Although these inventions have been disclosed in the context of certain preferred embodiments and examples, it will be understood by those skilled in the art that this application extends beyond the specifically disclosed embodiments to other alternative embodiments and/or uses of the invention and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or sub-combinations of the specific features and aspects of the embodiments may be made and still fall within the scope of the application. For example, the application contemplates the connection hub alone or in combination with any of the other modules could comprise a separate aspect. Or, any one or a combination of the modules could be directly connected to an umbrella hub or overhead support to form another separate aspect. Accordingly, it should be understood that various features and aspects of the disclosed embodiments can be combined with or substituted for one another in order to form varying modes of the disclosed embodiments. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A method of positioning a medical prosthesis comprising:
    establishing a vertical plane with a measuring device;
    projecting a pattern of light onto the leg of a patient;
    recording the incidence of light on the leg of a patient;
    replacing the joint by inserting a cup, wherein one or more angles of the cup are measured relative to the vertical plane;
    projecting the pattern light onto the leg of the patient after replacing the joint;
    repositioning the leg to align the recording of the incidence of light with the pattern of light.

2. The method of claim 1, further comprising determining a change in leg length in the vertical plane.

3. The method of claim 1, further comprising determining a change in joint offset in a plane perpendicular to the vertical plane.

4. The method of claim 1, further comprising establishing a horizontal plane with a measuring device, wherein the vertical plane and the horizontal plane define a reference frame.

5. The method of claim 4, further comprising recording a point in the reference frame.

6. The method of claim 4, further comprising recording a point pre-operatively in the reference frame.

7. The method of claim 4, further comprising recording a point post-operatively in the reference frame.

8. The method of claim 1, further comprising recording a position of a probe when contacting a point pre-dislocation.

9. The method of claim 1, further comprising recording a position of a probe when contacting a point post-instrumentation.

10. The method of claim 1, further comprising determining a change in leg length.

11. The method of claim 1, further comprising determining a change in joint offset.

12. A method of positioning a medical prosthesis comprising:
coupling a measuring device and probe to a patient;
positioning the probe to contact a first point;
recording the position of the probe when the probe is contacting the first point;
positioning the probe to contact a second point;
recording the position of the probe when the probe is contacting the second point;
positioning the probe to contact a third point;
recording the position of the probe when the probe is contacting the third point wherein the first point, the second point, and the third point define a plane; and
establishing an adjusted plane by rotating the plane by the direction of gravity.

13. The method of claim 12, further comprising positioning the probe horizontally to measure the direction of gravity.

14. The method of claim 12, further comprising determining cup angles relative to the reference plane.

15. The method of claim 12, further comprising positioning a medical prosthesis at an angle relative to the adjusted plane.

16. The method of claim 12, wherein the first point and the second point define the inter-ASIS line.

17. The method of claim 12, wherein the first point, the second point, and the third point define the anterior pelvic plane.

18. The method of claim 12, wherein the first point is the ipsilateral ASIS.

19. The method of claim 12, wherein the second point is the contralateral ASIS.

20. The method of claim 12, wherein the third point is the anterior surface of the pubic symphysis.

* * * * *

UNITED STATES PATENT AND TRADEMARK OFFICE
CERTIFICATE OF CORRECTION

PATENT NO. : 10,918,499 B2
APPLICATION NO. : 15/920216
DATED : February 16, 2021
INVENTOR(S) : Jonathan Nielsen et al.

Page 1 of 1

It is certified that error appears in the above-identified patent and that said Letters Patent is hereby corrected as shown below:

In the Claims

In Column 71, Line 13 (Approx.), Claim 12, delete "point" and insert --point,--.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*